US008614237B2

(12) United States Patent
Djaballah et al.

(10) Patent No.: US 8,614,237 B2
(45) Date of Patent: Dec. 24, 2013

(54) BENZOFURAN-4,5-DIONES AS SELECTIVE PEPTIDE DEFORMYLASE INHIBITORS

(75) Inventors: Hakim Djaballah, Scarsdale, NY (US); Christophe Antczak, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 193 days.

(21) Appl. No.: 13/318,573

(22) PCT Filed: May 5, 2010

(86) PCT No.: PCT/US2010/001334
§ 371 (c)(1),
(2), (4) Date: Dec. 8, 2011

(87) PCT Pub. No.: WO2010/129049
PCT Pub. Date: Nov. 11, 2010

(65) Prior Publication Data
US 2012/0071523 A1    Mar. 22, 2012

Related U.S. Application Data

(60) Provisional application No. 61/175,756, filed on May 5, 2009.

(51) Int. Cl.
*A61K 31/426* (2006.01)
*C07D 417/14* (2006.01)

(52) U.S. Cl.
USPC .......................................... 514/365; 548/525

(58) Field of Classification Search
USPC .......................................... 514/365; 548/525
See application file for complete search history.

(56) References Cited

U.S. PATENT DOCUMENTS

| 7,747,395 | B2 | 6/2010 | Scheinberg et al. |
| 2004/0002117 | A1 | 1/2004 | Hogan et al. |
| 2008/0124808 | A1 | 5/2008 | Rodgers et al. |
| 2008/0254442 | A1 | 10/2008 | Scheinberg et al. |
| 2009/0023783 | A1 | 1/2009 | Zhang et al. |

FOREIGN PATENT DOCUMENTS

| CN | 101 274 925 A | 10/2008 |
| WO | WO 02/095361 | 11/2002 |
| WO | WO 03/000671 | 1/2003 |
| WO | WO 03/104209 | 12/2003 |

OTHER PUBLICATIONS

Extended European Search Report for EP 10772382.7, mailed Sep. 28, 2012.
Grinev et al., Action of acidic and alkaline agents on dioxonaphthofuran derivatives. Chemistry of Heterocyclic Compounds. 1980;16(6):578-80.
Grinev et al., Investigation in the field of quinones. LIII. Synthesis of monoaryl hydrazones of tetraoxy derivatives in the benzofuran and indole series. Pharmaceutical Chemistry Journal. 1972;6(5):273-75.
Grinev et al., Synthesis and some transformations of halogen-substituted o-quinones in the benzofuran series. Chemistry of Heterocyclic Compounds. 1975;11(6):639-42.
Grinev et al., Synthesis of 4,5-dihydroxy-7-(2-aminopropyl)- and 4,5-dihydroxy-7-(2-phenyl-2-aminoethyl)benzofuran derivatives. Chemistry of Heterocyclic Compounds. 1983;19(9):945-48.
Huang et al., Synthesis of tanshinone IIA analogues and their inhibitory activities against Cdc25 phosphatases. Chinese Chem Lett. 2009;20(12):1461-64.
Mukhanova et al., Synthesis of amino derivatives of naphtho[1,2-b]furan. Pharmaceutical Chemistry Journal. 1990;24(11):802-05.
Stankyavichus et al., Rearrangement of 3-ethoxycarbonyl-5-hydroxyimino-2-methyl-4-oxonaphtho[1,2-b]furan and 3-ethoxycarbonyl-5-hydroxyimino-2-methyl-4-oxo-1-phenylbenzo[g]indole by the action of benzenesulfonyl chloride in an alkaline medium. Chemistry of Heterocyclic Compounds. 1999;35(11):1272-75.
International Search Report and Written Opinion for PCT/US2010/001334 mailed Jun. 29, 2010.
International Preliminary Report on Patentability for PCT/US2010/001334 mailed Nov. 17, 2011.
[No Author Listed] Collaborative Computational Project, No. 4. The CCP4 suite: programs for protein crystallography. Acta Crystallogr D Biol Crystallogr. Sep. 1, 1994;50(Pt 5):760-3.
Al-Mousawi et al., Studies with Enaminones: Reactivity of 1,5-Disubstituted-1,4-pentadien-3-ones Toward Electrophilic Reagents. A Novel Route to Azolylazines, Benzofuranals, Pyranones. J Heterocyclic Chem. 2001;38:949-53.
Altschul et al., Basic local alignment search tool. J Mol Biol. Oct. 5, 1990;215(3):403-10.
Antczak et al., A profiling platform for the identification of selective metalloprotease inhibitors. J Biomol Screen. Apr. 2008;13(4):285-94. Epub Mar. 18, 2008.
Antczak et al., High-throughput identification of inhibitors of human mitochondrial peptide deformylase. J Biomol Screen. Jun. 2007;12(4):521-35. Epub Apr. 13, 2007.
Apfel et al., Peptide deformylase as an antibacterial drug target: target validation and resistance development. Antimicrob Agents Chemother. Apr. 2001;45(4):1058-64.
Atkinson et al., The Kinetics and Mechanisms of Additions to Olefinic Substances. Part 16. Addition of Halogens to 1,4-Benzoquinone and to I ,4-Naphthoquinone, and Dehydrohalogenation of the Resulting Adducts. J Chem Soc Perkin Trans II. 1983:271-9.
Balakrishnon et al., Metalloprotease inhibitors GM6001 and Tapi-0 inhibit the obligate intracellular human pathogen *Chlamydia trachomatis* by targeting peptide deformylase of the bacterium. J Biol Chem. Ju. 16, 2006;281(24):16691-9. Epub Mar. 24, 2006.
Baldwin et al., Crystal structure of type II peptide deformylase from *Staphylococcus aureus*. J Biol Chem. Aug. 23, 2002;277(34):31163-71. Epub Jun. 4, 2002.
Barrero et al., New Routes Toward Drimanes and *nor*-Drimanes from (−)-Sclareol. Synlett. 2000;11:1561-4.
Bartlett et al., Molecular Recognition in Chemical and Biological Problems. Royal Chem Soc. 1989;78:182-96.

(Continued)

*Primary Examiner* — Taofiq A Solola
(74) *Attorney, Agent, or Firm* — Wolf, Greenfield & Sacks, P.C.; C. Hunter Baker

(57) ABSTRACT

The instant invention provides novel benzofuran-4,5-diones and pharmaceutical compositions thereof useful for inhibiting PDF and for treating proliferative and infectious diseases. Compounds may be selective for eukaryotic (e.g., human) PDF or prokaryotic PDF.

19 Claims, 17 Drawing Sheets

(56) References Cited

OTHER PUBLICATIONS

Becker et al., Iron center, substrate recognition and mechanism of peptide deformylase. Nat Struct Biol. Dec. 1998;5(12):1053-8.

Becker et al., Structure of peptide deformylase and identification of the substrate binding site. J Biol Chem. May 8, 1998;273(19):11413-6.

Berge et al., Pharmaceutical salts. J Pharm Sci. Jan. 1977;66(1):1-19.

Bevan et al., A high-throughput screening method for the determination of aqueous drug solubility using laser nephelometry in microtiter plates. Anal Chem. Apr. 15, 2000;72(8):1781-7.

Bingel-Erlenmeyer et al., A peptide deformylase-ribosome complex reveals mechanism of nascent chain processing. Nature. Mar. 6, 2008;452(7183):108-11. Epub Feb. 20, 2008.

Böhm, The computer program LUDI: a new method for the de novo design of enzyme inhibitors. J Comput Aided Mol Des. Feb. 1992;6(1):61-78.

Bonnet et al., A mitochondria-K+ channel axis is suppressed in cancer and its normalization promotes apoptosis and inhibits cancer growth. Cancer Cell. Jan. 2007;11(1):37-51.

Boularot et al., Discovery and refinement of a new structural class of potent peptide deformylase inhibitors. J Med Chem. Jan. 11, 2007;50(1):10-20.

Brisson et al., Discovery and characterization of novel small molecule inhibitors of human Cdc25B dual specificity phosphatase. Mol Pharmacol. Oct. 2004;66(4):824-33. Epub Jul. 1, 2004.

Brünger et al., Crystallography & NMR system: A new software suite for macromolecular structure determination. Acta Crystallogr D Biol Crystallogr. Sep. 1, 1998;54(Pt 5):905-21.

Chan et al., Crystal structure of the *Escherichia coli* peptide deformylase. Biochemistry. Nov. 11, 1997;36(45):13904-9.

Chen et al., Actinonin, a naturally occurring antibacterial agent, is a potent deformylase inhibitor. Biochemistry. Feb. 15, 2000;39(6):1256-62.

Clamp et al., The Jalview Java alignment editor. Bioinformatics. Feb. 12, 2004;20(3):426-7. Epub Jan. 22, 2004.

Clements et al., Antibiotic activity and characterization of BB-3497, a novel peptide deformylase inhibitor. Antimicrob Agents Chemother. Feb. 2001;45(2):563-70.

Cohen et al., Molecular modeling software and methods for medicinal chemistry. J Med Chem. Mar. 1990;33(3):883-94.

Don et al., Mitochondria as cancer drug targets. Trends Mol Med. Aug. 2004;10(8):372-8.

Escobar-Alvarez et al., Structure and activity of human mitochondrial peptide deformylase, a novel cancer target. J Mol Biol. Apr. 17, 2009;387(5):1211-28. Epub Feb. 21, 2009.

Fearnley et al., Two overlapping genes in bovine mitochondrial DNA encode membrane components of ATP synthase. Embo J. Aug. 1986;5(8):2003-8.

Fieulaine et al., The crystal structure of mitochondrial (Type 1A) peptide deformylase provides clear guidelines for the design of inhibitors specific for the bacterial forms. J Biol Chem. Dec. 23, 2005;280(51):42315-24. Epub Sep. 28, 2005.

Giglione et al., Control of protein life-span by N-terminal methionine excision. Embo J. Jan. 2, 2003;22(1):13-23.

Giglione et al., Identification of eukaryotic peptide deformylases reveals universality of N-terminal protein processing mechanisms. Embo J. Nov. 1, 2000;19(21):5916-29.

Giglione et al., Organellar peptide deformylases: universality of the N-terminal methionine cleavage mechanism. Trends Plant Sci. Dec. 2001;6(12):566-72.

Golovchenko et al., Analysis of pH-dependent protein interactions with gel filtration medium. J Chromatogr. Feb. 7, 1992;591(1-2):121-8.

Good et al., Hydrogen ion buffers for biological research. Biochemistry. Feb. 1966;5(2):467-77.

Goodford, A computational procedure for determining energetically favorable binding sites on biologically important macromolecules. J Med Chem. Jul. 1985;28(7):849-57.

Goodsell et al., Automated docking of substrates to proteins by simulated annealing. Proteins. 1990;8(3):195-202.

Gordon et al., Actinonin: an antibiotic substance produced by an actinomycete. Nature. Aug. 18, 1962;195:701-2.

Grant et al., Inhibition and structure-activity studies of methionine hydroxamic acid derivatives with bacterial peptide deformylase. Bioorg Chem. Aug. 2001;29(4):211-22.

Grinev et al., Synthesis of derivatives of naphthofuran and benzindole. J Gen Chem. USSR. 1962;32:1931-6.

Grujic et al., Actinonin induces apoptosis in U937 leukemia cells. Cancer Lett. Jun. 8, 2005;223(2):211-8. Epub Dec. 13, 2004.

Guilloteau et al., The crystal structures of four peptide deformylases bound to the antibiotic actinonin reveal two distinct types: a platform for the structure-based design of antibacterial agents. J Mol Biol. Jul. 26, 2002;320(5):951-62.

Harris et al., Co-crystallization of *Staphylococcus aureus* peptide deformylase (PDF) with potent inhibitors. Acta Crystallogr D Biol Crystallogr. Dec. 2002;58(Pt 12):2153-6. Epub Nov. 23, 2002.

Hooker, Action of lighton β-hydroxy-α-naphthoquinone. Journal of the American Chemical Society. 1936;58:1212-6.

Howard et al., A novel class of inhibitors of peptide deformylase discovered through high-throughput screening and virtual ligand screening. J Med Chem. Dec. 30, 2004;47(27):6669-72.

Jain et al., Bacterial Peptide deformylase inhibitors: a new class of antibacterial agents. Curr Med Chem. 2005;12(14):1607-21.

Jenkins et al., Catalytic domain of human immunodeficiency virus type 1 integrase: identification of a soluble mutant by systematic replacement of hydrophobic residues. Proc Natl Acad Sci U S A. Jun. 20, 1995;92(13):6057-61.

Jones et al., Potential utility of a peptide deformylase inhibitor (NVP PDF-713) against oxazolidinone-resistant or streptogramin-resistant Gram-positive organism isolates. J Antimicrob Chemother. May 2004;53(5):804-7. Epub Mar. 31, 2004.

Kang et al., Inhibition of the calcineurin-NFAT interaction by small organic molecules reflects binding at an allosteric site. J Biol Chem. Nov. 11, 2005;280(45):37698-706. Epub Sep. 7, 2005.

Kayser et al., In vitro leishmanicidal activity of monomeric and dimeric naphthoquinones. Acta Trop. Dec. 1, 2000;77(3):307-14.

Kierzek et al., Models of protein crystal growth. Biophys Chem. Jun. 15, 2001;91(1):1-20.

Kreusch et al., Structure analysis of peptide deformylases from *Streptococcus pneumoniae, Staphylococcus aureus, Thermotoga maritima* and *Pseudomonas aeruginosa*: snapshots of the oxygen sensitivity of peptide deformylase. J Mol Biol. Jul. 4, 2003;330(2):309-21.

Kroemer, Mitochondria in cancer. Oncogene. Aug. 7, 2006;25(34):4630-2.

Kuntz et al., A geometric approach to macromolecule-ligand interactions. J Mol Biol. Oct. 25, 1982;161(2):269-88.

Laatsch, Methylation of 3,3'-dihydroxylated 2,2'binaphtho-1,4'-quinones. Chemical Sciences. 1990;45(3):393-400.

Lazennec et al., Formate dehydrogenase-coupled spectrophotometric assay of peptide deformylase. Anal Biochem. Jan. 1, 1997;244(1):180-2.

Lee et al., A new human peptide deformylase inhibitable by actinonin. Biochem Biophys Res Commun. Dec. 12, 2003;312(2):309-15.

Lee et al., Human mitochondrial peptide deformylase, a new anticancer target of actinonin-based antibiotics. J Clin Invest. Oct. 2004;114(8):1107-16.

Leeds et al., Peptide deformylase as an antibacterial target: a critical assessment. Curr Opin Pharmacol. Oct. 2006;6(5):445-52. Epub Aug. 9, 2006.

Liao et al., Identification and initial characterization of translational initiation factor 2 from bovine mitochondria. J Biol Chem. Aug. 15, 1990;265(23):13618-22.

Lofland et al., In vitro antibacterial activity of the peptide deformylase inhibitor BB-83698. J Antimicrob Chemother. Apr. 2004;53(4):664-8. Epub Feb. 18, 2004.

Martin, 3D database searching in drug design. J Med Chem. Jun. 12, 1992;35(12):2145-54.

Mazel et al., Genetic characterization of polypeptide deformylase, a distinctive enzyme of eubacterial translation. Embo J. Feb. 15, 1994;13(4):914-23.

(56) References Cited

OTHER PUBLICATIONS

Mbing et al., Two biflavonoids from Ouratea flava stem bark. Phytochemistry. 2003;63(4):427-31.
McCcafferty et al., Mutational analysis of potential zinc-binding residues in the active site of the enterococcal D-Ala-D-Ala dipeptidase VanX. Biochemistry. Aug. 26, 19976;36(34):10498-505.
Meinnel et al., A new subclass of the zinc metalloproteases superfamily revealed by the solution structure of peptide deformylase. J Mol Biol. Sep. 27, 1996;262(3):375-86.
Meinnel et al., Characterization of the *Thermus thermophilus* locus encoding peptide deformylase and methionyl-tRNA(fMet) formyltransferase. J Bacteriol. Dec. 1994;176(23):7387-90.
Meinnel et al., Design and synthesis of substrate analogue inhibitors of peptide deformylase. Biochemistry. Apr. 6, 1999;38(14):4287-95.
Miranker et al., Functionality maps of binding sites: a multiple copy simultaneous search method. Proteins. 1991;11(1):29-34.
Mukhanova et al., New approach to synthesis of derivatives of 2-(5-hydroxybenzofuryl-3)naphthofurans. Chemistry of Heterocyclic Compounds. 1998;34(6):651-7.
Murshudov et al., Refinement of macromolecular structures by the maximum-likelihood method. Acta Crystallogr D Biol Crystallogr. May 1, 1997;53(Pt 3):240-55.
Navaza, AmoRe: an Automated Package for Molecular Replacement. Acta Cryst. 1994;A50:157-63.
Navia et al., Use of structural informatino in dug design. Curr Opin Struct Biol. 1992;2;202-10.
Nguyen et al., Characterization of a human peptide deformylase: implications for antibacterial drug design. Biochemistry. Aug. 26, 2003;42(33):9952-8.
Nishibata et al., Automatic Creation of Drug Canidate Structures Based on Receptor Structure. Starting Point for Artificial Lead Generation. Tetrahedron. 1991;47:8985-90.
O'Brien et al., Investigation of the Alamar Blue (resazurin) fluorescent dye for the assessment of mammalian cell cytotoxicity. Eur J Biochem. Sep. 2000;267(17):5421-6.
Park et al., Crystallization and preliminary X-ray crystallographic analysis of peptide deformylase (PDF) from *Bacillus cereus* in ligand-free and actinonin-bound forms. Acta Crystallogr Sect F Struct Biol Cryst Commun. Jan. 1, 2005;61(Pt 1):150-2. Epub Dec. 24, 2004.
Ragusa et al., Substrate recognition and selectivity of peptide deformylase. Similarities and differences with metzincins and thermolysin. J Mol Biol. Jun. 25, 1999;289(5):1445-57.
Roehrl et al., Discovery of small-molecule inhibitors of the NFAT—calcineurin interaction by competitive high-throughput fluorescence polarization screening. Biochemistry. Dec. 28, 2004;43(50:16067-75.
Roehrl et al., Selective inhibition of calcineurin-NFAT signaling by blocking protein-protein interaction with small organic molecules. Proc Natl Acad Sci U S A. May 18, 2004;101(20):7554-9. Epub May 6, 2004.
Schechter et al., On the active site of proteases. III. Mapping the active site of papain; specific peptide inhibitors of papain. Biochem Biophys Res Commun. Sep. 6, 1968;32(5):898-902.
Schechter et al., On the size of the active site in proteases. I. Papain. Biochem Biophys Res Commun. Apr. 20, 1967;27(2):157-62.
Schwede et al., Swiss-Model: An automated protein homology-modeling server. Nucleic Acids Res. Jul. 1, 2003;31(13):3381-5.
Serero et al., An unusual peptide deformylase features in the human mitochondrial N-terminal methionine excision pathway. J Biol Chem. Dec. 26, 2003;278(52):52953-63. Epub Oct. 7, 2003.
Sharma et al., Structure of the mammalian mitochondrial ribosome reveals an expanded functional role for its component proteins. Cell. Oct. 3, 2003;115(1):97-108.
Smith et al., Structural variation and inhibitor binding in polypeptide deformylase from four different bacterial species. Protein Sci. Feb. 2003;12(2):349-60.
Spencer et al., Interaction of mitochondrial initiation factor 2 with mitochondrial fMet-tRNA. Nucleic Acids Res. Oct. 11, 2004;32(18):5464-70. Print 2004.
Takenaga et al., In vitro metabolism of a new anticancer agent, 6-N-formylamino-12, 13-dihydro-1,11-dihydroxy-13-(beta-D-glucopyranosil)5H-indolo+ ++[2,3-a]pyrrolo[3,4-c]carbazole-5,7(6H)-dione (NB-506), in mice, rats, dogs, and humans. Drug Metab Dispos. Feb. 1999;27(2):213-20.
Takeuchi et al., Mammalian mitochondrial methionyl-tRNA transformylase from bovine liver. Purification, characterization, and gene structure. J Biol Chem. Jun. 12, 1998;273(24):15085-90.
Takeuchi et al., Recognition of tRNAs by Methionyl-tRNA transformylase from mammalian mitochondria. J Biol Chem. Jun. 8, 2001;276(23):20064-8. Epub Mar. 23, 2001.
Tan et al., Stereocelective Synthesis of over Two Million Compounds Having Structural Features Both Reminiscent of Natural Products and compatible with Miniaturized Cell-Based Assays. J Am Chem Soc. 1998;120:8565-66.
Teo et al., Peptide deformylase inhibitors as potent antimycobacterial agents. Antimicrob Agents Chemother. Nov. 2006;50(11):3665-73. Epub Sep. 11, 2006.
Thompson et al., Clustal W: improving the sensitivity of progressive multiple sequence alignment through sequence weighting, position-specific gap penalties and weight matrix choice. Nucleic Acids Res. Nov. 11, 1994;22(22):4673-80.
Tisler, Heterocyclic Quinones. Advances in Heterocyclic Chemistry. Alan R. Katritzky, eds, Academic Press. 1989;45:54-5.
Turk, Targeting proteases: successes, failures and future prospects. Nat Rev Drug Discov. Sep. 2006;5(9):785-99.
Walker et al., Identification of the subunits of F1F0-ATPase from bovine heart mitochondria. Biochemistry. Jun. 4, 1991;30(22):5369-78.
Wallace et al., LIGPLOT: a program to generate schematic diagrams of protein-ligand interactions. Protein Eng. Feb. 1995;8(2):127-34.
Wang et al., Docking studies of nickel-peptide deformylase (PDF) inhibitors: exploring the new binding pockets. Biophys Chem. Jun. 20, 2006;122(1):43-9. Epub Mar. 6, 2006.
Watters et al., Antimicrobial activity of a novel peptide deformylase inhibitor, LBM415, tested against respiratory tract and cutaneous infection pathogens: a global surveillance report (2003-2004). J Antimicrob Chemother. May 2006;57(5):914-23. Epub Mar. 20, 2006.
Wei et al., Continuous spectrophotometric assay of peptide deformylase. Anal Biochem. Jul. 15, 1997;250(1):29-34.
Weisburg et al., Intracellular pH and multidrug resistance regulate complement-mediated cytotoxicity of nucleated human cells. J Biol Chem. Apr. 16, 1999;274(16):10877-88.
Weiss et al., Global indicators of X-ray data quality. J. Appl. Crystallogr. 2001;34:130-35.
Wiencek, New strategies for protein crystal growth. Annu Rev Biomed Eng. 1999;1:505-34.
Wilen et al., Tetrahedron Report No. 38. Strategies in Optical Resolutions. Tetrahedron. 1977;33:2725-36.
Wise et al., In vitro activities of peptide deformylase inhibitors against gram-positive pathogens. Antimicrob Agents Chemother. Apr. 2002;46(4):1117-8.
Xu et al., Antitumor activity of actinonin in vitro and in vivo. Clin Cancer Res. Jan. 1998;4(1):171-6.
Yagi et al., Identification of the dicyclohexylcarbodiimide-binding subunit of NADH-ubiquinone oxidoreductase (Complex I). J Biol Chem. Nov. 5, 1988;263(31):16150-5.
Yoon et al., Crystal structure of peptide deformylase from *Staphylococcus aureus* in complex with actinonin, a naturally occurring antibacterial agent. Proteins. Nov. 15, 2004;57(3):639-42.
Yu et al., Convenient preparations of the three 2,3-dihalo-1,4-benzoquinone. Synthetic Communications. 1999;29(5):821-5.
Zhou et al., Co-crystallization of *Leptospira interrogans* peptide deformylase with a potent inhibitor and molecular-replacement schemes with eight subunits in an asymmetric unit. Acta Crystallogr D Biol Crystallogr. Jan. 2004;60(Pt 1):137-9. Epub Dec. 18, 2003.

(56) References Cited

OTHER PUBLICATIONS

Zhou et al., Novel conformational states of peptide deformylase from pathogenic bacterium *Leptospira interrogans*: implications for population shift. J Biol Chem. Dec. 23, 2005;280(51):42391-6. Epub Oct. 20, 2005.

Zhou et al., Unique structural characteristics of peptide deformylase from pathogenic bacterium *Leptospira interrogans*. J Mol Biol. May 21, 2004;339(1):207-15.

| Supplier ID | HsPDF %I 100uM | HsPDF %I 10uM | EcPDF %I 100uM | EcPDF %I 10uM | APN %I 100uM | MMP-1 %I 100uM |
|---|---|---|---|---|---|---|
| SKC-BF-13 | | | 32 | 32 | 50 | 38 |
| SKC-BF-12 | | | 53 | 35 | | 46 |
| SKC-BF-09 | | | 65 | 43 | | 41 |
| SKC-BF-10 | | | 68 | 24 | | 46 |
| SKC-BF-04 | | | 11 | -6 | 54 | 11 |
| SKC-BF-08 | | | 22 | 20 | 41 | 23 |
| SKC-BF-11 | | | 27 | 14 | 50 | 32 |
| SKC-BF-05 | | | 1 | 0 | 50 | -19 |
| SKC-BF-07 | | 33 | 26 | 6 | 64 | 8 |
| SKC-BF-03 | | 82 | 13 | -6 | 68 | 10 |
| SKC-BF-02 | | 76 | 24 | 1 | 4 | 6 |
| SKC-BF-01 | | 68 | 32 | 11 | 5 | 7 |
| SKC-BF-06 | | 29 | 5 | -2 | 21 | 26 |
| SKC-NF-03 | 41 | 25 | 21 | 18 | -2 | 21 |
| SKC-BF-Int10D | 26 | 21 | 3 | 4 | -3 | -7 |
| SKC-NF-02 | 36 | 18 | 30 | 17 | 20 | 21 |
| SKC-NF-01 | 50 | 15 | 23 | 30 | 22 | 27 |
| SKC-BF-Int22 | 18 | 14 | -2 | 4 | 2 | -14 |
| SKC-BF-Int7B | 11 | 14 | 9 | 18 | 5 | -19 |
| SKC-BF-Int9 | 7 | 11 | -10 | 5 | 4 | -2 |
| SKC-BF-Int4 | 24 | 8 | 1 | 6 | 6 | -20 |
| SKC-BF-Int19 | 31 | 4 | 7 | -1 | 12 | 19 |
| SKC-BF-Int10F | 13 | 4 | -3 | -1 | -4 | 14 |
| SKC-BF-Int14 | -15 | 3 | -20 | 3 | -6 | -20 |
| SKC-BF-Int7C | -20 | 3 | -4 | -4 | -14 | -14 |
| SKC-BF-Int7D | -9 | 0 | -8 | 11 | -2 | -14 |
| SKC-BF-Int10E | 9 | -2 | -4 | -3 | -4 | -4 |
| SKC-BF-Int3 | 11 | -3 | 7 | 7 | 10 | -1 |
| SKC-BF-Int8 | -8 | -4 | 3 | -16 | -4 | 2 |
| SKC-BF-Int13 | 8 | -6 | 7 | -26 | -7 | 3 |
| SKC-BF-Int21 | 5 | -13 | 7 | 4 | 10 | -3 |
| SKC-BF-Int7A | -5 | -17 | -14 | -8 | -17 | 10 |
| SKC-BF-Int16 | -21 | -24 | -6 | 4 | -1 | -15 |

-26 ▬▬ 124
% inhibition

Figure 5

| Supplier ID | HsPDF %I 100uM | HsPDF IC50 | HL-60 IC50 | RV+ IC50 | Molt3 IC50 | Jurkat IC50 | ALL-3 IC50 | CWR22 IC50 | HEK293 IC50 | Y79 IC50 | Meso47 IC50 |
|---|---|---|---|---|---|---|---|---|---|---|---|
| SKC-BF-13 | | | | | | | | | | 38 | 37 |
| SKC-BF-10 | | | 69 | 100 | 71 | 67 | 69 | 68 | 100 | 66 | 72 |
| SKC-BF-12 | | | 47 | 64 | | | 36 | 100 | 100 | 100 | 100 |
| SKC-BF-05 | 35 | | | 43 | | | | 50 | 38 | 66 | 100 |
| SKC-BF-07 | | | | 38 | | | 35 | 46 | 36 | 63 | 100 |
| SKC-BF-03 | | | | 48 | | | 47 | 59 | 40 | 74 | 100 |
| SKC-BF-11 | | | 36 | 55 | | | 49 | 67 | 67 | 64 | 100 |
| SKC-BF-06 | 39 | 48 | 67 | | | 48 | 71 | 54 | 100 | 71 |
| SKC-BF-02 | 34 | | | | | | | 55 | | 31 | 100 |
| SKC-BF-04 | | 40 | 33 | 67 | 47 | 57 | 59 | 69 | 100 | 67 | 71 |
| SKC-BF-09 | | 45 | 72 | 100 | 31 | 46 | 69 | 72 | 100 | 100 | 100 |
| SKC-BF-01 | | 59 | | | | | | 46 | | 36 | 63 |
| SKC-BF-08 | | 65 | 53 | 100 | 49 | 55 | 70 | 70 | 100 | 68 | 100 |
| SKC-NF-01 | 50 | 100 | 40 | | | | 42 | 39 | 44 | 55 | 39 |
| SKC-NF-03 | 41 | N.D. | 61 | 100 | 50 | 100 | 100 | 100 | 100 | 100 | 100 |
| SKC-NF-02 | 36 | N.D. | 100 | 100 | 100 | 100 | 100 | 100 | 100 | 100 | 100 |
| SKC-BF-Int19 | 31 | N.D. | | 43 | | | | 100 | 100 | 100 | 100 |
| SKC-BF-Int10D | 26 | N.D. | | 100 | | 32 | 100 | 100 | 63 | 100 | 100 |
| SKC-BF-Int4 | 24 | N.D. | 100 | 100 | 100 | 100 | 100 | 100 | 100 | 100 | 100 |
| SKC-BF-Int22 | 18 | N.D. | 100 | 100 | 100 | 100 | 100 | 100 | 100 | 100 | 100 |
| SKC-BF-Int10F | 13 | N.D. | 100 | 100 | 100 | 100 | 100 | 100 | 100 | 100 | 100 |
| SKC-BF-Int3 | 11 | N.D. | 100 | 100 | 100 | 100 | 100 | 100 | 100 | 100 | 100 |
| SKC-BF-Int7B | 11 | N.D. | 100 | 100 | 100 | 100 | 100 | 100 | 100 | 100 | 100 |
| SKC-BF-Int10E | 9 | N.D. | 100 | 100 | 100 | 100 | 100 | 100 | 100 | 100 | 100 |
| SKC-BF-Int13 | 8 | N.D. | 100 | 100 | 100 | 100 | 100 | 100 | 100 | 100 | 100 |
| SKC-BF-Int21 | 5 | N.D. | 79 | 100 | 100 | 62 | 60 | 100 | 58 | 100 | 100 |
| SKC-BF-Int7A | 5 | N.D. | 100 | 100 | 72 | 100 | 100 | 47 | 100 | 100 | 100 |
| SKC-BF-Int9 | 7 | N.D. | 100 | 100 | | 39 | 100 | 100 | 100 | 100 | 100 |
| SKC-BF-Int8 | 8 | N.D. | 100 | 100 | 100 | 100 | 100 | 100 | 100 | 100 | 100 |
| SKC-BF-Int7D | -9 | N.D. | | 40 | | | 68 | 57 | 31 | 64 | 100 |
| SKC-BF-Int14 | -15 | N.D. | 57 | 100 | 53 | 37 | 100 | 100 | 100 | 100 | 100 |
| SKC-BF-Int7C | -20 | N.D. | 100 | 100 | 100 | 100 | 100 | 100 | 100 | 100 | 100 |
| SKC-BF-Int16 | -21 | N.D. | 100 | 100 | 100 | 100 | 100 | 100 | 100 | 100 | 100 |

N.D.: not determined  -21 ▓ 125     5 ▓ >100
                      % inhibition    IC$_{50}$ (µM)

Figure 7

| R1 | R2 | R3 | SKI ID | Enzymatic functional assay IC$_{50}$, µM | | Alamar Blue viability assay IC$_{50}$, µM | | | | | | | | Nuclear count proliferation assay IC$_{50}$, µM | | Solubility limit, µM |
|---|---|---|---|---|---|---|---|---|---|---|---|---|---|---|---|---|
| | | | | HsPDF | EcPDF | HL60 | RV+ | Molt-3 | Jurkat | ALL3 | Y79 | CWR22 | Meso47 | CWR 22 | Meso47 | |
| phenyl | | | 417508 | 3.4 | 10 | 10 | 10 | 4.5 | 5.8 | 10 | 10 | 10 | 10 | 10 | 10 | 10 |
| 4-NO2-phenyl | | | 417503 | 10 | 10 | 10 | 10 | 10 | 10 | 10 | 10 | 10 | 10 | 10 | 10 | 10 |
| 3-Me-phenyl | | | 417500 | 10 | 10 | 10 | 10 | 10 | 10 | 10 | 10 | 10 | 10 | 10 | 10 | 10 |
| 4-Cl-phenyl | | | 417498 | 10 | 10 | 10 | 10 | 10 | 10 | 10 | 10 | 10 | 10 | 10 | 10 | 10 |
| 3,4-diCl-phenyl | | | 417507 | 10 | 10 | 10 | 10 | 3.8 | 5.3 | 10 | 10 | 10 | 10 | 10 | 10 | 10 |
| 4-Cl-phenyl | | | 417511 | 10 | 10 | 10 | 10 | 3.8 | 6.1 | 10 | 10 | 10 | 10 | 10 | 10 | 10 |
| 2-Cl-phenyl | | | 417516 | 0.96 | 10 | 4.5 | 4.2 | 1.6 | 4.3 | 4.4 | 7.5 | 5.3 | 10 | 2.9 | 10 | 5 |
| 4-F-phenyl | | | 417506 | 10 | 10 | 10 | 10 | 4.2 | 4 | 10 | 10 | 10 | 10 | 10 | 10 | 10 |
| 3-CF3-phenyl | | | 417509 | 10 | 10 | 10 | 10 | 4.5 | 4.7 | 10 | 10 | 10 | 10 | 10 | 10 | 10 |
| 3-OMe-phenyl | | | 417505 | 10 | 10 | 10 | 10 | 10 | 10 | 10 | 10 | 10 | 10 | 10 | 10 | 10 |
| 4-OEt-phenyl | | | 417523 | 10 | 10 | 10 | 10 | 4.5 | 10 | 10 | 10 | 10 | 10 | 10 | 10 | 10 |
| 2-Cl-4-OEt-phenyl | | | 417517 | 10 | 10 | 10 | 10 | 10 | 10 | 10 | 10 | 10 | 10 | 10 | 10 | 10 |
| 2,6-diMe-phenyl | | | 417514 | 10 | 10 | 10 | 10 | 10 | 10 | 10 | 10 | 10 | 10 | 10 | 10 | 10 |
| 2-OMe-phenyl | | | 417513 | 10 | 10 | 10 | 10 | 10 | 10 | 10 | 10 | 10 | 10 | 10 | 10 | 10 |

Figure 14

| R1 | R2 | R3 | SKI ID | Enzymatic functional assay IC$_{50}$, µM | | Alamar Blue viability assay IC$_{50}$, µM | | | | | | | | Nuclear count proliferation assay IC$_{50}$, µM | | Solubility limit, µM |
|---|---|---|---|---|---|---|---|---|---|---|---|---|---|---|---|---|
| | | | | HsPDF | EcPDF | HL60 | RV+ | Molt-3 | Jurkat | ALL3 | Y79 | CWR22 | Meso47 | CWR 22 | Meso47 | |
| (4-Cl-benzoyl) | Cl | Cl | 417519 | 0.69 | 10 | 10 | 10 | 4.6 | 10 | 10 | 10 | 10 | 10 | 10 | 10 | 10 |
| (4-Br-benzoyl) | Br | Br | 417518 | 2.3 | 10 | 10 | 10 | 10 | 10 | 10 | 10 | 10 | 10 | 10 | 10 | 10 |
| (4-Cl-phenoxyacetyl) | Cl | Cl | 417521 | 0.32 | 10 | 10 | 10 | 5 | 10 | 10 | 10 | 10 | 10 | 10 | 10 | 10 |
| (4-Br-phenoxyacetyl) | Br | Br | 417520 | 0.88 | 10 | 10 | 10 | 4.2 | 4.6 | 10 | 10 | 10 | 10 | 10 | 10 | 10 |
| (benzofuran) | Br | Br | 417510 | 10 | 10 | 10 | 10 | 4.4 | 5.9 | 10 | 10 | 10 | 10 | 10 | 10 | 10 |
| (benzofuran) | Cl | Cl | 417515 | 10 | 10 | 10 | 10 | 10 | 10 | 10 | 10 | 10 | 10 | 10 | 10 | 10 |
| (benzodioxole) | Br | Br | 417502 | 10 | 10 | 10 | 10 | 10 | 10 | 10 | 10 | 10 | 10 | 10 | 10 | 10 |
| (benzodioxin) | Br | Br | 417504 | 2.3 | 10 | 10 | 10 | 10 | 10 | 6.1 | 10 | 10 | 10 | 10 | 10 | 10 |
| (4-pyrazolyl-phenyl) | Br | Br | 417499 | 1.8 | 10 | 10 | 10 | 6.4 | 10 | 3.9 | 10 | 10 | 10 | 10 | 10 | 10 |
| (4-oxazolylmethoxy-phenyl) | Br | Br | 417522 | 10 | 10 | 10 | 10 | 4 | 5.4 | 10 | 10 | 10 | 10 | 10 | 10 | 10 |
| (thiophene) | Br | Br | 417501 | 10 | 10 | 10 | 10 | 10 | 10 | 10 | 10 | 10 | 10 | 10 | 10 | 10 |
| (thiophene) | Cl | Cl | 417512 | 1.8 | 10 | 10 | 10 | 3.9 | 4.6 | 6.8 | 10 | 10 | 10 | 10 | 10 | 10 |

Figure 14 (continued)

BENZOFURAN-4,5-DIONES AS SELECTIVE PEPTIDE DEFORMYLASE INHIBITORS

PRIORITY INFORMATION

The present application is a national stage filing under 35 U.S.C. §371 of international PCT application, PCT/US2010/001334, filed May 5, 2010, which claims priority under 35U.S.C. §119(e) to U.S. provisional patent application, U.S. Ser. No. 61/175,756, filed May 5, 2009, each of which is incorporated herein by reference.

GOVERNMENT SUPPORT

This invention was made with U.S. Government support under grant number 1R21NS57008 awarded by the National Institutes of Health. The U.S. Government has certain rights in the invention.

BACKGROUND OF THE INVENTION

Peptide deformylase (PDF) has been long recognized as important in protein synthesis. Removal of the formyl moiety on the N-terminal methionine of nascent proteins by PDF is a necessary activity for prokaryotic cell viability (Mazel et al., *Embo. J.* 1994, 13, 914-923). The central role of PDF in bacterial protein synthesis has led to significant efforts to discover antibiotics that selectively target bacterial PDFs (Howard et al., *J. Med. Chem.* 2004, 47, 6669-6672; Leeds et al., *Current Opinion in Pharmacology* 2006, 6, 445-452). PDF inhibitors are a promising drug class, as has been demonstrated by the broad spectrum activity in vitro against drug resistant bacterial strains of the clinical drug candidates LBM415 (Watters et al., *J. Antimicrob. Chemother.* 2006, 57, 914-923) and BB-83698 (Lofland et al., *J. Antimicrob. Chemother.* 2004, 53, 664-668). The PDF inhibitor BB-83698 has been proposed as a tuberculosis treatment (Teo et al., *Antimicrob. Agents Chemother.* 2006, 50, 3665-3673).

PDF activity was not believed to be important in eukaryotic cells until recently because nuclear encoded proteins are not N-formylated (Serero et al., *J. Biol. Chem.* 2003, 278, 52953-52963). However, in eukaryotes, mitochondrial protein synthesis involves the formylation and deformylation of proteins, as evidenced by the presence of the enzymatic machinery to perform these activities in mammals and plants, among other eukaryotes (Giglione et al., *Embo. J.* 2000, 19, 5916-5929; Takeuchi et al., *J. Biol. Chem.* 2001, 276, 20064-20068; Takeuchi et al., *J. Biol. Chem.* 1998, 273, 15085-15090). The human mitochondrial *Homo sapiens* peptide deformylase (HsPDF) protein, which participates in the N-methionine excision pathway of newly synthesized peptides encoded by the mitochondrial genome, removes the N-terminal formyl group on the initiator methionine, and is important for cancer cell viability (Lee et al., *Biochem. Biophys. Res. Commun.* 2003, 312, 309-315; Lee et al., *J. Clin. Invest.* 2004, 114, 1107-1116; Serero et al., 2003 supra). For example, cancer cell lines appear to be more sensitive to HsPDF inhibition than normal non-cancer cell lines (Lee 2003 and Lee 2004 supra). As well, ATP depletion and mitochondrial membrane depolarization result from the inhibition of HsPDF with the PDF inhibitor actinonin. siRNA interference and pharmacologic inhibition both decrease human cell growth. Furthermore, the PDF inhibitor actinonin and its analogs exhibit anti-cancer activity in vitro and in vivo (Xu et al., *Clin. Cancer Res.* 1998, 4, 171-176).

As of today, most of the research for PDF inhibitors has been focused on the identification of bacterial PDF inhibitors. Nearly all bacterial PDF inhibitors currently in development share a common scaffold based on a peptidomimetic backbone linked to a chelating moiety (Jain et al., *Curr. Med. Chem.* 2005, 12, 1607-1621). Indeed, many of the reported screens were performed on small "rationally" designed libraries, often focused on chelator-based compounds (Gordon et al., *Nature,* 1962, 195, 701-702; Jain et al., *Curr. Med. Chem.* 2005, 12, 1607-1621; Clements et al., *Antimicrob. Agents. Chemother.* 2001, 45, 563-570). Issues related to the lack of selectivity of such compounds were recently highlighted (Turk et al., *Nat. Rev. Drug Discov.* 2006, 5, 785-799). Thus, there remains a need to identify PDF inhibitors structurally different from known bacterial PDF inhibitors, such that they might be selective for HsPDF. These observations led to a screen for novel non-peptidomimetic and non-hydroxamic acid based inhibitors of HsPDF as potentially new anti-proliferative agents.

SUMMARY OF THE INVENTION

The present invention pertains to benzofuran-4,5-diones as non-peptidomimetic, non-hydroxamic acid-based inhibitors of peptide deformylase. Preferably, the inhibitors are selective for HsPDF. Also described herein are pharmaceutical compositions comprising benzofuran-4,5-diones and methods of using such compounds and compositions thereof in vitro and in vivo for research purposes and/or for the treatment of diseases such as, for instance, proliferative diseases or infectious diseases.

Certain compounds of the present invention were identified during a high-throughput screening campaign using binding assays adapted specifically to identify compounds active toward HsPDF. Of the primary hits identified, six included a benzofuran-4,5-dione scaffold. These six hits were further characterized to assess their dose response and specificity profiles and were found to demonstrate good selectivity for HsPDF over other metalloproteases. Specifically, the invention discloses the first inhibitors selective for human PDF over *E. coli* PDF with selectivity of up to greater than 77 fold in a functional assay. Additionally, most of the newly identified HsPDF inhibitors have broad cytotoxicity activity toward cancer cells.

In one aspect, the present invention provides novel benzofuran-4,5-diones and salts thereof. In another aspect, the present invention provides compounds and compositions that may be used to inhibit HsPDF in vivo or in vitro. In yet another aspect, the present invention provides compounds that may be used in the treatment of a disease associated with PDF activity such as, for instance, a proliferative disease or an infectious disease. The invention additionally provides pharmaceutical compositions of the inventive compounds and optionally a pharmaceutically acceptable excipient, and uses thereof.

In certain embodiments, the inventive compounds are of the formula:

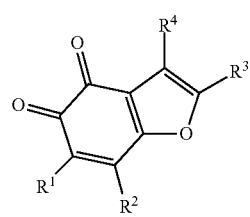

wherein:

R¹ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$^a$; —C(=O)R$^a$; —CO$_2$R$^a$; —CN; —SCN; —SR$^a$; —SOR$^a$; —SO$_2$R$^a$; —NO$_2$; —N$_3$; —N(R$^a$)$_2$; —NR$^a$C(=O)R$^a$; —NR$^a$C(=O)N(R$^a$)$_2$; —OC(=O)OR$^a$; —OC(=O)R$^a$; —OC(=O)N(R$^a$)$_2$; —NR$^a$C(=O)OR$^a$; or —C(R$^a$)$_3$; wherein each occurrence of R$^a$ is independently hydrogen; halogen; a protecting group; an optionally substituted aliphatic or heteroaliphatic moiety; an acyl moiety; or an optionally substituted aryl or heteroaryl moiety;

R² is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$^b$; —C(=O)R$^b$; —CO$_2$R$^b$; —CN; —SCN; —SR$^b$; —SOR$^b$; —SO$_2$R$^b$; —NO$_2$; —N$_3$; —N(R$^b$)$_2$; —NR$^b$C(=O)R$^a$; —NR$^b$C(=O)N(R$^b$)$_2$; —OC(=O)OR$^b$; —OC(=O)R$^b$; —OC(=O)N(R$^b$)$_2$; —NR$^b$C(=O)OR$^b$; or —C(R$^b$)$_3$; wherein each occurrence of R$^b$ is independently hydrogen; halogen; a protecting group; an optionally substituted aliphatic or heteroaliphatic moiety; an acyl moiety; or an optionally substituted aryl or heteroaryl moiety;

wherein R¹ and R² when taken together form an optionally substituted, saturated or unsaturated aromatic, heteroaromatic, or nonaromatic 3-8 membered monocyclic or bicyclic ring optionally containing one or more heteroatoms selected from the group consisting of N, O, or S;

R³ is hydrogen; halogen; cyclic or acyclic, substituted or unsubstituted, branched or unbranched aliphatic; cyclic or acyclic, substituted or unsubstituted heteroaliphatic; substituted or unsubstituted, branched or unbranched acyl; substituted or unsubstituted aryl; substituted or unsubstituted heteroaryl; —OR$^c$; —C(=O)R$^c$; —CO$_2$R$^c$; —CN; —SCN; —SR$^c$; —SOR$^c$; —SO$_2$R$^c$; —NO$_2$; —N$_3$; —N(R$^c$)$_2$; —NR$^c$C(=O)R$^c$; —NR$^c$C(=O)N(R$^c$)$_2$; —OC(=O)OR$^c$; —OC(=O)R$^c$; —OC(=O)N(R$^c$)$_2$; —NR$^c$C(=O)OR$^c$; or —C(R$^c$)$_3$; wherein each occurrence of R$^c$ is independently hydrogen; halogen; a protecting group; an optionally substituted aliphatic or heteroaliphatic moiety; an acyl moiety; or an optionally substituted aryl or heteroaryl moiety; and R⁴ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$^d$; —C(=O)R$^d$; —CO$_2$R$^d$; —CN; —SCN; —SR$^d$; —SOR$^d$; —SO$_2$R$^d$; —NO$_2$; —N$_3$; —N(R$^d$)$_2$; —NR$^d$C(=O)R$^d$; —NR$^d$C(=O)N(R$^d$)$_2$; —OC(=O)OR$^d$; —OC(=O)R$^d$; —OC(=O)N(R$^d$)$_2$; —NR$^d$C(=O)OR$^d$; or —C(R$^d$)$_3$; wherein each occurrence of R$^d$ is independently hydrogen; halogen; a protecting group; an optionally substituted aliphatic or heteroaliphatic moiety; an acyl moiety; or an optionally substituted aryl or heteroaryl moiety, or a pharmaceutically acceptable salt thereof; and wherein the compound is not of one of the formulae:

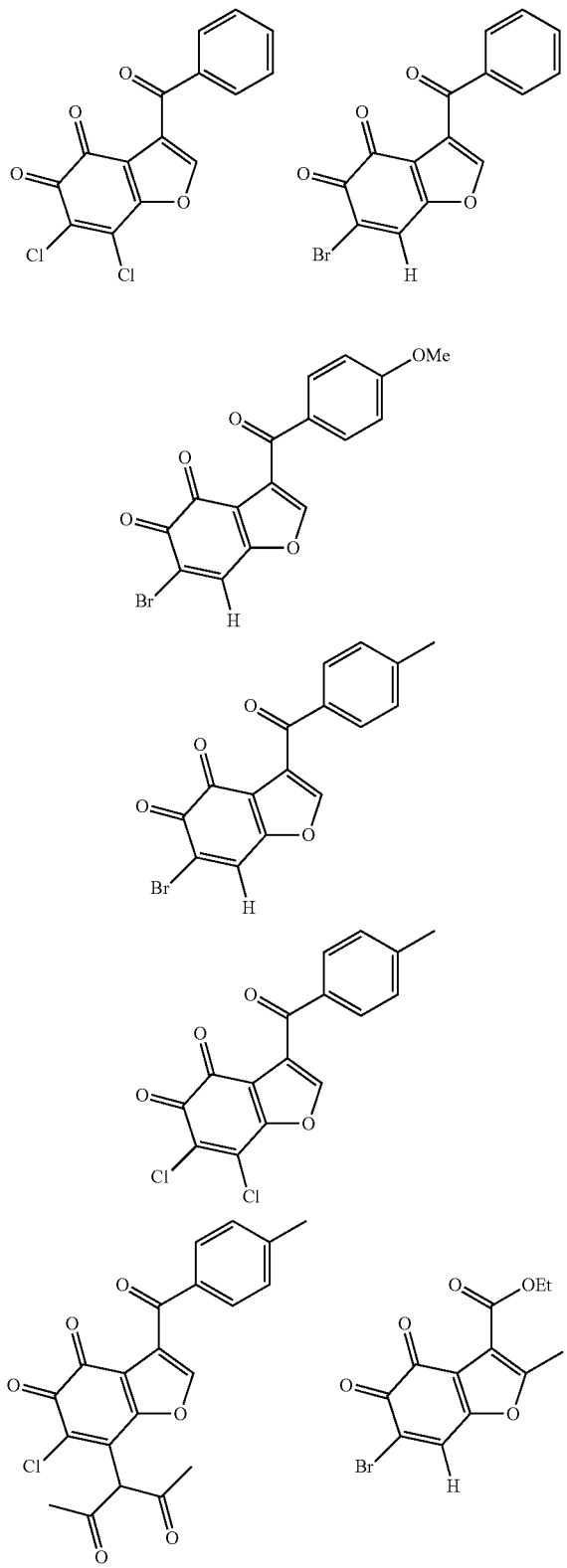

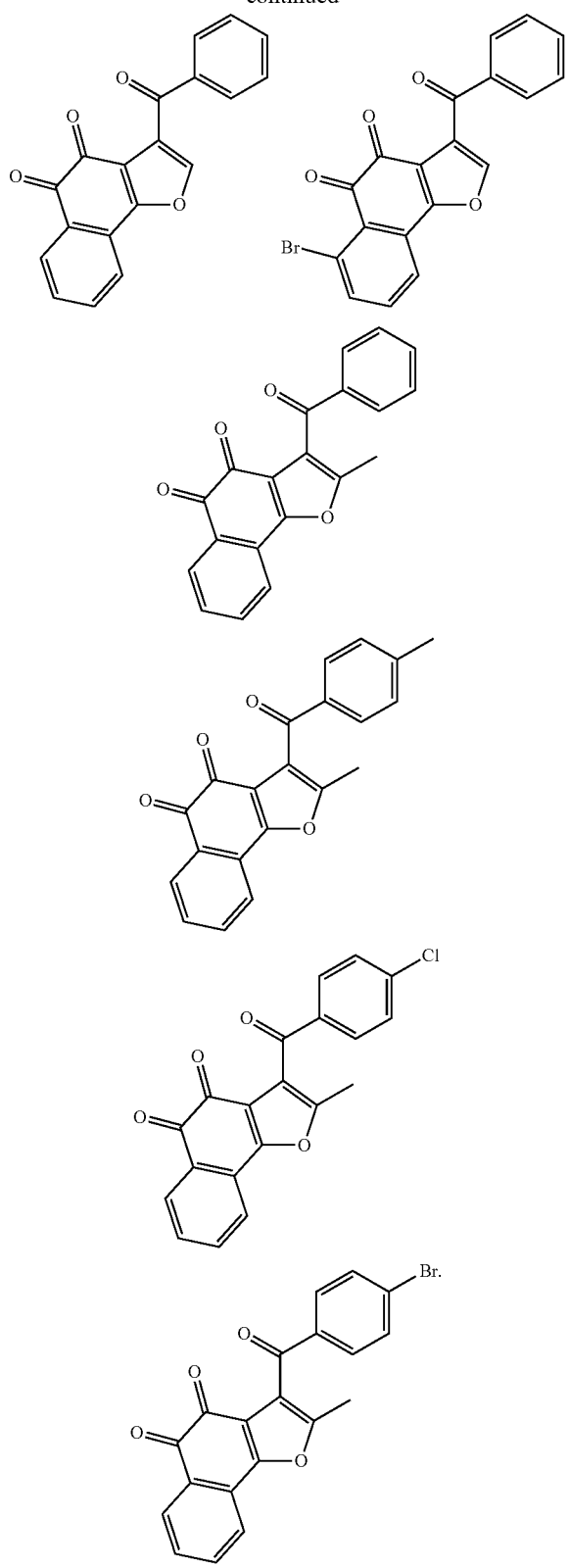

In some embodiments, the present invention provides novel pharmaceutical compositions comprising a therapeutically effective amount of a compound of the formula:

wherein:
R$^1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$^a$; —C(=O)R$^a$; —CO$_2$R$^a$; —CN; —SCN; —SR$^a$; —SOR$^a$; —SO$_2$R$^a$; —NO$_2$; —N$_3$; —N(R$^a$)$_2$; —NR$^a$C(=O)R$^a$; —NR$^a$C(=O)N(R$^a$)$_2$; —OC(=O)OR$^a$; —OC(=O)R$^a$; —OC(=O)N(R$^a$)$_2$; —NR$^a$C(=O)OR$^a$; or —C(R$^a$)$_3$; wherein each occurrence of R$^a$ is independently hydrogen; halogen; a protecting group; an optionally substituted aliphatic or heteroaliphatic moiety; an acyl moiety; or an optionally substituted aryl or heteroaryl moiety;

R$^2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$^b$; —C(=O)R$^b$; —CO$_2$R$^b$; —CN; —SCN; —SR$^b$; —SOR$^b$; —SO$_2$R$^b$; —NO$_2$; —N$_3$; —N(R$^b$)$_2$; —NR$^b$C(=O)R$^a$; —NR$^b$C(=O)N(R$^b$)$_2$; —OC(=O)OR$^b$; —OC(=O)R$^b$; —OC(=O)N(R$^b$)$_2$; —NR$^b$C(=O)OR$^b$; or —C(R$^b$)$_3$; wherein each occurrence of R$^b$ is independently hydrogen; halogen; a protecting group; an optionally substituted aliphatic or heteroaliphatic moiety; an acyl moiety; or an optionally substituted aryl or heteroaryl moiety;

wherein R$^1$ and R$^2$ when taken together form an optionally substituted, saturated or unsaturated aromatic, heteroaromatic, or nonaromatic 3-8 membered monocyclic or bicyclic ring optionally containing one or more heteroatoms selected from the group consisting of N, O, or S;

R$^3$ is hydrogen; halogen; cyclic or acyclic, substituted or unsubstituted, branched or unbranched aliphatic; cyclic or acyclic, substituted or unsubstituted heteroaliphatic; substituted or unsubstituted, branched or unbranched acyl; substituted or unsubstituted aryl; substituted or unsubstituted heteroaryl; —OR$^c$; —C(=O)R$^c$; —CO$_2$R$^c$; —CN; —SCN; —SR$^c$; —SOR$^c$; —SO$_2$R$^c$; —NO$_2$; —N$_3$; —N(R$^c$)$_2$; —NR$^c$C(=O)R$^c$; —NR$^c$C(=O)N(R$^c$)$_2$; —OC(=O)OR$^c$; —OC(=O)R$^c$; —OC(=O)N(R$^c$)$_2$; —NR$^c$C(=O)OR$^c$; or —C(R$^c$)$_3$; wherein each occurrence of R$^c$ is independently hydrogen; halogen; a protecting group; an optionally substituted aliphatic or heteroaliphatic moiety; an acyl moiety; or an optionally substituted aryl or heteroaryl moiety; and R$^4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$^d$; —C(=O)R$^d$; —CO$_2$R$^d$; —CN; —SCN; —SR$^d$; —SOR$^d$; —SO$_2$R$^d$; —NO$_2$; —N$_3$; —N(R$^d$)$_2$; —NR$^d$C(=O)R$^d$; —NR$^d$C(=O)N(R$^d$)$_2$; —OC(=O)OR$^d$; —OC(=O)R$^d$; —OC(=O)N(R$^d$)$_2$;

—NR$^d$C(=O)OR$^d$; or —C(R$^d$)$_3$; wherein each occurrence of R$^d$ is independently hydrogen; halogen; a protecting group; an optionally substituted aliphatic or heteroaliphatic moiety; an acyl moiety; or an optionally substituted aryl or heteroaryl moiety, or a pharmaceutically acceptable salt thereof; and optionally a pharmaceutically acceptable excipient.

In another aspect, the invention provides methods of inhibiting PDF or uses of the inventive compounds for inhibiting PDF. PDF may be inhibited in vivo or in vitro. Methods of inhibiting PDF in vivo may comprise administering to a subject in need thereof a benzofuran-4,5-dione in an amount effective to inhibit PDF. Methods of inhibiting PDF in vitro may comprise contacting a cell or biological sample with a benzofuran-4,5-dione in an amount effective to inhibit PDF. In certain embodiments, the inhibited PDF is a eukaryotic PDF. In certain embodiments, the eukaryotic PDF is human PDF (HsPDF). In certain embodiments, the inhibited PDF is a prokaryotic PDF. In certain embodiments, the inhibited PDF is a bacterial PDF.

Conditions and/or diseases that may be treated using the inventive compounds, compositions, or methods include, by way of nonlimiting example, conditions, and/or diseases wherein the inhibition of PDF is desirable (e.g., a proliferative, infectious, or inflammatory disease). In certain embodiments, the inhibition of a eukaryotic PDF is desirable (e.g., in the treatment of a proliferative disease). In certain embodiments, the inhibition of human PDF is desirable. In certain embodiments, the inhibition of a prokaryotic PDF is desirable (e.g., in the treatment of an infectious disease). In some embodiments, the invention provides methods of inducing apoptosis in a cell in vivo or in vitro using an inventive benzofuran-4,5-dione. In some embodiments, the invention provides methods of inhibiting the proliferation of cancer cells in vivo or in vitro using an inventive benzofuran-4,5-dione. In some embodiments, the invention provides methods of inhibiting growth of a microorganism in vivo or in vitro using a benzofuran-4,5-dione. In certain embodiments, the microorganism is bacterial. In certain embodiments, the microorganism is fungal. All methods of use and/or treatment described herein may comprise the use of a benzofuran-4,5-dione of the present invention or a composition containing a benzofuran-4,5-dione of the present invention, and/or salts thereof.

In some embodiments, the invention provides methods for preparing benzofuran-4,5-diones.

All publications and patent documents cited in this application are incorporated by reference in their entirety for all purposes to the same extent as if the contents of each individual publication or patent document were included herein.

Definitions

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March, *March's Advanced Organic Chemistry*, 5$^{th}$ Edition, John Wiley & Sons, Inc., New York, 2001; Larock, Comprehensive Organic Transformations, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure is substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic, aliphatic and heteroaliphatic, carbon and heteroatom substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example of proliferative diseases, including, but not limited to cancer. The term "stable", as used herein, typically refers to compounds which possess stability sufficient to allow manufacture and which maintain the integrity of the compound for a sufficient period of time to be detected and preferably for a sufficient period of time to be useful for the purposes detailed herein.

Certain compounds of the present invention can comprise one or more asymmetric centers, and thus can exist in various isomeric forms, e.g., stereoisomers and/or diastereomers. Thus, inventive compounds and pharmaceutical compositions thereof may be in the form of an individual enantiomer, diastereomer, or geometric isomer, or may be in the form of a mixture of stereoisomers. In certain embodiments, the compounds of the invention are enantiopure compounds. In certain other embodiments, mixtures of stereoisomers or diastereomers are provided.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. In addition to the above-mentioned compounds per se, the invention also encompasses pharmaceutically acceptable derivatives of these compounds and compositions comprising one or more compounds.

Where a particular enantiomer is desired, it may, in some embodiments be provided substantially free of the corresponding enantiomer, and may also be referred to as "optically enriched." "Optically enriched," as used herein, means that the compound is made up of a significantly greater proportion of one enantiomer. In certain embodiments the compound is made up of at least about 90% by weight of a particular enantiomer. In other embodiments the compound is made up of at least about 95%, 96%, 97%, 98%, or 99% by weight of a desired enantiomer. A desired enantiomer may be isolated from a racemic mixture by any method known to those skilled in the art, including chiral high pressure liquid chromatography (HPLC) or the formation and crystallization of chiral salts, or the enantiomer may be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); Wilen, *Tables of Resolving Agents and Optical Resolutions* p. 268 (E. L. Eliel, Ed., Univ. of Notre Dame Press, Notre Dame, Ind. 1972).

The term "acyl", as used herein, refers to a carbonyl-containing functionality, e.g., —C(=O)R % wherein R' is an aliphatic, alycyclic, heteroaliphatic, heterocyclic, aryl, heteroaryl, (aliphatic)aryl, (heteroaliphatic)aryl, heteroaliphatic (aryl), or heteroaliphatic(heteroaryl) moiety, whereby each of the aliphatic, heteroaliphatic, aryl, or heteroaryl moieties is substituted or unsubstituted, or is a substituted (e.g., hydrogen; or aliphatic, heteroaliphatic, aryl, or heteroaryl moieties) oxygen or nitrogen containing functionality (e.g., forming a carboxylic acid, ester, or amide functionality).

The term "aliphatic", as used herein, includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, and alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (substituted or unsubstituted, branched or unbranched) having 1-6 carbon atoms.

In certain embodiments, the alkyl, alkenyl, and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alicyclic", as used herein, refers to compounds which combine the properties of aliphatic and cyclic compounds and include but are not limited to cyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —$CH_2$-cyclopropyl, cyclobutyl, —$CH_2$-cyclobutyl, cyclopentyl, —$CH_2$-cyclopentyl, cyclohexyl, —$CH_2$-cyclohexyl, cyclohexenylethyl, cyclohexanylethyl, norborbyl moieties and the like, which again, may bear one or more substituents.

The term "alkoxy" (or "alkyloxy"), or "thioalkyl" as used herein refers to an alkyl group, as previously defined, attached to the parent molecular moiety through an oxygen atom or through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkoxy, include but are not limited to, methoxy, ethoxy, propoxy, isopropoxy, n-butoxy, tert-butoxy, neopentoxy, and n-hexoxy. Examples of thioalkyl include, but are not limited to, methylthio, ethylthio, propylthio, isopropylthio, n-butylthio, and the like.

The term "alkylamino" refers to a group having the structure —NHR' wherein R' is alkyl, as defined herein. The term "aminoalkyl" refers to a group having the structure —$NH_2$R', wherein R' is alkyl, as defined herein. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkylamino include, but are not limited to, methylamino, ethylamino, iso-propylamino, and the like.

Some examples of substituents of the above-described aliphatic (and other) moieties include, but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —C(O)$R_x$; —$CO_2(R_x)$; —CON($R_x$)$_2$; —OC(O)$R_x$; —$OCO_2R_x$; —OCON($R_x$)$_2$; —N($R_x$)$_2$; —S(O)$_2R_x$; —$NR_x$(CO)$R_x$; wherein each occurrence of $R_x$ independently includes, but is not limited to, aliphatic, alycyclic, heteroaliphatic, heterocyclic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

In general, the term "aryl", as used herein, refers to a stable mono- or polycyclic, unsaturated moiety having preferably 3-14 carbon atoms, each of which may be substituted or unsubstituted. In certain embodiments, the term "aryl" refers to a planar ring having p-orbitals perpendicular to the plane of the ring at each ring atom and satisfying the Huckel rule where the number of pi electrons in the ring is (4n+2) wherein n is an integer. A mono- or polycyclic, unsaturated moiety that does not satisfy one or all of these criteria for aromaticity is defined herein as "non-aromatic", and is encompassed by the term "alicyclic".

In general, the term "heteroaryl", as used herein, refers to a stable mono- or polycyclic, unsaturated moiety having preferably 3-14 carbon atoms, each of which may be substituted or unsubstituted; and comprising at least one heteroatom selected from O, S, and N within the ring (i.e., in place of a ring carbon atom). In certain embodiments, the term "heteroaryl" refers to a planar ring comprising at least one heteroatom, having p-orbitals perpendicular to the plane of the ring at each ring atom, and satisfying the Huckel rule where the number of pi electrons in the ring is (4n+2) wherein n is an integer.

It will also be appreciated that aryl and heteroaryl moieties, as defined herein may be attached via an alkyl or heteroalkyl moiety and thus also include -(alkyl)aryl, -(heteroalkyl)aryl, -(heteroalkyl)heteroaryl, and -(heteroalkyl)heteroaryl moieties. Thus, as used herein, the phrases "aryl or heteroaryl moieties" and "aryl, heteroaryl, -(alkyl)aryl, -(heteroalkyl)aryl, -(heteroalkyl)heteroaryl, and -(heteroalkyl)heteroaryl" are interchangeable. Substituents include, but are not limited to, any of the previously mentioned substituents, i.e., the substituents recited for aliphatic moieties, or for other moieties as disclosed herein, resulting in the formation of a stable compound.

The term "aryl", as used herein, does not differ significantly from the common meaning of the term in the art and refers to an unsaturated cyclic moiety comprising at least one aromatic ring. In certain embodiments, "aryl" refers to a mono- or bicyclic carbocyclic ring system having one or two aromatic rings including, but not limited to, phenyl, naphthyl, tetrahydronaphthyl, indanyl, indenyl, and the like.

The term "heteroaryl", as used herein, does not differ significantly from the common meaning of the term in the art and refers to a cyclic aromatic radical having from five to ten ring atoms of which one ring atom is selected from S, O, and N; zero, one or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)R$_x$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl, or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or -(alkyl)heteroaryl substituents described above and herein may be substituted or unsubstituted. Additionally, it will be appreciated that any two adjacent groups taken together may represent a 4, 5, 6, or 7-membered substituted or unsubstituted alicyclic or heterocyclic moiety. Additional examples of generally applicable substituents are illustrated by the specific embodiments described herein.

The term "cycloalkyl," as used herein, refers specifically to groups having three to seven, preferably three to ten, carbon atoms. Suitable cycloalkyls include, but are not limited to cyclopropyl, cyclobutyl, cyclopentyl, cyclohexyl, cycloheptyl, and the like, which, as in the case of aliphatic, alicyclic, heteroaliphatic or heterocyclic moieties, may optionally be substituted with substituents including, but not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$; wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments described herein.

The term "heteroaliphatic", as used herein, refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, e.g., in place of carbon atoms. Heteroaliphatic moieties may be linear or branched, and saturated or unsaturated. In certain embodiments, heteroaliphatic moieties are substituted by independent replacement of one or more of the hydrogen atoms thereon with one or more moieties including, but not limited, to aliphatic; alicyclic; heteroaliphatic; heterocyclic; aromatic; heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$ R$_x$; —NR$_x$(CO)R$_x$, wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments described herein.

The term "heterocycloalkyl," "heterocycle," or "heterocyclic," as used herein, refers to compounds which combine the properties of heteroaliphatic and cyclic compounds and include, but are not limited to, saturated and unsaturated mono- or polycyclic cyclic ring systems having 5-16 atoms wherein at least one ring atom is a heteroatom selected from O, S, and N (wherein the nitrogen or sulfur heteroatom may optionally be oxidized), wherein the ring systems are optionally substituted with one or more functional groups, as defined herein. In certain embodiments, the term "heterocycloalkyl," "heterocycle," or "heterocyclic" refers to a non-aromatic 5-, 6- or 7-membered ring or a polycyclic group wherein at least one ring atom is a heteroatom selected from O, S, and N (wherein the nitrogen and sulfur heteroatoms may be optionally be oxidized), including, but not limited to, a bi- or tri-cyclic group, comprising fused six-membered rings having between one and three heteroatoms independently selected from oxygen, sulfur and nitrogen, wherein (i) each 5-membered ring has 0 to 2 double bonds, each 6-membered ring has 0 to 2 double bonds and each 7-membered ring has 0 to 3 double bonds, (ii) the nitrogen and sulfur heteroatoms may be optionally be oxidized, (iii) the nitrogen heteroatom may optionally be quaternized, and (iv) any of the above heterocyclic rings may be fused to an aryl or heteroaryl ring. Representative heterocycles include, but are not limited to, heterocycles such as furanyl, thiofuranyl, pyranyl, pyrrolyl, thienyl, pyrrolidinyl, pyrazolinyl, pyrazolidinyl, imidazolinyl, imidazolidinyl, piperidinyl, piperazinyl, oxazolyl, oxazolidinyl, isooxazolyl, isoxazolidinyl, dioxazolyl, thiadiazolyl, oxadiazolyl, tetrazolyl, triazolyl, thiatriazolyl, oxatriazolyl, thiadiazolyl, oxadiazolyl, morpholinyl, thiazolyl, thiazolidinyl, isothiazolyl, isothiazolidinyl, dithiazolyl, dithiazolidinyl, tetrahydrofuryl, and benzofused derivatives thereof. In certain embodiments, a "substituted heterocycle, or heterocycloalkyl or heterocyclic" group is utilized and as used herein, refers to a heterocycle, or heterocycloalkyl or heterocyclic group, as defined above, substituted by the independent replacement of one, two, or three of the hydrogen atoms thereon with, but are not limited to, aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substitutents described above and herein may be substituted or unsubstituted. Additional examples or generally applicable substituents are illustrated by the specific embodiments described herein.

Additionally, it will be appreciated that any of the alicyclic or heterocyclic moieties described above and herein may comprise an aryl or heteroaryl moiety fused thereto. Additional examples of generally applicable substituents are illustrated by the specific embodiments described herein. The terms "halo" and "halogen" as used herein refer to an atom selected from fluorine, chlorine, bromine, and iodine.

The terms "halo" and "halogen" as used herein refer to an atom selected from fluorine, chlorine, bromine, and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "amino", as used herein, refers to a primary (—NH$_2$), secondary (—NHR$_x$), tertiary (—NR$_x$R$_y$), or quaternary (—N$^+$R$_x$R$_y$R$_z$) amine, where R$_x$, R$_y$ and R$_z$ are independently an aliphatic, alicyclic, heteroaliphatic, heterocyclic, aryl, or heteroaryl moiety, as defined herein. Examples of amino groups include, but are not limited to, methylamino, dimethylamino, ethylamino, diethylamino, diethylaminocarbonyl, methylethylamino, iso-propylamino, piperidino, trimethylamino, and propylamino.

The term "alkylidene", as used herein, refers to a substituted or unsubstituted, linear or branched saturated divalent radical consisting solely of carbon and hydrogen atoms, having from one to n carbon atoms, having a free valence "-" at both ends of the radical. In certain embodiments, the alkylidene moiety has 1 to 6 carbon atoms.

The term "alkenylidene", as used herein, refers to a substituted or unsubstituted, linear or branched unsaturated divalent radical consisting solely of carbon and hydrogen atoms, having from two to n carbon atoms, having a free valence "-" at both ends of the radical, and wherein the unsaturation is present only as double bonds and wherein a double bond can exist between the first carbon of the chain and the rest of the molecule. In certain embodiments, the alkenylidene moiety has 2 to 6 carbon atoms.

The term "alkynylidene", as used herein, refers to a substituted or unsubstituted, linear or branched unsaturated divalent radical consisting solely of carbon and hydrogen atoms, having from two to n carbon atoms, having a free valence "-" at both ends of the radical, and wherein the unsaturation is present only as triple or double bonds and wherein a triple or double bond can exist between the first carbon of the chain and the rest of the molecule. In certain embodiments, the alkynylidene moiety has 2 to 6 carbon atoms.

Unless otherwise indicated, as used herein, the terms "alkyl", "alkenyl", "alkynyl", "heteroalkyl", "heteroalkenyl", "heteroalkynyl", "alkylidene", alkenylidene", -(alkyl) aryl, -(heteroalkyl)aryl, -(heteroalkyl)aryl, -(heteroalkyl)heteroaryl, and the like encompass substituted and unsubstituted, and linear and branched groups. Similarly, the terms "aliphatic", "heteroaliphatic", and the like encompass substituted and unsubstituted, saturated and unsaturated, and linear and branched groups. Similarly, the terms "cycloalkyl", "heterocycle", "heterocyclic", and the like encompass substituted and unsubstituted, and saturated and unsaturated groups. Additionally, the terms "cycloalkenyl", "cycloalkynyl", "heterocycloalkenyl", "heterocycloalkynyl", "aromatic", "heteroaromatic", "aryl", "heteroaryl" and the like encompass both substituted and unsubstituted groups.

The phrase, "pharmaceutically acceptable derivative," as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety, which is susceptible to removal in vivo yielding the parent molecule as the pharmacologically active species. An example of a pro-drug is an ester, which is cleaved in vivo to yield a compound of interest. Pro-drugs of a variety of compounds, and materials and methods for derivatizing the parent compounds to create the pro-drugs, are known and may be adapted to the present invention.

The biological activity of pro-drugs and pro-drugs may also be altered by appending a functionality onto the compound, which may be catalyzed by an enzyme. Also, included are oxidation and reduction reactions, including enzyme-catalyzed oxidation and reduction reactions. Certain exemplary pharmaceutical compositions and pharmaceutically acceptable derivatives will be discussed in more detail herein below.

By the term "protecting group", as used herein, it is meant that a particular functional moiety, e.g., O, S, or N, is temporarily blocked so that a reaction can be carried out selectively at another reactive site in a multifunctional compound. In certain embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen, and carbon protecting groups may be utilized. For example, in certain embodiments, as detailed herein, certain exemplary oxygen protecting groups are utilized. These oxygen protecting groups include, but are not limited to methyl ethers, substituted methyl ethers (e.g., MOM (methoxymethyl ether), MTM (methylthiomethyl ether), BOM (benzyloxymethyl ether), PMBM or MPM (p-methoxybenzyloxymethyl ether), to name a few), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether), to name a few), esters (e.g., formate, acetate, benzoate (Bz), trifluoroacetate, dichloroacetate, to name a few), carbonates, cyclic acetals and ketals. In certain other exemplary embodiments, nitrogen protecting groups are utilized. These nitrogen protecting groups include, but are not limited to, carbamates (including methyl, ethyl and substituted ethyl carbamates (e.g., Troc), to name a few) amides, cyclic imide derivatives, N-Alkyl and N-Aryl amines, imine derivatives, and enamine derivatives, to name a few. Certain other exemplary protecting groups are detailed herein, however, it will be appreciated that the present invention is not intended to be limited to these protecting groups; rather, a variety of additional equivalent protecting groups can be readily identified using the above criteria and utilized in the present invention. Additionally, a variety of protecting groups are described in *Protective Groups in Organic Synthesis*, Third Ed. Greene, T. W. and Wuts, P. G., Eds., John Wiley & Sons, New York: 1999, the entire contents of which are hereby incorporated by reference.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Other pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

Additionally, as used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of the compounds of the present invention which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As used herein, the term "tautomer" includes two or more interconvertable compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol; amide-to-imide; lactam-to-lactim; enamine-to-imine; and enamine-to-(a different) enamine tautomerizations.

As used herein, the term "isomers" includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, an isomer/enantiomer may, in some embodiments, be provided substantially free of the corresponding enantiomer, and may also be referred to as "optically enriched." "Optically-enriched," as used herein, means that the compound is made up of a significantly greater proportion of one enantiomer. In certain embodiments the compound of the present invention is made up of at least about 90% by weight of a particular enantiomer. In other embodiments the compound is made up of at least about 95%, 98%, or 99% by weight of a particular enantiomer. A desired enantiomer may be isolated from a racemic mixture by any method known to those skilled in the art, including chiral high pressure liquid chromatography (HPLC) or the formation and crystallization of chiral salts, or the enantiomer may be prepared by asymmetric syntheses. See, for example, Jacques, et al., Enantiomers, Racemates and Resolutions (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

"Small Molecule": As used herein, the term "small molecule" refers to a non-peptidic, non-oligomeric organic compound either synthesized in the laboratory or found in nature. Small molecules, as used herein, can refer to compounds that are "natural product-like", however, the term "small molecule" is not limited to "natural product-like" compounds. Rather, a small molecule is typically characterized in that it contains several carbon-carbon bonds, and has a molecular weight of less than 2000 g/mol, preferably less than 1500 g/mol, although this characterization is not intended to be limiting for the purposes of the present invention. Examples of "small molecules" that occur in nature include, but are not limited to, taxol, dynemicin, and rapamycin. Examples of "small molecules" that are synthesized in the laboratory include, but are not limited to, compounds described in Tan et al., ("Stereoselective Synthesis of over Two Million Compounds Having Structural Features Both Reminiscent of Natural Products and Compatible with Miniaturized Cell-Based Assays" *J. Am. Chem. Soc.* 120:8565, 1998; incorporated herein by reference). In certain other embodiments, natural-product-like small molecules are utilized.

As used herein the term "biological sample" includes, without limitation, cell cultures or extracts thereof; biopsied material obtained from an animal (e.g., mammal) or extracts thereof; and blood, saliva, urine, feces, semen, tears, or other body fluids or extracts thereof. For example, the term "biological sample" refers to any solid or fluid sample obtained from, excreted by or secreted by any living organism, including single-celled micro-organisms (such as bacteria and yeasts) and multicellular organisms (such as plants and animals, for instance a vertebrate or a mammal, and in particular a healthy or apparently healthy human subject or a human subject affected by a condition or disease to be diagnosed or investigated).

The biological sample can be in any form, including a solid material such as a tissue, cells, a cell pellet, a cell extract, cell homogenates, or cell fractions; or a biopsy, or a biological fluid. The biological fluid may be obtained from any site (e.g., blood, saliva (or a mouth wash containing buccal cells), tears, plasma, serum, urine, bile, cerebrospinal fluid, amniotic fluid, peritoneal fluid, and pleural fluid, or cells therefrom, aqueous or vitreous humor, or any bodily secretion), a transudate, an exudate (e.g., fluid obtained from an abscess or any other site of infection or inflammation), or fluid obtained from a joint (e.g., a normal joint or a joint affected by disease such as rheumatoid arthritis, osteoarthritis, gout or septic arthritis).

The biological sample can be obtained from any organ or tissue (including a biopsy or autopsy specimen) or may comprise cells (whether primary cells or cultured cells) or medium conditioned by any cell, tissue or organ. Biological samples may also include sections of tissues such as frozen sections taken for histological purposes. Biological samples also include mixtures of biological molecules including proteins, lipids, carbohydrates, and nucleic acids generated by partial or complete fractionation of cell or tissue homogenates. Although the sample is preferably taken from a human subject, biological samples may be from any animal, plant, bacteria, virus, yeast, etc. If desired, the biological sample may be subjected to preliminary processing, including preliminary separation techniques.

The term animal, as used herein, refers to humans as well as non-human animals, at any stage of development, including, for example, mammals, birds, reptiles, amphibians, fish, worms and single cells. In certain embodiments, the non-human animal is a mammal (e.g., a rodent, a mouse, a rat, a rabbit, a monkey, a dog, a cat, a sheep, cattle, a primate, or a pig). An animal may be a transgenic animal.

As used herein, the term "test subject" or "subject" refers to any organism to which a composition of this invention may be administered, e.g., for experimental, diagnostic, prophylactic, and/or therapeutic purposes. Typical subjects include animals (e.g., mammals such as mice, rats, rabbits, non-human primates, and humans; insects; worms; etc.). In some embodiments, a subject may be infected with, suffering from, and/or susceptible to a disease, disorder, and/or condition.

The term HsPDF as used herein refers to not only to native HsPDF (SEQ ID NO.:1), but also includes any structural modifications thereof. Structural modifications include any additions, deletions, and/or substitutions to the native HsPDF amino acid sequence, of bound metal(s), and/or of coordinating solvates, hydrates, or non-covalently bound ligands.

The term PDF as used herein refers to both bacterial and eukaryotic peptide deformylase proteins. Exemplary bacterial PDF include, but are not limited to, *Escherichia coli* PDF; *Streptococcus pneumoniae* PDF; *Haemophilus influenzae* PDF; *Sthaphylococcus aureus* PDF; *Arabidopsis thaliana* PDF; *Pseudomonas aeruginosa* PDF; *Leptospira interrogans* PDF; *Thermotoga maritima* PDF; *Bacillus stearothermophilus* PDF; *B. subtilis* PDF; *P. aeruginosa* PDF; Malaria parasite (*Plasmodium falciparum* PDF); *Thermus thermophilus* PDF; *T. maritima* PDF; *Chlamydia trachomatis* PDF; *C. pneumoniae* PDF; *C. psittaci* PDF; and *C. pecorum* PDF.

BRIEF DESCRIPTION OF THE DRAWINGS

FIG. 5. Specificity profiling of the derivatives of benzofuran-4,5-diones.

FIG. 7. Cytotoxicity profiling for the thirty-three (33) derivatives of benzofuran-4,5-diones toward HsPDF and EcPDF. The $IC_{50}$ in µM for each compound toward each cell line is summarized as a heat map.

FIG. 14. Cytotoxicity profiling of 26 benzofuran-4,5-diones using a panel of eight cancer cell lines. $R_1$, $R_2$, and $R_3$ are based on the chemical structures in FIG. 10.

DETAILED DESCRIPTION OF CERTAIN EMBODIMENTS OF THE INVENTION

Figure 1:
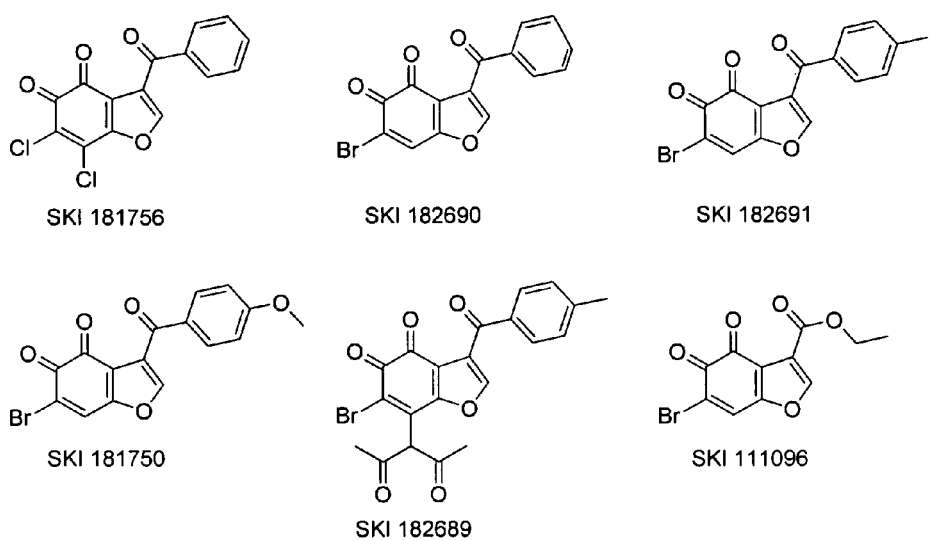
FIG. 1. Structures of the six primary hits from high-throughput screening with the benzofuran-4,5-dione scaffold.

In prokaryotes and a small subset of eukaryotes, protein synthesis is initiated with an N-formylated methionine. In bacteria, the N-formyl group is subsequently removed from most proteins by peptide deformylase (PDF). The resulting free amine moiety then undergoes further processing by methionine aminopeptidase and other enzymes to yield mature proteins. HsPDF (human mitochondrial peptide deformylase) is a specific type of peptide deformylase recently discovered to exhibit selective anti-proliferative properties in cancer cells. Thus, HsPDF provides an exciting new target for broadly acting anti-proliferative agents.

The majority of research on PDF inhibitors has focused on bacterial PDF inhibitors, most of which currently in development have a peptidomimetic backbone linked to a chelating moiety. However, these chelator-based compounds often lack selectivity. Thus, there remains a need to identify novel non-peptidomimetic and non-hydroxamic acid-based inhibitors with improved selectivity toward human PDF.

Compounds of the present invention were originally identified during a high-throughput screening campaign. This campaign used binding assays specifically adapted to identify compounds active toward human PDF. Six of the primary hits obtained have a benzofuran-4,5-dione scaffold. These six compounds were subsequently characterized to assess their dose response and specificity profiles by using fluorescence polarization profiling methods and fluorescamine-based functional assays adapted specifically for human PDF (Antczak et al., *J. Biomol. Screen* 2007, 12:5, 21-35; Antczak et al., *J. Biomol. Screen* 2008, 13, 285-294). Indeed, the six lead compounds were found to demonstrate good selectivity for human PDF over certain other metalloproteases (e.g., *E. coli* PDF). In addition to their enhanced selectivity, most of the newly identified human PDF inhibitors also have broad cytotoxicity activity toward cancer cells. Data obtained from the above-mentioned study led to the design, synthesis, and analysis of a series of benzofuran-4,5-dione derivatives.

Exemplary cancer cell lines screened herein include HL-60 (human acute promyelocytic leukemia), Jurkat (human acute T cell leukemia), Molt3 (acute lymphoblastic leukemia), CWR22 (prostate carcinoma), HEK293 (human embryonic kidney), K562 (human chronic myeloid leukemia lymphoblasts), Y79 (human retinoblastoma), NCEB-1 (human non-hodgkin lymphoma), HL-60/RV+ (a P-glycoprotein-overexpressing multi-drug resistant HL-60 variant selected by continuous exposure to vincristine), and ALL-3 (acute lymphoblastic leukemia). Cancer cells may also be derived from a tumor.

Exemplary cancers that may be treated using an inventive benzofuran-4,5-dione, or composition thereof, include bone cancer, brain cancer, blood cancer, breast cancer, pancreatic cancer, lung cancer, kidney cancer, stomach cancer, ovarian cancer, prostate cancer, colorectal cancer, endometrial cancer, bladder cancer, non-Hodgkin lymphoma, leukemia, neuroblastoma, lymphomas, rhabdomyosacroma, Wilms' tumor, osteosarcoma and Ewing's sarcoma. In certain embodiments, the cancer is leukemia.

The subject with one of the above-mentioned cancers can be a mammal, e.g., a human, mouse, rat, guinea pig, dog, cat, horse, cow, pig, or non-human primate, such as a monkey, chimpanzee, or baboon. In some embodiments, the subject is a bird, reptile, amphibian, fish, and/or worm. In some embodiments, an animal may be an experimental animal, a transgenic animal, genetically-engineered animal, and/or a clone.

Compounds of the Invention

In part, the present invention encompasses the recognition that there remains a need to identify structurally diverse PDF inhibitors that are structurally different from known bacterial PDF inhibitors and are potentially selective for human, bacterial, or prokaryotic PDF. In one aspect, the present invention provides novel compounds that may be used in the treatment of an infectious and/or proliferative disease. In certain embodiments, inventive compounds described herein are of the formula:

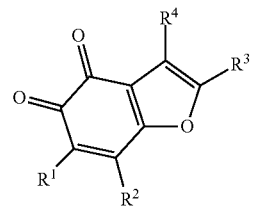

wherein:

$R^1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$^a$; —C(=O)R$^a$; —CO$_2$R$^a$; —CN; —SCN; —SR$^a$; —SOR$^a$; —SO$_2$R$^a$; —NO$_2$; —N$_3$; —N(R$^a$)$_2$; —NR$^a$C(=O)R$^a$; —NR$^a$C(=O)N(R$^a$)$_2$; —OC(=O)OR$^a$; —OC(=O)R$^a$; —OC(=O)N(R$^a$)$_2$; —NR$^a$C(=O)OR$^a$; or —C(R$^a$)$_3$; wherein each occurrence of $R^a$ is independently hydrogen; halogen; a protecting group; an optionally substituted aliphatic or heteroaliphatic moiety; an acyl moiety; or an optionally substituted aryl or heteroaryl moiety;

$R^2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$^b$; —C(=O)R$^b$; —CO$_2$R$^b$; —CN; —SCN; —SR$^b$; —SOR$^b$; —SO$_2$R$^b$; —NO$_2$; —N$_3$; —N(R$^b$)$_2$; —NR$^b$C(=O)R$^a$; —NR$^b$C(=O)N(R$^b$)$_2$; —OC(=O)OR$^b$; —OC(=O)R$^b$; —OC(=O)N(R$^b$)$_2$; —NR$^b$C(=O)OR$^b$; or —C(R$^b$)$_3$; wherein each occurrence of $R^b$ is independently hydrogen; halogen; a protecting group; an optionally substituted aliphatic or heteroaliphatic moiety; an acyl moiety; or an optionally substituted aryl or heteroaryl moiety;

wherein $R^1$ and $R^2$ when taken together form an optionally substituted, saturated or unsaturated aromatic, heteroaromatic, or nonaromatic 3-8 membered monocyclic or bicyclic ring optionally containing one or more heteroatoms selected from the group consisting of N, O, or S;

$R^3$ is hydrogen; halogen; cyclic or acyclic, substituted or unsubstituted, branched or unbranched aliphatic; cyclic or acyclic, substituted or unsubstituted heteroaliphatic; substituted or unsubstituted, branched or unbranched acyl; substituted or unsubstituted aryl; substituted or unsubstituted heteroaryl; —OR$^c$; —C(=O)R$^c$; —CO$_2$R$^c$; —CN; —SCN; —SR$^c$; —SOR$^c$; —SO$_2$R$^c$; —NO$_2$; —N$_3$; —N(R$^c$)$_2$; —NR$^c$C(=O)R$^c$; —NR$^c$C(=O)N(R$^c$)$_2$; —OC(=O)OR$^c$; —OC(=O)R$^c$; —OC(=O)N(R$^c$)$_2$; —NR$^c$C(=O)OR$^c$; or —C(R$^c$)$_3$; wherein each occurrence of $R^c$ is independently hydrogen; halogen; a protecting group; an optionally substituted aliphatic or heteroaliphatic moiety; an acyl moiety; or an optionally substituted aryl or heteroaryl moiety; and $R^4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$^d$; —C(=O)R$^d$; —CO$_2$R$^d$; —CN; —SCN; —SR$^d$; —SOR$^d$; —SO$_2$R$^d$; —NO$_2$; —N$_3$; —N(R$^d$)$_2$; —NR$^d$C(=O)R$^d$; —NR$^d$C(=O)N(R$^d$)$_2$; —OC(=O)OR$^d$; —OC(=O)R$^d$; —OC(=O)N(R$^d$)$_2$; —NR$^d$C(=O)OR$^d$; or —C(R$^d$)$_3$; wherein each occurrence of $R^d$ is independently hydrogen; halogen; a protecting group; an optionally substituted aliphatic or heteroaliphatic moiety; an acyl moiety; or an optionally substituted aryl or heteroaryl moiety, or a pharmaceutically acceptable salt thereof.

In certain embodiments, the inventive compound is not of the following formulae:

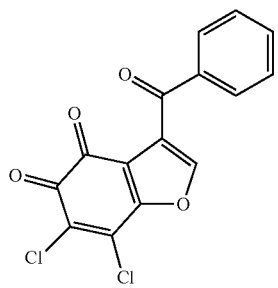
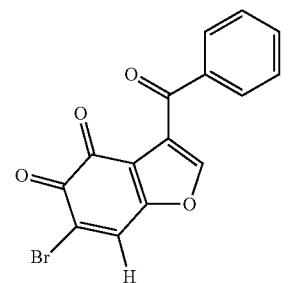

-continued

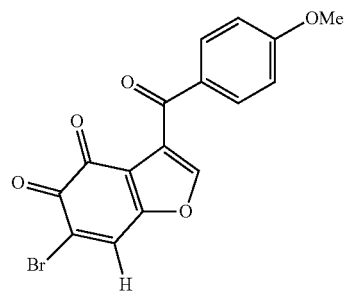

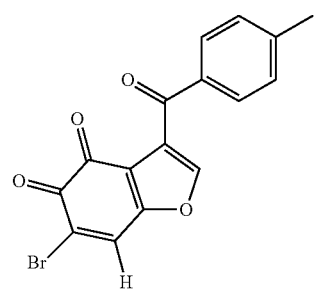

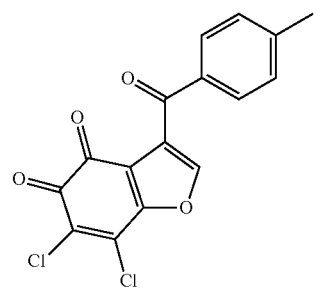

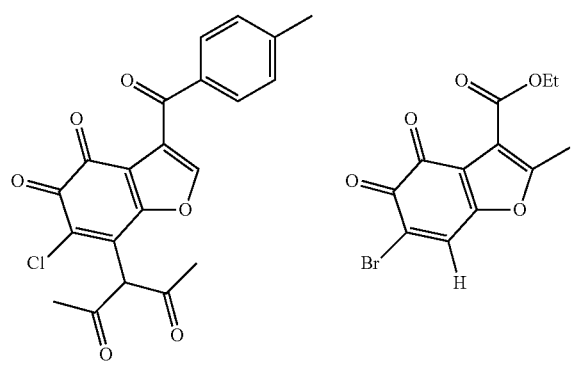

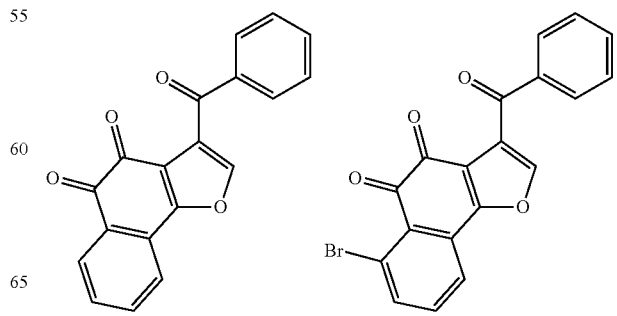

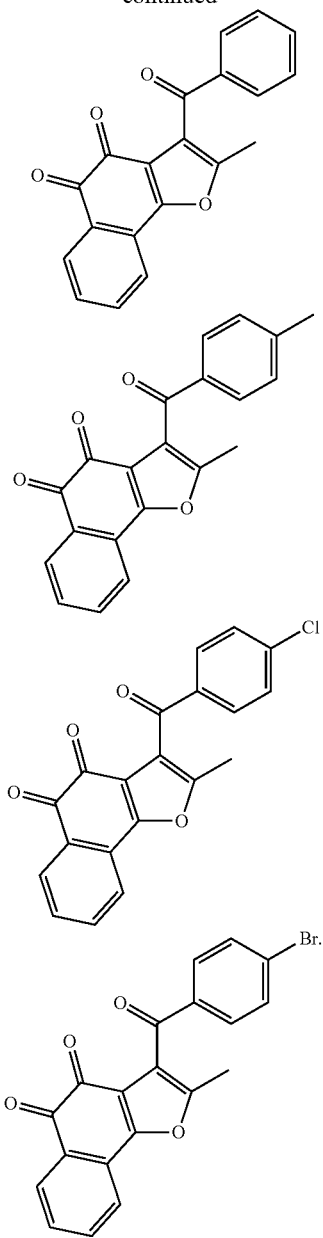

In some embodiments, $R^1$ is hydrogen. In some embodiments, $R^1$ is halogen. In certain embodiments, $R^1$ is fluorine. In certain embodiments, $R^1$ is chlorine. In certain embodiments, $R^1$ is bromine. In certain embodiments, $R^1$ is iodine. In some embodiments, $R^1$ is cyclic aliphatic. In some embodiments, $R^1$ is acyclic aliphatic. In some embodiments, $R^1$ is substituted aliphatic. In some embodiments, $R^1$ is unsubstituted aliphatic. In some embodiments, $R^1$ is branched aliphatic. In some embodiments, $R^1$ is unbranched aliphatic. In some embodiments, $R^1$ is $C_{1-6}$ alkyl. In some embodiments, $R^1$ is methyl. In some embodiments, $R^1$ is ethyl. In some embodiments, $R^1$ is propyl. In some embodiments, $R^1$ is butyl. In some embodiments, $R^1$ is pentyl. In some embodiments, $R^1$ is hexyl. In some embodiments, $R^1$ is cyclic heteroaliphatic. In some embodiments, $R^1$ is acyclic heteroaliphatic. In some embodiments, $R^1$ is substituted heteroaliphatic. In some embodiments, $R^1$ is unsubstituted heteroaliphatic. In some embodiments, $R^1$ is branched heteroaliphatic. In some embodiments, $R^1$ is unbranched heteroaliphatic. In some embodiments, $R^1$ is substituted acyl. In some embodiments, $R^1$ is unsubstituted acyl. In some embodiments, $R^1$ is branched acyl. In some embodiments, $R^1$ is unbranched acyl. In some embodiments, $R^1$ is substituted aryl. In some embodiments, $R^1$ is unsubstituted aryl. In some embodiments, $R^1$ is substituted hetereoaryl. In some embodiments, $R^1$ is unsubstituted heteroaryl. In some embodiments, $R^1$ is —$OR^a$. In some embodiments, $R^1$ is —$C(=O)R^a$. In some embodiments, $R^1$ is —$CO_2R^a$. In some embodiments, $R^1$ is —$CN$. In some embodiments, $R^1$ is —$SCN$. In some embodiments, $R^1$ is —$SR^a$. In some embodiments, $R^1$ is —$SOR^a$. In some embodiments, $R^1$ is —$SO_2R^a$. In some embodiments, $R^1$ is —$NO_2$. In some embodiments, $R^1$ is —$N_3$. In some embodiments, $R^1$ is —$N(R^a)_2$. In some embodiments, $R^1$ is —$NR^aC(=O)R^a$. In some embodiments, $R^1$ is —$NR^aC(=O)N(R^a)_2$. In some embodiments, $R^1$ is —$OC(=O)OR^a$. In some embodiments, $R^1$ is —$OC(=O)R^a$. In some embodiments, $R^1$ is —$OC(=O)N(R^a)_2$. In some embodiments, $R^1$ is —$NR^aC(=O)OR^a$. In some embodiments, $R^1$ is —$C(R^a)_3$. In some embodiments, each occurrence of $R^a$ is independently hydrogen. In some embodiments, each occurrence of $R^a$ is independently halogen. In some embodiments, each occurrence of $R^a$ is independently a protecting group. In some embodiments, each occurrence of $R^a$ is independently an optionally substituted aliphatic. In some embodiments, each occurrence of $R^a$ is independently a heteroaliphatic moiety. In some embodiments, each occurrence of $R^a$ is independently an acyl moiety. In some embodiments, each occurrence of $R^a$ is independently an optionally substituted aryl moiety. In some embodiments, each occurrence of $R^a$ is independently a heteroaryl moiety.

In some embodiments, $R^2$ is hydrogen. In some embodiments, $R^2$ is halogen. In certain embodiments, $R^2$ is fluorine. In certain embodiments, $R^2$ is chlorine. In certain embodiments, $R^2$ is bromine. In certain embodiments, $R^2$ is iodine. In some embodiments, $R^2$ is cyclic aliphatic. In some embodiments, $R^2$ is acyclic aliphatic. In some embodiments, $R^2$ is substituted aliphatic. In some embodiments, $R^2$ is unsubstituted aliphatic. In some embodiments, $R^2$ is branched aliphatic. In some embodiments, $R^2$ is unbranched aliphatic. In some embodiments, $R^2$ is $C_{1-6}$ alkyl. In some embodiments, $R^2$ is methyl. In some embodiments, $R^2$ is ethyl. In some embodiments, $R^2$ is propyl. In some embodiments, $R^2$ is butyl. In some embodiments, $R^2$ is pentyl. In some embodiments, $R^2$ is hexyl. In some embodiments, $R^2$ is cyclic heteroaliphatic. In some embodiments, $R^2$ is acyclic heteroaliphatic. In some embodiments, $R^2$ is substituted heteroaliphatic. In some embodiments, $R^2$ is unsubstituted heteroaliphatic. In some embodiments, $R^2$ is branched heteroaliphatic. In some embodiments, $R^2$ is unbranched heteroaliphatic. In some embodiments, $R^2$ is substituted acyl. In some embodiments, $R^2$ is unsubstituted acyl. In some embodiments, $R^2$ is branched acyl. In some embodiments, $R^2$ is unbranched acyl. In some embodiments, $R^2$ is substituted aryl. In some embodiments, $R^2$ is unsubstituted aryl. In some embodiments, $R^2$ is substituted hetereoaryl. In some embodiments, $R^2$ is unsubstituted heteroaryl. In some embodiments, $R^2$ is —$OR^b$. In some embodiments, $R^2$ is —$C(=O)R^b$. In some embodiments, $R^2$ is —$CO_2R^b$. In some embodiments, $R^2$ is —$CN$. In some embodiments, $R^2$ is —$SCN$. In some embodiments, $R^2$ is —$SR^b$. In some embodiments, $R^2$ is —$SOR^b$. In some embodiments, $R^2$ is —$SO_2R^b$. In some embodiments, $R^2$ is —$NO_2$. In some embodiments, $R^2$ is —$N_3$. In some embodiments, $R_2$ is —$N(R^b)_2$. In some embodiments, $R^2$ is —$NR^bC(=O)R^b$. In some embodiments, $R^2$ is —$NR^bC(=O)N(R^b)_2$. In some embodiments, $R^2$ is —OC(=O)OR$^b$. In some embodiments, R$^2$ is —OC(=O)R$^b$. In some embodiments, R$^2$ is —OC(=O)N(R$^b$)$_2$. In some embodiments, R$^2$ is —NR$^b$C(=O)OR$^b$. In some embodiments, R$^2$ is —C(R$^b$)$_3$. In some embodiments, each occurrence of R$^b$ is independently hydrogen. In some embodiments, each occurrence of R$^b$ is independently halogen. In some embodiments, each occurrence of R$^b$ is independently a protecting group. In some embodiments, each occurrence of R$^b$ is independently an optionally substituted aliphatic. In some embodiments, each occurrence of R$^b$ is independently a heteroaliphatic moiety. In some embodiments, each occurrence of R$^b$ is independently an acyl moiety. In some embodiments, each occurrence of R$^b$ is independently an optionally substituted aryl moiety. In some embodiments, each occurrence of R$^b$ is independently an optionally substituted heteroaryl moiety.

In certain embodiments, at least one occurrence of R$^1$ and R$^2$ is hydrogen. In certain embodiments, both R$^1$ and R$^2$ are hydrogen. In some embodiments, at least one occurrence of R$^1$ or R$^2$ is a halogen. In some embodiments, at least one occurrence of R$^1$ or R$^2$ is a halogen, and the other is hydrogen. In some embodiments, at least one occurrence of R$^1$ or R$^2$ is fluorine. In some embodiments, at least one occurrence of R$^1$ or R$^2$ is bromine. In some embodiments, at least one occurrence of R$^1$ or R$^2$ is chlorine. In some embodiments, each occurrence of R$^1$ and R$^2$ is independently a halogen. In some embodiments, both R$^1$ and R$^2$ are fluorine. In some embodiments, both R$^1$ and R$^2$ are bromine. In some embodiments, both R$^1$ and R$^2$ are chlorine. In some embodiments, at least one occurrence of R$^1$ or R$^2$ is an isotopic label. By way of nonlimiting example, isotopic labels include $^{18}$F, $^{123}$I, $^{125}$I, $^{131}$I, $^{11}$C, $^{13}$N, and/or $^{15}$O.

In certain embodiments, R$^1$ and R$^2$ taken together form a fused aryl or heteroaryl. In certain embodiments, R$^1$ and R$^2$ taken together form a fused aryl. In certain embodiments, R$^1$ and R$^2$ taken together form a fused phenyl. In certain embodiments, R$^1$ and R$^2$ taken together form a fused unsubstituted phenyl.

In some embodiments, R$^3$ is hydrogen. In some embodiments, R$^3$ is halogen. In certain embodiments, R$^3$ is fluorine. In certain embodiments, R$^3$ is chlorine. In certain embodiments, R$^3$ is bromine. In certain embodiments, R$^3$ is iodine. In some embodiments, R$^3$ is cyclic aliphatic. In some embodiments, R$^3$ is acyclic aliphatic. In some embodiments, R$^3$ is substituted aliphatic. In some embodiments, R$^3$ is unsubstituted aliphatic. In some embodiments, R$^3$ is branched aliphatic. In some embodiments, R$^3$ is unbranched aliphatic. In some embodiments, R$^3$ is C$_{1-6}$ alkyl. In some embodiments, R$^3$ is methyl. In some embodiments, R$^3$ is ethyl. In some embodiments, R$^3$ is propyl. In some embodiments, R$^3$ is butyl. In some embodiments, R$^3$ is pentyl. In some embodiments, R$^3$ is hexyl. In some embodiments, R$^3$ is cyclic heteroaliphatic. In some embodiments, R$^3$ is acyclic heteroaliphatic. In some embodiments, R$^3$ is substituted heteroaliphatic. In some embodiments, R$^3$ is unsubstituted heteroaliphatic. In some embodiments, R$^3$ is branched heteroaliphatic. In some embodiments, R$^3$ is unbranched heteroaliphatic. In some embodiments, R$^3$ is substituted acyl. In some embodiments, R$^3$ is unsubstituted acyl. In some embodiments, R$^3$ is branched acyl. In some embodiments, R$^3$ is unbranched acyl. In some embodiments, R$^3$ is substituted aryl. In some embodiments, R$^3$ is unsubstituted aryl. In some embodiments, R$^3$ is substituted hetereoaryl. In some embodiments, R$^3$ is unsubstituted heteroaryl. In some embodiments, R$^3$ is —OR$^c$. In some embodiments, R$^3$ is —C(=O)R$^c$. In some embodiments, R$^3$ is —CO$_2$R$^c$. In some embodiments, R$^3$ is —CN. In some embodiments, R$^3$ is —SCN. In some embodiments, R$^3$ is —SR$^c$. In some embodiments, R$^3$ is —SOR$^c$. In some embodiments, R$^3$ is —SO$_2$R$^c$. In some embodiments, R$^3$ is —NO$_2$. In some embodiments, R$^3$ is —N$_3$. In some embodiments, R$^3$ is —N(R$^c$)$_2$. In some embodiments, R$^3$ is —NR$^c$C(=O)R$^c$. In some embodiments, R$^3$ is —NR$^c$C(=O)N(R$^c$)$_2$. In some embodiments, R$^3$ is —OC(=O)OR$^c$. In some embodiments, R$^3$ is —OC(=O)R$^c$. In some embodiments, R$^3$ is —OC(=O)N(R$^c$)$_2$. In some embodiments, R$^3$ is —NR$^3$C(=O)OR$^c$. In some embodiments, R$^3$ is —C(R$^c$)$_3$. In some embodiments, at least one occurrence of R$^c$ is independently hydrogen. In some embodiments, at least one occurrence of R$^c$ is independently halogen. In some embodiments, at least one occurrence of R$^c$ is independently a protecting group. In some embodiments, at least one occurrence of R$^c$ is independently an optionally substituted aliphatic. In some embodiments, at least one occurrence of R$^c$ is independently a heteroaliphatic moiety. In some embodiments, at least one occurrence of R$^c$ is independently an acyl moiety. In some embodiments, at least one occurrence of R$^c$ is independently an optionally substituted aryl moiety. In some embodiments, at least one occurrence of R$^c$ is independently a heteroaryl moiety.

In some embodiments, R$^4$ is hydrogen. In some embodiments, R$^4$ is halogen. In certain embodiments, R$^4$ is fluorine. In certain embodiments, R$^4$ is chlorine. In certain embodiments, R$^4$ is bromine. In certain embodiments, R$^4$ is iodine. In some embodiments, R$^4$ is cyclic aliphatic. In some embodiments, R$^4$ is acyclic aliphatic. In some embodiments, R$^4$ is substituted aliphatic. In some embodiments, R$^4$ is unsubstituted aliphatic. In some embodiments, R$^4$ is branched aliphatic. In some embodiments, R$^4$ is unbranched aliphatic. In some embodiments, R$^4$ is C$_{1-6}$ alkyl. In some embodiments, R$^4$ is methyl. In some embodiments, R$^4$ is ethyl. In some embodiments, R$^4$ is propyl. In some embodiments, R$^4$ is butyl. In some embodiments, R$^4$ is pentyl. In some embodiments, R$^4$ is hexyl. In some embodiments, R$^4$ is cyclic heteroaliphatic. In some embodiments, R$^4$ is acyclic heteroaliphatic. In some embodiments, R$^4$ is substituted heteroaliphatic. In some embodiments, R$^4$ is unsubstituted heteroaliphatic. In some embodiments, R$^4$ is branched heteroaliphatic. In some embodiments, R$^4$ is unbranched heteroaliphatic. In some embodiments, R$^4$ is substituted acyl. In some embodiments, R$^4$ is unsubstituted acyl. In some embodiments, R$^4$ is branched acyl. In some embodiments, R$^4$ is unbranched acyl. In some embodiments, R$^4$ is optionally substituted benzoyl. In some embodiments, R$^4$ is substituted aryl. In some embodiments, R$^4$ is unsubstituted aryl. In some embodiments, R$^4$ is substituted hetereoaryl. In some embodiments, R$^4$ is unsubstituted heteroaryl. In some embodiments, R$^4$ is —OR$^d$. In some embodiments, R$^4$ is —C(=O)R$^d$. In some embodiments, R$^4$ is —CO$_2$R$^d$. In some embodiments, R$^4$ is —CN. In some embodiments, R$^4$ is —SCN. In some embodiments, R$^4$ is —SR$^d$. In some embodiments, R$^4$ is —SOR$^d$. In some embodiments, R$^4$ is —SO$_2$R$^d$. In some embodiments, R$^4$ is —NO$_2$. In some embodiments, R$^4$ is —N$_3$. In some embodiments, R$^4$ is —N(R$^d$)$_2$. In some embodiments, R$^4$ is —NR$^d$C(=O)R$^d$. In some embodiments, R$^4$ is —NR$^d$C(=O)N(R$^d$)$_2$. In some embodiments, R$^4$ is —OC(=O)OR$^d$. In some embodiments, R$^4$ is —OC(=O)R$^d$. In some embodiments, R$^4$ is —OC(=O)N(R$^d$)$_2$. In some embodiments, R$^4$ is —NR$^3$C(=O)OR$^d$. In some embodiments, R$^4$ is —C(R$^d$)$_3$. In some embodiments, at least one occurrence of R$^d$ is independently hydrogen. In some embodiments, at least one occurrence of R$^d$ is independently halogen. In some embodiments, at least one occurrence of R$^d$ is independently a protecting group. In some embodiments, at least one occurrence of R$^d$ is independently an optionally substituted aliphatic. In some embodiments, at least one occurrence of $R^d$ is independently a heteroaliphatic moiety. In some embodiments, at least one occurrence of $R^d$ is independently an acyl moiety. In some embodiments, at least one occurrence of $R^d$ is independently an optionally substituted aryl moiety. In some embodiments, at least one occurrence of $R^d$ is independently a heteroaryl moiety.

In certain embodiments, the compound is of the formula:

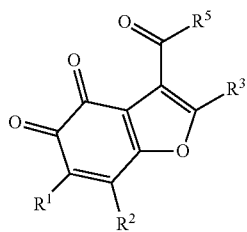

wherein $R^1$, $R^2$, and $R^3$ are as described above; and $R^5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —$OR^e$; —$SR^e$; —$N(R^e)_2$; —$NR^eC(=O)R^e$; —$NR^eC(=O)N(R^e)_2$; —$OC(=O)OR^e$; —$OC(=O)R^e$; —$OC(=O)N(R^e)_2$; —$NR^eC(=O)OR^e$; or —$C(R^e)_3$; wherein at least one occurrence of $R^e$ is independently hydrogen; halogen; a protecting group; an optionally substituted aliphatic or heteroaliphatic moiety; an acyl moiety; or an optionally substituted aryl or heteroaryl moiety, or a pharmaceutically acceptable salt thereof.

In certain embodiments, $R^5$ is hydrogen. In certain embodiments, $R^5$ is cyclic aliphatic. In certain embodiments, $R^5$ is acyclic aliphatic. In certain embodiments, $R^5$ is substituted aliphatic. In certain embodiments, $R^5$ is unsubstituted aliphatic. In certain embodiments, $R^5$ is branched aliphatic. In certain embodiments, $R^5$ is unbranched aliphatic. In some embodiments, $R^5$ is unbranched aliphatic. In some embodiments, $R^5$ is $C_{1-6}$ alkyl. In some embodiments, $R^5$ is methyl. In some embodiments, $R^5$ is ethyl. In some embodiments, $R^5$ is propyl. In some embodiments, $R^5$ is butyl. In some embodiments, $R^5$ is pentyl. In some embodiments, $R^5$ is hexyl. In certain embodiments, $R^5$ is cyclic heteroaliphatic. In certain embodiments, $R^5$ is acyclic heteroaliphatic. In certain embodiments, $R^5$ is substituted heteroaliphatic. In certain embodiments, $R^5$ is unsubstituted heteroaliphatic. In certain embodiments, $R^5$ is branched heteroaliphatic. In certain embodiments, $R^5$ is unbranched heteroaliphatic. In certain embodiments, $R^5$ is substituted aryl. In certain embodiments, $R^5$ is unsubstituted aryl. In some embodiments, $R^5$ optionally substituted phenyl. In certain embodiments, $R^5$ is substituted heteroaryl. In certain embodiments, $R^5$ is unsubstituted heteroaryl. In certain embodiments, $R^5$ is substituted heteroaryl. In certain embodiments, $R^5$ is substituted or unsubstituted 5-membered heteroaryl. In certain embodiments, $R^5$ is a substituted or unsubstituted heteroaryl moiety selected from the group consisting of furanyl, thiophenyl, pyrrolyl, pyrrolidinyl, oxazolyl, thiazolyl, imidazolyl, pyrazolyl, pyrazolinyl, isoxazolyl, isothiazolyl, oxadiazolyl, triazolyl, tetrazolyl, thiadiazolyl, pyranyl, pyridinyl, piperidinyl, dioxanyl, morpholinyl, dithianyl, thiomorpholinyl, pyridazinyl, pyrazinyl, piperazinyl, triazinyl, trithianyl, indolizinyl, indolyl, isoindolyl, indolinyl, benzofuranyl, benzothiophenyl, indazolyl, benzimidazolyl, benzthiazolyl, purinyl, quinolizinyl, quinolinyl, isoquinolinyl, cinnolinyl, phthalazinyl, quinazolinyl, quinoxalinyl, naphthyridinyl, pteridinyl, quinuclidinyl, carbazolyl, acridinyl, phenazinyl, phenothialinyl, phenoxazinyl, indenyl, naphthalenyl, azulenyl, fluorenyl, anthracenyl, norbornanyl, and adamatanyl. In certain embodiments, $R^5$ is substituted or unsubstituted 6-membered heteroaryl. In certain embodiments, $R^5$ is thiophenyl. In certain embodiments, $R^5$ is 2-thiophenyl. In certain embodiments, $R^5$ is 3-thiophenyl. In certain embodiments, $R^5$ is a substituted or unsubstituted, bicyclic heterocyclic moiety. In certain embodiments, $R^5$ is an unsubstituted heterocyclic bicycle. In certain embodiments, $R^5$ is a substituted or unsubstituted, bicyclic heteroaryl moiety. In certain embodiments, $R^5$ is —$OR^e$. In certain embodiments, $R^5$ is —OH. In certain embodiments, $R^5$ is —$SR^e$. In certain embodiments, $R^5$ is —$N(R^e)_2$. In certain embodiments, $R^5$ is —$NR^eC(=O)R^e$. In certain embodiments, $R^5$ is —$NR^eC(=O)N(R^e)_2$. In certain embodiments, $R^5$ is —$OC(=O)OR^e$. In certain embodiments, $R^5$ is —$OC(=O)R^e$. In certain embodiments, $R^5$ is —$OC(=O)N(R^e)_2$. In certain embodiments, $R^5$ is —$NR^eC(=O)OR^e$. In certain embodiments, $R^5$ is or —$C(R^e)_3$. In certain embodiments, at least one occurrence of $R^e$ is independently hydrogen. In certain embodiments, at least one occurrence of $R^e$ is independently halogen. In certain embodiments, at least one occurrence of $R^e$ is independently a protecting group. In certain embodiments, at least one occurrence of $R^e$ is independently optionally substituted aliphatic. In some embodiments, $R^e$ is $C_{1-6}$ alkyl. In some embodiments, $R^e$ is methyl. In some embodiments, $R^e$ is ethyl. In some embodiments, $R^e$ is propyl. In some embodiments, $R^e$ is butyl. In some embodiments, $R^e$ is pentyl. In some embodiments, $R^e$ is hexyl. In certain embodiments, at least one occurrence of $R^e$ is independently optionally substituted heteroaliphatic. In certain embodiments, at least one occurrence of $R^e$ is independently an acyl moiety. In certain embodiments, at least one occurrence of $R^e$ is independently an optionally substituted aryl. In certain embodiments, at least one occurrence of $R^e$ is independently an optionally substituted heteroaryl moiety.

In certain embodiments, $R^5$ is —$OR^e$, wherein $R^e$ is $C_{1-6}$ alkyl. In certain embodiments, $R^5$ is —$OR^e$, wherein $R^e$ is methyl. In certain embodiments, $R^5$ is —$OR^e$, wherein $R^e$ is ethyl. In certain embodiments, $R^5$ is —$OR^e$, wherein $R^e$ is propyl. In certain embodiments, $R^5$ is —$OR^e$, wherein $R^e$ is butyl. In certain embodiments, $R^5$ is —$OR^e$, wherein $R^e$ is phenyl.

In certain embodiments, $R^5$ is —$SR^e$, wherein $R^e$ is $C_{1-6}$ alkyl. In certain embodiments, $R^5$ is —$SR^e$, wherein $R^e$ is methyl. In certain embodiments, $R^5$ is —$SR^e$, wherein $R^e$ is ethyl. In certain embodiments, $R^5$ is —$SR^e$, wherein $R^e$ is propyl. In certain embodiments, $R^5$ is —$SR^e$, wherein $R^e$ is butyl. In certain embodiments, $R^5$ is —$SR^e$, wherein $R^e$ is phenyl.

In certain embodiments, $R^5$ is —$N(R^e)_2$, wherein at least one occurrence of $R^e$ is independently $C_{1-6}$ alkyl. In certain embodiments, $R^5$ is —$N(R^e)_2$, wherein at least one occurrence of $R^e$ is independently methyl. In certain embodiments, $R^5$ is —$N(R^e)_2$, wherein at least one occurrence of $R^e$ is independently ethyl. In certain embodiments, $R^5$ is —$N(R^e)_2$, wherein at least one occurrence of $R^e$ is independently propyl. In certain embodiments, $R^5$ is —$N(R^e)_2$, wherein at least one occurrence of $R^e$ is independently butyl. In certain embodiments, $R^5$ is —$N(R^e)_2$, wherein at least one occurrence of $R^e$ is independently phenyl.

In certain embodiments, the compound is of the formula:

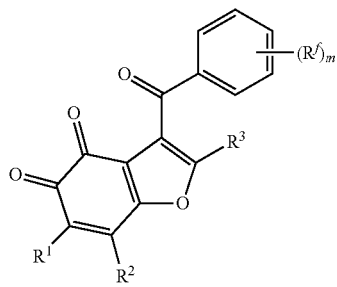

wherein:
R$^1$, R$^2$, and R$^3$ are as described herein;
m is an integer between 0-5, inclusive; and
at least one occurrence of R$^f$ is independently hydrogen; halogen; cyclic or acyclic, substituted or unsubstituted, branched or unbranched aliphatic; cyclic or acyclic, substituted or unsubstituted heteroaliphatic; substituted or unsubstituted, branched or unbranched acyl; substituted or unsubstituted aryl; substituted or unsubstituted heteroaryl; —OR$^g$; —C(=O)R$^g$; —CO$_2$R$^g$; —CN; —SCN; —SR$^g$; —SOR$^g$; —SO$_2$R$^g$; —NO$_2$; —N$_3$; —N(R$^g$)$_2$; —NR$^g$C(=O)R$^g$; —NR$^g$C(=O)N(R$^g$)$_2$; —OC(=O)OR$^g$; —OC(=O)R$^g$; —OC(=O)N(R$^g$)$_2$; —NR$^g$C(=O)OR$^g$; or —C(R$^g$)$_3$; wherein at least one occurrence of R$^g$ is independently hydrogen; halogen; a protecting group; an optionally substituted aliphatic or heteroaliphatic moiety; an acyl moiety; or an optionally substituted aryl or heteroaryl moiety, or a pharmaceutically acceptable salt or derivative thereof.

In certain embodiments, m is 0. In certain embodiments, m is 1. In certain embodiments, m is 2. In certain embodiments, m is 3. In certain embodiments, m is 4. In certain embodiments, m is 5.

In certain embodiments, at least one occurrence of R$^f$ is independently hydrogen. In certain embodiments, at least one occurrence of R$^f$ is independently halogen. In certain embodiments, at least one occurrence of R$^f$ is independently fluorine. In certain embodiments, at least one occurrence of R$^f$ is independently chlorine. In certain embodiments, at least one occurrence of R$^f$ is independently bromine. In certain embodiments, at least one occurrence of R$^f$ is independently iodine. In certain embodiments, at least one occurrence of R$^f$ is independently cyclic aliphatic. In certain embodiments, at least one occurrence of R$^f$ is independently acyclic aliphatic. In certain embodiments, at least one occurrence of R$^f$ is independently substituted aliphatic. In certain embodiments, at least one occurrence of R$^f$ is independently unsubstituted aliphatic. In certain embodiments, at least one occurrence of R$^f$ is independently branched aliphatic. In certain embodiments, at least one occurrence of R$^f$ is independently unbranched aliphatic. In certain embodiments, at least one occurrence of R$^f$ is independently C$_{1-6}$ alkyl. In certain embodiments, at least one occurrence of R$^f$ is independently methyl. In certain embodiments, at least one occurrence of R$^f$ is independently ethyl. In certain embodiments, at least one occurrence of R$^f$ is independently propyl. In certain embodiments, at least one occurrence of R$^f$ is independently butyl. In certain embodiments, at least one occurrence of R$^f$ is independently pentyl. In certain embodiments, at least one occurrence of R$^f$ is independently hexyl. In certain embodiments, at least one occurrence of R$^f$ is independently cyclic heteroaliphatic. In certain embodiments, at least one occurrence of R$^f$ is independently acyclic heteroaliphatic. In certain embodiments, at least one occurrence of R$^f$ is independently substituted heteroaliphatic. In certain embodiments, at least one occurrence of R$^f$ is independently unsubstituted heteroaliphatic. In certain embodiments, at least one occurrence of R$^f$ is independently substituted acyl. In certain embodiments, at least one occurrence of R$^f$ is independently unsubstituted acyl. In certain embodiments, at least one occurrence of R$^f$ is independently branched acyl. In certain embodiments, at least one occurrence of R$^f$ is independently unbranched aryl. In certain embodiments, at least one occurrence of R$^f$ is independently substituted aryl. In certain embodiments, at least one occurrence of R$^f$ is independently unsubstituted aryl. In certain embodiments, at least one occurrence of R$^f$ is independently substituted phenyl. In certain embodiments, at least one occurrence of R$^f$ is independently unsubstituted phenyl. In certain embodiments, at least one occurrence of R$^f$ is independently substituted heteroaryl. In certain embodiments, at least one occurrence of R$^f$ is independently unsubstituted heteroaryl. In certain embodiments, at least one occurrence of R$^f$ is —OR$^g$. In certain embodiments, at least one occurrence of R$^f$ is —C(=O)R$^g$. In certain embodiments, at least one occurrence of R$^f$ is —CO$_2$R$^g$. In certain embodiments, at least one occurrence of R$^f$ is —CO$_2$H. In certain embodiments, at least one occurrence of R$^f$ is —CN. In certain embodiments, at least one occurrence of R$^f$ is —SCN. In certain embodiments, at least one occurrence of R$^f$ is —SR$^g$. In certain embodiments, at least one occurrence of R$^f$ is —SOR$^g$. In certain embodiments, at least one occurrence of R$^f$ is —SO$_2$R$^g$. In certain embodiments, at least one occurrence of R$^f$ is —NO$_2$. In certain embodiments, at least one occurrence of R$^f$ is —N$_3$. In certain embodiments, at least one occurrence of R$^f$ is —N(R$^g$)$_2$. In certain embodiments, at least one occurrence of R$^f$ is —NR$^g$C(=O)R$^g$. In certain embodiments, at least one occurrence of R$^f$ is —NR$^g$C(=O)N(R$^g$)$_2$. In certain embodiments, at least one occurrence of R$^f$ is —OC(=O)OR$^g$. In certain embodiments, at least one occurrence of R$^f$ is —OC(=O)R$^g$. In certain embodiments, at least one occurrence of R$^f$ is —OC(=O)N(R$^g$)$_2$. In certain embodiments, at least one occurrence of R$^f$ is —NR$^g$C(=O)OR$^g$. In certain embodiments, at least one occurrence of R$^f$ is —C(R$^g$)$_3$. In certain embodiments, at least one occurrence of R$^g$ is independently hydrogen. In certain embodiments, at least one occurrence of R$^g$ is independently halogen. In certain embodiments, at least one occurrence of R$^g$ is independently a protecting group. In certain embodiments, at least one occurrence of R$^g$ is independently optionally substituted aliphatic. In certain embodiments, at least one occurrence of R$^g$ is independently C$_{1-6}$ alkyl. In certain embodiments, at least one occurrence of R$^g$ is independently methyl. In certain embodiments, at least one occurrence of R$^g$ is independently ethyl. In certain embodiments, at least one occurrence of R$^g$ is independently propyl. In certain embodiments, at least one occurrence of R$^g$ is independently butyl. In certain embodiments, at least one occurrence of R$^g$ is independently pentyl. In certain embodiments, at least one occurrence of R$^g$ is independently hexyl. In certain embodiments, at least one occurrence of R$^g$ is independently optionally substituted heteroaliphatic. In certain embodiments, at least one occurrence of R$^g$ is independently an acyl moiety. In certain embodiments, at least one occurrence of R$^g$ is independently optionally substituted aryl. In certain embodiments, at least one occurrence of R$^g$ is independently optionally substituted heteroaryl.

In certain embodiments, $R^5$ is of the formula:

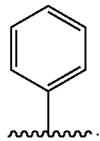

In certain embodiments, $R^5$ is of one of the formulae:

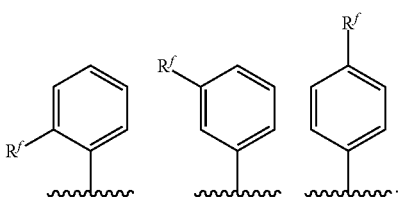

In certain embodiments, $R^5$ is of the formula:

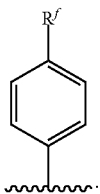

In certain embodiments, $R^5$ is of one of the formulae:

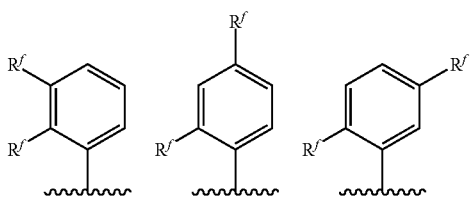

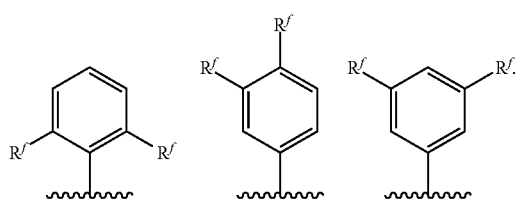

In certain embodiments, the two $R^f$ form a cyclic structure with the intervening carbon atoms. In certain embodiments, the cyclic structure is five-membered or six-membered. In certain embodiments, the two $R^f$ form a carbocyclic structure with the intervening carbon atoms. In certain embodiments, the two $R^f$ form a heterocyclic structure with the intervening carbon atoms. In certain embodiments, $R^5$ is of the formula:

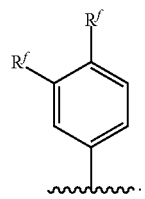

In certain embodiments, the two $R^f$ form a cyclic structure with the intervening carbon atoms. In certain embodiments, the cyclic structure is five-membered or six-membered. In certain embodiments, the two $R^f$ form a carbocyclic structure with the intervening carbon atoms. In certain embodiments, the two $R^f$ form a heterocyclic structure with the intervening carbon atoms.

In certain embodiments, $R^5$ is of one of the formulae:

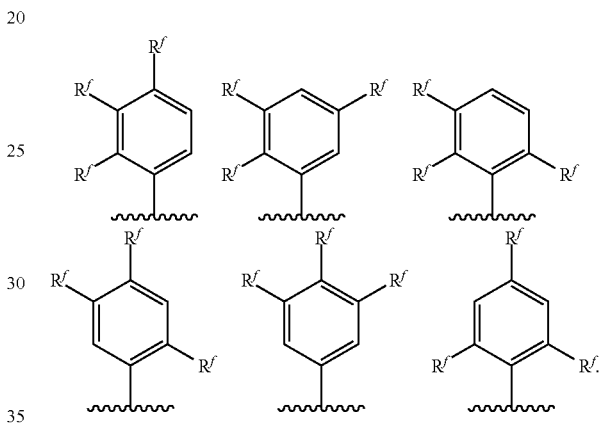

In certain embodiments, $R^5$ is of the formula:

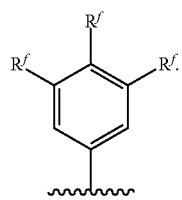

In certain embodiments, the two $R^f$ form a cyclic structure with the intervening carbon atoms. In certain embodiments, the cyclic structure is five-membered or six-membered. In certain embodiments, the two $R^f$ form a carbocyclic structure with the intervening carbon atoms. In certain embodiments, the two $R^f$ form a heterocyclic structure with the intervening carbon atoms.

In certain embodiments, $R^5$ is of one of the formulae:

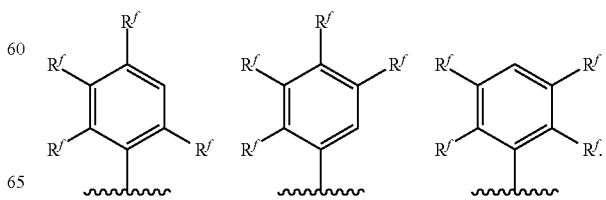

In certain embodiments, $R^5$ is of the formula:

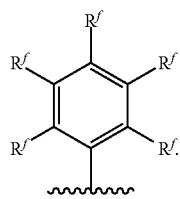

In some embodiments, at least one occurrence of $R^f$ is —$OR^g$. In some embodiments, at least one occurrence of $R^f$ is —OH. In some embodiments, at least one occurrence of $R^f$ is —$OR^g$, wherein $R^g$ is a protecting group. In some embodiments, at least one occurrence of $R^f$ is —$OR^g$, wherein $R^g$ is $C_{1-6}$ alkyl. In some embodiments, at least one occurrence of $R^f$ is —$OR^g$, wherein $R^g$ is methyl, ethyl, propyl, or butyl. In some embodiments, at least one occurrence of $R^f$ is —OMe. In some embodiments, at least two occurrences of $R^f$ are —OMe. In some embodiments, at least three occurrences of $R^f$ are —OMe. In some embodiments, at least four occurrences of $R^f$ are —OMe. In some embodiments, at least five occurrences of $R^f$ are —OMe. In some embodiments, all occurrences of $R^f$ are —OMe. In some embodiments, at least one occurrence of $R^f$ is —OEt. In some embodiments, at least two occurrences of $R^f$ are —OEt. In some embodiments, at least three occurrences of $R^f$ are —OEt. In some embodiments, at least four occurrences of $R^f$ are —OEt. In some embodiments, all five occurrences of $R^f$ are —OEt. In some embodiments, all occurrences of $R^f$ are —OEt.

In some embodiments, at least one occurrence of $R^f$ is —$SR^g$. In some embodiments, at least one occurrence of $R^f$ is —SH. In some embodiments, at least one occurrence of $R^f$ is —$SR^g$, wherein $R^g$ is a protecting group. In some embodiments, at least one occurrence of $R^f$ is —$SR^g$, wherein $R^g$ is $C_{1-6}$ alkyl. In some embodiments, at least one occurrence of $R^f$ is —$SR^g$, wherein $R^g$ is methyl, ethyl, propyl, or butyl. In some embodiments, at least one occurrence of $R^f$ is —SMe. In some embodiments, at least two occurrences of $R^f$ are —SMe. In some embodiments, at least three occurrences of $R^f$ are —SMe. In some embodiments, at least four occurrences of $R^f$ are —SMe. In some embodiments, at least five occurrences of $R^f$ are —SMe. In some embodiments, all occurrences of $R^f$ are —SMe. In some embodiments, at least one occurrence of $R^f$ is —SEt. In some embodiments, at least two occurrences of $R^f$ are —SEt. In some embodiments, at least three occurrences of $R^f$ are —SEt. In some embodiments, at least four occurrences of $R^f$ are —SEt. In some embodiments, all five occurrences of $R^f$ are —SEt. In some embodiments, all occurrences of $R^f$ are —SEt.

In some embodiments, at least one occurrence of $R^f$ is —$N(R^g)_2$. In some embodiments, at least one occurrence of $R^f$ is —$NH(R^g)$. In some embodiments, at least one occurrence of $R^f$ is —$NH_2$. In some embodiments, at least one occurrence of $R^f$ is —$N(R^g)_2$, wherein at least once occurrence of $R^g$ is a protecting group. In some embodiments, at least one occurrence of $R^f$ is —$NH(R^g)$, wherein $R^g$ is a protecting group. In some embodiments, at least one occurrence of $R^f$ is —$N(R^g)_2$, wherein at least one occurrence of $R^g$ is a $C_{1-6}$ alkyl.

In some embodiments, at least one occurrence of $R^f$ is a halogen. In some embodiments, at least one occurrence of $R^f$ is fluorine. In some embodiments, at least one occurrence of $R^f$ is chlorine. In some embodiments, at least one occurrence of $R^f$ is bromine. In some embodiments, at least one occurrence of $R^f$ is iodine.

In some embodiments, at least one occurrence of $R^f$ comprises an isotopic label. Exemplary isotopic labels include $^2H$, $^3H$, $^{18}F$, $^{123}I$, $^{125}I$, $^{131}I$, $^{11}C$, $^{14}C$, $^{13}N$, and/or $^{15}O$. In certain embodiments, at least one occurrence of $R^f$ is $^{18}F$. In certain embodiments, at least one occurrence of $R^f$ is $^{123}I$. In some embodiments, at least one occurrence of $R^f$ is $^{125}I$. In some embodiments, at least one occurrence of $R^f$ is $^{131}I$.

In certain embodiments, at least one occurrence of $R^f$ is $C_{1-6}$ alkyl. In certain embodiments, at least two occurrences of $R^f$ are $C_{1-6}$ alkyl. In certain embodiments, at least three occurrences of $R^f$ are $C_{1-6}$ alkyl. In certain embodiments, at least four occurrences of $R^f$ are $C_{1-6}$ alkyl. In certain embodiments, all five occurrences of $R^f$ are $C_{1-6}$ alkyl. In certain embodiments, at least one occurrence of $R^f$ is methyl. In certain embodiments, at least two occurrences of $R^f$ are methyl. In certain embodiments, at least three occurrences of $R^f$ are methyl. In certain embodiments, at least four occurrences of $R^f$ are methyl. In certain embodiments, all five occurrences of $R^f$ are methyl. In certain embodiments, at least one occurrence of $R^f$ is ethyl. In certain embodiments, at least two occurrences of $R^f$ are ethyl. In certain embodiments, at least three occurrences of $R^f$ are ethyl. In certain embodiments, at least four occurrences of $R^f$ are ethyl. In certain embodiments, all five occurrences of $R^f$ are ethyl. In certain embodiments, at least one occurrence of $R^f$ is propyl. In certain embodiments, at least two occurrences of $R^f$ are propyl. In certain embodiments, at least three occurrences of $R^f$ are propyl. In certain embodiments, at least four occurrences of $R^f$ are propyl. In certain embodiments, all five occurrences of $R^f$ are propyl. In certain embodiments, at least one occurrence of $R^f$ is butyl. In certain embodiments, at least two occurrences of $R^f$ are butyl. In certain embodiments, at least three occurrences of $R^f$ are butyl. In certain embodiments, at least four occurrences of $R^f$ are butyl. In certain embodiments, all five occurrences of $R^f$ are butyl. In certain embodiments, at least one occurrence of $R^f$ is pentyl. In certain embodiments, at least one occurrence of $R^f$ is hexyl. In some embodiments, at least one occurrence of $R^f$ is an aliphatic moiety optionally substituted with one or more halogens selected from the group consisting of fluorine, chlorine, bromine, or iodine. Exemplary moities include, but are not limited to, —$CF_3$, —$CF_2H$, —$CFH_2$, and —$CF_2CF_3$.

In some embodiments, m is 1, and $R^f$ is —$OR^g$.

In some embodiments, m is 2 and at least one occurrence of $R^f$ is —$OR^g$.

In some embodiments, m is 3 and at least one occurrence of $R^f$ is —$OR^g$.

In some embodiments, m is 4 and at least one occurrence of $R^f$ is —$OR^g$.

In some embodiments, m is 5 and at least one occurrence of $R^f$ is —$OR^g$.

In certain embodiments, at least one occurrence of $R^g$ is hydrogen. In certain embodiments, at least two occurrences of $R^g$ are hydrogen. In certain embodiments, at least three occurrences of $R^g$ are hydrogen. In certain embodiments, at least four occurrences of $R^g$ are hydrogen. In certain embodiments, all five occurrences of $R^g$ are hydrogen.

In certain embodiments, at least one occurrence of $R^g$ is $C_{1-6}$ alkyl. In certain embodiments, at least two occurrences of $R^g$ are $C_{1-6}$ alkyl. In certain embodiments, at least three occurrences of $R^g$ are $C_{1-6}$ alkyl. In certain embodiments, at least four occurrences of $R^g$ are $C_{1-6}$ alkyl. In certain embodiments, all five occurrences of $R^g$ are $C_{1-6}$ alkyl. In certain embodiments, at least one occurrence of $R^g$ is methyl. In certain embodiments, at least two occurrences of $R^g$ are methyl. In certain embodiments, at least three occurrences of $R^g$ are methyl. In certain embodiments, at least four occurrences of $R^g$ are methyl. In certain embodiments, all five occurrences of $R^g$ are methyl. In certain embodiments, at least one occurrence of $R^g$ is ethyl. In certain embodiments, at least two occurrences of $R^g$ are ethyl. In certain embodiments, at least three occurrences of $R^g$ are ethyl. In certain embodiments, at least four occurrences of $R^g$ are ethyl. In certain embodiments, all five occurrences of $R^g$ are ethyl. In certain embodiments, at least one occurrence of $R^g$ is propyl. In certain embodiments, at least two occurrences of $R^g$ are propyl. In certain embodiments, at least three occurrences of $R^g$ are propyl. In certain embodiments, at least four occurrences of $R^g$ are propyl. In certain embodiments, all five occurrences of $R^g$ are propyl. In certain embodiments, at least one occurrence of $R^g$ is butyl. In certain embodiments, at least two occurrences of $R^g$ are butyl. In certain embodiments, at least three occurrences of $R^g$ are butyl. In certain embodiments, at least four occurrences of $R^g$ are butyl. In certain embodiments, all five occurrences of $R^g$ are butyl. In certain embodiments, at least one occurrence of $R^g$ is pentyl. In certain embodiments, at least one occurrence of $R^g$ is hexyl.

In certain embodiments, at least one occurrence of $R^g$ is a protecting group. Exemplary protecting groups include silyl protecting groups, acyl groups, benzyl groups, benzoyl groups, and sulfonates.

In some embodiments, at least one occurrence of $R^g$ is an aliphatic moiety optionally substituted with one or more halogens selected from the group consisting of fluorine, chlorine, bromine, or iodine. Exemplary moities include, but are not limited to, $-CF_3$, $-CF_2H$, $-CFH_2$, and $-CF_2CF_3$.

In certain embodiments, $R^5$ is of the formula:

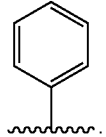

In certain embodiments, $R^5$ is of the formula:

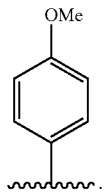

In certain embodiments, $R^5$ is of the formula:

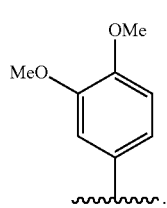 [SMILES: *c1ccc(OC)c(OC)c1]

In certain embodiments, $R^5$ is of the formula:

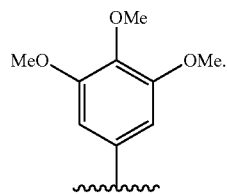 [SMILES: *c1cc(OC)c(OC)c(OC)c1]

In certain embodiments, $R^5$ is one of the formulae:

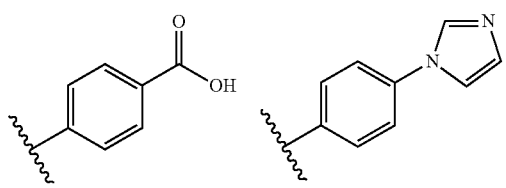

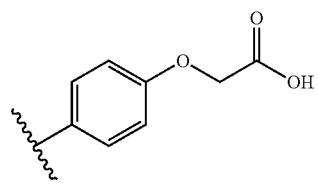

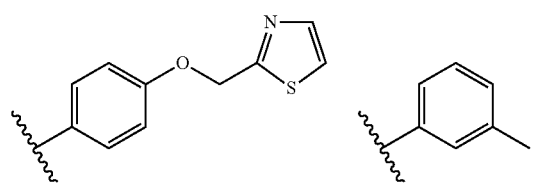

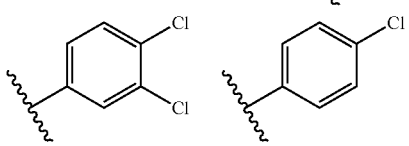

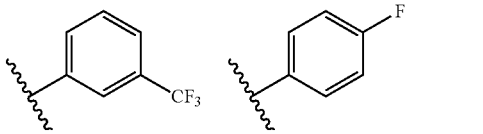

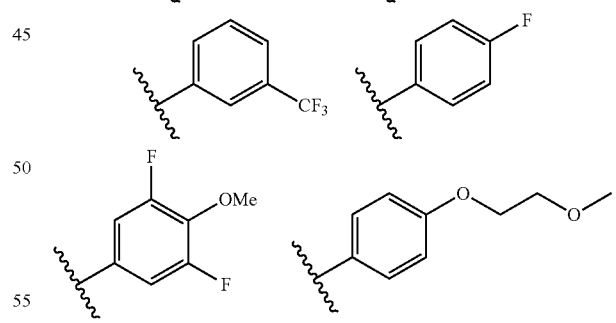

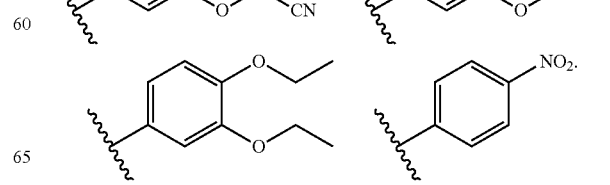

In certain embodiments, $R^5$ is one of the formulae:

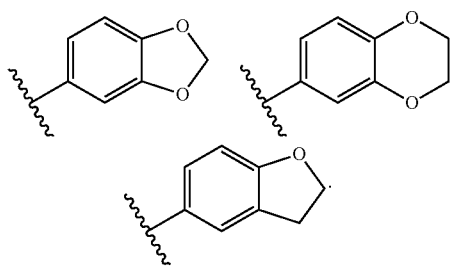

In certain embodiments, $R^5$ is one of the formulae:

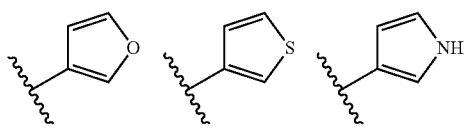

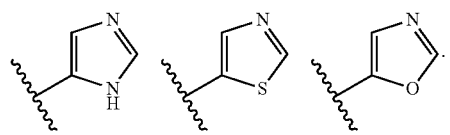

In certain embodiments, $R^5$ is of the formula:

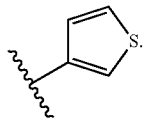 [SMILES: *c1ccsc1]

In certain embodiments, the compound is of the formula:

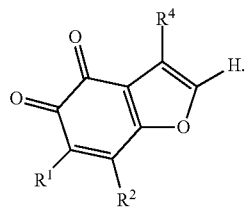

In certain embodiments, the compound is of the formula:

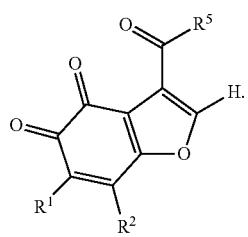

In other embodiments, the compound of the invention is of any one of the formulae:

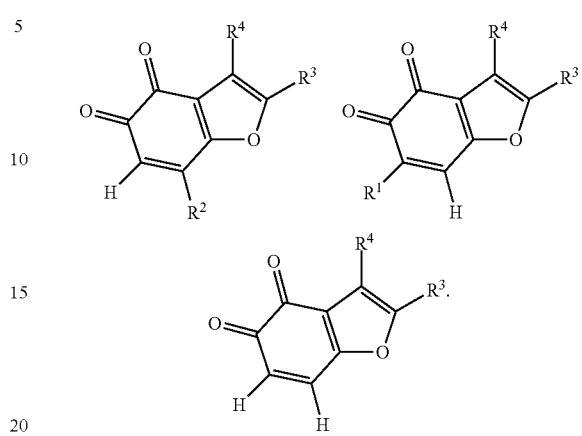

In certain embodiments, the compound is of any one of the formulae:

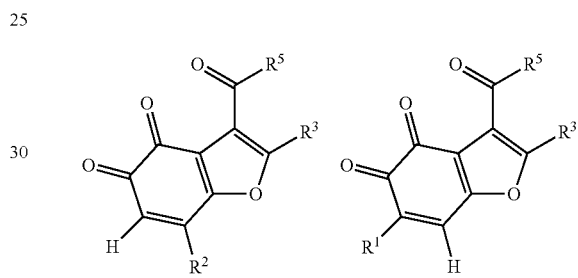

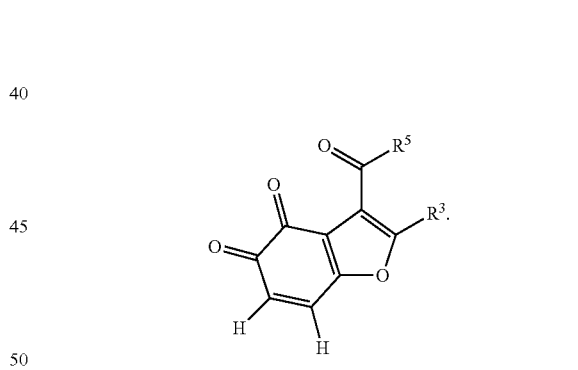

In certain embodiments, the compound is of any one of the formulae:

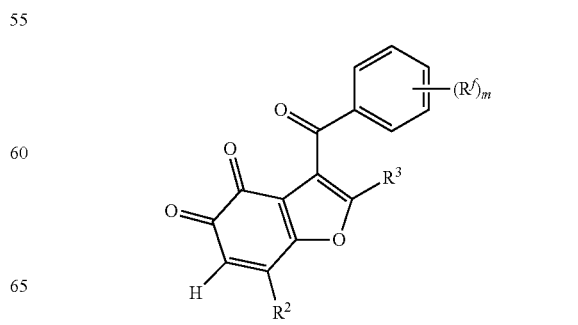

-continued
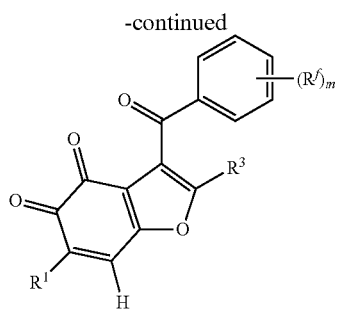
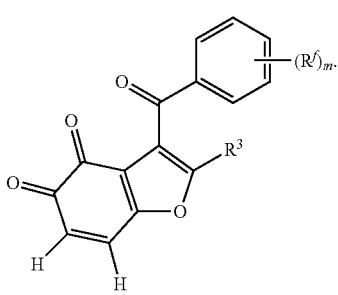
In certain embodiments, the compound is of any one of the formulae:
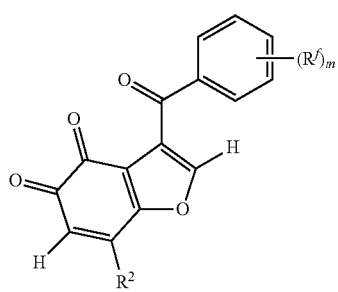
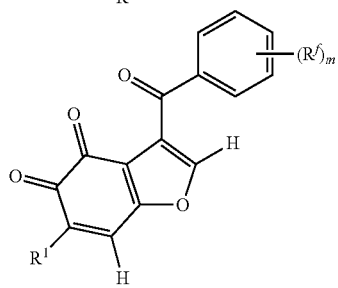
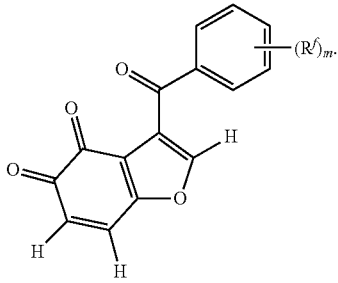
In certain embodiments, the compound is of any one of the formulae:
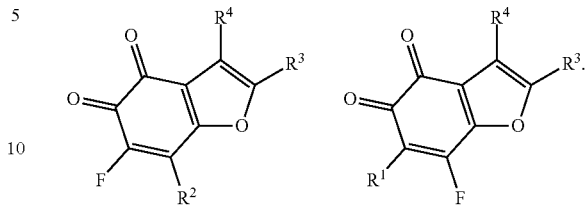
In certain embodiments, the compound is of any one of the formulae:
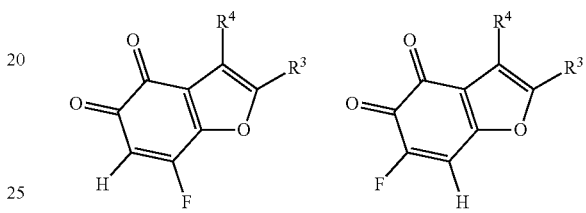
In certain embodiments, the compound is of any one of the formulae:
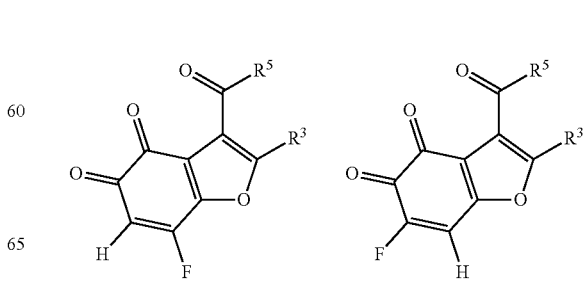
In certain embodiments, the compound is of any one of the formulae:

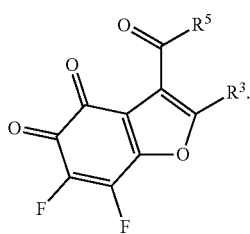
In certain embodiments, the compound is of any one of the formulae:
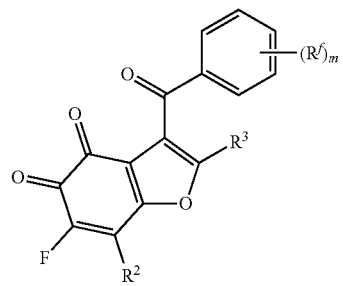
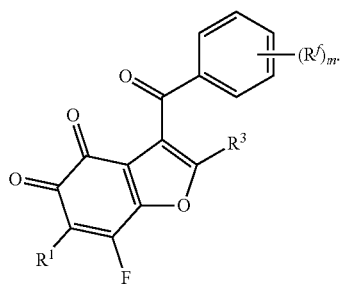
In certain embodiments, the compound is of any one of the formulae:
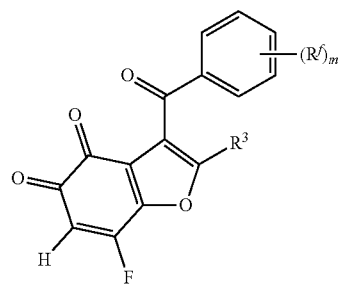
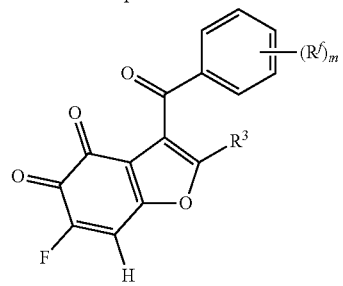
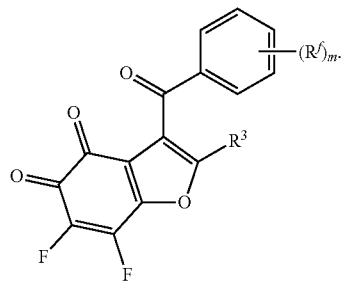
In certain embodiments, the compound is of any one of the formulae:
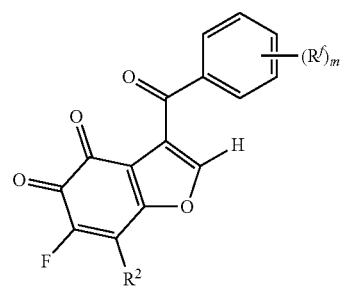
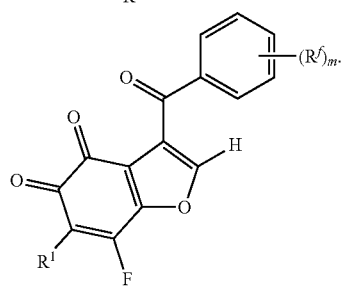
In certain embodiments, the compound is of any one of the formulae:
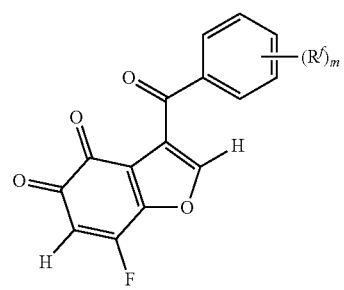
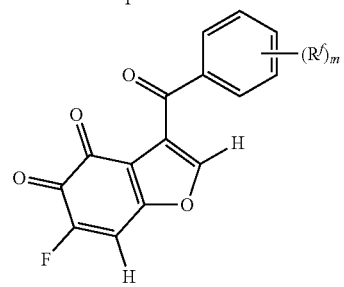

-continued

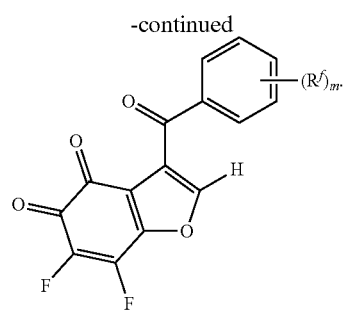

In certain embodiments, the compound is of any one of the formulae:

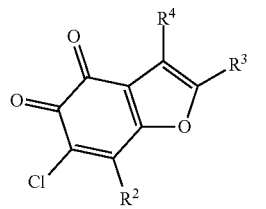 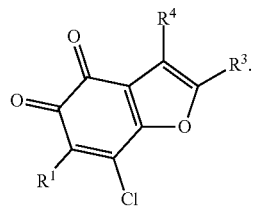

In certain embodiments, the compound is of any one of the formulae:

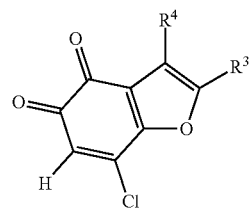 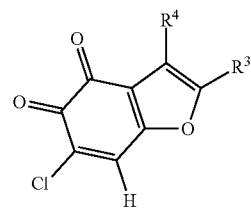

In certain embodiments, the compound is of any one of the formulae:

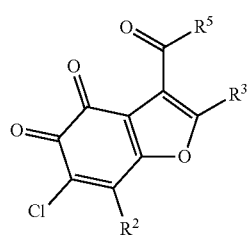

In certain embodiments, the compound is of any one of the formulae:

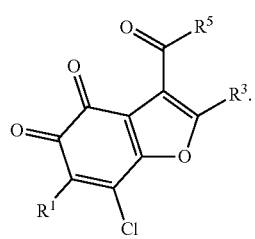

In certain embodiments, the compound is of any one of the formulae:

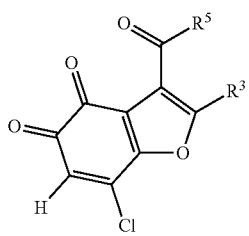 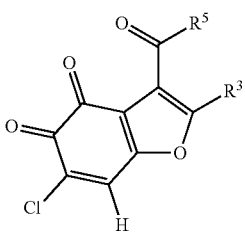

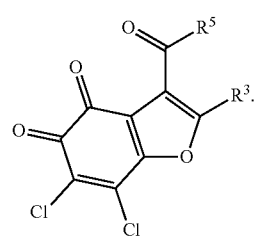

In certain embodiments, the compound is of any one of the formulae:

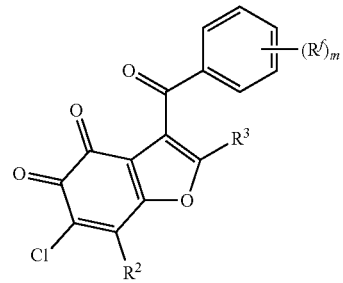

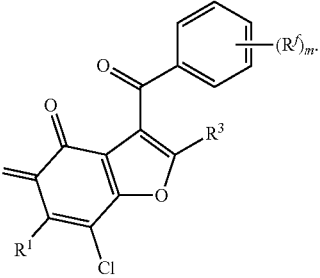

In certain embodiments, the compound is of any one of the formulae:

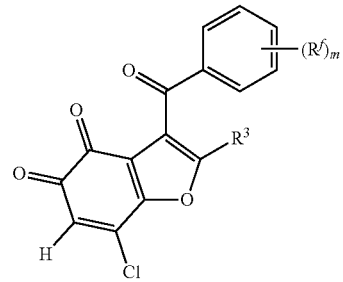

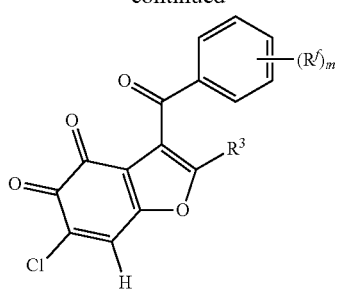
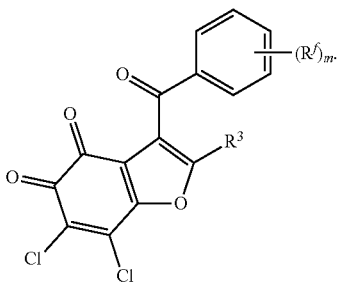
In certain embodiments, the compound is of any one of the formula:
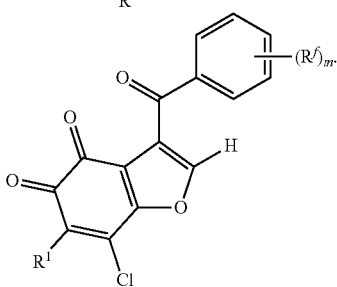
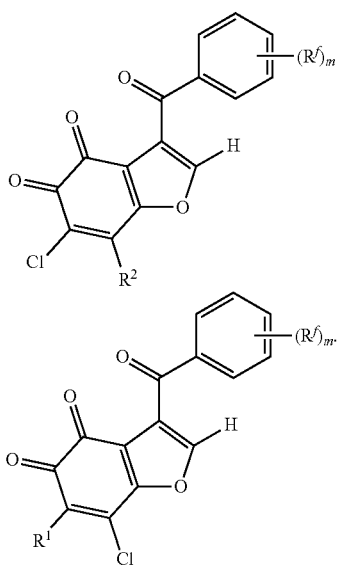
In certain embodiments, the compound is of any one of the formulae:
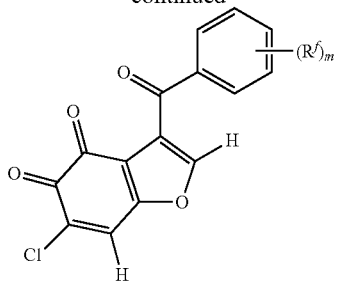
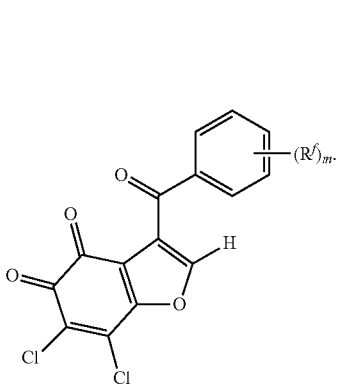
In certain embodiments, the compound is of any one of the formulae:
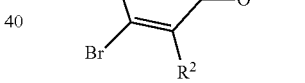
In certain embodiments, the compound is of any one of the formulae:
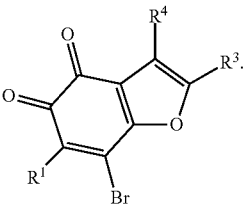
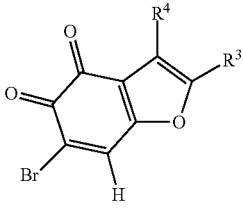
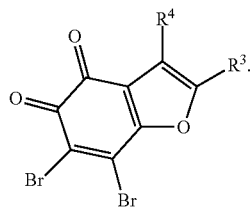

In certain embodiments, the compound is of any one of the formulae:
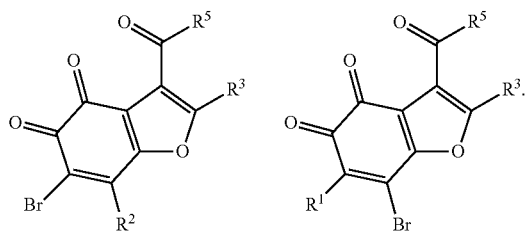
In certain embodiments, the compound is of any one of the formulae:
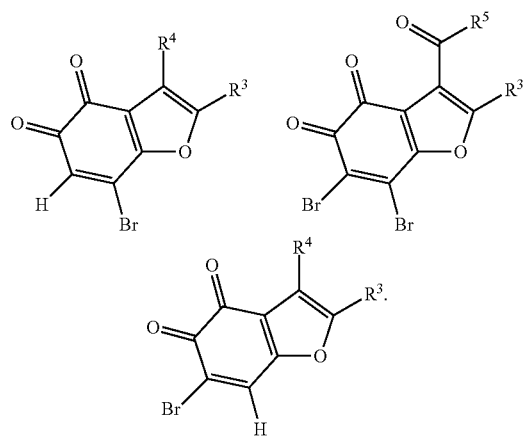
In certain embodiments, the compound is of any one of the formulae:
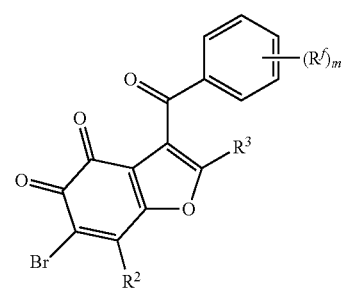
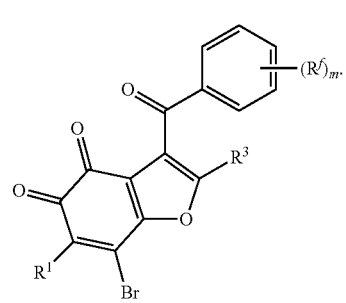
In certain embodiments, the compound is of any one of the formulae:
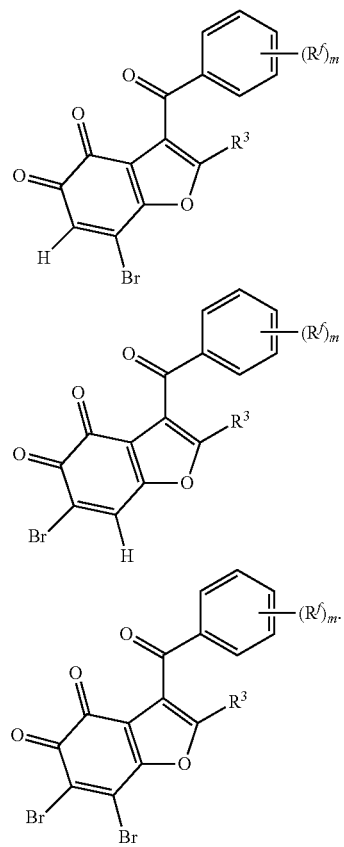
In certain embodiments, the compound is of any one of the formulae:
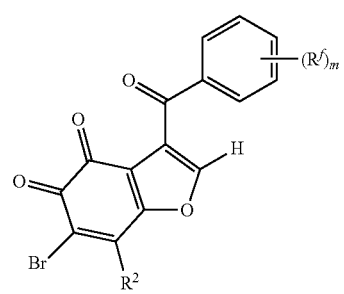
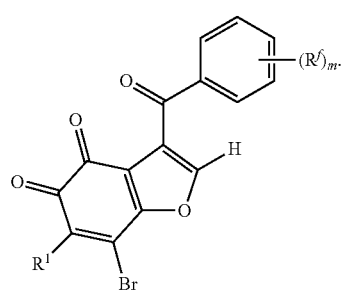

In certain embodiments, the compound is of any one of the formulae:
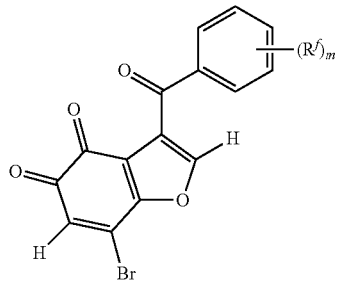
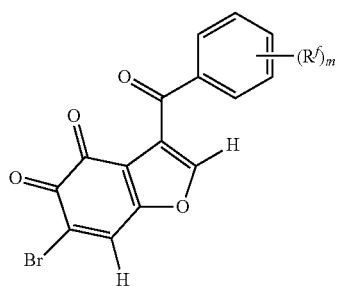
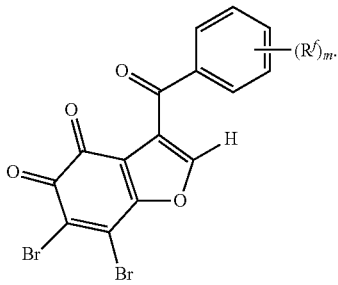
In certain embodiments, the compound is any one of the formulae:
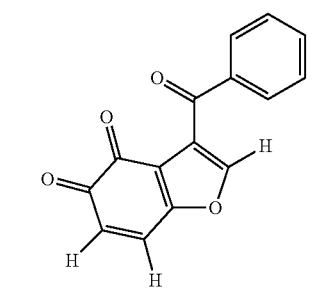
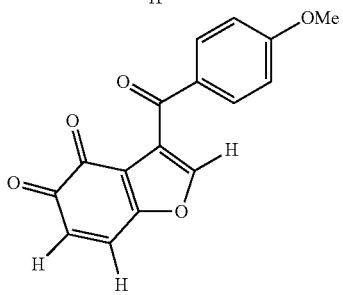
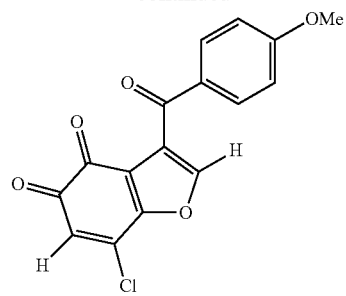
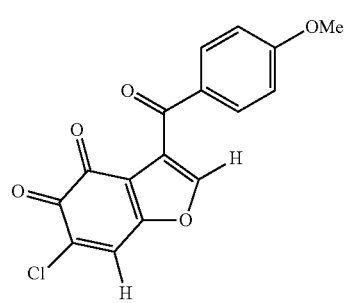
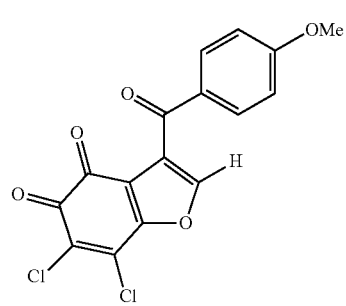
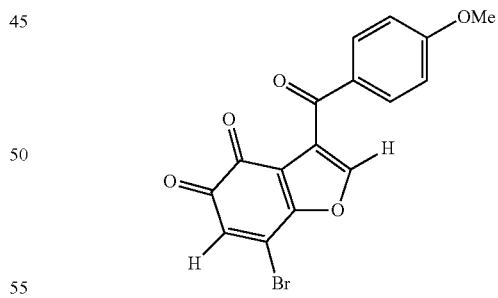
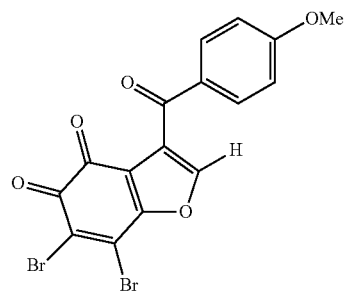

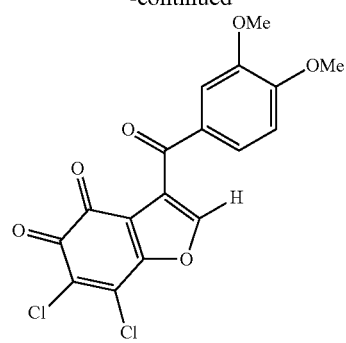
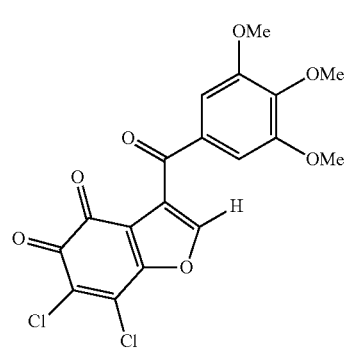
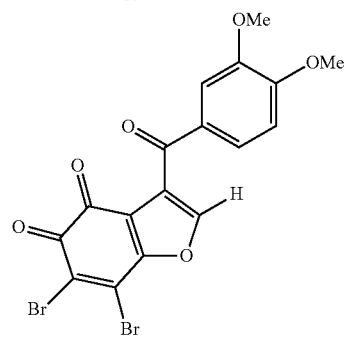
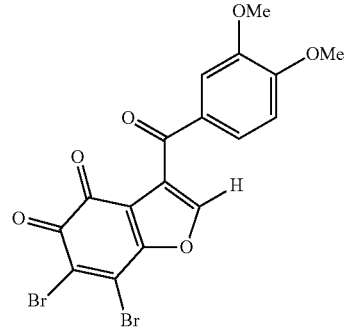
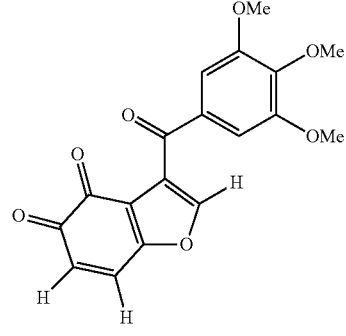
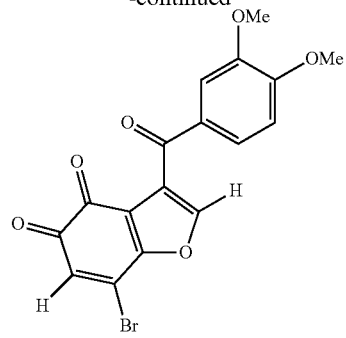
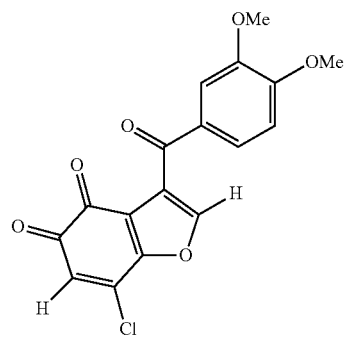
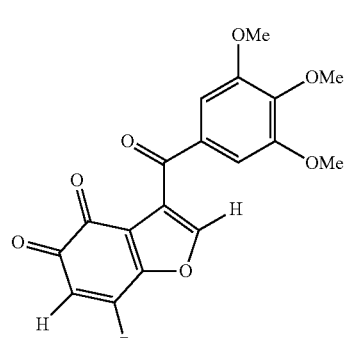
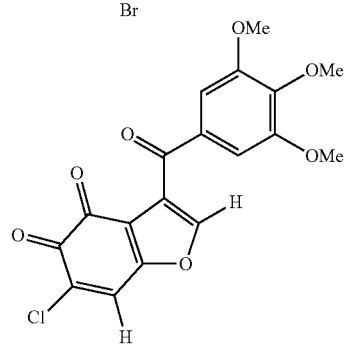
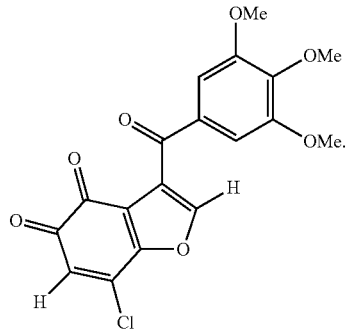 [SMILES: COc1cc(C(=O)c2coc3c2C(=O)C(=O)C=C3Cl)cc(OC)c1OC]

In certain embodiments, the compound is any one of the formulae:
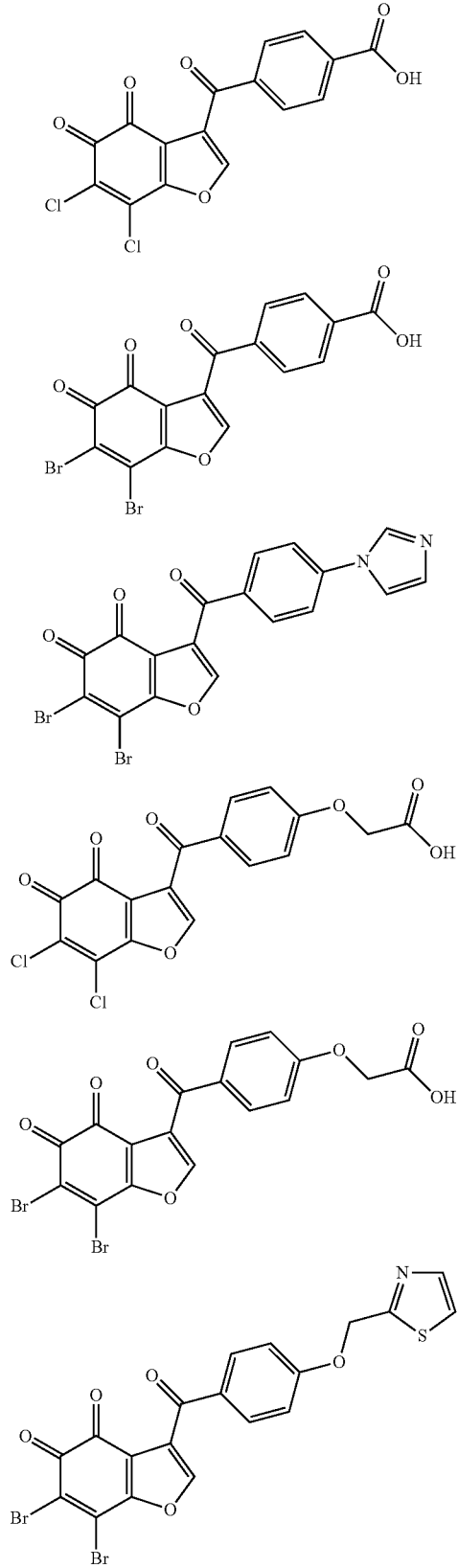
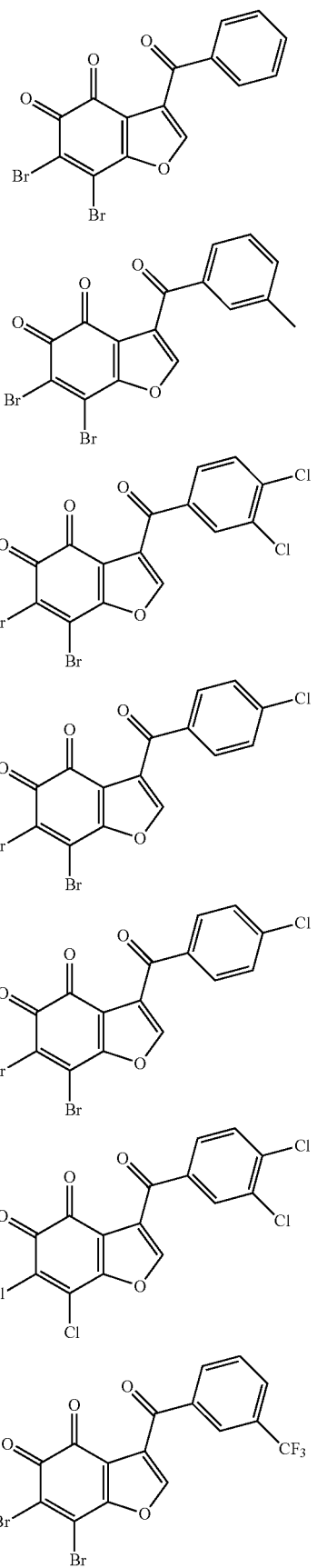

55
-continued
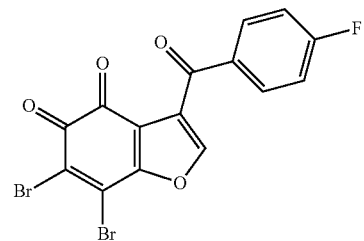
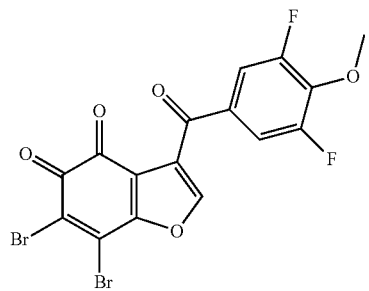
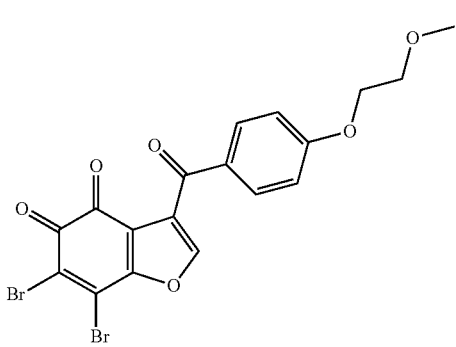
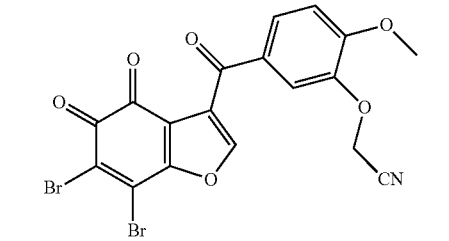
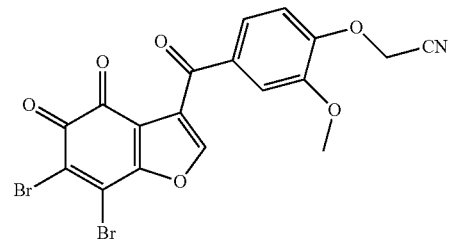
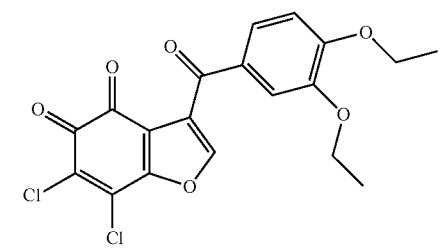
56
-continued
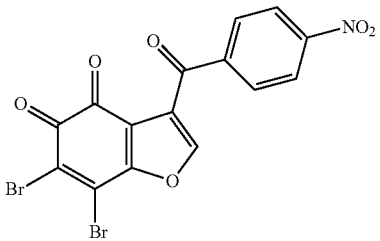
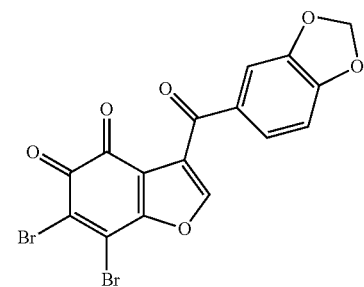
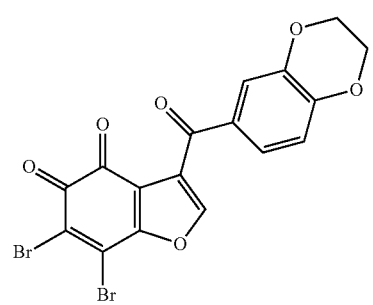
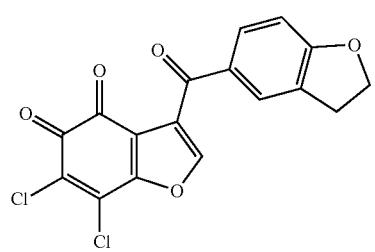
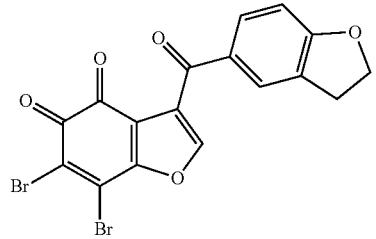
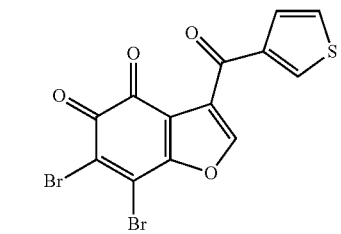

-continued

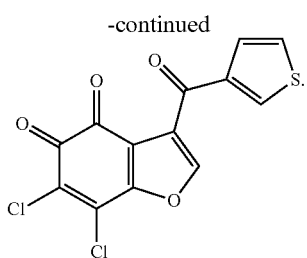

In certain embodiments, the compound is of the formula:

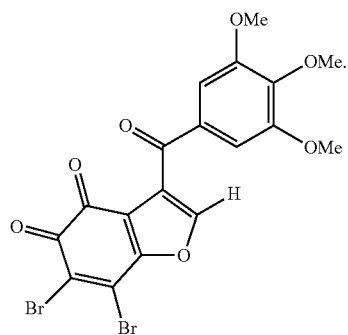

In certain embodiments, the compound is of the formula:

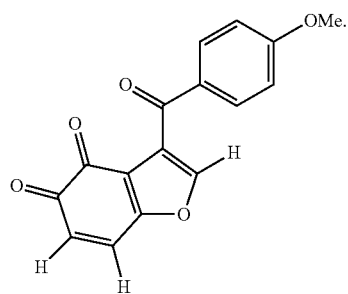 [SMILES: COc1ccc(C(=O)c2coc3c2C(=O)C(=O)C=C3)cc1]

In certain embodiments, the compound is of the formula:

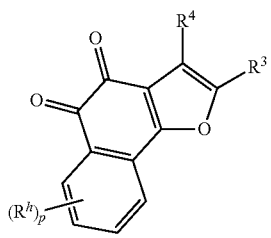

wherein:
$R^3$ and $R^4$ are as defined herein;
p is an integer between 0 and 4, inclusive; and
at least one occurrence of $R^h$ is independently hydrogen; halogen; cyclic or acyclic, substituted or unsubstituted, branched or unbranched aliphatic; cyclic or acyclic, substituted or unsubstituted heteroaliphatic; substituted or unsubstituted, branched or unbranched acyl; substituted or unsubstituted aryl; substituted or unsubstituted heteroaryl; —$OR^i$; —$C(=O)R^i$; —$CO_2R^i$; —CN; —SCN; —$SR^i$; —$SOR^i$; —$SO_2R^i$; —$NO_2$; —$N_3$; —$N(R^i)_2$; —$NR^iC(=O)R^i$; —$NR^iC(=O)N(R^i)_2$; —$OC(=O)OR^i$; —$OC(=O)R^i$; —$OC(=O)N(R^i)_2$; —$NR^iC(=O)OR^i$; or —$C(R^i)_3$; wherein at least one occurrence of $R^i$ is independently hydrogen; halogen; a protecting group; an optionally substituted aliphatic or heteroaliphatic moiety; an acyl moiety; or an optionally substituted aryl or heteroaryl moiety, or a pharmaceutically acceptable salt thereof.

In certain embodiments, p is 0. In certain embodiments, p is 1. In certain embodiments, p is 2. In certain embodiments, p is 3. In certain embodiments, p is 4.

In certain embodiments, at least one occurrence of $R^h$ is independently hydrogen. In certain embodiments, at least one occurrence of $R^h$ is independently halogen. In certain embodiments, at least one occurrence of $R^h$ is independently cyclic aliphatic. In certain embodiments, at least one occurrence of $R^h$ is independently acyclic aliphatic. In certain embodiments, at least one occurrence of $R^h$ is independently substituted aliphatic. In certain embodiments, at least one occurrence of $R^h$ is independently unsubstituted aliphatic. In certain embodiments, at least one occurrence of $R^h$ is independently branched aliphatic. In certain embodiments, at least one occurrence of $R^h$ is independently or unbranched aliphatic. In certain embodiments, at least one occurrence of $R^h$ is independently cyclic heteroaliphatic. In certain embodiments, at least one occurrence of $R^h$ is independently acyclic heteroaliphatic. In certain embodiments, at least one occurrence of $R^h$ is independently substituted heteroaliphatic. In certain embodiments, at least one occurrence of $R^h$ is independently unsubstituted heteroaliphatic. In certain embodiments, at least one occurrence of $R^h$ is independently substituted acyl. In certain embodiments, at least one occurrence of $R^h$ is independently unsubstituted acyl. In certain embodiments, at least one occurrence of $R^h$ is independently branched acyl. In certain embodiments, at least one occurrence of $R^h$ is independently unbranched acyl. In certain embodiments, at least one occurrence of $R^h$ is independently substituted aryl. In certain embodiments, at least one occurrence of $R^h$ is independently unsubstituted aryl. In certain embodiments, at least one occurrence of $R^h$ is independently substituted heteroaryl. In certain embodiments, at least one occurrence of $R^h$ is independently unsubstituted heteroaryl. In certain embodiments, at least one occurrence of $R^h$ is independently —$OR^i$. In certain embodiments, at least one occurrence of $R^h$ is independently —$C(=O)R^i$. In certain embodiments, at least one occurrence of $R^h$ is independently —$CO_2R^i$. In certain embodiments, at least one occurrence of $R^h$ is independently —CN. In certain embodiments, at least one occurrence of $R^h$ is independently —SCN. In certain embodiments, at least one occurrence of $R^h$ is independently —$SR^i$. In certain embodiments, at least one occurrence of $R^h$ is independently —$SOR^i$. In certain embodiments, at least one occurrence of $R^h$ is independently —$SO_2R^i$. In certain embodiments, at least one occurrence of $R^h$ is independently —$NO_2$. In certain embodiments, at least one occurrence of $R^h$ is independently —$N_3$. In certain embodiments, at least one occurrence of $R^h$ is independently —$N(R^i)_2$. In certain embodiments, at least one occurrence of $R^h$ is independently —$NR^iC(=O)R^i$. In certain embodiments, at least one occurrence of $R^h$ is independently —$NR^iC(=O)N(R^i)_2$. In certain embodiments, at least one occurrence of $R^h$ is independently —$OC(=O)OR^i$. In certain embodiments, at least one occurrence of $R^h$ is independently —$OC(=O)R^i$. In certain embodiments, at least one occurrence of $R^h$ is independently —$OC(=O)N(R^i)_2$. In certain embodiments, at least one occurrence of $R^h$ is independently —$NR^iC(=O)OR^i$. In certain embodiments, at least one occurrence of $R^h$ is independently or —$C(R^i)_3$. In certain embodiments, at least one occurrence of $R^i$ is independently hydrogen. In certain embodiments, at least one occurrence of $R^i$ is independently halogen. In certain embodiments, at least one occurrence of $R^i$ is independently a protecting group. In certain embodiments, at least one occurrence of $R^i$ is independently optionally substituted aliphatic. In certain embodiments, at least one occurrence of $R^i$ is independently optionally substituted heteroaliphatic. In certain embodiments, at least one occurrence of $R^i$ is independently an acyl moiety. In certain embodiments, at least one occurrence of $R^i$ is independently optionally substituted aryl. In certain embodiments, at least one occurrence of $R^i$ is independently optionally substituted heteroaryl.

In some embodiments, at least one occurrence of $R^h$ comprises an isotopic label. By way of nonlimiting example, isotopic labels include $^2H$, $^3H$, $^{18}F$, $^{123}I$, $^{125}I$, $^{131}I$, $^{11}C$, $^{14}C$, $^{13}N$, and/or $^{15}O$.

In some embodiments, at least one occurrence of $R^h$ is hydrogen. In some embodiments, at least two occurrences of $R^h$ are hydrogen. In some embodiments, at least three occurrences of $R^h$ are hydrogen. In some embodiments, at least four occurrences of $R^h$ are hydrogen.

In certain embodiments, the compound is of the formula:

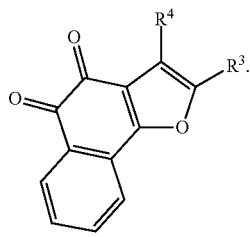

In certain embodiments, the compound is of the formula:

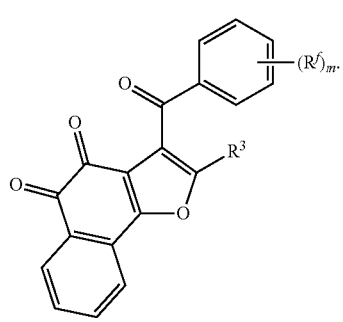

In certain embodiments, the compound is of the formula:

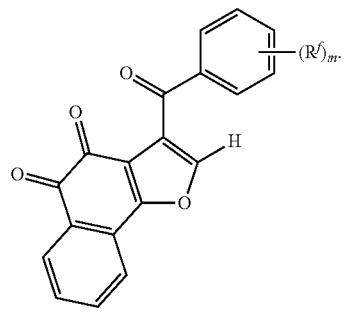

In certain embodiments, the compound is of one of the formulae:

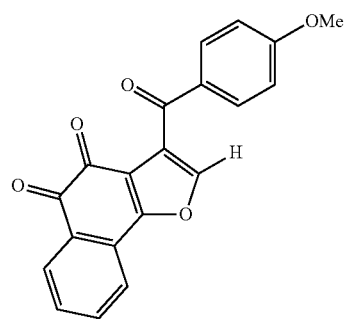

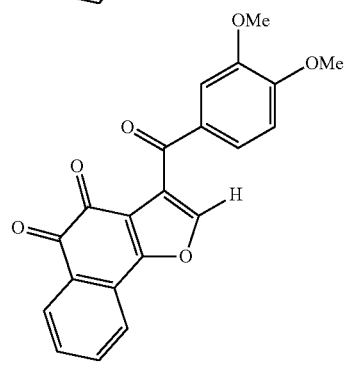

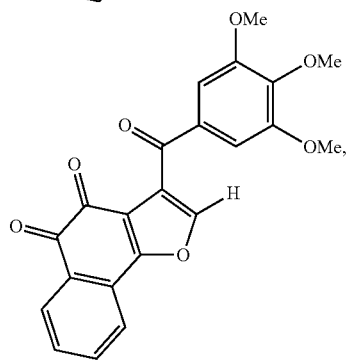

or a pharmaceutically acceptable salt thereof.

Synthesis of Compounds

Compounds of the present invention and intermediates thereto may be synthesized in a variety of ways known to those of skill in the art.

Scheme 1. Synthesis of halogenation paraquinones.

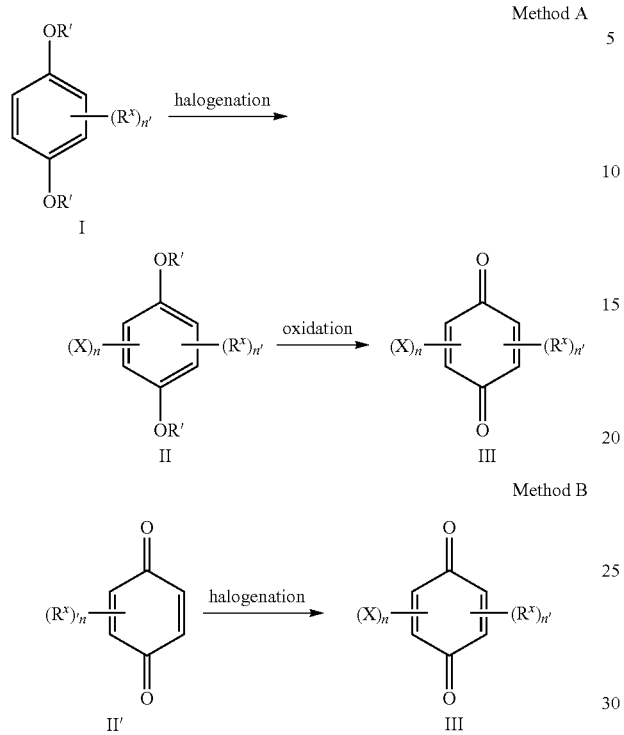

Synthetic intermediates I and II' may be commercially available or synthesized from a commercially available starting material. In certain embodiments, quinone II' or benzoquinone I is halogenated. In embodiments according to method A (above), the benzoquinone (e.g., methoxy-protected benzoquinone or hydroquinone) is halogenated with a halogenating agent such as, for instance, bromine or chlorine. Subsequent oxidation of the halogenated benzoquinone using, for instance, ceric ammonium nitrate (CAN) affords the desired halogenated quinone. Alternatively, in certain embodiments according to method B (above), a paraquinone is halogenated using a suitable halogenating reagent (e.g., bromine or $SO_2Cl_2$) followed immediately by treatment with $Ag_2O$ under acidic conditions (e.g., $H_2SO_4$). Depending on the reagents and starting material selected, the compound being halogenated may undergo one or more halogenations to afford a product containing one or more halogens. The solvent used during halogenation may be any suitable solvent known to those in the art, such as, for instance, methyl tert-butyl ether (MTBE), ether, chloroform, acetic acid, or combinations thereof. Solvents used during the oxidation may be aqueous solvents, organic solvents, or combinations thereof.

Scheme 2. Synthesis of benzofuran-4,5-diones.

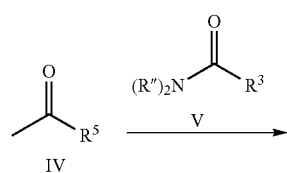

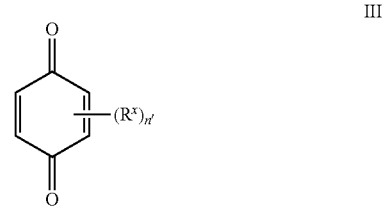

Synthetic intermediates IV and V may be prepared using any of the methods known in the art or may be commercially available. In some embodiments, compounds of the present invention may be synthesized using the synthetic route shown above. In embodiments shown above, ketone IV (e.g., acetophenone) is added to amide V (e.g., DMF). Subsequent dehydration furnishes vinylogous amide VI, which is then coupled to quinone III under acidic conditions (e.g., acetic acid). Oxidation of the resulting benzofuran moiety of VII using any one of the oxidants known in the art (e.g., $HNO_3$, Dess-Martin periodinane, or Fremy's salt) affords benzofuran-4,5,-dione VIII.

In some embodiments, synthesis of benzofuran-4,5-diones comprises the step of reacting a compound of formula III:

III wherein:
    n' is an integer between 0 and 3, inclusive;
    each occurrence of $R^x$ is independently $R^1$ or $R^2$; wherein each occurrence of $R^1$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl;

—OR$^a$; —C(=O)R$^a$; —CO$_2$R$^a$; —CN; —SCN; —SR$^a$; —SOR$^a$; —SO$_2$R$^a$; —NO$_2$; —N$_3$; —N(R$^a$)$_2$; —NR$^a$C(=O)R$^a$; —NR$^a$C(=O)N(R$^a$)$_2$; —OC(=O)OR$^a$; —OC(=O)R$^a$; —OC(=O)N(R$^a$)$_2$; —NR$^a$C(=O)OR$^a$; or —C(R$^a$)$_3$; wherein each occurrence of R$^a$ is independently hydrogen; halogen; a protecting group; an optionally substituted aliphatic or heteroaliphatic moiety; an acyl moiety; or an optionally substituted aryl or heteroaryl moiety;

each occurrence of R$^2$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$^b$; —C(=O)R$^b$; —CO$_2$R$^b$; —CN; —SCN; —SR$^b$; —SOR$^b$; —SO$_2$R$^b$; —NO$_2$; —N$_3$; —N(R$^b$)$_2$; —NR$^b$C(=O)R$^a$; —NR$^b$C(=O)N(R$^b$)$_2$; —OC(=O)OR$^b$; —OC(=O)R$^b$; —OC(=O)N(R$^b$)$_2$; —NR$^b$C(=O)OR$^b$; or —C(R$^b$)$_3$; wherein each occurrence of R$^b$ is independently hydrogen; halogen; a protecting group; an optionally substituted aliphatic or heteroaliphatic moiety; an acyl moiety; or an optionally substituted aryl or heteroaryl moiety; and wherein R$^1$ and R$^2$ when taken together form an optionally substituted, saturated or unsaturated aromatic, heteroaromatic, or nonaromatic 3-8 membered monocyclic or bicyclic ring optionally containing one or more heteroatoms selected from the group consisting of N, O, or S;
with a compound of formula IV:

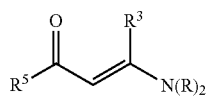

wherein:
each occurrence of R is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; —C(=O)R$^s$; —C(=O)OR$^s$; or —C(R$^s$)$_3$; wherein each occurrence of R$^s$ is independently hydrogen; a protecting group; an optionally substituted aliphatic or heteroaliphatic moiety; or an optionally substituted aryl or heteroaryl moiety;

R$^3$ is hydrogen; halogen; cyclic or acyclic, substituted or unsubstituted, branched or unbranched aliphatic; cyclic or acyclic, substituted or unsubstituted heteroaliphatic; substituted or unsubstituted, branched or unbranched acyl; substituted or unsubstituted aryl; substituted or unsubstituted heteroaryl; or —C(R$^c$)$_3$; wherein each occurrence of R$^c$ is independently hydrogen; halogen; a protecting group; an optionally substituted aliphatic or heteroaliphatic moiety; an acyl moiety; or an optionally substituted aryl or heteroaryl moiety; and R$^5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —OR$^e$; —SR$^e$; —N(R$^e$)$_2$; —NR$^e$C(=O)R$^e$; —NR$^e$C(=O)N(R$^e$)$_2$; —OC(=O)OR$^e$; —OC(=O)R$^e$; —OC(=O)N(R$^e$)$_2$; —NR$^e$C(=O)OR$^e$; or —C(R$^e$)$_3$; wherein each occurrence of R$^e$ is independently independently hydrogen; a protecting group; an optionally substituted aliphatic or heteroaliphatic moiety; an acyl moiety; or an optionally substituted aryl or heteroaryl moiety; under suitable conditions to afford a compound of formula VII:

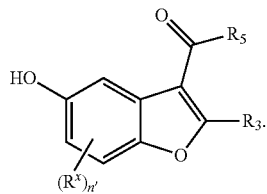

In some embodiments, the step of reacting a compound of formula III with a compound of formula IV comprises one or more additional reagents and one or more solvents. In certain embodiments, the one or more additional reagents may comprise an acid such as, for instance, acetic acid. In some embodiments, the acid is also the solvent.

Reaction times may vary depending on the individual substrates. In some embodiments, the reaction time is less than 0.5 h. In some embodiments, the reaction time is less than 1 h. In some embodiments, the reaction time is from about 1 h to about 50 h. In some embodiments, the reaction time is from about 1 h to about 40 h. In some embodiments, the reaction time is from about 1 h to about 35 h. In some embodiments, the reaction time is from about 1 h to about 25 h. In some embodiments, the reaction time is from about 1 h to about 20 h. In some embodiments, the reaction time is from about 1 h to about 10 h. In some embodiments, the reaction time is about 5 hours. In certain embodiments, the reaction time is about 20 hours. In certain embodiments, the reaction time is about 24 hours. In certain embodiments, the reaction time is about 36 hours.

Reaction temperatures may vary depending on the substrates, solvents, and other reagent used. In some embodiments, the reaction temperature is less than 0° C. In some embodiments, the reaction temperature ranges from about 0° C. to about 100° C. In some embodiments, the reaction temperature ranges from about 0° C. to about 90° C. In some embodiments, the reaction temperature ranges from about 0° C. to about 80° C. In some embodiments, the reaction temperature ranges from about 0° C. to about 70° C. In some embodiments, the reaction temperature ranges from about 0° C. to about 60° C. In some embodiments, the reaction temperature ranges from about 0° C. to about 50° C. In some embodiments, the reaction temperature ranges from about 0° C. to about 40° C. In some embodiments, the reaction temperature ranges from about 0° C. to about 30° C. In some embodiments, the reaction temperature ranges from about 0° C. to about 25° C. In some embodiments, the reaction temperature ranges from about 5° C. to about 25° C. In some embodiments, the reaction temperature ranges from about 10° C. to about 25° C.

In certain embodiments, the invention provides a method of oxidizing a compound of formula VII:

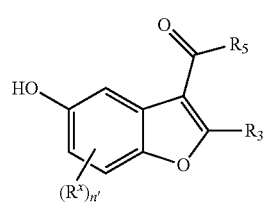

wherein:

n' is an integer between 0 and 3, inclusive;

each occurrence of $R^x$ is independently $R^1$ or $R^2$; wherein each occurrence of $R^1$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^a$; —$C(=O)R^a$; —$CO_2R^a$; —CN; —SCN; —$SR^a$; —$SOR^a$; —$SO_2R^a$; —$NO_2$; —$N_3$; —$N(R^a)_2$; —$NR^aC(=O)R^a$; —$NR^aC(=O)N(R^a)_2$; —$OC(=O)OR^a$; —$OC(=O)R^a$; —$OC(=O)N(R^a)_2$; —$NR^aC(=O)OR^a$; or —$C(R^a)_3$; wherein each occurrence of $R^a$ is independently hydrogen; halogen; a protecting group; an optionally substituted aliphatic or heteroaliphatic moiety; an acyl moiety; or an optionally substituted aryl or heteroaryl moiety; and wherein each occurrence of $R^2$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^b$; —$C(=O)R^b$; —$CO_2R^b$; —CN; —SCN; —$SR^b$; —$SOR^b$; —$SO_2R^b$; —$NO_2$; —$N_3$; —$N(R^b)_2$; —$NR^bC(=O)R^a$; —$NR^bC(=O)N(R^b)_2$; —$OC(=O)OR^b$; —$OC(=O)R^b$; —$OC(=O)N(R^b)_2$; —$NR^bC(=O)OR^b$; or —$C(R^b)_3$; wherein each occurrence of $R^b$ is independently hydrogen; halogen; a protecting group; an optionally substituted aliphatic or heteroaliphatic moiety; an acyl moiety; or an optionally substituted aryl or heteroaryl moiety; and wherein $R^1$ and $R^2$ when taken together form an optionally substituted, saturated or unsaturated aromatic, heteroaromatic, or nonaromatic 3-8 membered monocyclic or bicyclic ring optionally containing one or more heteroatoms selected from the group consisting of N, O, or S;

$R^3$ is hydrogen; halogen; cyclic or acyclic, substituted or unsubstituted, branched or unbranched aliphatic; cyclic or acyclic, substituted or unsubstituted heteroaliphatic; substituted or unsubstituted, branched or unbranched acyl; substituted or unsubstituted aryl; substituted or unsubstituted heteroaryl; —$OR^c$; —$C(=O)R^c$; —$CO_2R^c$; —CN; —SCN; —$SR^c$; —$SOR^c$; —$SO_2R^c$; —$NO_2$; —$N_3$; —$N(R^c)_2$; —$NR^cC(=O)R^c$; —$NR^cC(=O)N(R^c)_2$; —$OC(=O)OR^c$; —$OC(=O)OR^c$; —$OC(=O)N(R^c)_2$; —$NR^cC(=O)OR^c$; or —$C(R^c)_3$; wherein each occurrence of $R^c$ is independently hydrogen; halogen; a protecting group; an optionally substituted aliphatic or heteroaliphatic moiety; an acyl moiety; or an optionally substituted aryl or heteroaryl moiety; and $R^5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —$OR^e$; —$SR^e$; —$N(R^e)_2$; —$NR^eC(=O)R^e$; —$NR^eC(=O)N(R^e)_2$; —$OC(=O)OR^e$; —$OC(=O)R^e$; —$OC(=O)N(R^e)_2$; —$NR^eC(=O)OR^e$; or —$C(R^e)_3$; wherein each occurrence of $R^e$ is independently independently hydrogen; halogen; a protecting group; an optionally substituted aliphatic or heteroaliphatic moiety; an acyl moiety; or an optionally substituted aryl or heteroaryl moiety; in the presence of a suitable oxidant to afford a compound of the formula:

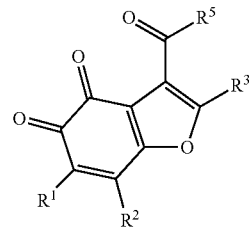

wherein $R^1$, $R^2$, $R^3$, and $R^5$ are as defined herein.

Suitable oxidants include any oxidant known in the art. Exemplary oxidants include, but are not limited to, $HNO_3$, periodinanes (e.g., Dess-Martin periodinane), hypervalent iodides (e.g., PIFA), metal salts (e.g., $CuCl_2$, Co(salen)), peroxides (e.g., $H_2O_2$), potassium nitrosodisulfonate (Fremy's salt), and ceric ammonium nitrate (CAN).

In some embodiments, the invention provides a method for preparing a compound of the formula:

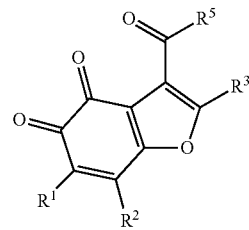

wherein:

$R^1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^a$; —$C(=O)R^a$; —$CO_2R^a$; —CN; —SCN; —$SR^a$; —$SOR^a$; —$SO_2R^a$; —$NO_2$; —$N_3$; —$N(R^a)_2$; —$NR^aC(=O)R^a$; —$NR^aC(=O)N(R^a)_2$; —$OC(=O)OR^a$; —$OC(=O)R^a$; —$OC(=O)N(R^a)_2$; —$NR^aC(=O)OR^a$; or —$C(R^a)_3$; wherein each occurrence of $R^a$ is independently hydrogen; halogen; a protecting group; an optionally substituted aliphatic or heteroaliphatic moiety; an acyl moiety; or an optionally substituted aryl or heteroaryl moiety;

$R^2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^b$; —$C(=O)R^b$; —$CO_2R^b$; —CN; —SCN; —$SR^b$; —$SOR^b$; —$SO_2R^b$; —$NO_2$; —$N_3$; —$N(R^b)_2$; —$NR^bC(=O)R^a$; —$NR^bC(=O)N(R^b)_2$; —$OC(=O)OR^b$; —$OC(=O)R^b$; —$OC(=O)N(R^b)_2$; —$NR^bC(=O)OR^b$; or —$C(R^b)_3$; wherein each occurrence of $R^b$ is independently hydrogen; halogen; a protecting group; an optionally substituted aliphatic or heteroaliphatic moiety; an acyl moiety; or an optionally substituted aryl or heteroaryl moiety;

wherein $R^1$ and $R^2$ when taken together form an optionally substituted, saturated or unsaturated aromatic, heteroaromatic, or nonaromatic 3-8 membered monocyclic or bicyclic ring optionally containing one or more heteroatoms selected from the group consisting of N, O, or S;

$R^3$ is hydrogen; halogen; cyclic or acyclic, substituted or unsubstituted, branched or unbranched aliphatic; cyclic or acyclic, substituted or unsubstituted heteroaliphatic; substituted or unsubstituted, branched or unbranched acyl; substituted or unsubstituted aryl; substituted or unsubstituted heteroaryl; or —C($R^c$)$_3$; wherein each occurrence of $R^c$ is independently hydrogen; halogen; a protecting group; an optionally substituted aliphatic or heteroaliphatic moiety; an acyl moiety; or an optionally substituted aryl or heteroaryl moiety; and $R^5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —OR$^e$; —SR$^e$; —N(R$^e$)$_2$; —NR$^e$C(=O)R$^e$; —NR$^e$C(=O)N(R$^e$)$_2$; —OC(=O)OR$^e$; —OC(=O)R$^e$; —OC(=O)N(R$^e$)$_2$; —NR$^e$C(=O)OR$^e$; or —C(R$^e$)$_3$; wherein each occurrence of $R^e$ is independently independently hydrogen; halogen; a protecting group; an optionally substituted aliphatic or heteroaliphatic moiety; an acyl moiety; or an optionally substituted aryl or heteroaryl moiety, or a pharmaceutically acceptable salt thereof;

comprising the steps of:

(1) reacting a compound of formula III:

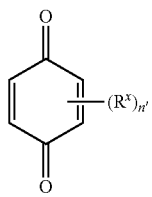

III wherein:

n' is an integer between 0 and 3, inclusive; and each occurrence of $R^x$ is independently $R^1$ or $R^2$, and wherein $R^1$ and $R^2$ are as defined above;

with a compound of formula VI:

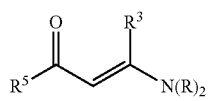

VI wherein:

$R^3$ and $R^5$ are as defined above; and each occurrence of R is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; —C(=O)R$^s$; —C(=O)OR$^s$; or —C(R$^s$)$_3$; wherein each occurrence of R$^s$ is independently hydrogen; a protecting group; an optionally substituted aliphatic or heteroaliphatic moiety; or an optionally substituted aryl or heteroaryl moiety; under suitable conditions to afford a compound of formula VII:

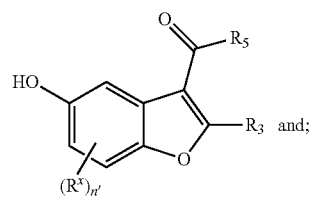

VII (2) oxidizing the compound of formula VII.

In certain embodiments, the invention provides methods of making a library of benzofuran-4,5-dione derivatives containing modifications designed to facilitate structure-activity relationship studies (SARS). In certain embodiments, benzofuran-4,5-dione derivatives are designed and synthesized to contain isosteres or particular substituents of interest in order to determine the effect of a particular atom or substituent on the activity of a compound. Substituents of interest may include, for instance, halogens at the α and β positions on the 4,5-orthodione moiety. Alternatively, in embodiments wherein $R^5$ is optionally substituted aryl, derivatives can be designed to include particular substituents of interest around the aryl ring, such as alkoxy groups. In certain embodiments, the substituents of interest remain the same but the substitution around the aryl ring is varied. In certain other embodiments, the benzofurandione moiety is replaced with a naphthofurandione moiety.

Some of the foregoing compounds include one or more asymmetric centers, and thus can exist in various isomeric forms, e.g., stereoisomers and/or diastereomers. Thus, compounds useful in the present invention and pharmaceutical compositions thereof may be in the form of an individual enantiomer, diastereomer, or geometric isomer, or may be in the form of a mixture of stereoisomers. In certain embodiments, the compositions utilized in the invention include only one stereoisomer of a compound of the invention. In certain other embodiments, mixtures of stereoisomers or diastereomers are utilized.

The invention additionally encompasses the compounds as individual isomers substantially free of other isomers and alternatively, as mixtures of various isomers, e.g., racemic mixtures of stereoisomers. In addition to the compounds described herein, the invention also encompasses pharmaceutically acceptable derivatives of these compounds, and compositions comprising one or more inventive compounds and/or one or more pharmaceutically acceptable excipients.

Compounds utilized in the invention may be prepared by crystallization of the compound under different conditions and may exist as one or a combination of polymorphs of the compound. For example, different polymorphs may be identified and/or prepared using different solvents, or different mixtures of solvents for recrystallization; by performing crystallizations at different temperatures; or by using various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffractogram, and/or other techniques. Compounds utilized in the invention may also exist as amorphous compounds. The present invention encompasses the inventive compounds, their derivatives, their tautomers, their pro-drugs, their stereoisomers, their polymorphs, their pharmaceutically acceptable salts, their pharmaceutically acceptable solvates, their pharmaceutically acceptable hydrates, their pharmaceutically acceptable co-crystals, and pharmaceutically acceptable compositions thereof.

Compounds of the invention may be further characterized using any of the methods known to those of skill in the art.

Exemplary assays for determining the biological activity of inventive compounds may comprise the steps of first providing inventive compounds, contacting said inventive compounds with cells or proteins of interest, and incubating said compounds with cells or proteins of interest under suitable conditions to assay biological activity. A particular biological activity of the compounds of interest can be assessed using any of the methods known in the biological arts suitable for assessing that activity. In addition, the compounds may be screened using cytotoxicity assays or dose-response assays.

In certain embodiments, the methods used to screen the inventive compounds are high-throughput methods. For example, hundreds or thousands of inventive compounds may be evaluated in parallel. High-throughput screening assays may comprise binding assays, cytotoxicity assays, and/or dose-response assays. In certain embodiments, assays are adapted to identify compounds active toward a specific type of protein. In certain embodiments, the protein is a metalloprotease. Exemplary metalloprotease include PDF, APN, and MMP-1. In certain embodiments, the protein is PDF. In certain embodiments, the PDF is eukaryotic PDF. In certain embodiments, the PDF is bacterial PDF. In certain embodiments, the PDF is prokaryotic PDF. In certain embodiments, the PDF is human PDF.

In some embodiments, the binding assays used to identify compounds active toward a protein of interest comprise contacting a test compound with a protein of interest, incubating the test compound and the protein of interest under suitable conditions, adding an indicator to the mixture suitable for detecting the activity of a test compound toward a protein of interest, incubating for an additional period of time, and measuring the extent of activity of a test compound toward the protein of interest. In certain embodiments, the protein of interest is PDF, and the binding assay is specifically adapted to identify compounds active toward PDF. In certain embodiments, the binding assay is specifically adapted to identify compounds active toward eukaryotic PDF or prokaryotic PDF. In certain embodiments, the binding assay is specifically adapted to identify compounds active toward human PDF or bacterial PDF. Exemplary such binding assays include, for instance, fluorescence polarization assays.

In certain embodiments, a test compound is incubated with a protein of interest for approximately 1 minute to approximately 1 week. In certain embodiments, a test compound is incubated with a protein of interest for approximately 1 minute to approximately 1 week. In certain embodiments, a test compound is incubated with a protein of interest for approximately 12 hours to approximately 1 week. In certain embodiments, a test compound is incubated with a protein of interest for approximately 24 hours to approximately 1 week. In certain embodiments, a test compound is incubated with a protein of interest for approximately 36 hours to approximately 1 week. In certain embodiments, a test compound is incubated with a protein of interest for approximately 48 hours to approximately 1 week. In certain embodiments, a test compound is incubated with a protein of interest for approximately 48 hours to approximately 120 hours. In certain embodiments, a test compound is incubated with a protein of interest for approximately 48 hours to approximately 96 hours. In certain embodiments, a test compound is incubated with a protein of interest for approximately 62 hours to approximately 82 hours. In certain embodiments, a test compound is incubated with a protein of interest for approximately 72 hours. In certain embodiments, a test compound is incubated with a protein of interest for approximately 1, 2, 3, 4, 5, 6, or 7 days.

In some embodiments, a test compound is incubated with a protein of interest for approximately 1 minute to approximately 48 hours. In some embodiments, a test compound is incubated with a protein of interest for approximately 1 minute to approximately 36 hours. In some embodiments, a test compound is incubated with a protein of interest for approximately 1 minute to approximately 12 hours. In some embodiments a test compound is incubated with a protein of interest for approximately 1 minute to approximately 6 hours. In some embodiments, a test compound is incubated with a protein of interest for approximately 1 minute to approximately 5 hours. In some embodiments, a test compound is incubated with a protein of interest for approximately 1 minute to approximately 4 hours. In some embodiments, a test compound is incubated with a protein of interest for approximately 1 minute to approximately 3 hours. In some embodiments, a test compound is incubated with a protein of interest for approximately 1 minute to approximately 2 hours. In some embodiments, a test compound is incubated with a protein of interest for approximately 1 minute to approximately 1 hour. In certain embodiments, a test compound is incubated with a protein of interest for approximately 1 hour.

In certain embodiments, after a specified amount of time, an indicator is added and the mixture is incubated for an additional period of time. In some embodiments, this additional period of time ranges from approximately 1 minute to approximately 48 hours. In some embodiments, this additional period of time ranges from approximately 1 minute to approximately 36 hours. In some embodiments, this additional period of time ranges from approximately 1 minute to approximately 12 hours. In some embodiments, this additional period of time ranges from approximately 1 minute to approximately 6 hours. In some embodiments, this additional period of time ranges from approximately 1 minute to approximately 5 hours. In some embodiments, this additional period of time ranges from approximately 1 minute to approximately 4 hours. In some embodiments, this additional period of time ranges from approximately 1 minute to approximately 3 hours. In some embodiments, this additional period of time ranges from approximately 1 minute to approximately 2 hours. In some embodiments, this additional period of time ranges from approximately 1 minute to approximately 1 hour. In certain embodiments, this additional period of time is approximately 1 hour.

Activity may be measured using any of the methods and/or technology known in the art. In some embodiments, activity of a test compound (e.g., binding of a test compound to a protein of interest, etc.) is detected using a substance which produces a detectable signal that indicates activity. In some embodiments, activity is detected using an indicator which fluoresces (e.g., SKI 267088). In certain embodiments, a fluorescent indicator is measured by measuring fluorescence polarization. In certain embodiments, activity of a test compound is indicated by observing a variation in the measurement of fluorescence polarization. In certain embodiments, the activity of a test compound being measured is the ability of a test compound to bind to PDF. In certain embodiments, the PDF is human PDF. In certain embodiments, the test compound is a benzofuran-4,5-dione.

Test compounds may be known or novel compounds. In certain embodiments, test compounds comprise known benzofuran-4,5-diones and derivatives thereof. In certain embodiments, test compounds comprise inventive benzofuran-4,5-diones and derivatives thereof. In certain embodiments, test compounds comprise known and novel benzofuran-4,5-diones and derivatives thereof. The known and novel benzofuran-4,5-diones disclosed herein were first identified and assessed using the above-described screening and profiling methods. Exemplary benzofuran-4,5-diones include, but are not limited to, compounds of the formulae:

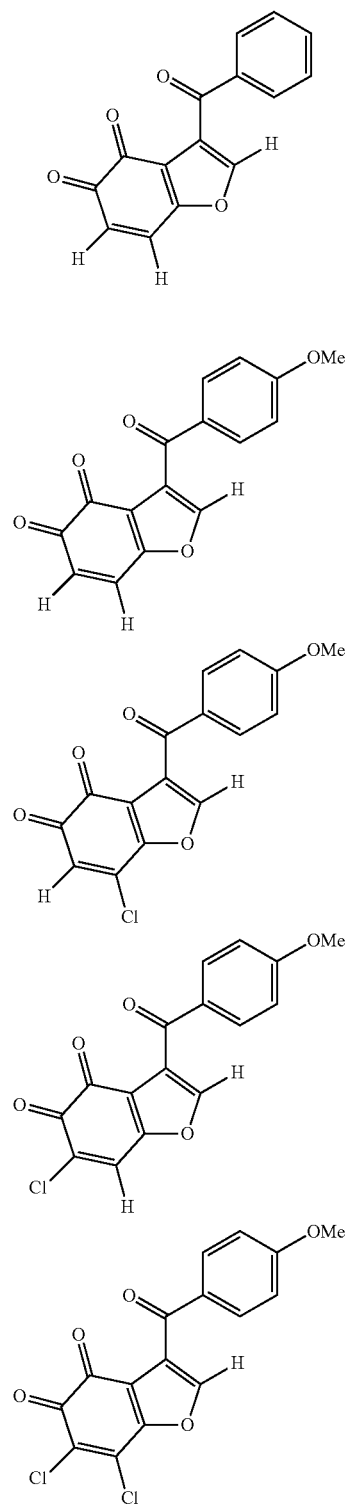

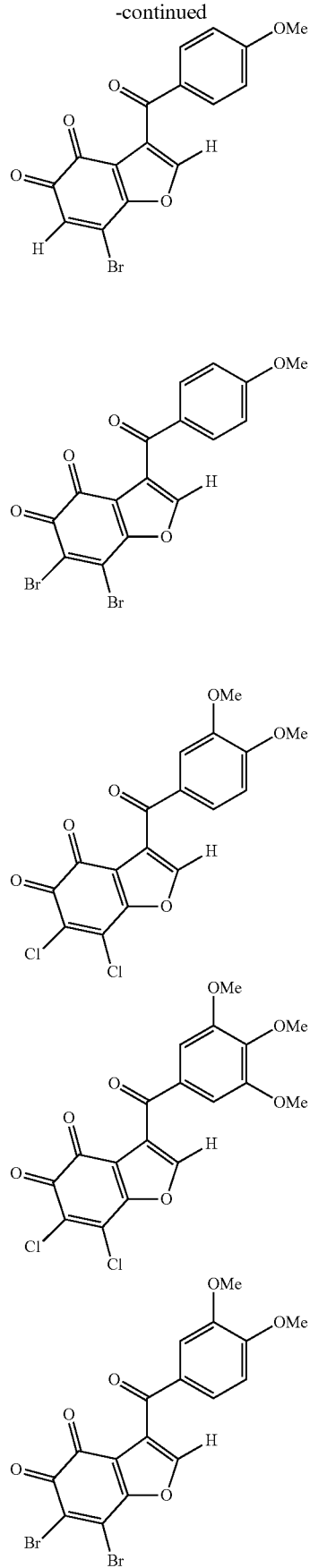

73
-continued
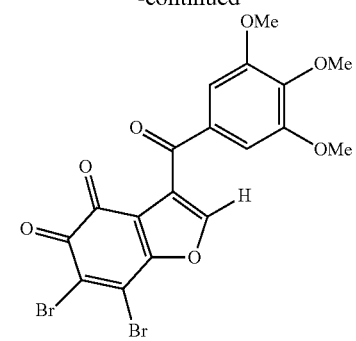
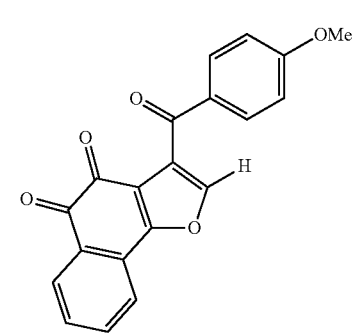
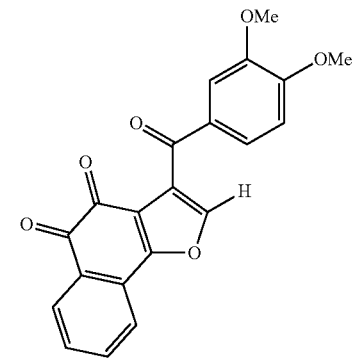
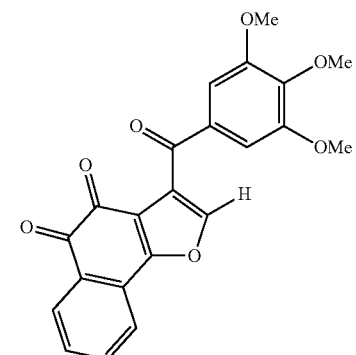
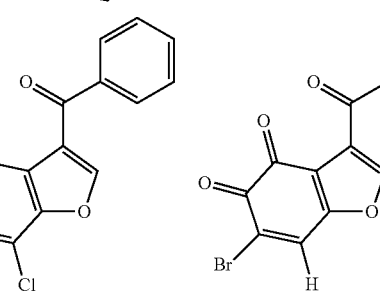
74
-continued
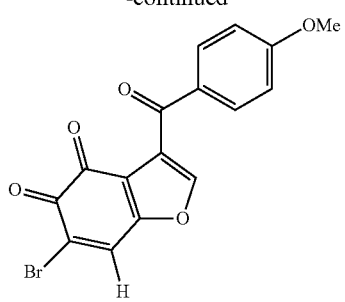
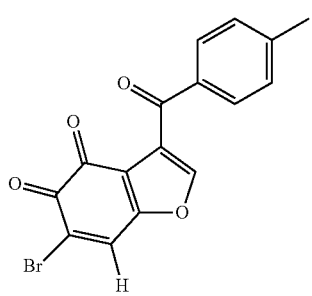
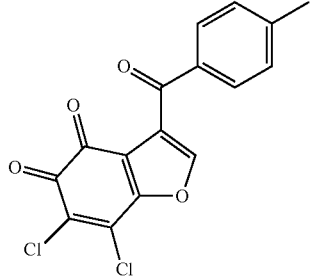
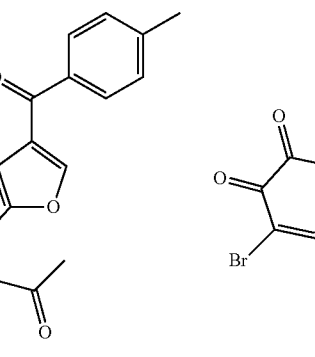
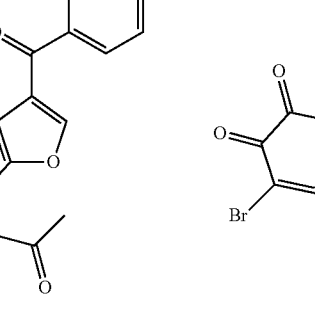
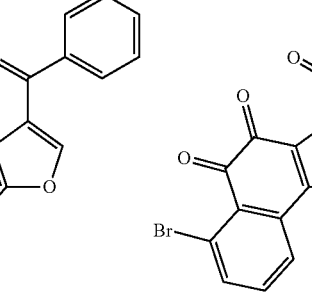
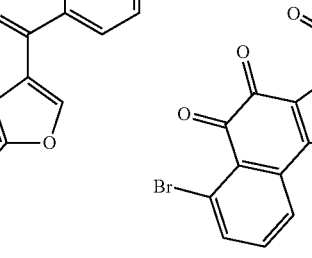
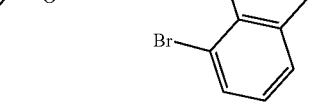

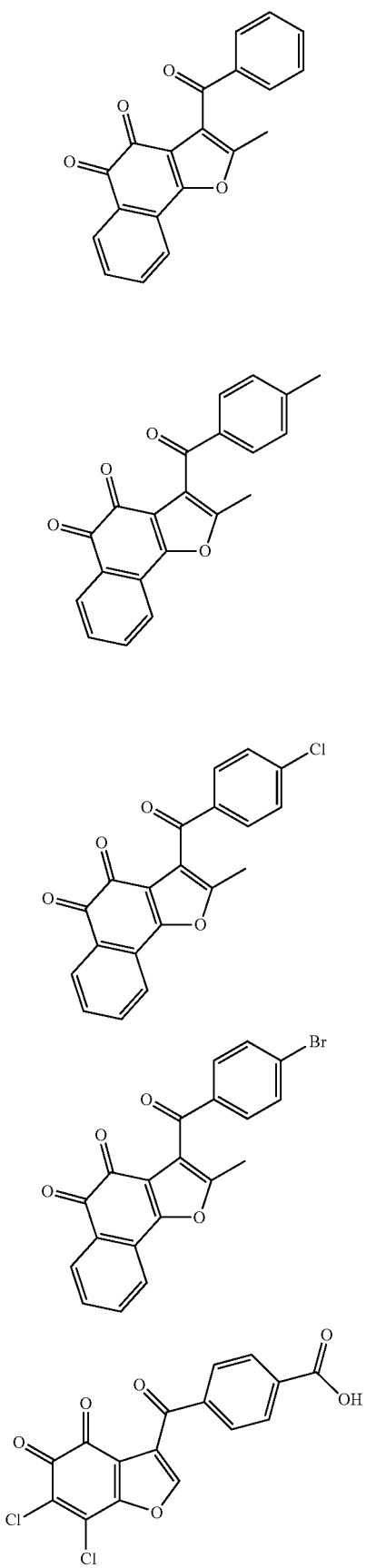
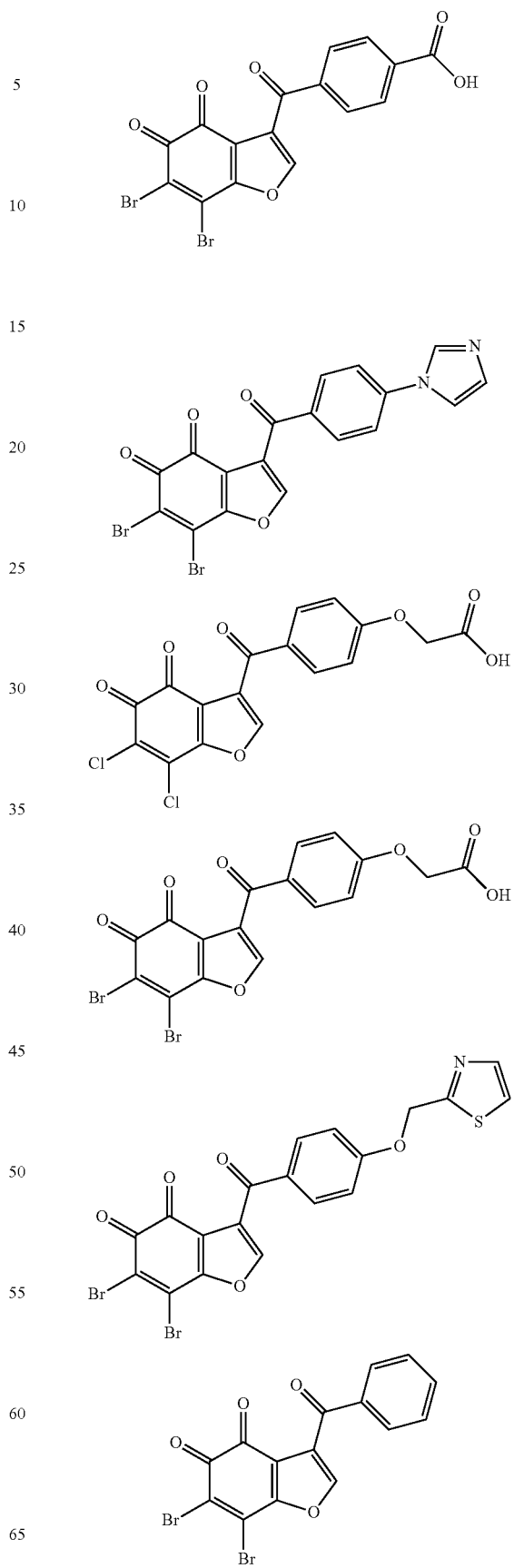

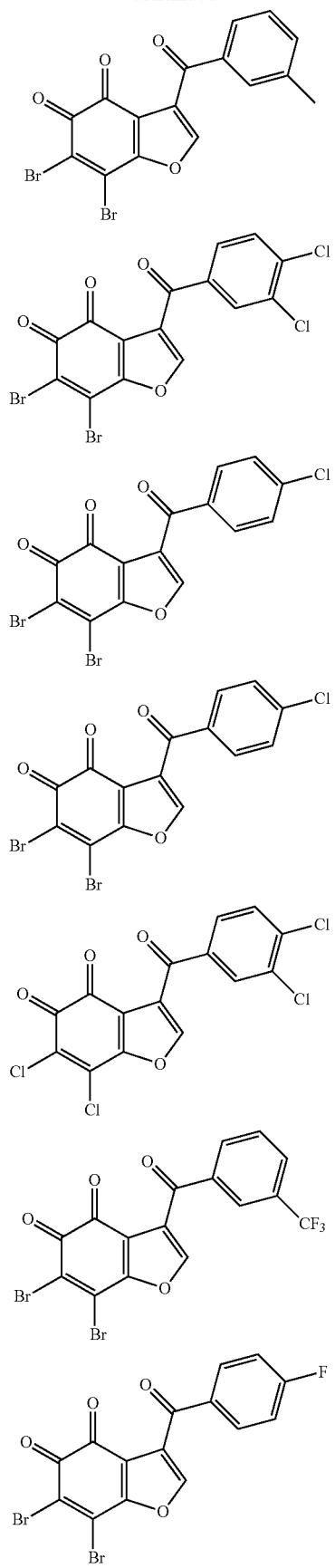
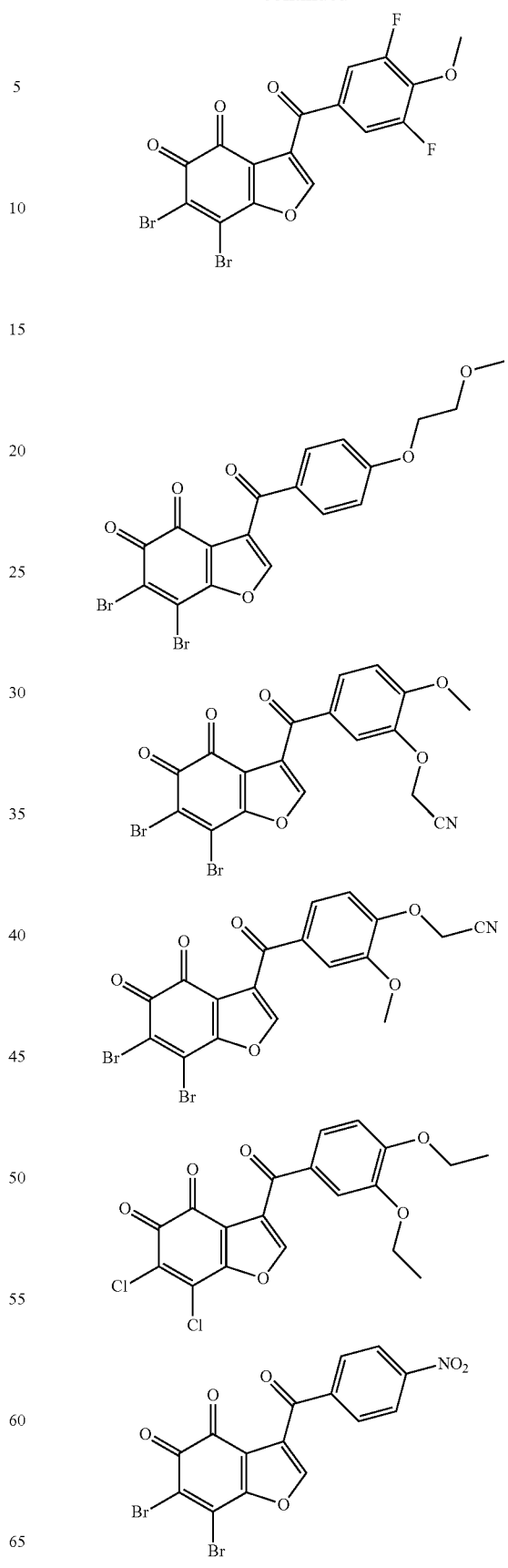

-continued

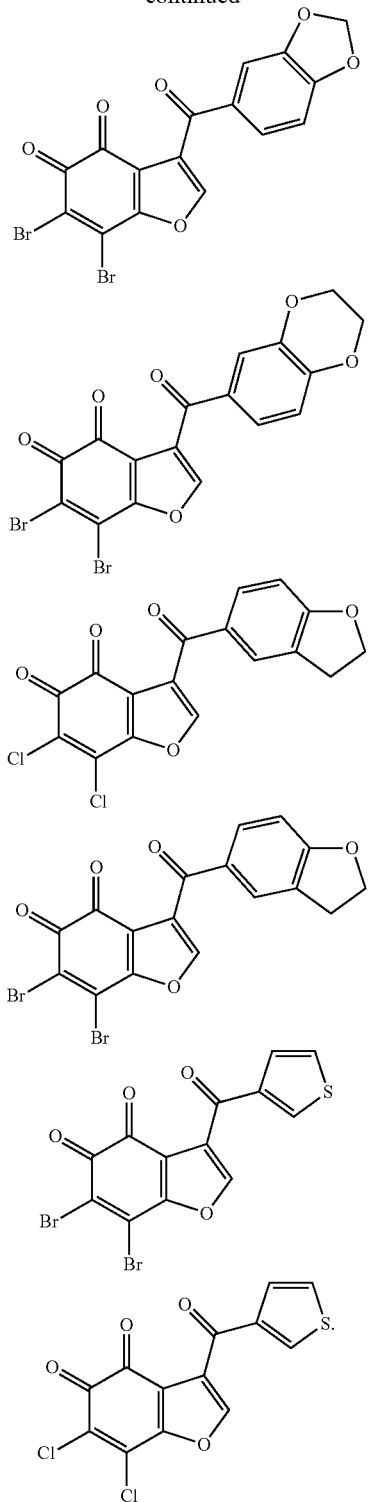

Methods of characterizing benzofuran-4,5-diones include assessing their cytotoxicity, dose response, and/or specificity profiles.

Cytotoxicity can be assessed in vitro using methods comprising the steps of providing a benzofuran-4,5-dione, contacting the benzofuran-4,5-dione with a cell, and incubating the cell with the benzofuran-4,5-dione under suitable conditions to determine the cytotoxicity of the compound. In certain embodiments, this method comprises adding an indicator of cell viability to assess cytotoxicity. In certain embodiments, the test compound is a benzofuran-4,5-dione. In certain embodiments, a test compound is cancer cells.

Cells may be derived from a cell line or a biological sample (e.g., a biopsy). In certain embodiments, the cells are normal cells. In certain embodiments, the cells are cancer cells. In certain embodiments, the cancer cells are derived from the cell line selected from the group consisting of HL-60, Jurkat, Molt3, CWR22, HEK293, K562, Y79, NCEB-1, HL-60/RV+, and ALL-3. In some embodiments, the cancer cell is derived from the HL-60 cell line. In some embodiments, the cancer cell is derived from the Jurkat cell line. In some embodiments, the cancer cell is derived from the Molt3 cell line. In some embodiments, the cancer cell is derived from the CWR22 cell line. In some embodiments, the cancer cell is derived from the HEK293 cell line. In some embodiments, the cancer cell is derived from the K562 cell line. In some embodiments, the cancer cell is derived from the Y79 cell line. In some embodiments, the cancer cell is derived from the NCEB-1 cell line. In some embodiments, the cancer cell is derived from the HL-60/RV+ cell line. In some embodiments, the cancer cell is derived from the HL-60/RV+ cell line. In some embodiments, the cancer cell is derived from the ALL-3 cell line.

In certain embodiments, the cells are incubated with a benzofuran-4,5-dione for approximately 1 minute to approximately 1 week. In certain embodiments, the cells are incubated with a benzofuran-4,5-dione for approximately 1 hour to approximately 1 week. In certain embodiments, the cells are incubated with a benzofuran-4,5-dione for approximately 12 hours to approximately 1 week. In certain embodiments, the cells are incubated with a benzofuran-4,5-dione for approximately 24 hours to approximately 1 week. In certain embodiments, the cells are incubated with a benzofuran-4,5-dione for approximately 36 hours to approximately 1 week. In certain embodiments, the cells are incubated with a benzofuran-4,5-dione for approximately 48 hours to approximately 1 week. In certain embodiments, the cells are incubated with a benzofuran-4,5-dione for approximately 48 hours to approximately 120 hours. In certain embodiments, the cells are incubated with a benzofuran-4,5-dione for approximately 48 hours to approximately 96 hours. In certain embodiments, the cells are incubated with a benzofuran-4,5-dione for approximately 62 hours to approximately 82 hours. In certain embodiments, the cells are incubated with a benzofuran-4,5-dione for approximately 72 hours. In certain embodiments, the cells are incubated with a benzofuran-4,5-dione for 1, 2, 3, 4, 5, 6, or 7 days.

In certain embodiments, after a specified amount of time (e.g., 72 hours) an indicator of cell viability (e.g., Alamar Blue) is added, and the mixture is incubated for an additional period of time. In some embodiments, this additional period of time ranges from approximately 1 hour to approximately 48 hours. In some embodiments, this additional period of time ranges from approximately 12 hour to approximately 36 hours. In some embodiments, this additional period of time is approximately 24 hours.

Cytotoxicity may be assessed using methods or technology known in the art. In some embodiments, cytotoxicity is measured by measuring cell viability. In some embodiments, cytotoxicity is quantified using one of any indicators known to those of ordinary skill in the art that produces a quantifiable signal, the intensity of which is detectable and proportional to cell viability. In some embodiments, cytotoxicity is quantified using an indicator which fluoresces. Exemplary indicators include Tyramide-Alexa Fluor 488, Alamar Blue, etc.

The dose response of benzofuran-4,5-diones can be determined using a cytotoxicity assay such as that described above. For instance, in some embodiments, dose response studies comprise iterations of the steps of providing a benzofuran-4,5-dione, contacting said benzofuran-4,5-dione with a cell, and incubating the cell with the benzofuran-4,5-dione under suitable conditions to determine the cytotoxicity of the benzofuran-4,5-dione. Indicators used to indicate cytotoxicity are as described above. Cytotoxicity assays are repeated using varied concentrations of a benzofuran-4,5-dione in order to calculate the $IC_{50}$. In certain embodiments, the cells are cancer cells.

Dose response may be assessed using dilutions with about 2, 10, 20, 30, 40, 50, 60, 70, 80, 90, or 100 µM test compound being the upper limit. In some embodiments, dose response is assessed using dilutions with about 100 µM test compound as the upper limit. In some embodiments, dose response is assessed using dilutions with about 10 µM test compound as the upper limit. In certain embodiments, the dilutions of test compound used include about 0.05, 0.1, 0.2, 0.4, 0.8, 1.5, 3, 6, 12, 25, 50, and 100 µM. In certain embodiments, the dilutions of test compound used include about 0.005, 0.01, 0.02, 0.04, 0.08, 0.15, 0.3, 0.6, 1.2, 2.5, 5, and 10 µM.

As detailed herein, in assays to determine the ability of a benzofuran-4,5-dione to inhibit cancer cell growth certain compounds may exhibit $IC_{50}$ values ≤100 µM. In certain other embodiments, the benzofuran-4,5-dione exhibits $IC_{50}$ values ≤50 µM. In certain other embodiments, the benzofuran-4,5-dione exhibits $IC_{50}$ values ≤40 µM. In certain other embodiments, the benzofuran-4,5-dione exhibits $IC_{50}$ values ≤30 µM. In certain other embodiments, the benzofuran-4,5-dione exhibits $IC_{50}$ values ≤20 µM. In certain other embodiments, the benzofuran-4,5-dione exhibits $IC_{50}$ values ≤10 µM. In certain other embodiments, the benzofuran-4,5-dione exhibits $IC_{50}$ values ≤7.5 µM. In certain embodiments, the benzofuran-4,5-dione exhibits $IC_{50}$ values ≤5 µM. In certain other embodiments, the benzofuran-4,5-dione exhibits $IC_{50}$ values ≤2.5 mM. In certain embodiments, the benzofuran-4,5-dione exhibits $IC_{50}$ values ≤1 W. In certain embodiments, the benzofuran-4,5-dione exhibits $IC_{50}$ values ≤0.75 µM. In certain embodiments, the benzofuran-4,5-dione exhibits $IC_{50}$ values ≤0.5 µM. In certain embodiments, the benzofuran-4,5-dione exhibits $IC_{50}$ values ≤0.25 µM. In certain embodiments, the benzofuran-4,5-dione exhibits $IC_{50}$ values ≤0.1 µM. In certain other embodiments, the benzofuran-4,5-dione exhibits $IC_{50}$ values ≤75 nM. In certain other embodiments, the benzofuran-4,5-dione exhibits $IC_{50}$ values ≤50 nM. In certain other embodiments, the benzofuran-4,5-dione exhibits $IC_{50}$ values ≤25 nM. In certain other embodiments, the benzofuran-4,5-dione exhibits $IC_{50}$ values ≤10 nM. In other embodiments, the benzofuran-4,5-dione exhibits $IC_{50}$ values ≤7.5 nM. In other embodiments, the benzofuran-4,5-dione exhibits $IC_{50}$ values ≤5 nM.

In some embodiments, the instant invention provides methods of assaying dose response in vivo comprising steps of first providing a benzofuran-4,5-dione, administering the benzofuran-4,5-dione in different concentrations to multiple test subjects, and monitoring the test subjects for signs of toxicity (e.g., weightloss).

A subject may be any animal. In certain embodiments, the subject is any mammal (e.g., humans, domestic/veternary/farm animals such as dogs, cats, cows, sheep, etc.). In some embodiments, the subject is a rodent. In certain embodiments, the subject is a human (e.g., child, juvenile, adult, male, female). In certain embodiments, the subject is an experimental animal such as a mouse, rat, dog, or non-human primate. In certain embodiments, the subject is mouse. In certain embodiments, the mouse is a male mouse about three weeks old.

The frequency and duration of administration of a benzofuran-4,5-dione to a test subject may vary. In some embodiments, the benzofuran-4,5-dione is administered 1, 2, 3, 4, or 5 times a day to a test subject. In some embodiments, the benzofuran-4,5-dione is administered at least every day. In some embodiments, the benzofuran-4,5-dione is administered at least every other day. In some embodiments, the benzofuran-4,5-dione is administered at least every third day. In some embodiments, the benzofuran-4,5-dione is administered at least every fourth day. In some embodiments, the benzofuran-4,5-dione is administered at least every fifth day. In some embodiments, the benzofuran-4,5-dione is administered at least every sixth day. In some embodiments, the benzofuran-4,5-dione is administered at least once a week. In some embodiments, the benzofuran-4,5-dione is administered at least once every two weeks. In some embodiments, the benzofuran-4,5-dione is administered at least once every three weeks. In some embodiments, the benzofuran-4,5-dione is administered at least once a month. In certain embodiments, the test subjects are mice treated with a benzofuran-4,5-dione twice a day for four days.

In certain embodiments, about 10, 20, 30, 40, 50, 60, 70, 80, 90, or 100 mg/kg of benzofuran-4,5-dione are administered to a test subject. In certain embodiments, about 10 mg/kg of benzofuran-4,5-dione are administered to a test subject. In certain embodiments, about 10, 9, 8, 7, 6, 5, 4, 3, 2, or 1 mg/kg of benzofuran-4,5-dione are administered to a test subject. In certain embodiments, less than 1 mg/kg of benzofuran-4,5-dione are administered to a test subject. In certain embodiments, about 1, 5, or 10 mg/kg of benzofuran-4,5-dione are administered to test subjects twice a day for four days.

Test subjects may be monitored for signs of toxicity over a period of time. In certain embodiments, test subjects are monitored for 1, 2, 3, 4, 5, 6, or 7 days. In certain embodiments, test subjects are monitored for 1, 2, 3, or 4 weeks. In certain embodiments, test subjects are monitored for 1, 2, 3, 4, 5, 6, 7, 8, 9, 10, 11, or 12 months. In certain embodiments, test subjects are monitored for 1 or more years.

Benzofuran-4,5-diones identified and characterized using the above methods may further be identified as possessing anti-bacterial, anti-viral, anti-parasitic, anti-inflammatory, and/or anti-cancer activity.

Exemplary bacterial diseases which these biologically active benzofuran-4,5-diones may be used to treat include, but are not limited to, Actinomycosis; Acute prostatitis; *Aeromonas hydrophila*; Annual ryegrass toxicity; Anthrax; Bacteremia; Bacterial meningitis; Bacterial pneumonia; Brazilian purpuric fever; Brodie's abscess; Bubonic plague; Brucellosis; *Burkholderia cepacia* complex; Buruli ulcer; Campylobacteriosis; *Capnocytophaga canimorsus*; Caries; Carrion's disease; *Chlamydia*; Cholera; Diphtheria; Diphtheritic stomatitis; Donovanosis; Erythema migrans; Fitz-Hugh-Curtis syndrome; Fournier gangrene; Group A streptococcal infection; Human granulocytic ehrlichiosis; Impetigo; Late congenital syphilis; Late congenital syphilitic oculopathy; *Legionella*; Lemierre's syndrome; Leprosy; Leptospirosis; Listeriosis; Ludwig's angina; Lyme disease; Melioidosis; Meningococcemia; Methicillin-resistant *Staphylococcus aureus*; Miliary tuberculosis; *Mycobacterium*; *Mycobacterium avium* complex; Necrotizing fasciitis; Nontuberculous mycobacteria; Omphalitis; Orbital cellulitis; Osteomyelitis; Paratyphoid fever; *Pasteurella multocida*; Periorbital cellulitis; Peritonsillar abscess; Pertussis; Pott's disease; Pseudomembranous colitis; Psittacosis; Pyomyositis; Q fever; Rheumatic fever; *Rickettsia prowazekii*; Rickettsialpox; Salmonellosis; Scarlet fever; Scrub typhus; Spondylitis; Staphylococcal infection; Strep throat; Syphilis; Syphilitic aortitis; Tetanus; Tuberculosis; Tularemia; Typhoid fever; Typhus.

Exemplary viral diseases which these biologically active benzofuran-4,5-dione may be used to treat include, but are not limited to, Acquired Immunodeficiency Syndrome; Adenoviridae Infections; Alphavirus Infections; Arbovirus Infections; Borna Disease; Bunyaviridae Infections; Caliciviridae Infections; Chickenpox; Condyloma Acuminata; Coronaviridae Infections; Coxsackievirus Infections; Cytomegalovirus Infections; Dengue; DNA Virus Infections; Eethyma; Encephalitis; Arbovirus; Epstein-Barr Virus Infections; Erythema Infectiosum; Hantavirus Infections; Hemorrhagic Fevers; Hepatitis; Herpes; Herpesviridae Infections; Infectious Mononucleosis; Influenza in birds; Influenza in humans; Lassa Fever; Measles; Molluscum Contagiosum; Mumps; Paramyxoviridae Infections; Phlebotomus Fever; Polyomavirus Infections; Rabies; Respiratory Syncytial Virus Infections; Rift Valley Fever; RNA Virus Infections; Rubella; Slow Virus Diseases; Smallpox; Subacute Sclerosing Panencephalitis; Tumor Virus Infections; Warts; West Nile Fever; Yellow Fever.

Exemplary parasitic diseases which these biologically active benzofuran-4,5-dione may be used to treat include, but are not limited to, Amebiasis; Anisakiasis; *Ascariasis*; Babesiosis; Blastocystis hominis infections; Cestode Infections; Chagas Disease; Cryptosporidiosis; Cyclosporiasis; Cysticercosis; Dientamoebiasis; Diphyllobothriasis; Dracunculiasis; Echinococcosis; Ectoparasitic Infestations; Filariasis; Giardiasis; Helminthiasis; Hookworm Infections; Intestinal Diseases, Parasitic; Larva Migrans; Leishmaniasis; Lice Infestations; Loiasis; Malaria; Mite Infestations; Myiasis; Neurocysticercosis; Onchocerciasis; Protozoan Infections; Scabies; Schistosomiasis; Skin Diseases, Parasitic; Strongyloidiasis; Taeniasis; Toxocariasis; Toxoplasmosis; Trichinosis; Trichomonas Infections; Trypanosomiasis; Whipworm Infections Exemplary inflammatory diseases which these biologically active benzofuran-4,5-dione may be used to treat include, but are not limited to, rheumatoid arthritis, osteoarthritis inflammatory lung disease, inflammatory bowel disease, atherosclerosis and psoriasis.

Exemplary cancers which these biologically active benzofuran-4,5-dione may be used to treat include, but are not limited to, bone cancer, brain cancer, blood cancer, breast cancer, pancreatic cancer, lung cancer, kidney cancer, stomach cancer, ovarian cancer, prostate cancer, colorectal cancer, endometrial cancer, bladder cancer, non-Hodgkin lymphoma, leukemia, neuroblastoma, lymphomas, rhabdomyosarcoma, Wilms' tumor, osteosarcoma and Ewing's sarcoma.

Method for Inhibiting PDF

This invention provides a method for inhibiting PDF comprising contacting a cell with a compound of the formula:

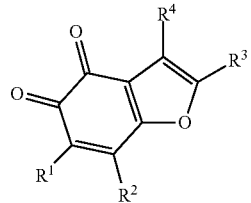

wherein $R^1$, $R^2$, $R^3$, and $R^4$ are as defined herein, or pharmaceutically acceptable salts or compositions thereof, in an amount effective to inhibit PDF. Contact of a benzofuran-4,5-dione with a cell may occur in vivo or in vitro.

In some embodiments, the instant invention provides a method of inhibiting PDF in vitro comprising the steps of first providing a benzofuran-4,5-dione, contacting the benzofuran-4,5-dione with a cell, and then incubating the cell under suitable conditions to inhibit PDF. The extent of inhibition can be assessed using methods known to detect inhibition.

In some embodiments, benzofuran-4,5-diones are selective for the inhibition of a specific type of PDF. In certain embodiments, the inhibited PDF is eukaryotic PDF. In certain embodiments, the inhibited PDF is prokaryotic PDF. In certain embodiments, the inhibited PDF is human PDF (e.g., HsPDF). In certain embodiments, the inhibited PDF is bacterial PDF (e.g., EcPDF).

The cells may be inside a subject or may be derived from a cell line or a biological sample (e.g., a biopsy). In certain embodiments, the cells are normal cells. In certain embodiments, the cells are cancer cells. In certain embodiments, the cancer cells are derived from the cell line selected from the group consisting of HL-60, Jurkat, Molt3, CWR22, HEK293, K562, Y79, NCEB-1, HL-60/RV+, and ALL-3. In some embodiments, the cancer cell is derived from the HL-60 cell line. In some embodiments, the cancer cell is derived from the Jurkat cell line. In some embodiments, the cancer cell is derived from the Molt3 cell line. In some embodiments, the cancer cell is derived from the CWR22 cell line. In some embodiments, the cancer cell is derived from the HEK293 cell line. In some embodiments, the cancer cell is derived from the K562 cell line. In some embodiments, the cancer cell is derived from the Y79 cell line. In some embodiments, the cancer cell is derived from the NCEB-1 cell line. In some embodiments, the cancer cell is derived from the HL-60/RV+ cell line. In some embodiments, the cancer cell is derived from the HL-60/RV+ cell line. In some embodiments, the cancer cell is derived from the ALL-3 cell line.

In certain embodiments, the cells are incubated with a benzofuran-4,5-dione for approximately 1 minute to approximately 1 week. In certain embodiments, the cells are incubated with a benzofuran-4,5-dione for approximately 1 hour to approximately 1 week. In certain embodiments, the cells are incubated with a benzofuran-4,5-dione for approximately 12 hours to approximately 1 week. In certain embodiments, the cells are incubated with a benzofuran-4,5-dione for approximately 24 hours to approximately 1 week. In certain embodiments, the cells are incubated with a benzofuran-4,5-dione for approximately 36 hours to approximately 1 week. In certain embodiments, the cells are incubated with a benzofuran-4,5-dione for approximately 48 hours to approximately 1 week. In certain embodiments, the cells are incubated with a benzofuran-4,5-dione for approximately 48 hours to approximately 120 hours. In certain embodiments, the cells are incubated with a benzofuran-4,5-dione for approximately 48 hours to approximately 96 hours. In certain embodiments, the cells are incubated with a benzofuran-4,5-dione for approximately 62 hours to approximately 82 hours. In certain embodiments, the cells are incubated with a benzofuran-4,5-dione for approximately 72 hours. In certain embodiments, the cells are incubated with a benzofuran-4,5-dione for 1, 2, 3, 4, 5, 6, or 7 days. In certain embodiments, the benzofuran-4,5-dione is of any one of the formulae described herein.

In certain embodiments, the instant invention provides a method of inhibiting PDF in vivo comprising the steps of first administering a benzofuran-4,5-dione to a subject and then monitoring the subject using any of the methods known in the art to assess the extent of inhibition of PDF.

In certain embodiments, the subject is a mammal. In certain embodiments, the subject is a rodent. In certain embodiments, the subject is a mouse or rat. In certain embodiments, the subject is a human. In certain embodiments, the subject has a proliferative disease such as cancer.

Method of Inducing Apoptosis

This invention provides a method of inducing apoptosis comprising contacting a cell with a compound of the formula:

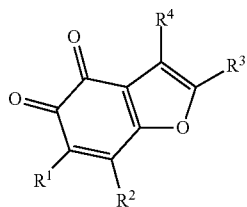

wherein $R^1$, $R^2$, $R^3$, and $R^4$ are as defined herein, or pharmaceutically acceptable salts, or compositions thereof, in an amount effective to induce apoptosis. In certain embodiments, the benzofuran-4,5-dione is of any one of the formulae described herein. Contact of a benzofuran-4,5-dione with a cell may occur in vivo or in vitro.

In some embodiments, the instant invention provides a method of inducing apoptosis in vitro comprising the steps of first providing a benzofuran-4,5-dione, contacting the benzofuran-4,5-dione with a cell, and then incubating the cell under suitable conditions to detect apoptosis. The extent of apoptosis can be assessed using methods known to detect cells undergoing apoptosis. In some embodiments, the extent of apoptosis is quantified using any one of the indicators known to those of ordinary skill in the art. In some embodiments, the extent of apoptosis is determined using an indicator medium which fluoresces.

Cells may be inside a subject or may be derived from a cell line or a biological sample (e.g., a biopsy). In certain embodiments, the cells are normal cells. In certain embodiments, the cells are infected cells. In certain embodiments, the cells are cancer cells. In certain embodiments, the cancer cells are derived from the cell line selected from the group consisting of HL-60, Jurkat, Molt3, CWR22, HEK293, K562, Y79, NCEB-1, HL-60/RV+, and ALL-3. In some embodiments, the cancer cell is derived from the HL-60 cell line. In some embodiments, the cancer cell is derived from the Jurkat cell line. In some embodiments, the cancer cell is derived from the Molt3 cell line. In some embodiments, the cancer cell is derived from the CWR22 cell line. In some embodiments, the cancer cell is derived from the HEK293 cell line. In some embodiments, the cancer cell is derived from the K562 cell line. In some embodiments, the cancer cell is derived from the Y79 cell line. In some embodiments, the cancer cell is derived from the NCEB-1 cell line. In some embodiments, the cancer cell is derived from the HL-60/RV+ cell line. In some embodiments, the cancer cell is derived from the HL-60/RV+ cell line. In some embodiments, the cancer cell is derived from the ALL-3 cell line.

In certain embodiments, the cells are incubated with a benzofuran-4,5-dione for approximately 1 minute to approximately 1 week. In certain embodiments, the cells are incubated with a benzofuran-4,5-dione for approximately 1 hour to approximately 1 week. In certain embodiments, the cells are incubated with a benzofuran-4,5-dione for approximately 12 hours to approximately 1 week. In certain embodiments, the cells are incubated with a benzofuran-4,5-dione for approximately 24 hours to approximately 1 week. In certain embodiments, the cells are incubated with a benzofuran-4,5-dione for approximately 36 hours to approximately 1 week. In certain embodiments, the cells are incubated with a benzofuran-4,5-dione for approximately 48 hours to approximately 1 week. In certain embodiments, the cells are incubated with a benzofuran-4,5-dione for approximately 48 hours to approximately 120 hours. In certain embodiments, the cells are incubated with a benzofuran-4,5-dione for approximately 48 hours to approximately 96 hours. In certain embodiments, the cells are incubated with a benzofuran-4,5-dione for approximately 62 hours to approximately 82 hours. In certain embodiments, the cells are incubated with a benzofuran-4,5-dione for approximately 72 hours. In certain embodiments, the cells are incubated with a benzofuran-4,5-dione for 1, 2, 3, 4, 5, 6, or 7 days. In certain embodiments, the benzofuran-4,5-dione is of any one of the formulae described herein.

In some embodiments, the instant invention provides a method of inducing apoptosis in vivo comprising the steps of first administering a benzofuran-4,5-dione to a subject and then monitoring the subject using any of the methods known in the art to assess the extent of apoptosis.

The method may further comprise administering one or more additional chemotherapeutic agents to the cell. Exemplary one or more additional chemotherapeutic agents are listed below in Methods of Treatment.

Method of Inhibiting Proliferation of Cells

This invention provides a method for inhibiting the proliferation of cells comprising contacting cells with a compound of the formula:

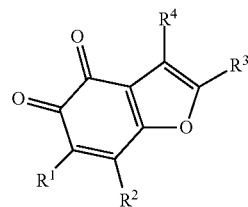

wherein $R^1$, $R^2$, $R^3$, and $R^4$ are as defined herein, or pharmaceutically acceptable salts or compositions thereof, in an amount effective to inhibit the proliferation. Contact of a benzofuran-4,5-dione with a cell may occur in vivo or in vitro.

Methods of inhibiting proliferation in vitro comprise the steps of first providing a benzofuran-4,5-dione, contacting the benzofuran-4,5-dione with a cell, and then incubating the cell under suitable conditions to inhibit proliferation. The extent of inhibition of proliferation can be assessed using methods known to detect the inhibition of proliferation.

The cells may be derived from a cell line or a biological sample (e.g., a biopsy). In certain embodiments, the cells are normal cells. In certain embodiments, the cells are cancer cells. In certain embodiments, the cancer cells are derived from the cell line selected from the group consisting of HL-60, Jurkat, Molt3, CWR22, HEK293, K562, Y79, NCEB-1, HL-60/RV+, and ALL-3. In some embodiments, the cancer cell is derived from the HL-60 cell line. In some embodiments, the cancer cell is derived from the Jurkat cell line. In some embodiments, the cancer cell is derived from the Molt3 cell line. In some embodiments, the cancer cell is derived from the CWR22 cell line. In some embodiments, the cancer cell is derived from the HEK293 cell line. In some embodiments, the cancer cell is derived from the K562 cell line. In some embodiments, the cancer cell is derived from the Y79 cell line. In some embodiments, the cancer cell is derived from the NCEB-1 cell line. In some embodiments, the cancer cell is derived from the HL-60/RV+ cell line. In some embodiments, the cancer cell is derived from the HL-60/RV+ cell line. In some embodiments, the cancer cell is derived from the ALL-3 cell line.

In certain embodiments, the cells are incubated with a benzofuran-4,5-dione for approximately 1 minute to approximately 1 week. In certain embodiments, the cells are incubated with a benzofuran-4,5-dione for approximately 1 hour to approximately 1 week. In certain embodiments, the cells are incubated with a benzofuran-4,5-dione for approximately 12 hours to approximately 1 week. In certain embodiments, the cells are incubated with a benzofuran-4,5-dione for approximately 24 hours to approximately 1 week. In certain embodiments, the cells are incubated with a benzofuran-4,5-dione for approximately 36 hours to approximately 1 week. In certain embodiments, the cells are incubated with a benzofuran-4,5-dione for approximately 48 hours to approximately 1 week. In certain embodiments, the cells are incubated with a benzofuran-4,5-dione for approximately 48 hours to approximately 120 hours. In certain embodiments, the cells are incubated with a benzofuran-4,5-dione for approximately 48 hours to approximately 96 hours. In certain embodiments, the cells are incubated with a benzofuran-4,5-dione for approximately 62 hours to approximately 82 hours. In certain embodiments, the cells are incubated with a benzofuran-4,5-dione for approximately 72 hours. In certain embodiments, the cells are incubated with a benzofuran-4,5-dione for 1, 2, 3, 4, 5, 6, or 7 days. In certain embodiments, the benzofuran-4,5-dione is of any one of the formulae described herein. In certain embodiments, the benzofuran-4,5-dione is of any one of the formulae described herein.

The instant invention also provides methods of inhibiting proliferation in vivo comprising the steps of first administering a benzofuran-4,5-dione to a subject with cancer and then monitoring the subject to assess the inhibition of proliferation of cancer cells. Subjects may be monitored using any of the methods known to those in the art. The efficacy of an inventive compound against tumor cells may be assayed in vivo by providing a therapeutically effective amount of a compound in a composition suitable for administration to a subject (e.g., host animal) with a tumor, administering said composition to a subject (e.g., host animal) with a tumor, and lastly assessing the antitumor effect of the compound by monitoring the tumor over a period of time.

In some embodiments, the tumors are artificially implanted tumors. In some embodiments, the tumors are xenografts. In some embodiments, the xenografts comprise cells derived from any one of the above-described cell lines.

Xenograft tumors are typically grown in the host animal to a certain size prior to administration of an inventive compound. In some embodiments, xenografts are grown to a size ranging from approximately 50 to approximately 500 mm$^3$. In some embodiments, xenografts are grown to a size ranging from approximately 100 to approximately 400 mm$^3$. In some embodiments, xenografts are grown to a size ranging from approximately 200 to approximately 300 mm$^3$. In some embodiments, xenografts are allowed to reach a size of at least approximately 250 mm$^3$ prior to administration of the compound.

The method comprises administration of an inventive compound in a therapeutically effective dose to a host animal. In some embodiments, a therapeutically effective dose comprises an amount ranging from approximately 0.1 mg/kg to approximately 50.0 mg/kg. In some embodiments, a therapeutically effective dose comprises an amount ranging from approximately 0.5 mg/kg to approximately 50.0 mg/kg. In some embodiments, a therapeutically effective dose comprises an amount ranging from approximately 0.5 mg/kg to approximately 40.0 mg/kg. In some embodiments, a therapeutically effective dose comprises an amount ranging from approximately 0.5 mg/kg to approximately 30.0 mg/kg. In some embodiments, a therapeutically effective dose comprises an amount ranging from approximately 1.0 mg/kg to approximately 25.0 mg/kg. In some embodiments, a therapeutically effective dose comprises an amount ranging from approximately 1.5 mg/kg to approximately 15.0 mg/kg. In some embodiments, treatment is administered locally. In some embodiments, treatment is administered by continuous infusion over a certain period of time.

In some embodiments, the efficacy of an inventive compound is measured by measuring tumor size over a period of time before, during, and/or after treatment with said compound. In some embodiments, tumor size is measured once a week. In some embodiments, tumor size is measured twice a week. In some embodiments, tumor size is measured daily. In some embodiments, tumor size is measured once a day. In some embodiments, tumor size is measured twice a day. In some embodiments, tumor size is measured once every other day. In some embodiments, tumor size is measured once every three days. In certain embodiments, tumor size is measured at intervals as required by any one of the methods known to those of skill in the art. In some embodiments, tumor size is measured externally twice a week with a caliper. In certain embodiments, tumor size is measured once a week using an imaging technique (e.g., MRI, X-ray, CT). In some embodiments, the imaging technique is bioluminescent imaging. In certain embodiments, bioluminescent imaging comprises anesthetization of the host animal, injection of a bioluminescent compound, and subsequent measurement of photonic emission. In some embodiments, imaging of the tumor is achieved using any of the methods known in the medical arts.

A subject may be any animal. In certain embodiments, the subject is any mammal (e.g., humans, domestic/veternary/farm animals such as dogs, cats, cows, sheep, etc.). In some embodiments, the subject is a rodent. In certain embodiments, the subject is a human (e.g., child, juvenile, adult, male, female). In certain embodiments, the subject is an experimental animal such as a mouse, rat, dog, or non-human primate. In certain embodiments, the subject is a human.

A therapeutically effective amount of a compound comprises administering an amount necessary to achieve a desired result. The exact amount required will vary from subject to subject, depending on the species, age, general condition of the subject, the severity of the disease, the particular anticancer agent, its mode of administration, the desired outcome, the xenograft, and the like.

In certain embodiments of the present invention, a "therapeutically effective amount" of a compound or pharmaceutical composition is that amount effective for inhibiting cell proliferation in a subject or a biological sample (e.g., in cells). In certain embodiments, cell proliferation is inhibited by about 10%, about 20%, about 30%, about 40%, about 50%, about 60%, about 70%, about 80%, about 90%, about 95%, or about 99%. In certain embodiments, the compound inhibits cell proliferation by at least about 25%, at least about 50%, at least about 75%, or at least about 90%.

In certain embodiments of the present invention, a "therapeutically effective amount" refers to an amount of a compound or composition sufficient to inhibit cell proliferation, or refers to an amount of a compound or composition sufficient to reduce the tumor burden in a subject. In certain embodiments, the tumor burden is reduced by about 1%, about 5%, about 10%, about 20%, about 30%, about 40%, about 50%, about 60%, about 70%, about 80%, about 90%, about 95%, or about 99%. In certain embodiments, the tumor burden is reduced by at least about 25%, at least about 50%, at least about 75%, or at least about 90%.

In certain embodiments of the present invention a "therapeutically effective amount" of the inventive compound or pharmaceutical composition is that amount effective for reducing or inhibiting the growth of tumor cells and/or killing tumor cells.

Methods of Inhibiting the Growth of a Microorganism

This invention provides a method of inhibiting the growth of a microorganism comprising contacting a cell with a compound of the formula:

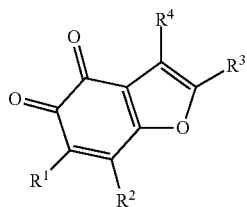

wherein $R^1$, $R^2$, $R^3$, and $R^4$ are as defined herein, or pharmaceutically acceptable salts or compositions thereof, in an amount effective to inhibit the growth of a microorganism. Contact of a benzofuran-4,5-dione with a cell may occur in vivo or in vitro.

In some embodiments, the instant invention provides a method of inhibiting the growth of a microorganism in vitro comprising the steps of first providing a benzofuran-4,5-dione, contacting the benzofuran-4,5-dione with a microorganism of interest, and then incubating the microorganism of interest under suitable conditions to inhibit growth. The extent of inhibition of growth can be assessed using any method known in the art to measure inhibition.

In certain embodiments, the instant invention provides a method of inhibiting the growth of a microorganism in vivo comprising the steps of first administering a benzofuran-4,5-dione to a subject infected with a microorganism and then monitoring the subject using any of the methods known in the art to assess the extent of inhibition of growth of a microorganism.

Exemplary classes of microorganisms include fungus, protozoa, bacteria (Gram-positive or Gram-negative), viruses, or parasites.

In certain embodiments of the present invention a "therapeutically effective amount" of the inventive compound or pharmaceutical composition is that amount effective for reducing or inhibiting the growth of microorganisms.

In certain embodiments of the present invention, a "therapeutically effective amount" of a compound or pharmaceutical composition is that amount effective for inhibiting the growth of a microorganism in a subject or a biological sample. In certain embodiments, the growth of a microorganism is inhibited by about 10%, about 20%, about 30%, about 40%, about 50%, about 60%, about 70%, about 80%, about 90%, about 95%, or about 99%. In certain embodiments, the compound inhibits the growth of a microorganism by at least about 25%, at least about 50%, at least about 75%, or at least about 90%.

A therapeutically effective amount of a compound comprises administering an amount necessary to achieve a desired result. The exact amount required will vary from subject to subject, depending on the species, age, general condition of the subject, the severity of the disease, the particular compounds or composition being administered, its mode of administration, the desired outcome, the microorganism, and the like.

Methods of Treatment

Another aspect of the invention is to provide methods for the treatment of a disease or disorder wherein the inhibition of PDF is desirable to treat that disease or disorder. Methods for the treatment of such diseases comprise administering to a subject in need thereof a therapeutically effective amount of a compound of the formula:

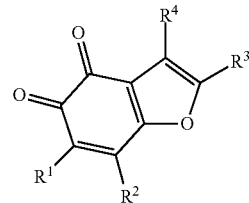

wherein $R^1$, $R^2$, $R^3$, and $R^4$ are as defined herein, and/or pharmaceutically acceptable salts, derivatives, or compositions thereof. In certain embodiments, the disease is a proliferative disease (e.g., cancer). In certain embodiments, the disease is an infectious disease (e.g., bacterial, viral, or parasitic infections). In certain embodiments, the disease is an inflammatory disease. In certain embodiments, the subject being treated is a host animal. In certain embodiments, the subject being treated is a mammal. In certain embodiments, the subject being treated is a human.

Exemplary proliferative diseases include bone cancer, brain cancer, blood cancer, breast cancer, pancreatic cancer, lung cancer, kidney cancer, stomach cancer, ovarian cancer, prostate cancer, colorectal cancer, endometrial cancer, bladder cancer, non-Hodgkin lymphoma, leukemia, neuroblastoma, lymphomas, rhabdomysosarcoma, Wilms' tumor, osteosarcoma, and Ewing's sarcoma.

Exemplary cancers of the blood, bone, or lymph nodes include leukemia (e.g., acute lymphoblastic leukemia, acute myelogenous leukemia, chronic myelogenous leukemia, chronic lymphocytic leukemia, and hairy cell leukemia), lymphoma (e.g., a type of Hodgkin's disease or a type of non-Hodgkin lymphoma) or multiple myeloma.

In certain embodiments, the proliferative disorder is myeloplastic syndrome or a myeloproliferative disease (e.g., polycythemia vera, essential thrombocytosis, myelofibrosis), or amyloidosis.

In certain embodiments of the present invention a "therapeutically effective amount" of the inventive compound or pharmaceutical composition is that amount effective for reducing or inhibiting the growth of tumor cells and/or killing tumor cells.

In some embodiments, the present methods for treating or preventing cancer can further comprise the administration of another anticancer agent. In some embodiments, the present invention provides methods for treating or preventing cancer, comprising the administration of an effective amount of a benzofuran-4,5-dione and another anticancer agent to a subject in need thereof. The benzofuran-4,5-dione and another anticancer agent can be administered concurrently. In this embodiment, the benzofuran-4,5-dione and another anticancer agent can be administered within the same composition, or can be administered from different compositions, via the same or different routes of administration. In another embodiment, the benzofuran-4,5-dione is administered during a time when the other anticancer agent exerts its prophylactic or therapeutic effect, or vice versa.

In some embodiments, the benzofuran-4,5-dione or other anticancer agent is administered in doses commonly employed when such agents are used as monotherapy for the treatment of cancer. In some embodiments, the benzofuran-4,5-dione and other anticancer agent are administered in doses that are lower than the doses commonly employed when such agents are used as monotherapy for the treatment of cancer.

In another embodiment, the benzofuran-4,5-dione and other anticancer agent act synergistically and are administered in doses that are lower than the doses commonly employed when such agents are used as monotherapy for the treatment of cancer. The dosage of the benzofuran-4,5-dione or other anticancer agent administered as well as the dosing schedule can depend on various parameters, including, but not limited to, the cancer being treated, the subject's general health, and the administering physician's discretion. A benzofuran-4,5-dione can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concurrently with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the other anticancer agent, to a subject in need thereof. In various embodiments a benzofuran-4,5-dione and the other anticancer agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, a benzofuran-4,5-dione and the other anticancer agent are administered within 3 hours. In another embodiment, a benzofuran-4,5-dione and the other anticancer agent are administered at 1 minute to 24 hours apart.

In some embodiments, an effective amount of a benzofuran-4,5-dione and an effective amount of other anticancer agent are present in the same composition. In some embodiments, this composition is useful for oral administration, in another embodiment, this composition is useful for intravenous administration. In some embodiments, the compositions comprise an amount of a benzofuran-4,5-dione and the other anticancer agent which together are effective to treat or prevent cancer.

In certain embodiments, the compositions comprise an effective amount of a pharmaceutically acceptable carrier or vehicle, and an effective amount of a benzofuran-4,5-dione. Exemplary benzofuran-4,5-diones include compounds of any one of the formulae:

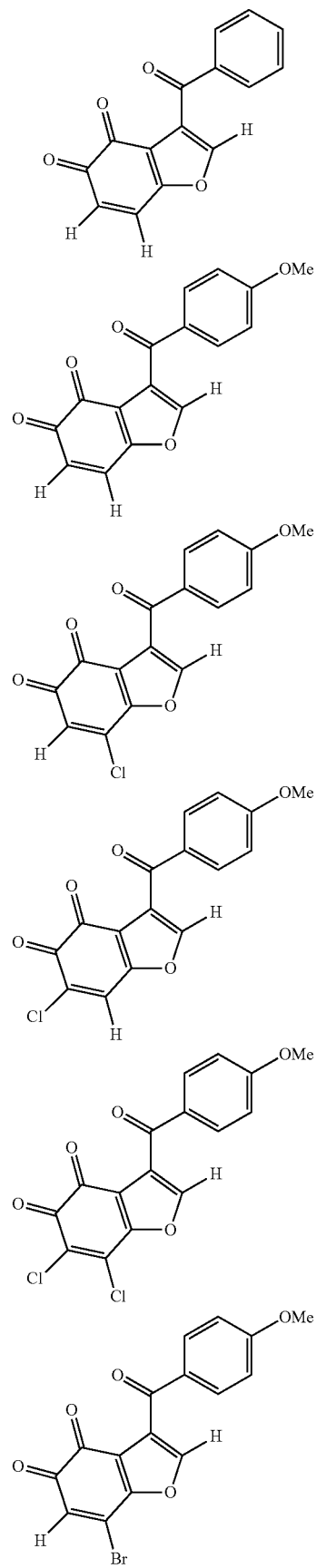 [SMILES: O=C1C=Cc2occ(C(=O)c3ccccc3)c2C1=O ; COc1ccc(C(=O)c2coc3c2C(=O)C(=O)C=C3)cc1 ; COc1ccc(C(=O)c2coc3c2C(=O)C(=O)C=C3Cl)cc1 ; COc1ccc(C(=O)c2coc3c2C(=O)C(=O)C(Cl)=C3)cc1 ; COc1ccc(C(=O)c2coc3c2C(=O)C(=O)C(Cl)=C3Cl)cc1 ; COc1ccc(C(=O)c2coc3c2C(=O)C(=O)C=C3Br)cc1]

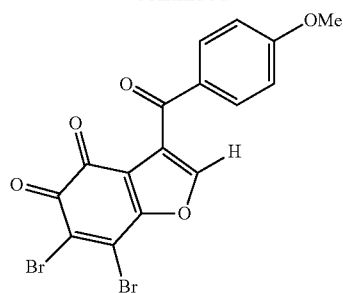
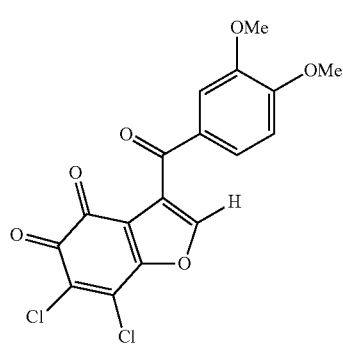
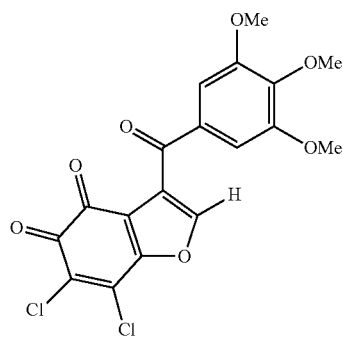
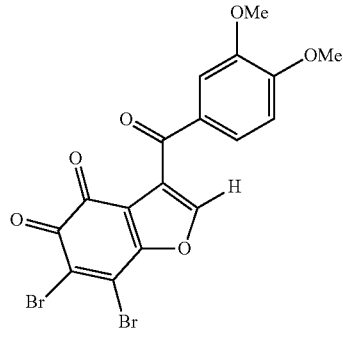
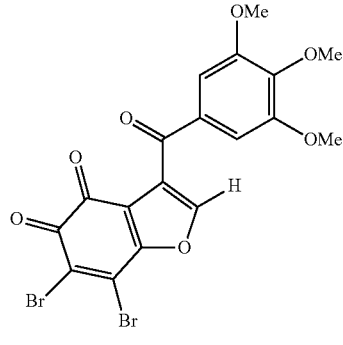
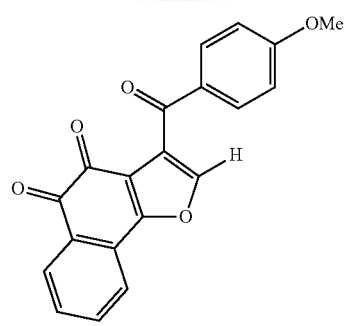
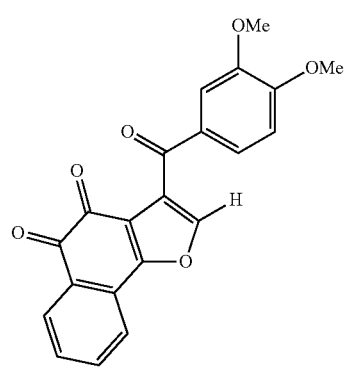
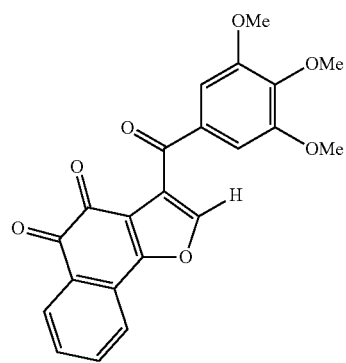
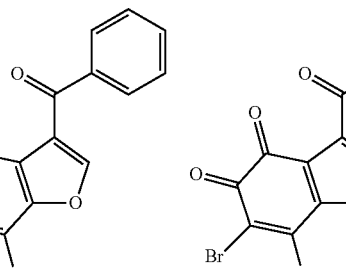
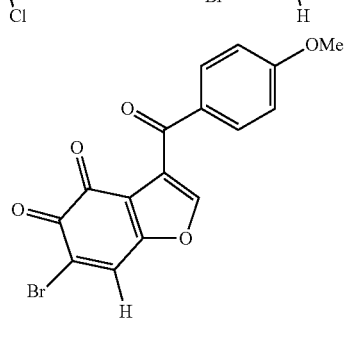

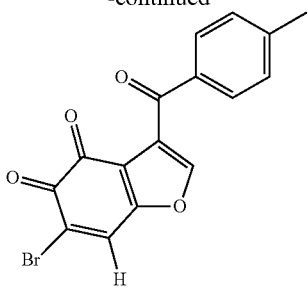
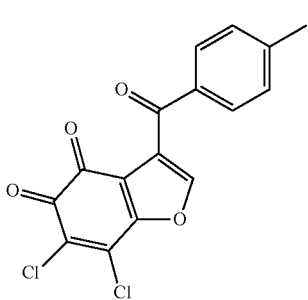
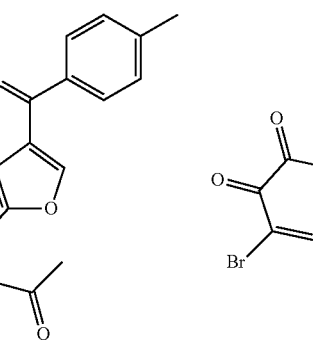
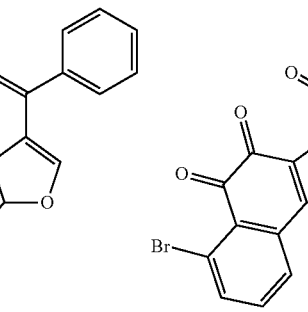
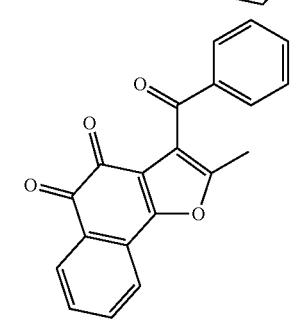
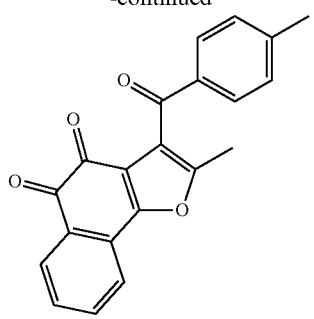
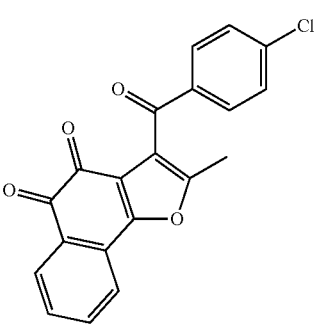
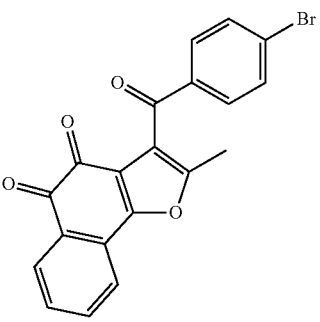
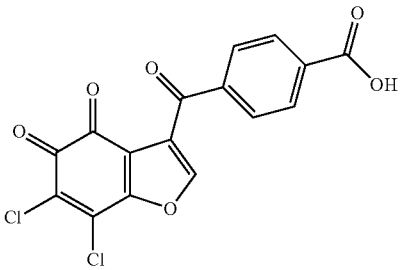
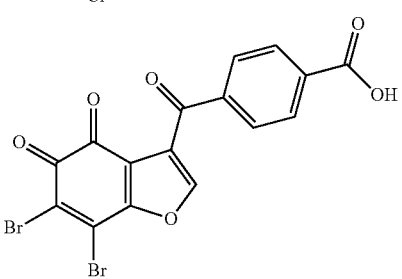

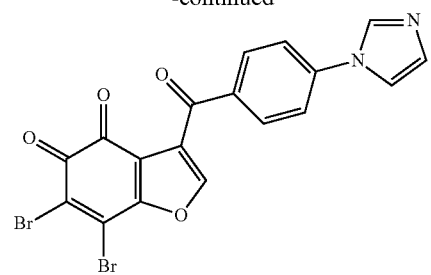
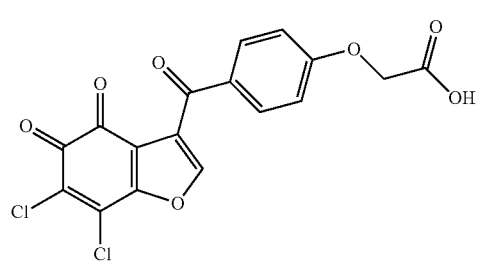
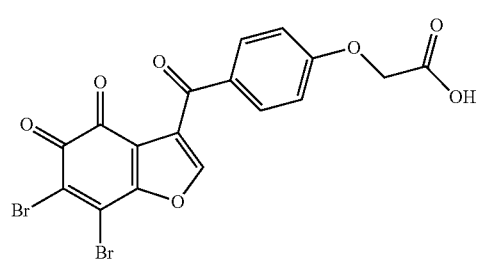
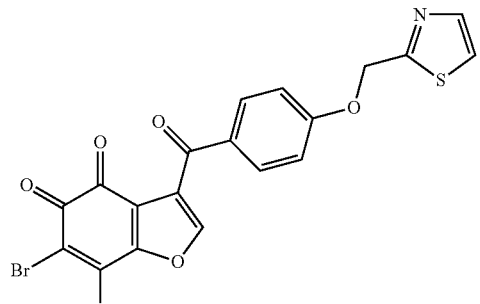
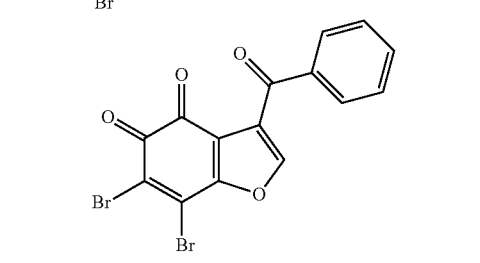
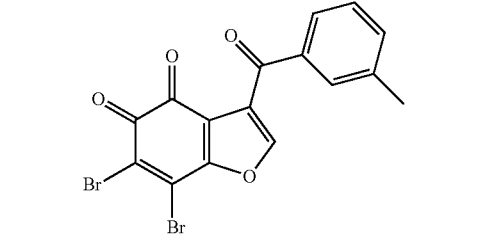
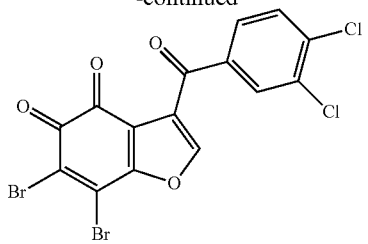
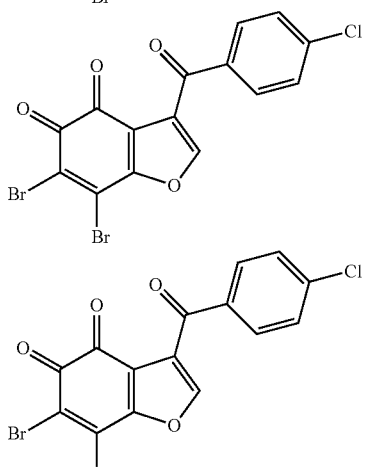
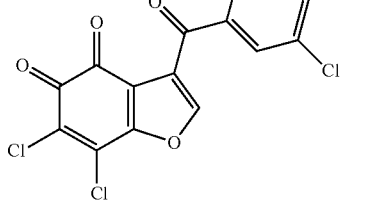
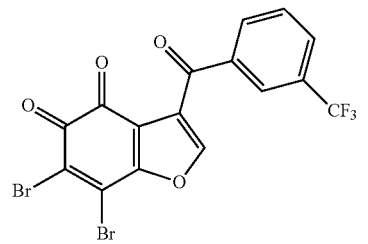
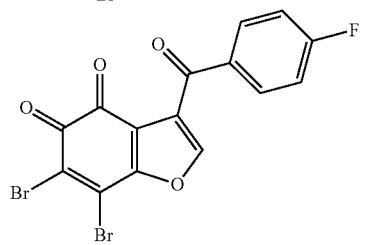
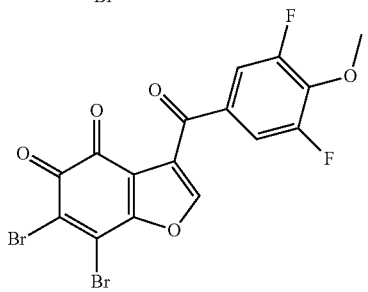

99
-continued
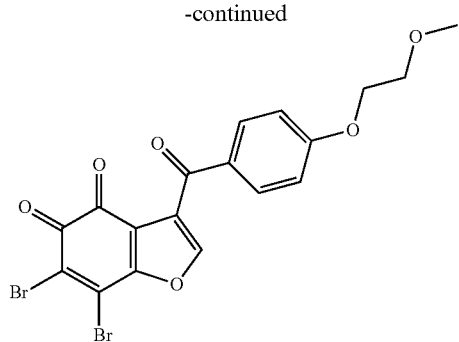
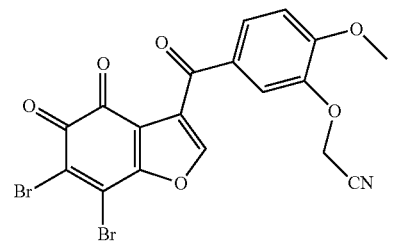
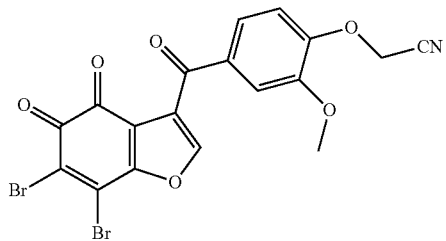
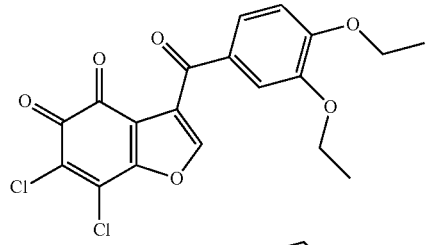
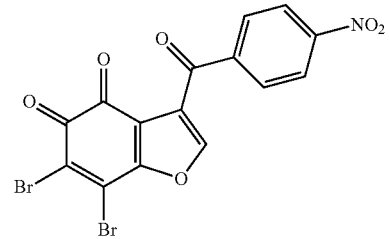
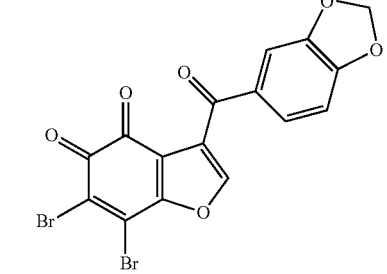
100
-continued
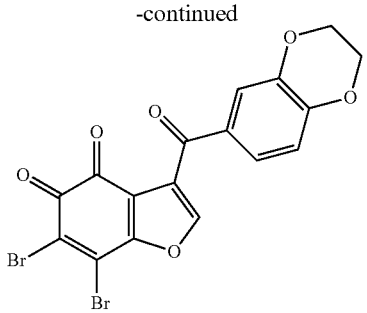
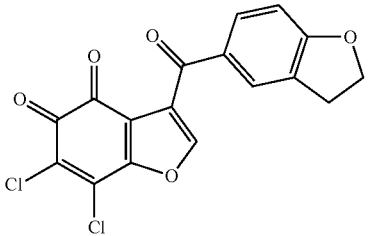
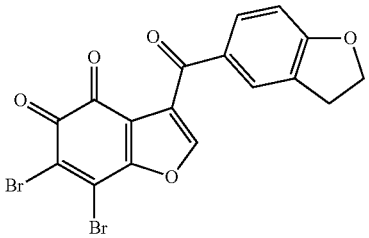
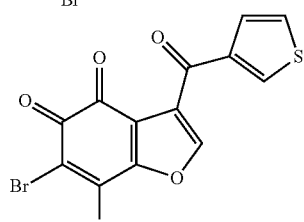
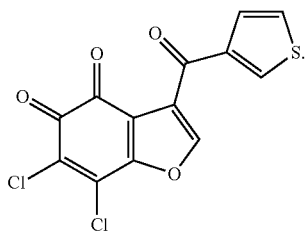 [SMILES: O=C1C(=O)c2c(C(=O)c3ccsc3)coc2C(Cl)=C1Cl]
In certain embodiments, the benzofuran-4,5-dione is
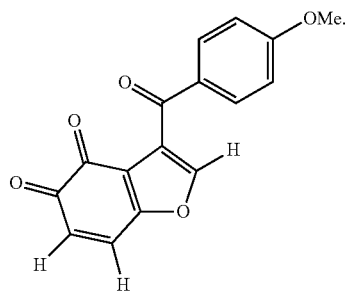

In certain embodiments, the benzofuran-4,5-dione is

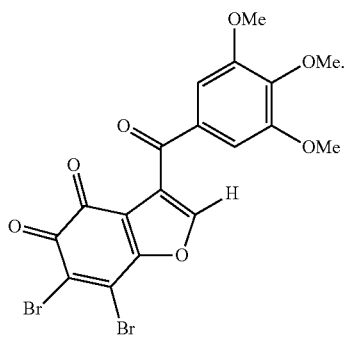

In one embodiment, the amount of a benzofuran-4,5-dione and the other anticancer agent is at least about 0.01% of the combined combination chemotherapy agents by weight of the composition. When intended for oral administration, this amount can be varied from about 0.1% to about 80% by weight of the composition. Some oral compositions can comprise from about 4% to about 50% of combined amount of a benzofuran-4,5-dione and the other anticancer agent by weight of the composition. Other compositions of the present invention are prepared so that a parenteral dosage unit contains from about 0.01% to about 2% by weight of the composition.

Cancers that can be treated or prevented by administering a benzofuran-4,5-dione and the other anticancer agent include, but are not limited to, bone cancer, brain cancer, blood cancer, breast cancer, pancreatic cancer, lung cancer, kidney cancer, stomach cancer, ovarian cancer, prostate cancer, colorectal cancer, endometrial cancer, bladder cancer, non-Hodgkin lymphoma, leukemia, neuroblastoma, lymphomas, rhabdomysosarcoma, Wilms' tumor, osteosarcoma, and Ewing's sarcoma.

Exemplary cancers of the blood, bone, or lymph nodes that can be treated or prevented by administering a benzofuran-4,5-dione and the other anticancer agent include leukemia (e.g., acute lymphoblastic leukemia, acute myelogenous leukemia, chronic myelogenous leukemia, chronic lymphocytic leukemia, and hairy cell leukemia), lymphoma (e.g., a type of Hodgkin's disease or a type of non-Hodgkin lymphoma) or multiple myeloma.

Exemplary other proliferative disorders that can be treated or prevented by administering a benzofuran-4,5-dione and the other anticancer agent is myeloplastic syndrome or a myeloproliferative disease (e.g., polycythemia vera, essential thrombocytosis, myelofibrosis), or amyloidosis.

The benzofuran-4,5-dione and other anticancer agent can act additively or synergistically. A synergistic combination of a benzofuran-4,5-dione and the other anticancer agent, might allow the use of lower dosages of one or both of these agents and/or less frequent administration of the agents to a subject with cancer. The ability to utilize lower dosages of one or both of the benzofuran-4,5-dione and other anticancer agent and/or to administer the agents less frequently can reduce any toxicity associated with the administration of the agents to a subject without reducing the efficacy of the agents in the treatment of cancer. In addition, a synergistic effect might result in the improved efficacy of these agents in the treatment of cancer and/or the reduction of any adverse or unwanted side effects associated with the use of either agent alone. In some embodiments, the administration of an effective amount of a benzofuran-4,5-dione and an effective amount of another anticancer agent inhibits the resistance of a cancer to the other anticancer agent. In one embodiment, the cancer is a tumor.

Suitable other anticancer agents useful in the methods and compositions of the present invention include, but are not limited to temozolomide, a topoisomerase I inhibitor, procarbazine, dacarbazine, gemcitabine, capecitabine, methotrexate, taxol, taxotere, mercaptopurine, thioguanine, hydroxyurea, cytarabine, cyclophosphamide, ifosfamide, nitrosoureas, cisplatin, carboplatin, mitomycin, dacarbazine, procarbizine, etoposide, teniposide, campathecins, bleomycin, doxorubicin, idarubicin, daunorubicin, dactinomycin, plicamycin, mitoxantrone, L-asparaginase, doxorubicin, epirubicin, 5-fluorouracil, taxanes such as docetaxel and paclitaxel, leucovorin, levamisole, irinotecan, estramustine, etoposide, nitrogen mustards, BCNU, nitrosoureas such as carmustine and lomustine, vinca alkaloids such as vinblastine, vincristine and vinorelbine, platinum complexes such as cisplatin, carboplatin and oxaliplatin, imatinib mesylate, hexamethylmelamine, topotecan, tyrosine kinase inhibitors, tyrphostins herbimycin A, genistein, erbstatin, and lavendustin A.

Other additional anticancer agents that are useful in the compositions and methods of the present invention include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefmgol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine hydrochloride; hydroxyurea; idarubicin hydrochloride; ifosfamide; ilmofosine; interleukin-2 (including recombinant interleukin-2, or rIL2), interferon alfa-2α; interferon alfa-2β; interferon alfa-n1; interferon alfa-n3; interferon beta-Iα; interferon gamma-Iβ; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamyciii; plomestane; porfimer sodium; porfiromycin; prednimustine; procarbazine hydrochloride; puromycin; puromycin hydrochloride; pyrazofurin; riboprine; rogletimide; safingol; safingol hydrochloride;

semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Further anticancer drugs that are useful in the methods and compositions of the invention include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta Lactam Derivatives; beta-alethine; betaclamycin B; betulinic acid; bFGF inhibitor; bicalutamide; bisantrene; bisaziridinylspermme; bisnafide; bistratene A; bizelesin; breflate; bropirimine; budotitane; buthionine sulfoximine; calcipotriol; calphostin C; camptothecin derivatives; canarypox IL-2; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin Analogue; conagenin; crambescidin 816; crisnatol; cryptoliycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemniii B; didox; diethylnorspermine; dihydro-5-acytidine; dihydrotaxol; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine Analogue; lipophilic disaccharide peptide; lipophilic platinum complexes; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin Analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drag resistance gene inhibitor; multiple tumor suppressor 1-based. therapy; mustard anticancer agents; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel Analogues; paclitaxel derivatives; palauamiiie; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum complexes; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone Bl; raboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfm; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurirt; tirapazamine; titanocene bichloride; topsentin;

toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; ver amine; verdins; verteporfm; vinorelbine; vinxaltine; vitaxin; vorozole; zanoterone; zeniplatin; zilascorb; and zinostatin stimalamer.

In another embodiment, the other anticancer agent is interferon-α. In another embodiment, the other anticancer agent is interleukin-2. In one embodiment, the other anticancer agent is an alkylating agent, such as a nitrogen mustard, a nitrosourea, an alkylsulfonate, a triazene, or a platinum-containing agent. In one embodiment, the other anticancer agent is a triazene alkylating agent. In one embodiment, the other anticancer agent is O-6-benzylguanine. In another embodiment, the other anticancer agent is O-6-benzylguanine and temozolomide. In another embodiment, the other anticancer agent is O-6-benzylguanineand procarbazine. In still another embodiment, the other anticancer agent is O-6-benzylguanine and dacarbazine.

The benzofuran-4,5-diones can be administered to a subject that has undergone or is currently undergoing one or more additional anticancer therapies including, but not limited to, surgery, radiation therapy, or immunotherapy, such as cancer vaccines.

In some embodiments, the invention provides methods for treating or preventing cancer comprising administering to a subject in need thereof an effective amount of a benzofuran-4,5-dione to treat or prevent cancer and another anticancer therapy including, but not limited to, surgery, radiation therapy, or immunotherapy, such as a cancer vaccine.

In some embodiments, the other anticancer therapy is radiation therapy. In another embodiment, the other anticancer therapy is surgery. In still another embodiment, the other anticancer therapy is immunotherapy.

In some embodiments, the present methods for treating or preventing cancer comprise administering an effective amount of a benzofuran-4,5-dione and radiation therapy. The radiation therapy can be administered concurrently with, prior to, or subsequent to the benzofuran-4,5-dione. In some embodiments, the radiation therapy can be administered at least an hour, five hours, 12 hours, a day, a week, a month, in another embodiment several months (e.g., up to three months), prior or subsequent to administration of the benzofuran-4,5-dione. Where the other anticancer therapy is radiation therapy, any radiation therapy protocol can be administered depending upon the type of cancer to be treated.

Compounds and/or pharmaceutical compositions of the invention may be used to treat an infectious disease. In certain embodiments, treatment of an infectious disease comprises inhibiting the growth of a microorganism such as a fungus, protozoa, virus, bacteria (Gram-positive or Gram-negative), or parasite.

Exemplary bacterial diseases which may be treated using the above-described methods of treatment include, but are not limited to, actinomycosis; acute prostatitis; *Aeromonas hydrophila*; annual ryegrass toxicity; Anthrax; Bacteremia; Bacterial meningitis; Bacterial pneumonia; Brazilian purpuric fever; Brodie's abscess; Bubonic plague; Brucellosis; *Burkholderia* cepacia complex; Buruli ulcer; Campylobacteriosis; *Capnocytophaga* canimorsus; Caries; Carrion's disease; chlamydia; cholera; diphtheria; Diphtheritic stomatitis; Donovanosis; Erythema migrans; Fitz-Hugh-Curtis syndrome; Fournier gangrene; Group A streptococcal infection; Human granulocytic ehrlichiosis; Impetigo; Late congenital syphilis; Late congenital syphilitic oculopathy; *Legionella*; Lemierre's syndrome; Leprosy; Leptospirosis; Listeriosis; Ludwig's angina; Lyme disease; Melioidosis; Meningococcemia; Methicillin-resistant *Staphylococcus aureus*; Miliary tuberculosis; *Mycobacterium; Mycobacterium avium* complex; Necrotizing fasciitis; Nontuberculous mycobacteria; Omphalitis; Orbital cellulitis; Osteomyelitis; Paratyphoid fever; *Pasteurella multocida*; Periorbital cellulitis; Peritonsillar abscess; Pertussis; Pott's disease; Pseudomembranous colitis; Psittacosis; Pyomyositis; Q fever; Rheumatic fever; *Rickettsia prowazekii*; Rickettsialpox; Salmonellosis; Scarlet fever; Scrub typhus; Spondylitis; Staphylococcal infection; Strep throat; Syphilis; Syphilitic aortitis; Tetanus; Tuberculosis; Tularemia; Typhoid fever; Typhus.

Exemplary viral diseases which may be treated using the above-described methods of treatment include, but are not limited to, Acquired Immunodeficiency Syndrome; Adenoviridae Infections; Alphavirus Infections; Arbovirus Infections; Borna Disease; Bunyaviridae Infections; Caliciviridae Infections; Chickenpox; Condyloma Acuminata; Coronaviridae Infections; Coxsackievirus Infections; Cytomegalovirus Infections; Dengue; DNA Virus Infections; Eethyma; Encephalitis; Arbovirus; Epstein-Barr Virus Infections; Erythema Infectiosum; Hantavirus Infections; Hemorrhagic Fevers; Hepatitis; Herpes; Herpesviridae Infections; Infectious Mononucleosis; Influenza in birds; Influenza in humans; Lassa Fever; Measles; Molluscum Contagiosum; Mumps; Paramyxoviridae Infections; Phlebotomus Fever; Polyomavirus Infections; Rabies; Respiratory Syncytial Virus Infections; Rift Valley Fever; RNA Virus Infections; Rubella; Slow Virus Diseases; Smallpox; Subacute Sclerosing Panencephalitis; Tumor Virus Infections; Warts; West Nile Fever; Yellow Fever.

Exemplary parasitic diseases which may be treated using the above-described methods of treatment include, but are not limited to, Amebiasis; Anisakiasis; *Ascariasis*; Babesiosis; Blastocystis hominis infections; Cestode Infections; Chagas Disease; Cryptosporidiosis; Cyclosporiasis; Cysticercosis; Dientamoebiasis; Diphyllobothriasis; Dracunculiasis; Echinococcosis; Ectoparasitic Infestations; Filariasis; Giardiasis; Helminthiasis; Hookworm Infections; Intestinal Diseases, Parasitic; Larva Migrans; Leishmaniasis; Lice Infestations; Loiasis; Malaria; Mite Infestations; Myiasis; Neurocysticercosis; Onchocerciasis; Protozoan Infections; Scabies; Schistosomiasis; Skin Diseases, Parasitic; Strongyloidiasis; Taeniasis; Toxocariasis; Toxoplasmosis; Trichinosis; Trichomonas Infections; Trypanosomiasis; Whipworm Infections Exemplary inflammatory diseases which may be treated using the above-described methods of treatment include, but are not limited to, rheumatoid arthritis, osteoarthritis inflammatory lung disease, inflammatory bowel disease, atherosclerosis and psoriasis. In certain embodiments, the inflammatory disease is an autoimmune disease.

In certain embodiments, compounds and/or pharmaceutical compositions of the invention may be administered via an infusion. The time of infusion ranges from approximately 1 minute to approximately 120 minutes. In some embodiments, the time of infusion ranges from approximately 1 minute to approximately 90 minutes. In some embodiments, the time of infusion ranges from approximately 1 minute to approximately 60 minutes. In some embodiments, the time of infusion ranges from approximately 5 minutes to approximately 45 minutes. In some embodiments, the time of infusion ranges from approximately 15 minutes to approximately 45 minutes. In some embodiments, the time of infusion is approximately 30 minutes. In certain embodiments, the treatment is repeated at least two times. In certain embodiments, the treatment is repeated at least three times. In certain embodiments, the treatment is repeated at least four times. In certain embodiments, the treatment is repeated 2, 3, 4, 5, 6, 7, 8, 9, 10 times. In some embodiments, the treatment is repeated upon recurrence of the disease. In certain embodiments, the treatment is repeated at least once a day. In certain embodiments, the treatment is repeated at least once every other day. In certain embodiments, the treatment is repeated at least once a week. In certain embodiments, the treatment is repeated at least twice a week. In certain embodiments, the treatment is repeated at least once a month. In certain embodiments, the treatment is repeated at least twice a month. In certain embodiments, the treatment is repeated at least three or four times a month. In certain embodiments, the treatment is repeated at least 1, 2, 3, 4, 5, 6, 7, 8, 9, or 10 times a month for as many months as necessary to achieve a desired outcome.

In certain embodiments, the compound of the invention may be administered at dosage levels of approximately 0.001 mg/kg to approximately 50 mg/kg, from approximately 0.01 mg/kg to approximately 25 mg/kg, or from approximately 0.1 mg/kg to approximately 10 mg/kg of subject body weight per day, one or more times a day, to obtain the desired therapeutic effect. It will also be appreciated that dosages smaller than approximately 0.001 mg/kg or greater than approximately 50 mg/kg can be administered to a subject.

The efficacy of the inventive treatment may be evaluated using any method known in the art. The treatment of the disease may be evaluated by physical examination, laboratory testing, imaging studies, etc. In some embodiments, the efficacy of the inventive treatment is evaluated using any combination of methods known in the medical arts.

Pharmaceutical Compositions

In another aspect, the present invention provides pharmaceutical compositions comprising a benzofuran-4,5-dione, or a pharmaceutically acceptable form thereof, and a pharmaceutically acceptable excipient. In certain embodiments, a therapeutically effective amount of a benzofuran-4,5-dione for the treatment of a proliferative, infectious, or inflammatory disease or condition is included in the pharmaceutical composition. In certain embodiments, a therapeutically effective amount of a benzofuran-4,5-dione for the treatment of cancer is included in the pharmaceutical composition. In certain embodiments, a therapeutically effective amount of a benzofuran-4,5-dione suitable for intravenous administration is included in the pharmaceutical composition.

In certain embodiments, the invention provides pharmaceutical compositions containing benzofuran-4,5-diones of the formula:

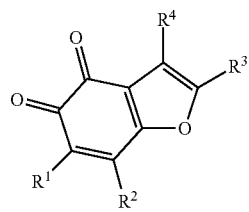

wherein $R^1$, $R^2$, $R^3$, and $R^4$ are as defined herein.

In some embodiments, the pharmaceutical composition may comprise a benzofuran-4,5-dione of any one of the formulae:

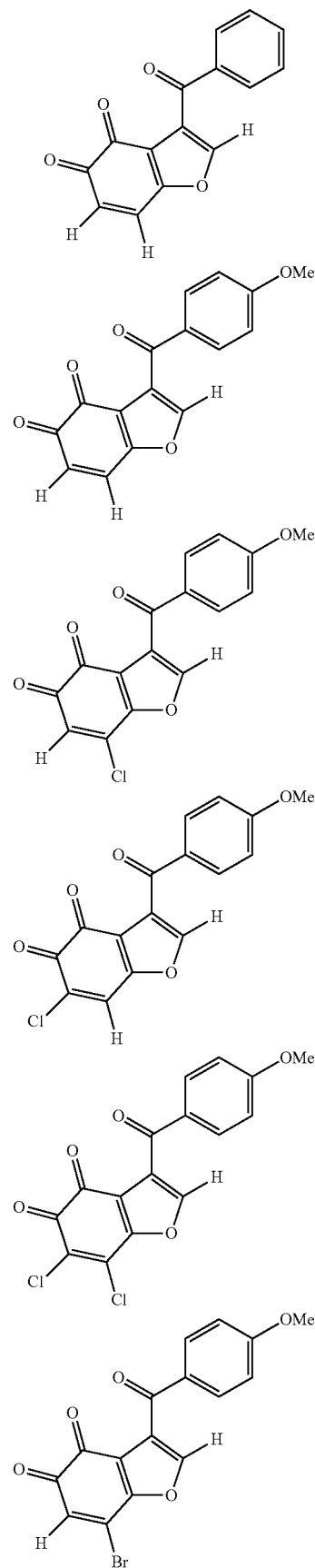 [SMILES: O=C1C=Cc2occ(C(=O)c3ccccc3)c2C1=O ; COc1ccc(C(=O)c2coc3c2C(=O)C(=O)C=C3)cc1 ; COc1ccc(C(=O)c2coc3c2C(=O)C(=O)C=C3Cl)cc1 ; COc1ccc(C(=O)c2coc3c2C(=O)C(=O)C(Cl)=C3)cc1 ; COc1ccc(C(=O)c2coc3c2C(=O)C(=O)C(Cl)=C3Cl)cc1 ; COc1ccc(C(=O)c2coc3c2C(=O)C(=O)C=C3Br)cc1]

-continued
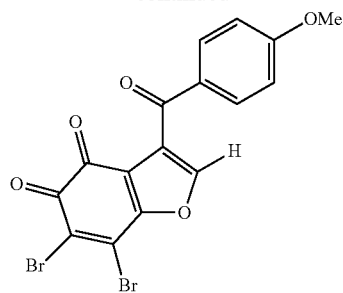
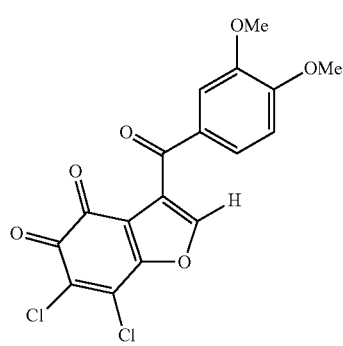
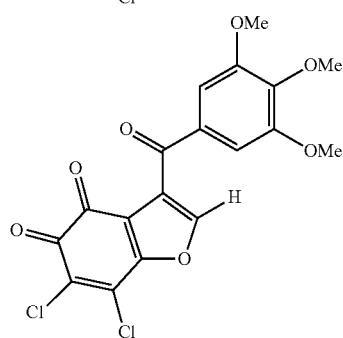
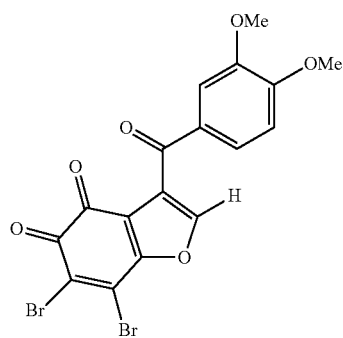
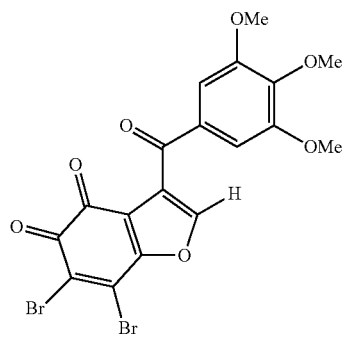 [SMILES: COc1cc(C(=O)c2coc3c2C(=O)C(=O)C(Br)=C3Br)cc(OC)c1OC]
-continued
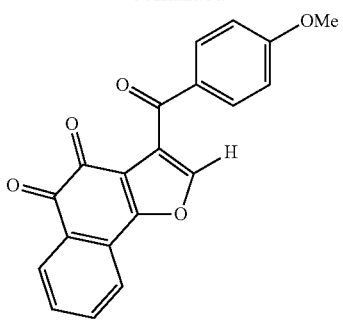
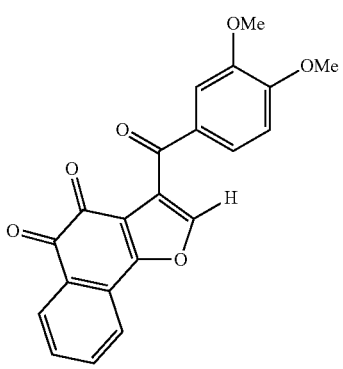
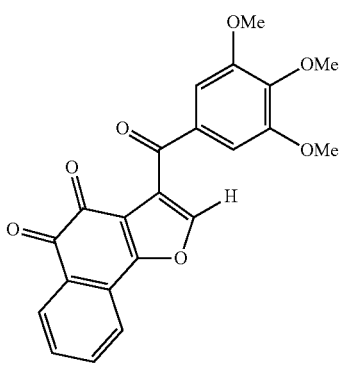
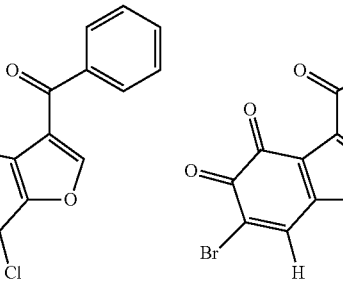
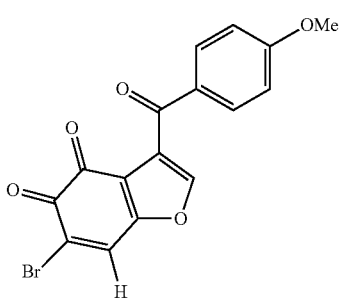

111
-continued
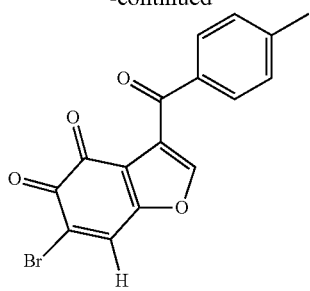
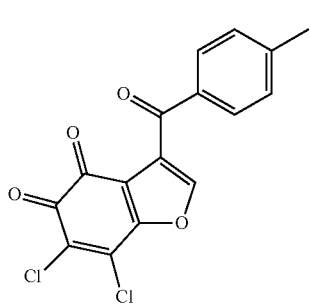
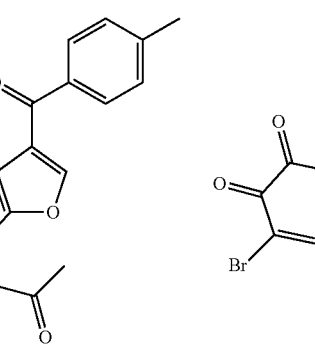
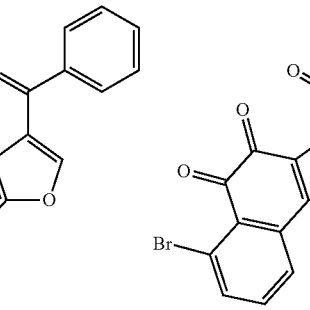
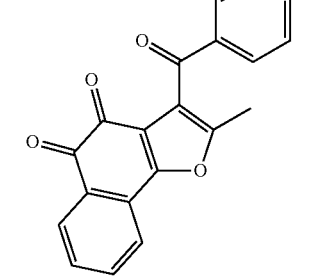
112
-continued
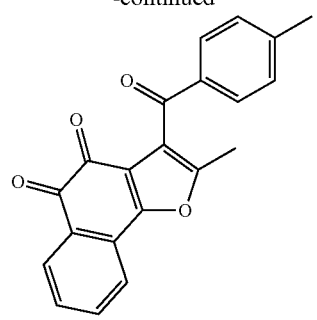
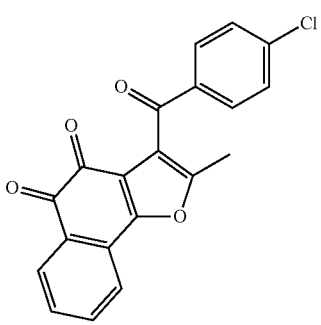
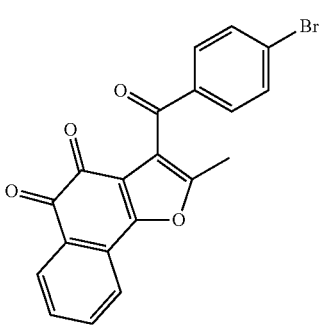
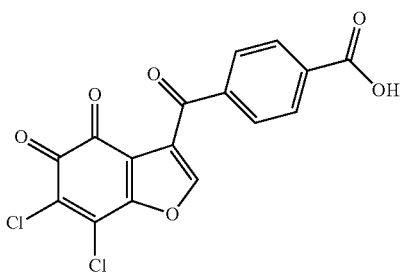
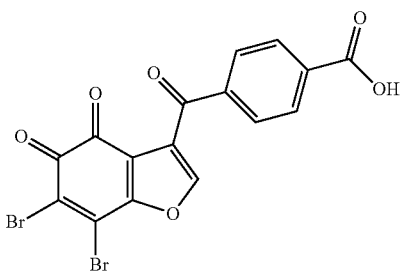

113
-continued
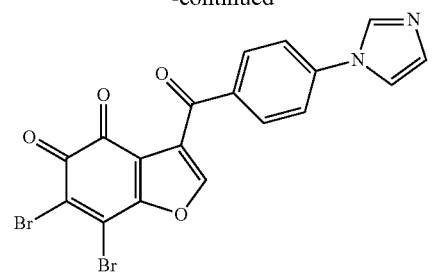
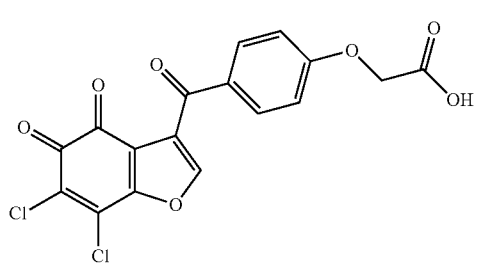
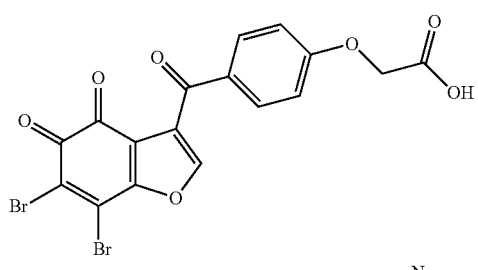
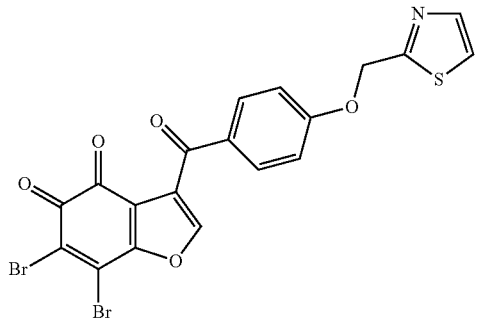
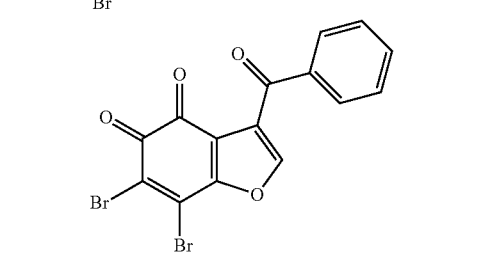
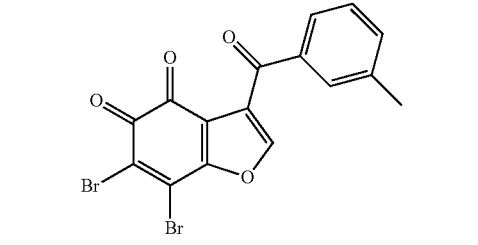
114
-continued
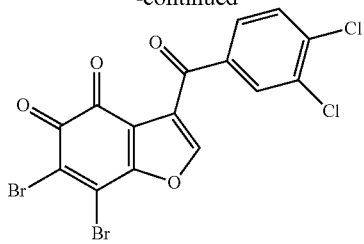
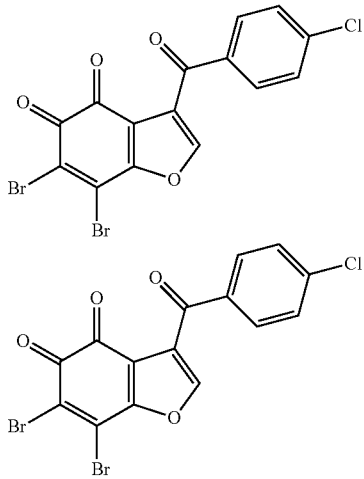
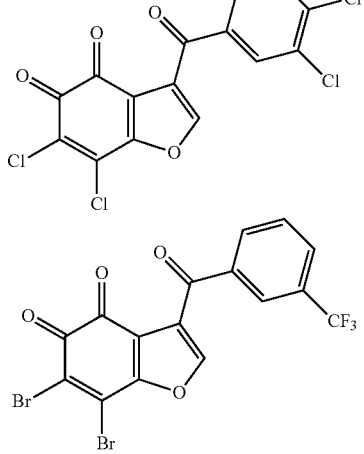
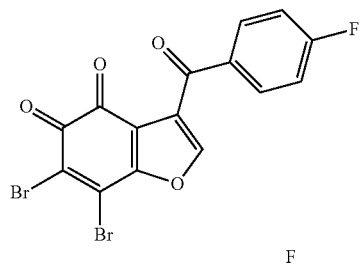
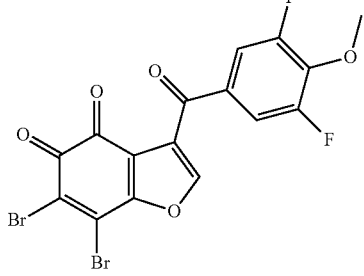

115
-continued
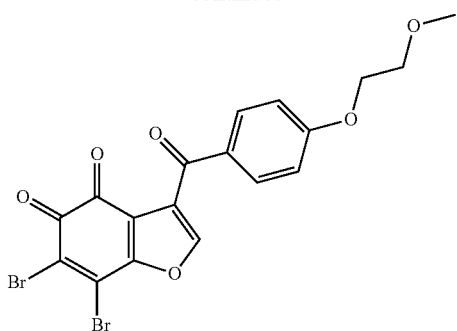
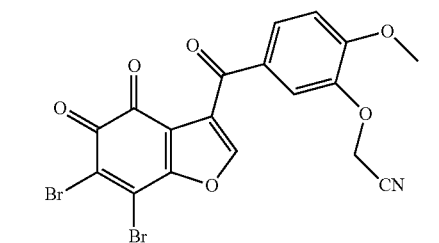
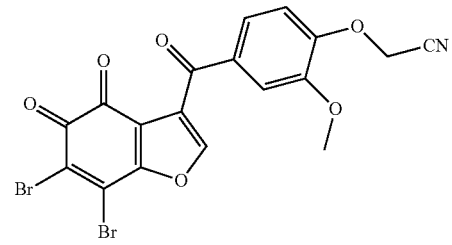
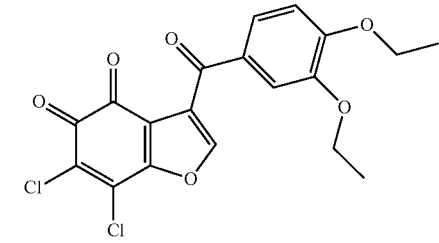
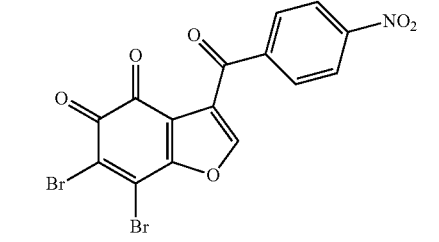
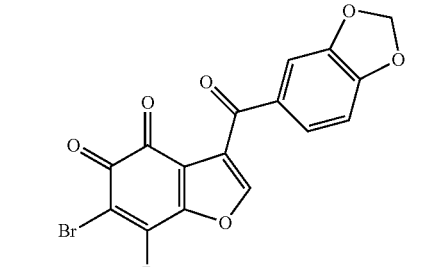
116
-continued
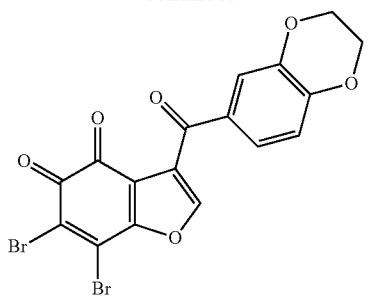
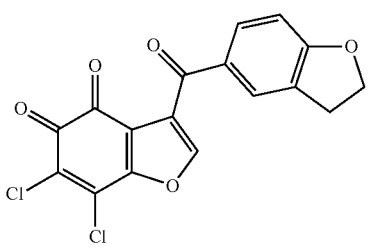
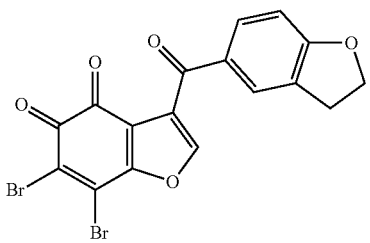
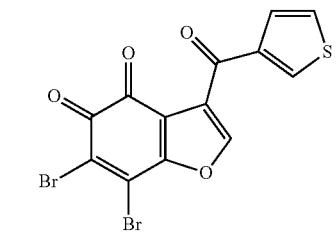
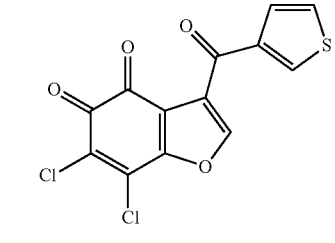 [SMILES: O=C1C(=O)c2c(C(=O)c3ccsc3)coc2C(Cl)=C1Cl]
or a pharmaceutically acceptable salt thereof.
In certain embodiments, the pharmaceutical composition may comprise a benzofuran-4,5-dione of the formula:

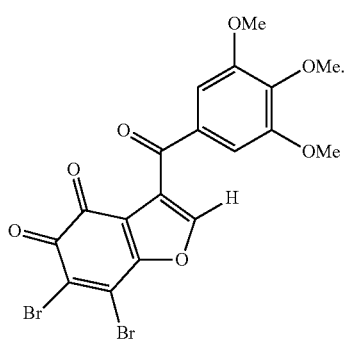

In certain embodiments, the pharmaceutical composition may comprise a benzofuran-4,5-dione of the formula:

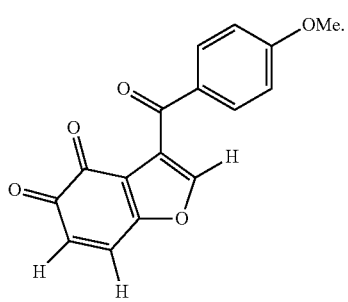 [SMILES: COc1ccc(C(=O)c2coc3c2C(=O)C(=O)C=C3)cc1]

In some embodiments, the pharmaceutical compositions comprising a benzofuran-4,5-dione, or a pharmaceutically acceptable form thereof, and a pharmaceutically acceptable excipient is used for the treatment of a bone cancer, brain cancer, blood cancer, breast cancer, pancreatic cancer, lung cancer, kidney cancer, stomach cancer, ovarian cancer, prostate cancer, colorectal cancer, endometrial cancer, bladder cancer, non-Hodgkin lymphoma, leukemia, neuroblastoma, lymphomas, rhabdomysosarcoma, Wilms' tumor, osteosarcoma, and Ewing's sarcoma.

In some embodiments, the pharmaceutical compositions comprising a benzofuran-4,5-dione, or a pharmaceutically acceptable form thereof, and a pharmaceutically acceptable excipient is used for the treatment of a cancer of the blood, bone, or lymph nodes including, but not limited to, leukemia (e.g., acute lymphoblastic leukemia, acute myelogenous leukemia, chronic myelogenous leukemia, chronic lymphocytic leukemia, and hairy cell leukemia), lymphoma (e.g., a type of Hodgkin's disease or a type of non-Hodgkin lymphoma) or multiple myeloma.

In some embodiments, the pharmaceutical compositions comprising a benzofuran-4,5-dione, or a pharmaceutically acceptable form thereof, and a pharmaceutically acceptable excipient is used for the treatment of a proliferative disorder other than cancer. Exemplary other proliferative disorders include, but are not limited to, myeloplastic syndrome or a myeloproliferative disease (e.g., polycythemia vera, essential thrombocytosis, myelofibrosis), or amyloidosis.

It will also be appreciated that the compound of the instant invention can exist in free form for treatment, or where appropriate, as a pharmaceutically acceptable form thereof. According to the present invention, a pharmaceutically acceptable form includes, but is not limited to, pharmaceutically acceptable salts, esters, salts of such esters, or a prodrug or other adduct or derivative of a compound of the instant invention which upon administration to a subject in need is capable of providing, directly or indirectly, a compound as otherwise described herein, or a metabolite thereof.

As described above, the pharmaceutical compositions of the present invention comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants, and the like, as suited to the particular dosage form desired. *Remington's Pharmaceutical Sciences*, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with a benzofuran-4,5-dione, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose, and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogenfree water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Injectable preparations, for example, sterile injectable aqueous or oleaginous may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland or fixed oil can be employed including synthetic mono- or diglycerides. In addition, fatty acids such as oleic acid are used in the preparation of injectables.

Compounds of the instant invention are preferably formulated in dosage unit form for ease of administration and uniformity of dosage. The expression "dosage unit form" as used herein refers to a physically discrete unit of therapeutic agent appropriate for the subject to be treated. It will be understood, however, that the total daily usage of the compound and/or composition of the present invention will be decided by the attending physician within the scope of sound medical judgment. The specific therapeutically effective dose level for any particular subject or organism will depend upon a variety of factors including the disorder being treated and the severity of the disorder; the activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed; and like factors well known in the medical arts (see, for example, Goodman and Gilman's, *The Pharmacological Basis of Therapeutics*, Tenth Edition, A. Gilman, J. Hardman and L. Limbird, eds., McGraw-Hill Press, 155-173, 2001, which is incorporated herein by reference in its entirety).

Furthermore, after formulation with an appropriate pharmaceutically acceptable excipient in a desired dosage, the pharmaceutical compositions of this invention can be administered to humans and other animals.

It will also be appreciated that the compound and/or pharmaceutical composition of the present invention can be formulated and employed in combination therapies, that is, the compound and/or pharmaceutical composition can be formulated with or administered concurrently with, prior to, or subsequent to, one or more other desired therapeutic agents. The particular combination of therapies (e.g., chemotherapy, radiation therapy, etc.) to be employed in a combination regimen will take into account compatibility of the desired therapeutics and/or therapies and the desired therapeutic effect to be achieved. It will also be appreciated that the therapies employed may achieve a desired effect for the same disorder (for example, an inventive compound may be administered concurrently with another anticancer agent, or they may achieve different effects (e.g., control of any adverse effects). In certain embodiments, pharmaceutical compositions of the present invention comprise a benzofuran-4,5-dione and any one or more of the chemotherapeutic agents listed herein.

Other therapies or anticancer agents that may be used in combination with an inventive compound include, for example, surgery, radiotherapy (e.g., γ-radiation, neutron beam radiotherapy, electron beam radiotherapy, proton therapy, brachytherapy, and systemic radioactive isotopes, etc.), endocrine therapy, biologic response modifiers (e.g., interferons, interleukins, and tumor necrosis factor (TNF)), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. For a more comprehensive discussion of updated cancer therapies see, *The Merck Manual*, Seventeenth Ed. 1999, the entire contents of which are hereby incorporated by reference. See also the National Cancer Institute (CNI) website (www.nci.nih.gov) and the Food and Drug Administration (FDA) website for a list of the FDA approved oncology drugs (www.fda.gov/cder/cancer/druglistframe).

In certain embodiments, the pharmaceutical composition of the present invention further comprises one or more additional therapeutic agents (e.g., chemotherapeutic and/or palliative agents). For example, additional therapeutic agents for conjoint administration or inclusion in a pharmaceutical composition with an inventive compound may be an approved chemotherapeutic agent and/or pallative agent, or it may be any one of a number of agents undergoing approval by the Food and Drug Administration. For purposes of the invention, the term "palliative" refers to treatment that is focused on the relief of symptoms of a disease and/or side effects of a therapeutic regimen, but is not curative. For example, palliative treatment encompasses painkillers and antinausea medications. In addition, chemotherapy, radiotherapy, and surgery can all be used palliatively (that is, to reduce symptoms without going for cure; e.g., for shrinking tumors and reducing pressure, bleeding, pain, and/or other symptoms or signs of cancer).

EXAMPLES

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that, unless otherwise indicated, the entire contents of each of the references cited herein are incorporated herein by reference to help illustrate the state of the art. The following examples contain important additional information, exemplification and guidance which can be adapted to the practice of this invention in its various embodiments and the equivalents thereof.

Example 1

Identification of Benzofuran-4,5-Diones as Novel and Selective HsPDF Inhibitors

Figure 2:
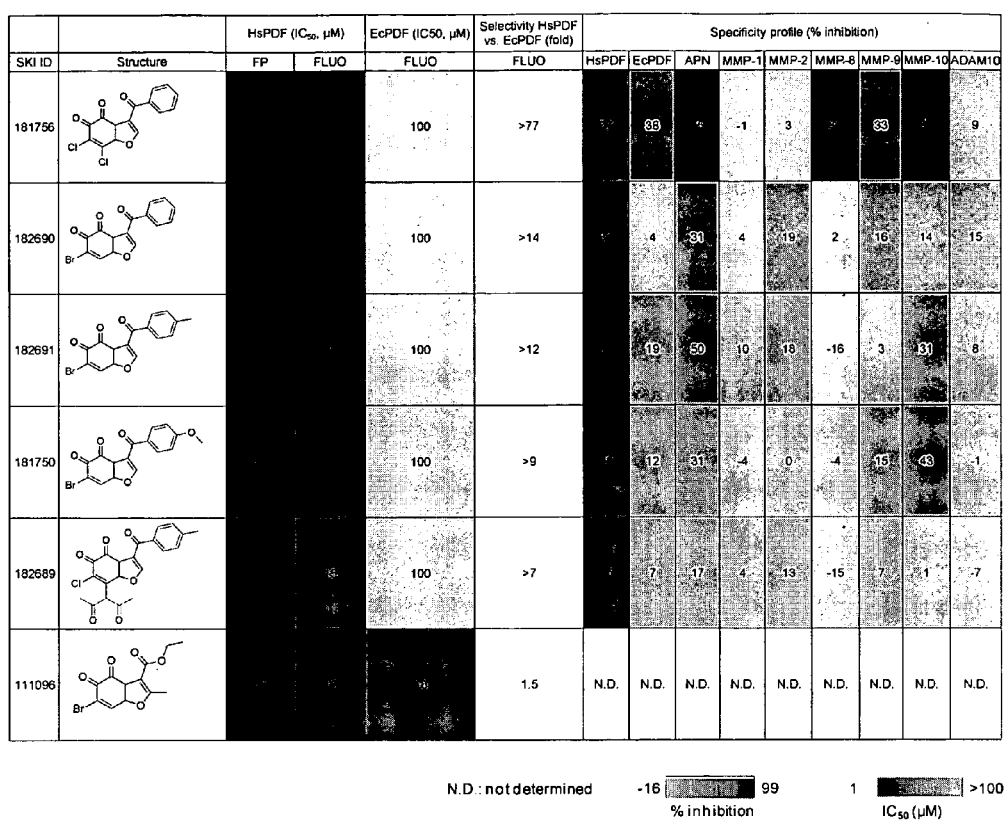
FIG. 2. Cytotoxicity profile of the six primary hits from high-throughput screening with a benzofuran-4,5-dione scaffold.
Figure 3:
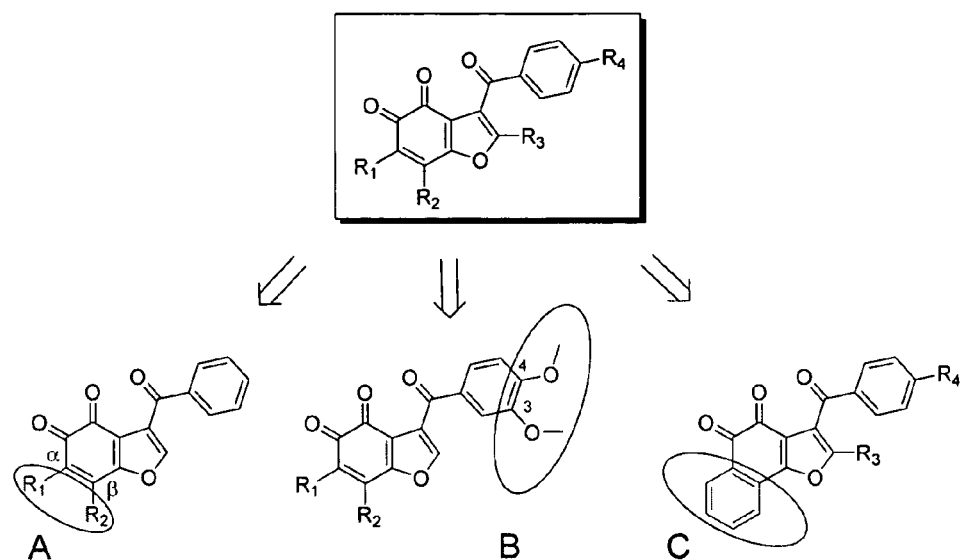
FIG. 3. Design of benzofuran-4,5-dione derivatives. A. Halogen substitutions at α- and β-positions on the 4,5-orthodione moiety. B. Effect of methoxy substituents at −2, −3 and −4 positions on the benzoyl moiety. C. Replacement of the benzofurandione moiety by a naphtofurandione moiety.

To identify novel HsPDF inhibitors, a high-throughput screening campaign was performed using a new fluorescence polarization (FP) binding assay developed previously (Antczak et al., *J. Biomol. Screen* 2007, 12:5, 21-35) (Example 6). Six primary hits belonging to the benzofuran-4,5-dione scaffold were identified (FIG. 1). For the purpose of characterizing those hits, dose response and specificity profiles were assessed using the previously described FP profiling method (Antczak et al., *J. Biomol. Screen* 2008, 13, 285-294) in addition to a functional assay based on fluorescamine previously adapted for HsPDF (Antczak et al., *J. Biomol. Screen* 2007, 12:5, 21-35 (Example 6). The specificity profile data for the six primary hits belonging to the benzofuran-4,5-dione scaffold is summarized in FIG. 2. Identified herein are the first HsPDF inhibitors selective for HsPDF over EcPDF with a selectivity of up to greater than 77 fold in the functional assay (FLUO). Most of the newly identified HsPDF inhibitors have good selectivity for HsPDF over other metalloproteases. The cytotoxicity profiling for those six primary hits was performed in a panel of seven cancer cell lines (Example 6). A heat map summarizes the calculated $IC_{50}$s (FIG. 3). Most of the newly identified HsPDF inhibitors have broad cytotoxic activity toward this panel of cancer cell lines.

Example 2

Exploratory Chemistry of Benzofuran-4,5-Diones and Methods for the Chemical Synthesis of the 33 New Derivatives of Benzofuran-4,5-Diones Exploratory chemistry efforts to establish basic structure activity relationships (SAR) for benzofuran-4,5-diones were initiated. During the design of the first round of derivatives, three types of modifications were explored for key features on this scaffold (Scheme 3):

(a) Halogen substitutions at α- and β-positions on the 4,5-orthodione moiety;
(b) Effect of methoxy substituents at −2, −3 and −4 positions on the benzoyl moiety; and
(c) Replacement of the benzofurandione moiety by a naphthofurandione moiety.

Scheme 3. Modifications A, B, and C.

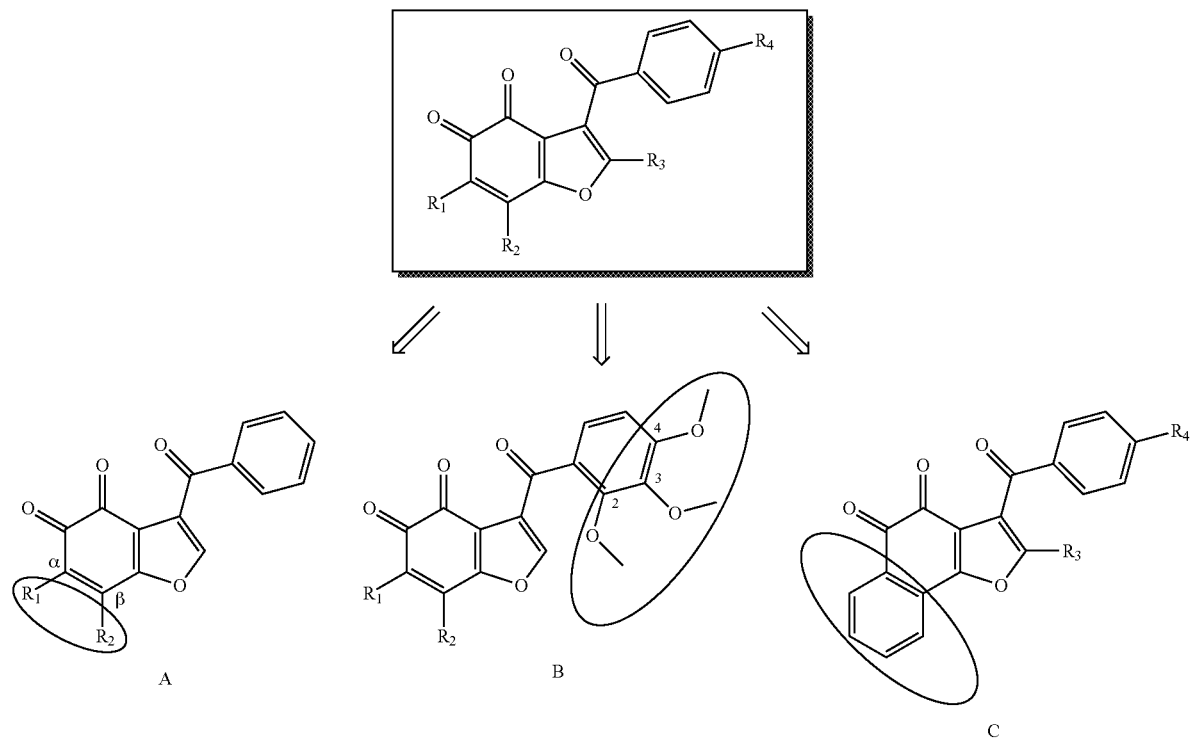

A series of 16 new derivatives (Table 1) were designed and synthesized for SAR studies. Seventeen intermediates of synthesis were also included in these studies, for a total of 33 compounds (Table 2). Synthetic routes for the 33 new derivatives of benzofuran-4,5-diones are described below.

TABLE 1

Sixteen benzofuran-4,5-dione derivatives were synthesized for SAR studies.

A modifications

SKC-BF-01

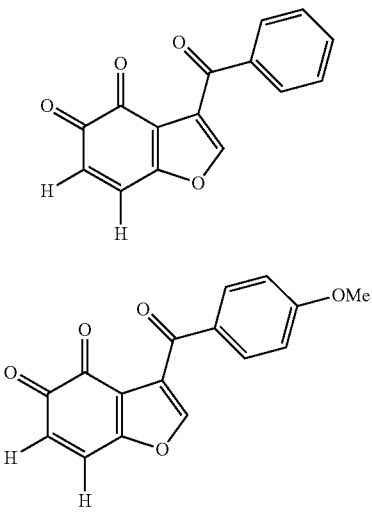

SKC-BF-02

TABLE 1-continued

Sixteen benzofuran-4,5-dione derivatives were synthesized for SAR studies.

SKC-BF-03

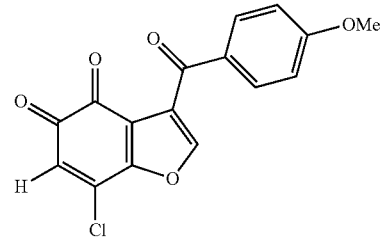 [SMILES: COc1ccc(C(=O)c2coc3c2C(=O)C(=O)C=C3Cl)cc1]

SKC-BF-04

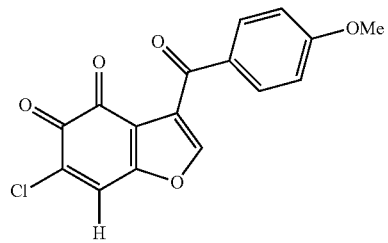 [SMILES: COc1ccc(C(=O)c2coc3c2C(=O)C(=O)C(Cl)=C3)cc1]

SKC-BF-05

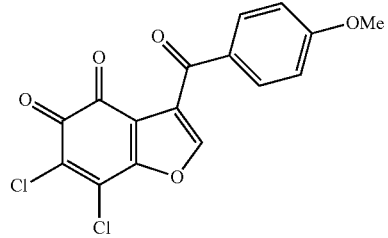 [SMILES: COc1ccc(C(=O)c2coc3c2C(=O)C(=O)C(Cl)=C3Cl)cc1]

TABLE 1-continued
Sixteen benzofuran-4,5-dione derivatives were synthesized for SAR studies.
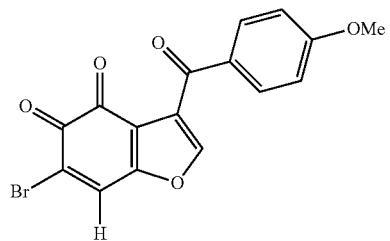
SKC-BF-06
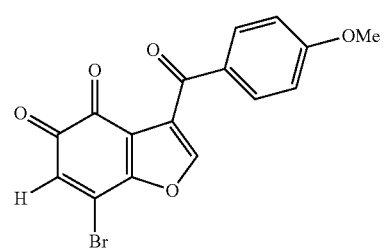 [SMILES: COc1ccc(C(=O)c2coc3c2C(=O)C(=O)C=C3Br)cc1]
SKC-BF-07
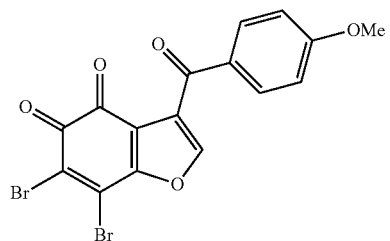
SKC-BF-08
A + B modifications
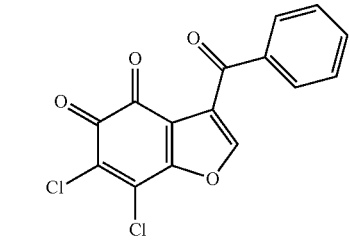 [SMILES: O=C1C(=O)c2c(C(=O)c3ccccc3)coc2C(Cl)=C1Cl]
SKC-BF-09
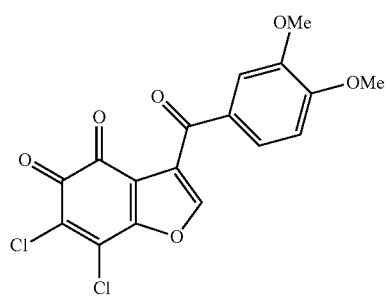
SKC-BF-10
TABLE 1-continued
Sixteen benzofuran-4,5-dione derivatives were synthesized for SAR studies.
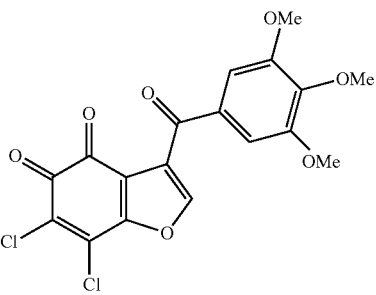
SKC-BF-11
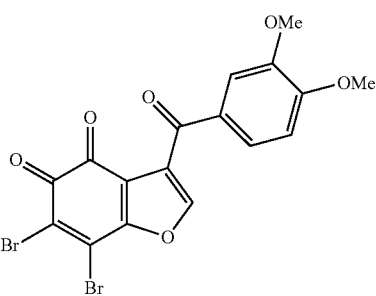 [SMILES: COc1ccc(C(=O)c2coc3c2C(=O)C(=O)C(Cl)=C3Cl)cc1OC]
SKC-BF-12
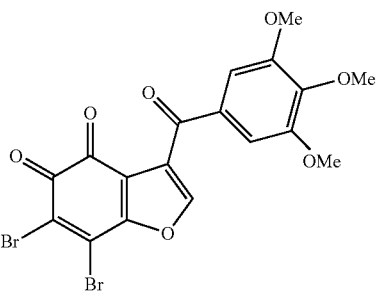 [SMILES: COc1cc(C(=O)c2coc3c2C(=O)C(=O)C(Cl)=C3Cl)cc(OC)c1OC]
SKC-BF-13
B + C modification
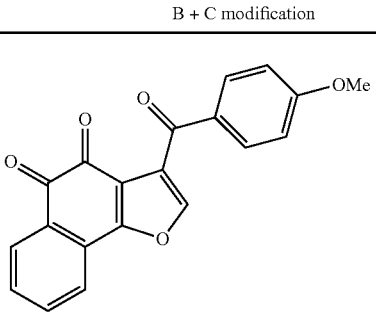
SKC-NF-01
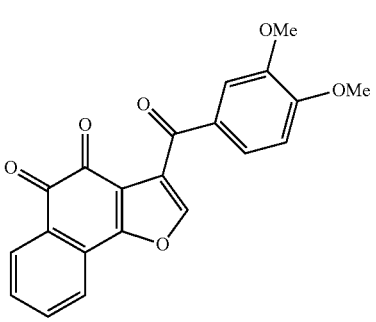 [SMILES: COc1ccc(C(=O)c2coc3c2C(=O)C(=O)c2ccccc2-3)cc1OC]
SKC-NF-02

TABLE 1-continued

Sixteen benzofuran-4,5-dione derivatives were synthesized for SAR studies.

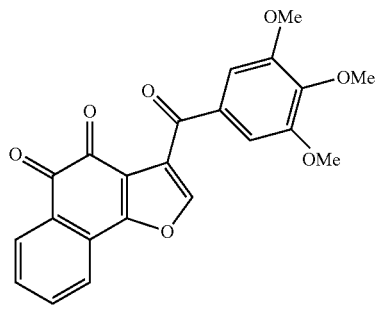 [SMILES: COc1cc(C(=O)c2coc3c2C(=O)C(=O)c2ccccc2-3)cc(OC)c1OC]

SKC-NF-03

TABLE 2

Synthetic intermediates screened in the first round of exploratory chemistry.

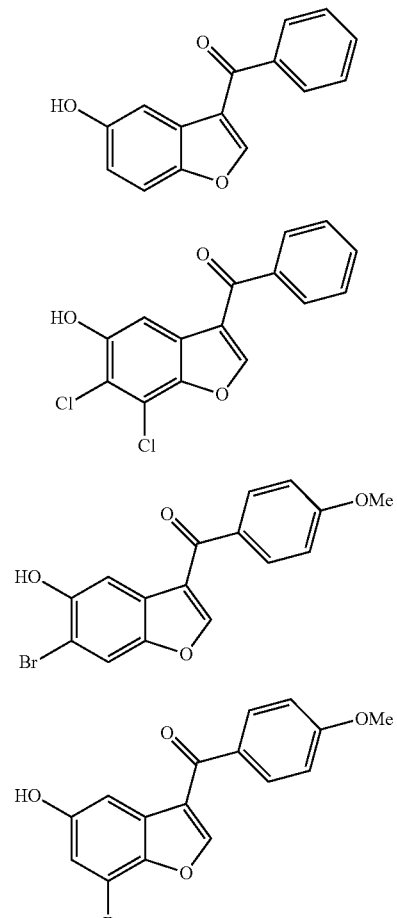

SKC-BF-Int3

SKC-BF-Int4

SKC-BF-Int7A

SKC-BF-Int7B

SKC-BF-Int7C

TABLE 2-continued

Synthetic intermediates screened in the first round of exploratory chemistry.

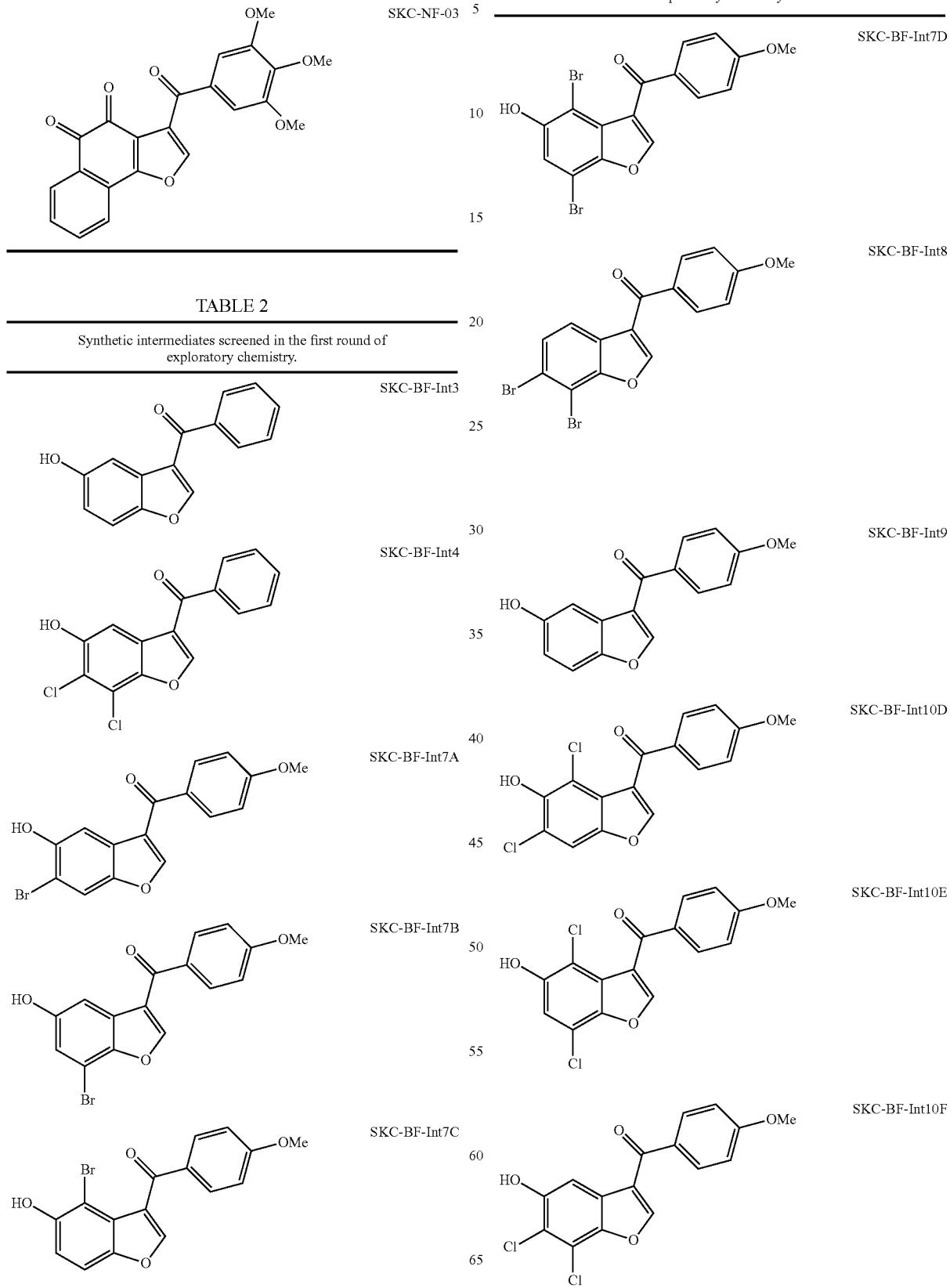

SKC-BF-Int7D

SKC-BF-Int8

SKC-BF-Int9

SKC-BF-Int10D

SKC-BF-Int10E

SKC-BF-Int10F

TABLE 2-continued
Synthetic intermediates screened in the first round of exploratory chemistry.
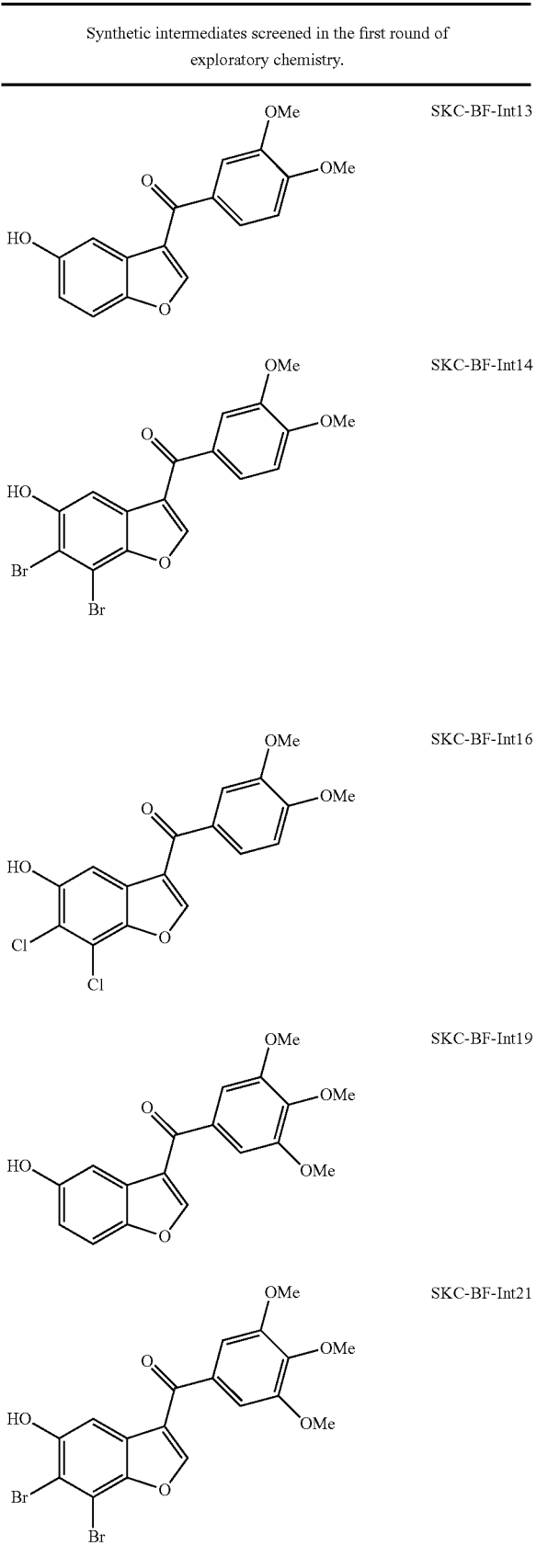
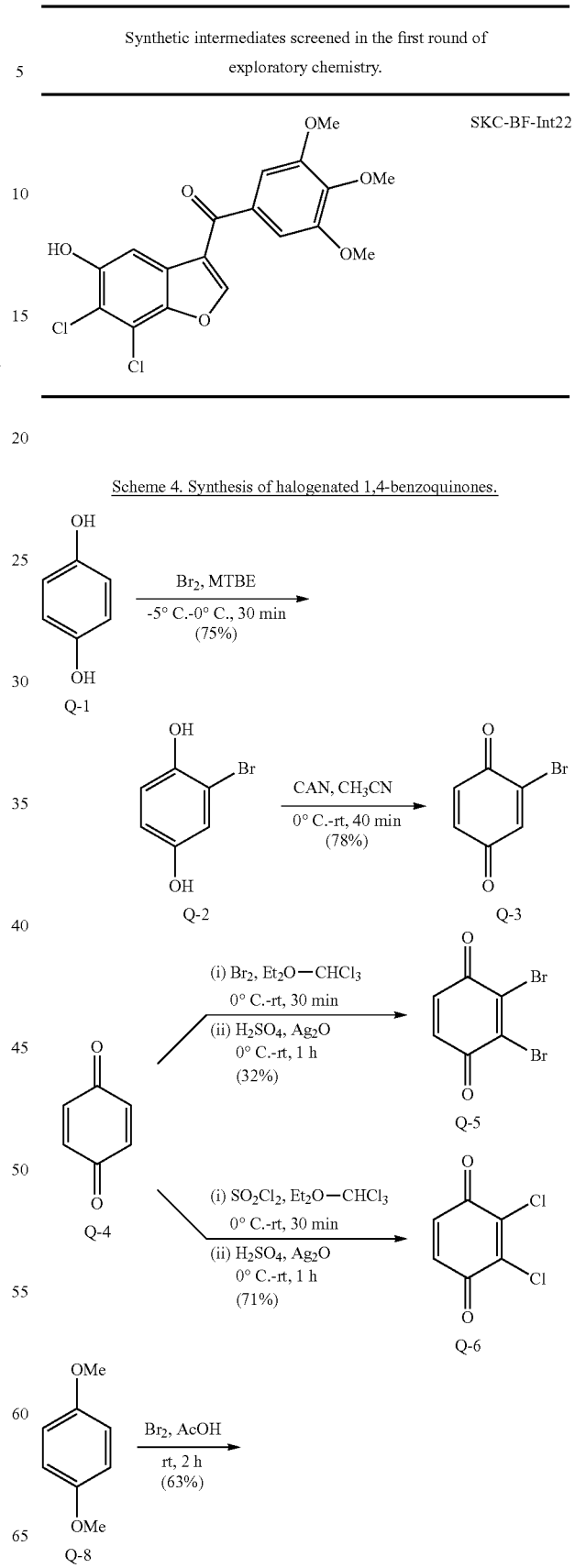

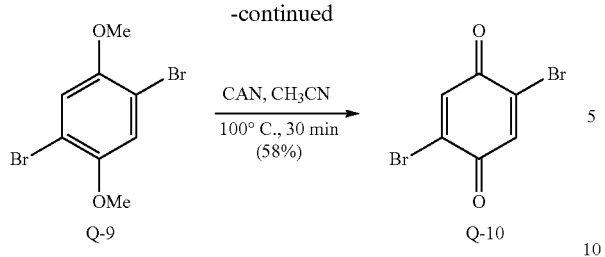

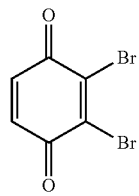

Q-9 → Q-10 (CAN, CH$_3$CN, 100° C., 30 min, 58%)

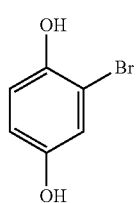

2-Bromo-benzene-1,4-diol (Q-2)

To a solution of hydroquinone Q-1 (10 g, 90.90 mmol) in MTBE (methyl tert-butyl ether) (100 mL) at −5° C. was added bromine (17.4 g, 90.90 mmol). The reaction mixture was stirred at 0° C. for 30 min. Solvent was removed in vacuo and the crude product was purified by column chromatography (SiO$_2$, 2% MeOH—CHCl$_3$) to afford compound Q-2 (13 g, 75%) as a solid. TLC R$_f$=0.6 (CHCl$_3$-MeOH, 9:1); $^1$H NMR (CDCl$_3$) δ 6.94 (app d, 1H), 6.88 (d, J=8.7 Hz, 1H), 6.72 (dd, J=8.7, 2.8 Hz, 1H), 5.19 (s, 2H) (*Synlett* 2000, 11, 1561-1564).

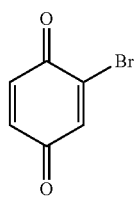

2-Bromo-[1,4]benzoquinone (Q-3)

To a solution of compound Q-2 (9 g, 47.62 mmol) in acetonitrile (300 mL) was added ceric ammonium nitrate (CAN, 40 g, 73.00 mmol) portion-wise over a period of 20 min at 0° C. The orange suspension was stirred at room temperature for 20 min, diluted with water (300 mL), and extracted with CHCl$_3$ (3×200 mL). The combined organic layers were dried (Na$_2$SO$_4$) and concentrated in vacuo to obtain compound Q-3 (7 g, 78%) as a yellow solid. TLC R$_f$=0.6 (petroleum ether-EtOAc, 7:3); $^1$H NMR (CDCl$_3$) δ 7.31 (d, J=2.4 Hz, 1H), 6.96 (d, J=10.0 Hz, 1H), 6.83 (dd, J=10.0 Hz, 2.1 Hz, 1H); MS (ES) m/z 186 (M+H)$^+$.

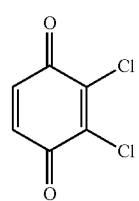

2,3-Dibromo-[1,4]benzoquinone (Q-5)

To a solution of 1,4-benzoquinone Q-4 (2.0 g, 18.52 mmol) in diethyl ether (75 mL) at 0° C. and under N$_2$ atmosphere was added a solution of bromine (2.95 g, 18.51 mmol) in CHCl$_3$-Et$_2$O (2:1, 30 mL) over a period of 10 min. The mixture was stirred at room temperature for 20 min, cooled to 0° C., treated with con. H$_2$SO$_4$ (50 mL), and stirred for another 30 min. The reaction mixture was poured onto crushed ice and the product was extracted with diethyl ether (3×100 mL). Silver (I) oxide (12.0 g, 51.78 mmol) was added to the combined organic layers and the mixture was stirred for 1 h. After filtration, the filtrate was concentrated in vacuo to obtain crude Q-5, which was purified by column chromatography (silica gel, 10% ethyl acetate-pet. ether) to afford compound Q-5 (1.6 g, 32%) as a pale yellow solid. TLC R$_f$=0.5 (petroleum ether-EtOAc, 9:1); $^1$H NMR (CDCl$_3$) δ 7.02 (s, 2H); MS (ES) m/z 266 (M−H)$^-$.

2,3-Dichloro-[1,4]benzoquinone (Q-6)

To a solution of 1,4-benzoquinone Q-4 (2.0 g, 18.52 mmol) in diethyl ether-chloroform (4:1, 90 mL) at 0° C. and under N$_2$ atmosphere was added sulfuryl chloride (3.0 mL, 37.0 mmol) dropwise over a period of 30 min. The reaction mixture was poured onto crushed ice, and extracted with diethyl ether (3×100 mL). Silver (I) oxide (10 g, 43.15 mmol) was added to the combined diethyl ether layers and the mixture was stirred for 1 h. After filtration, the filtrate was concentrated in vacuo to obtain crude Q-6, which was purified by column chromatography (silica gel, 10% ethyl acetate-pet. ether) to afford compound Q-6 (2.3 g, 71%) as a pale yellow solid. TLC R$_f$=0.6 (petroleum ether-EtOAc, 9:1); MS (ES) m/z 176 (M−H)$^-$.

131 132

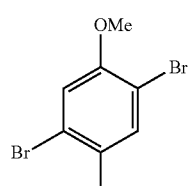
Q-9

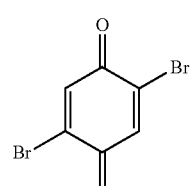
Q-10

1,4-Dibromo-2,5-dimethoxybenzene (Q-9)

To a solution of 1,4-dimethoxybenzene Q-8 (7.5 g, 53.57 mmol) in acetic acid (25 mL) was added a solution of bromine (17.4 g, 108.9 mmol) in acetic acid (5 mL) at room temperature. After stirring for 2 h, the solution was cooled to 10° C. The resulting fine precipitate was filtered, washed with water (20 mL), and dried under vacuum to obtain compound Q-9 (10 g, 63%) as a white solid. TLC $R_f$=0.5 (petroleum ether-EtOAc, 9.9:0.1); $^1$H NMR (CDCl$_3$) δ 7.10 (s, 2H), 3.84 (s, 6H).

2,5-Dibromo-[1,4]benzoquinone (Q-10)

A solution of compound Q-9 (5.0 g, 16.77 mmol) in CH$_3$CN (50 mL) was heated to 100° C., followed by the addition of a solution of ceric ammonium nitrate (CAN, 14 g, 25.54 mmol) in water (75 mL) over a period of 30 min. The reaction mixture was then allowed to cool to room temperature and stirred for another 30 min. The resulting precipitate was filtered, washed with water (20 mL), and dried under high vacuum to furnish compound Q-10 (2.6 g, 58%) as a yellow solid. TLC $R_f$=0.4 (petroleum ether-EtOAc, 9:1); MS (ES) m/z 266 (M−H)$^−$.

Scheme 5. Synthesis of SKC-BF derivatives.

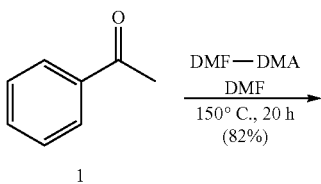

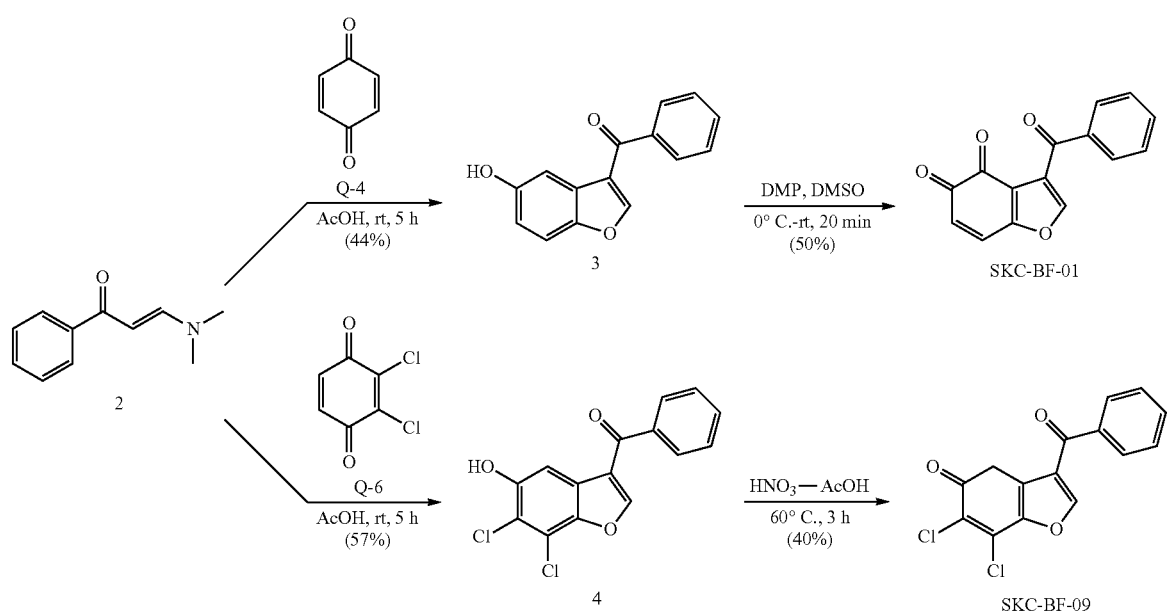

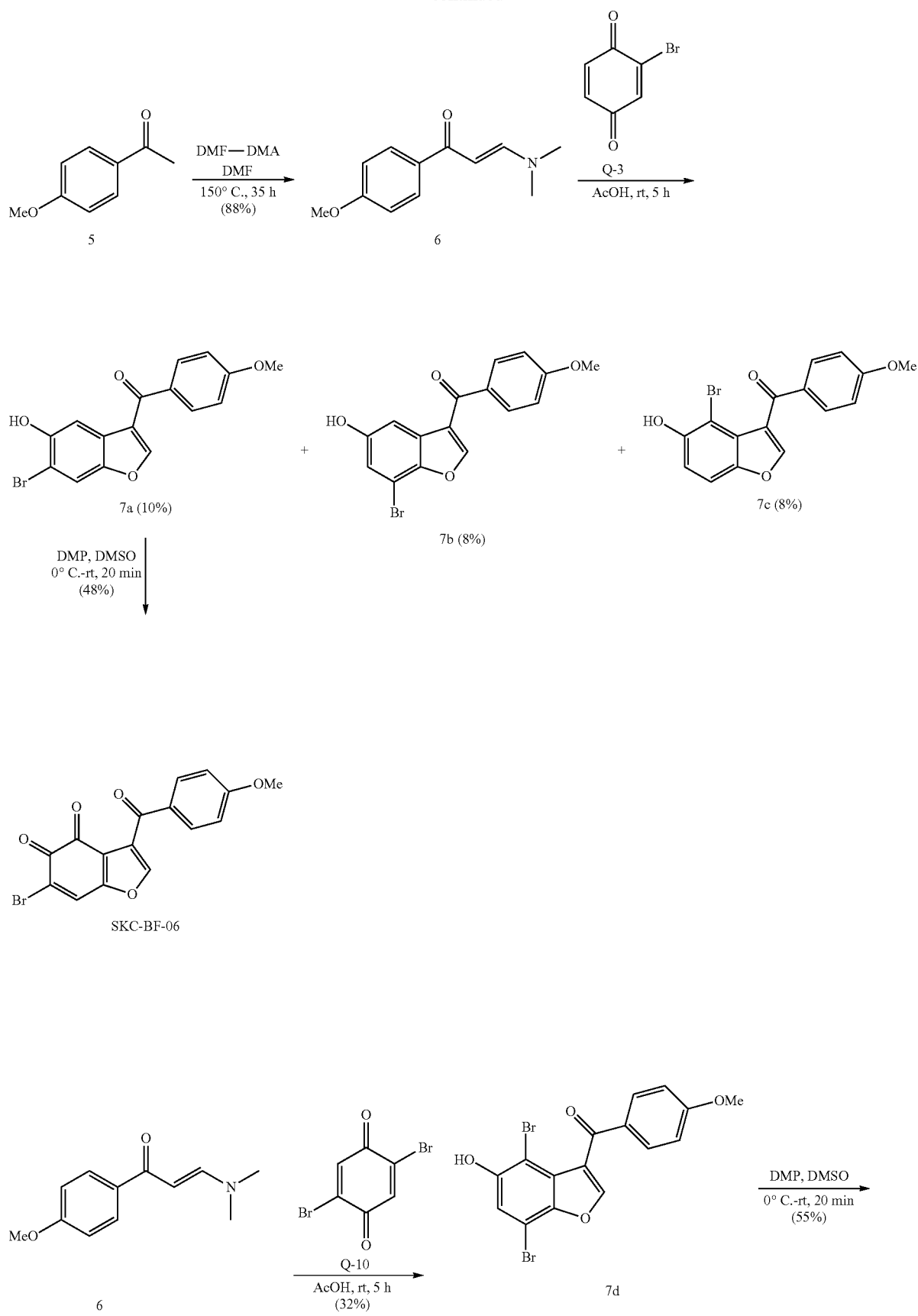

-continued
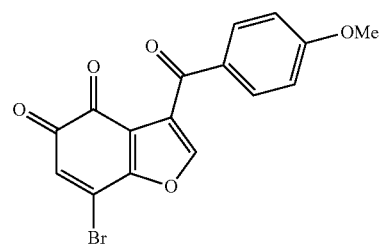
SKC-BF-07
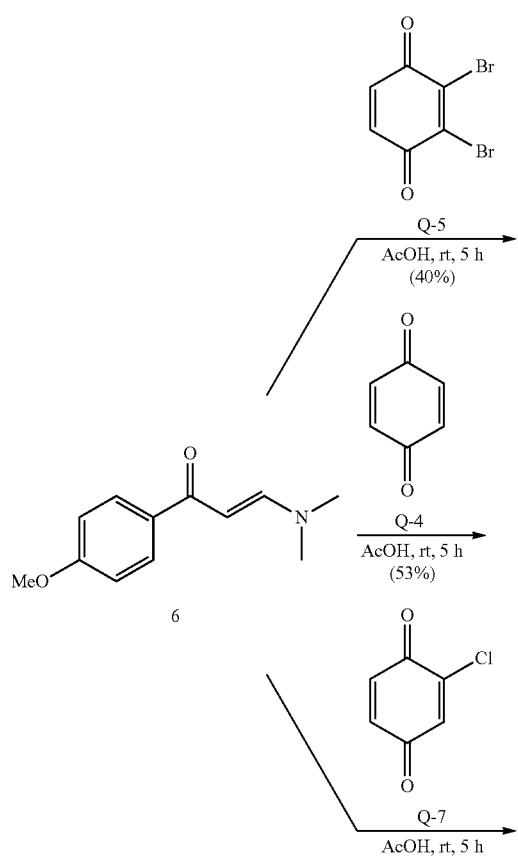
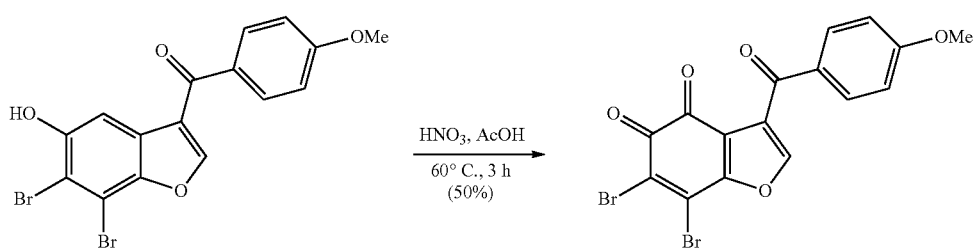

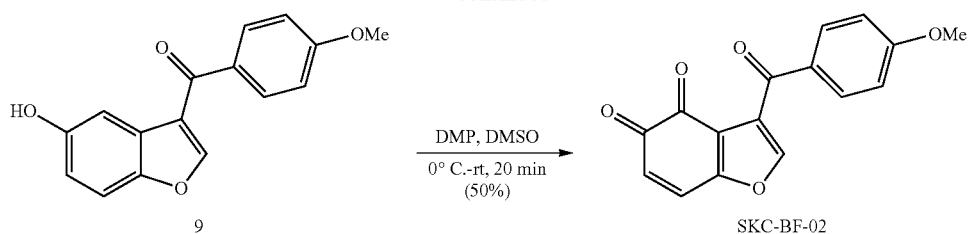
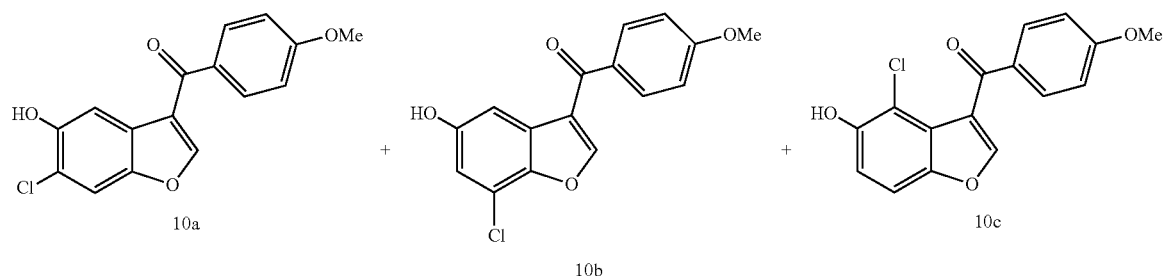
Scheme 7. Synthesis of SKC-BF derivatives.
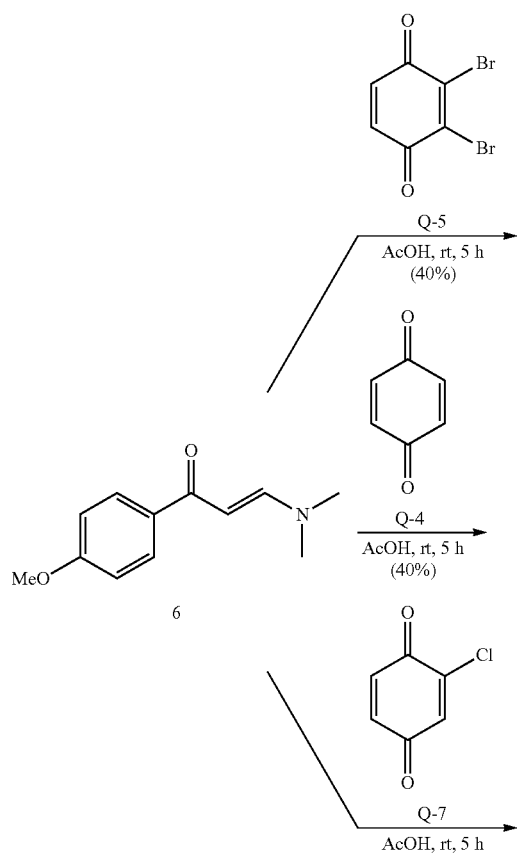

139                                    140
-continued
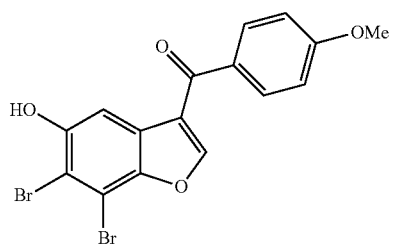
8
HNO₃, AcOH
60° C., 3 h
(48%)
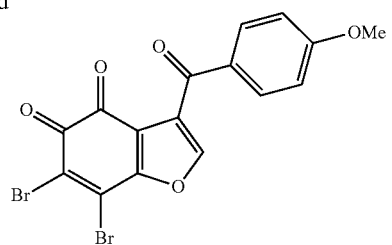
SKC-BF-08
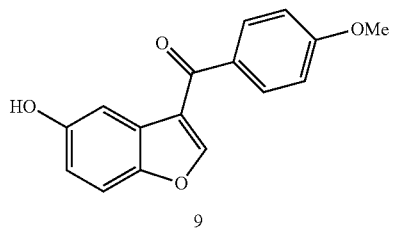
9
DMP, DMSO
0° C.-rt, 20 min
(50%)
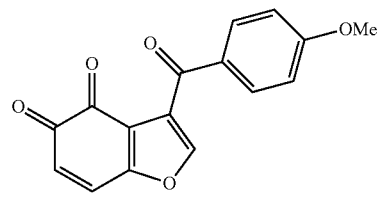
SKC-BF-02
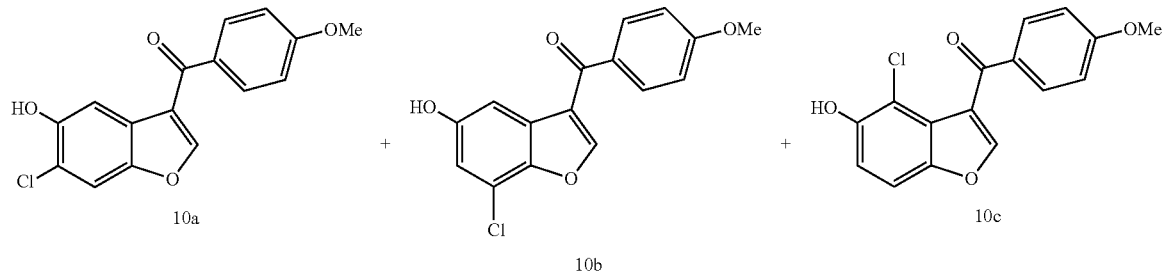
10a         +         10b         +         10c Scheme 8. Synthesis of SKC-BF derivatives.
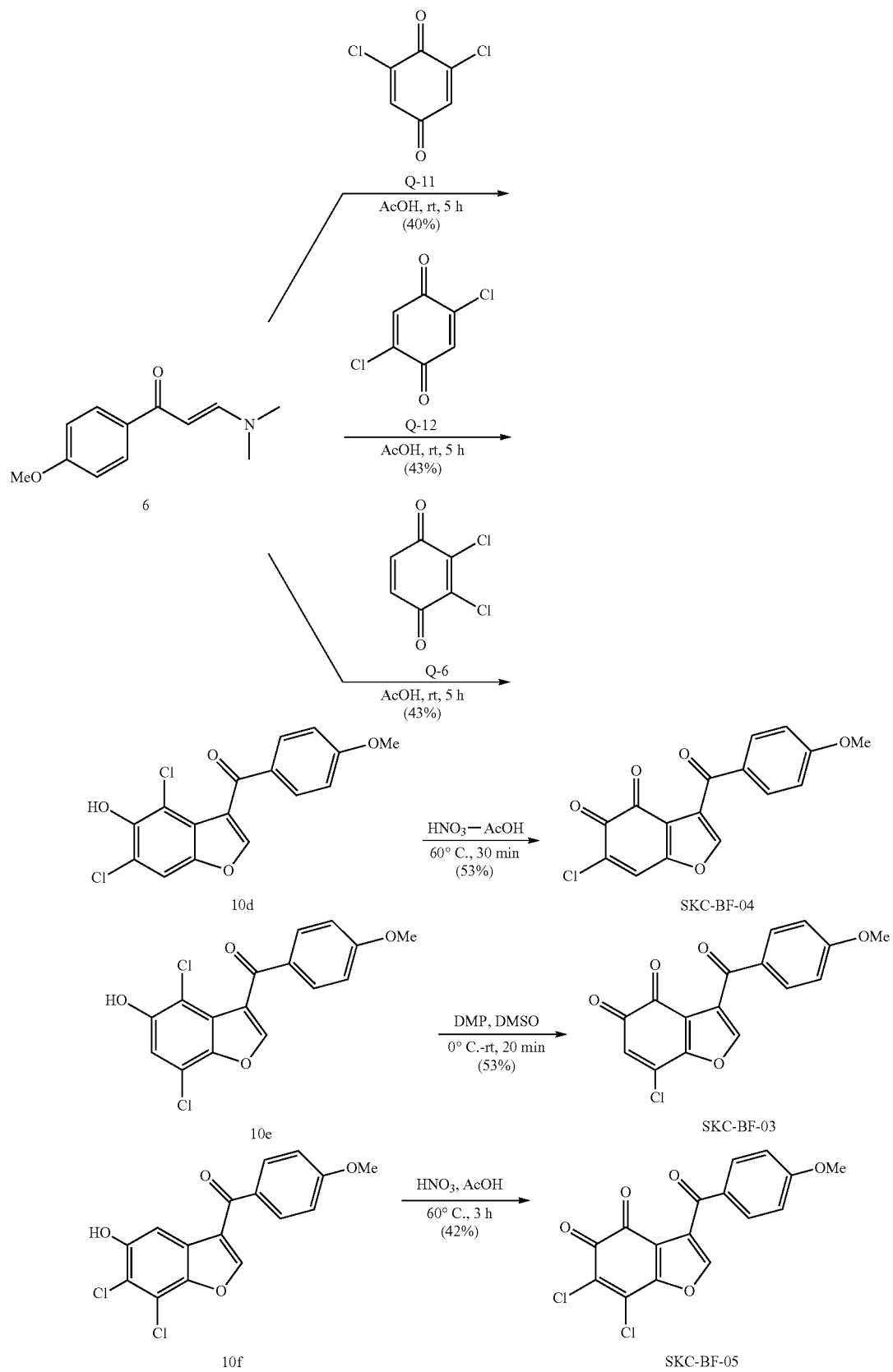

Scheme 9. Synthesis of SKC-BF derivatives.
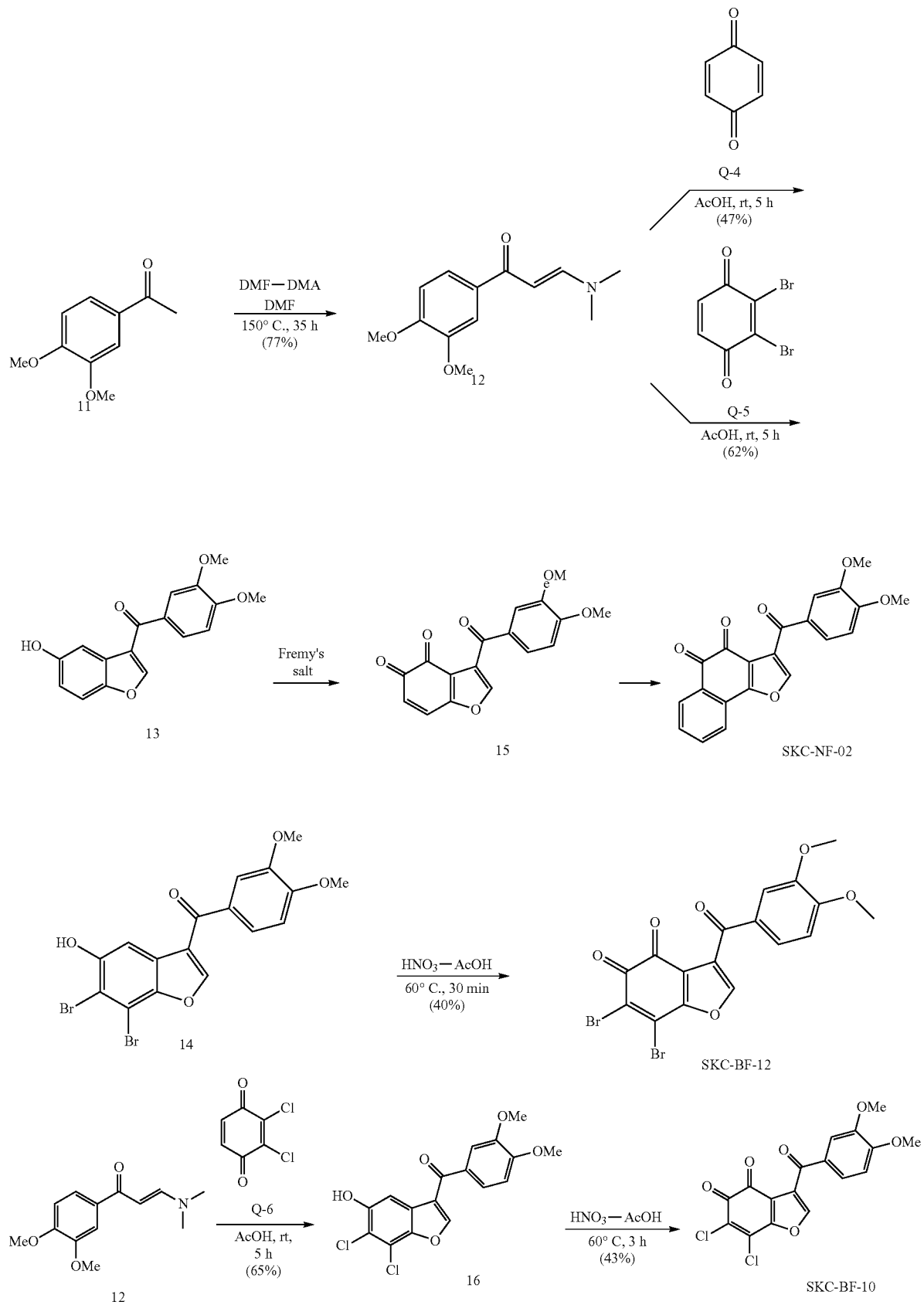

Scheme 10. Synthesis of SKC-BF derivatives.
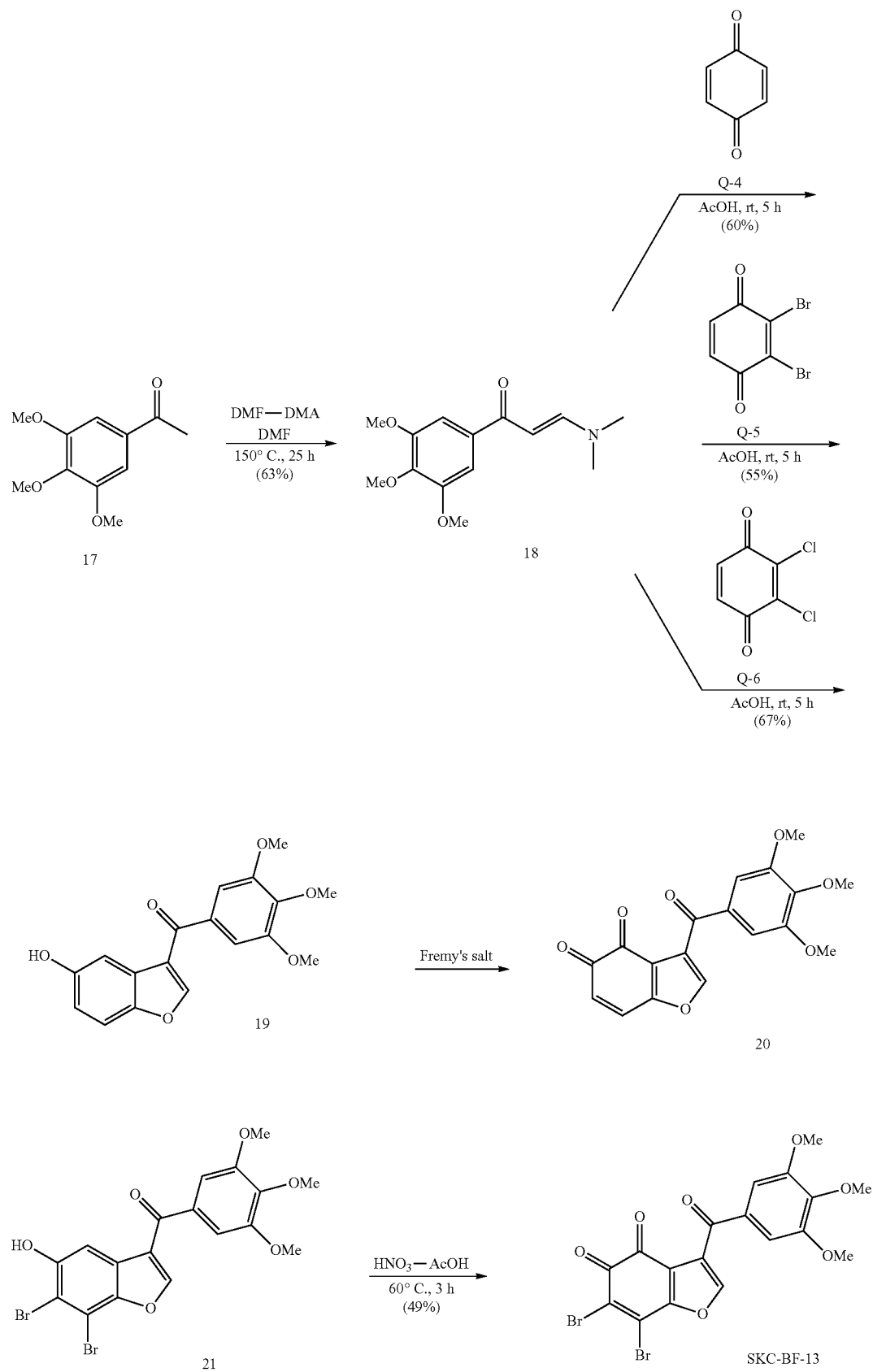

-continued
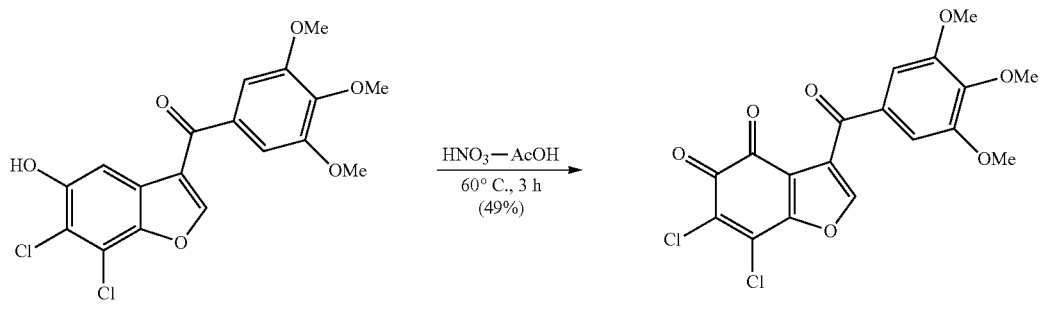
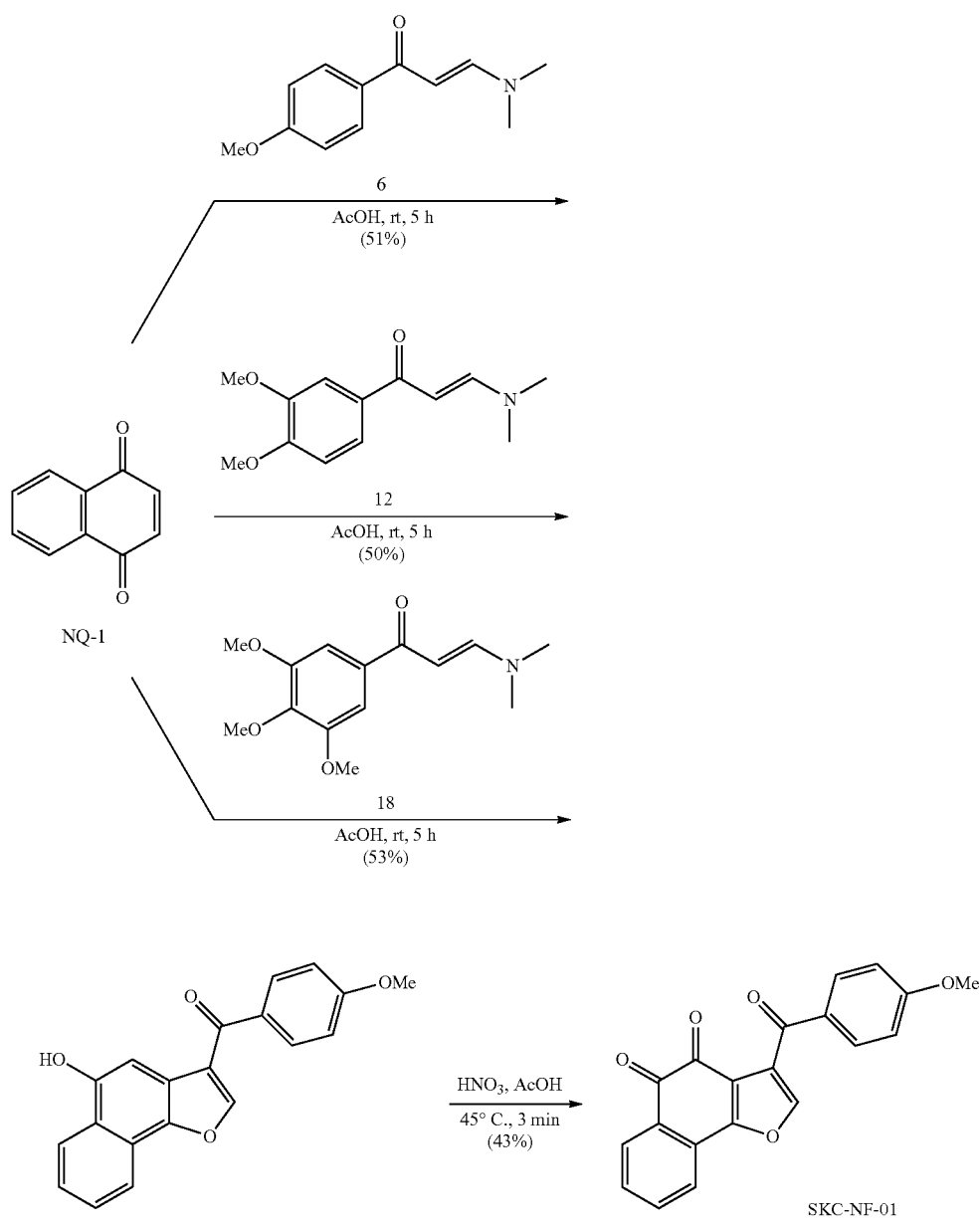
Scheme 11. Synthesis of SKC-NF derivatives.

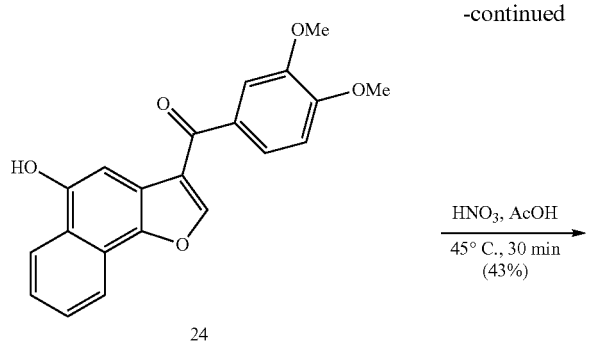

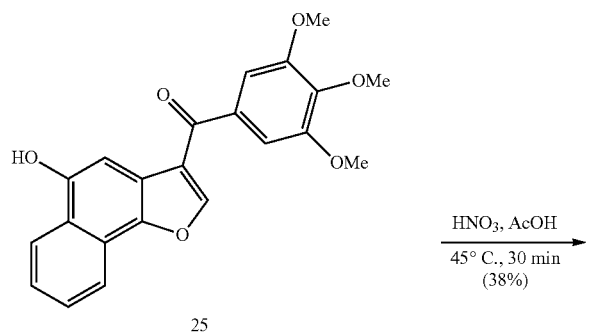

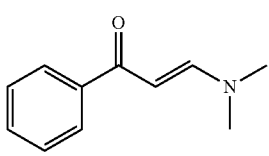

3-Dimethylamino-1-phenyl-propenone (2)

A mixture of acetophenone 1 (5.0 g, 41.66 mmol) and DMF-DMA (17.71 mL, 49.9 mmol) in DMF (10 mL) was heated to 150° C. under $N_2$ atmosphere. After stirring for 20 h at 150° C., the reaction mixture was concentrated in vacuo. The resulting residue was triturated with diethyl ether, filtered and dried under high vacuum to obtain compound 2 (6 g, 82%) as a yellow solid. TLC $R_f$=0.5 (CHCl$_3$-MeOH, 7:3); $^1$H NMR (CDCl$_3$) δ 7.88 (dd, J=7.8, 1.5 Hz, 2H), 7.8 (d, J=12.3 Hz, 1H), 7.42 (m, 3H), 5.71 (d, J=12.3 Hz, 1H), 3.1 (s, 6H); MS (ES) m/z 176 (M+H)$^+$.

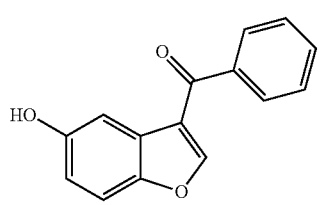 [SMILES: O=C(c1ccccc1)c1coc2ccc(O)cc12]

(5-Hydroxy-benzofuran-3-yl)-phenyl-methanone (3)

A suspension of enaminone 2 (2.0 g, 11.42 mmol) and compound Q-4 (1.23 g, 11.42 mmol) in acetic acid (15 mL) was stirred at room temperature under an atmosphere of $N_2$ for 5 h. The resulting precipitate was filtered and washed with water to afford compound 3 (1.2 g, 44%) as a pale, yellow solid. TLC $R_f$=0.6 (petroleum ether-EtOAc, 7:3); $^1$H NMR (CDCl$_3$) δ 9.47 (s, 1H), 8.58 (s, 1H), 7.9 (d, J=7.3 Hz, 2H), 7.68 (t, J=7.3 Hz, 1H), 7.5-7.6 (m, 4H), 6.9 (d, J=2.67 Hz, 1H); MS (ES) m/z 239 (M+H)$^+$.

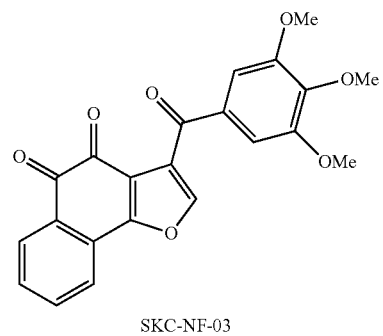

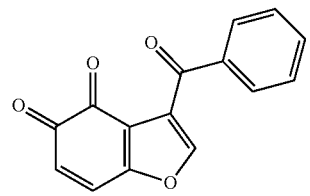

3-Benzoyl-benzofuran-4,5-dione (SKC-BF-01)

To a solution of compound 3 (100 mg, 0.42 mmol) in DMSO (1 mL) was added Dess-Martin periodinane (356 mg, 0.84 mmol) at 0° C. The resulting mixture was stirred at room temperature for 20 min and poured into ice water (2 mL). The resulting precipitate was filtered, washed with water, and dried under high vacuum to furnish compound SKC-BF-01 (50 mg, 50%) as a red solid. TLC $R_f$=0.6 (CHCl$_3$-MeOH, 9:1). NMR (CDCl$_3$) δ 7.88-7.85 (m, 3H), 7.61 (d, J=6.33 Hz, 1H), 7.49 (d, J=7.6 Hz, 2H), 7.41 (d, J=10.3 Hz, 1H), 6.34 (d, J=10.3 Hz, 1H); MS (ES) m/z 253 (M+H)$^+$.

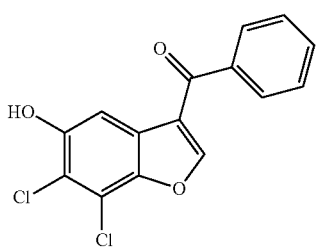 [SMILES: O=C(c1ccccc1)c1coc2c(Cl)c(Cl)c(O)cc12]

(6,7-Dichloro-5-hydroxy-benzofuran-3-yl)-phenyl-methanone (4)

A suspension of enaminone 2 (500 mg, 2.85 mmol) and compound Q-6 (500 mg, 2.85 mmol) in acetic acid (5 mL) was stirred at room temperature under an atmosphere of N$_2$ for 5 h. The resulting precipitate was filtered, washed with water, and dried under high vacuum to afford compound 4 (500 mg, 57%) as an off-white solid. TLC R$_f$=0.5 (petroleum ether-EtOAc, 7:3); $^1$H NMR (DMSO-d$_6$) δ 10.72 (s, 1H), 8.77 (s, 1H), 7.91 (d, J=7.0 Hz, 2H), 7.71 (m, 2H), 7.59 (app t, 2H); MS (ES) m/z 305 (M−H)$^-$.

SKC-BF-09

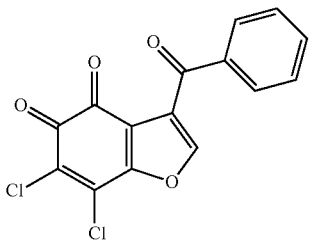

3-Benzoyl-6,7-dichloro-benzofuran-4,5-dione (SKC-BF-09)

To a solution of compound 4 (100 mg, 0.32 mmol) in glacial acetic acid (2 mL) at room temperature was added nitric acid (0.1 mL, d 1.35) dropwise with vigorous stirring. The mixture was heated at 60° C. for 3 h, allowed to cool to room temperature, and poured over crushed ice. The resulting precipitate was filtered, dried, and recrystallized (CH$_2$Cl$_2$-pet. ether) to afford compound SKC-BF-09 (40 mg, 40%) as brick red solid. TLC R$_f$=0.5 (petroleum ether-EtOAc, 7:3); $^1$H NMR (CDCl$_3$) δ 7.93 (s, 1H), 7.86 (d, J=6.9 Hz, 2H), 7.64 (app t, 1H), 7.50 (d, J=7.6 Hz, 2H); MS (ES) m/z 321 (M+H)$^+$.

6

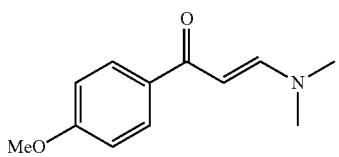

3-Dimethylamino-1-(4-methoxyphenyl)-propenone (6)

A mixture of 4-methoxyacetophenone 5 (5 g, 33.11 mmol) and DMF-DMA (3.9 g, 133.4 mmol) in DMF (10 mL) was heated to 150° C. under an atmosphere of N$_2$. After being stirred for 35 h at 150° C., the reaction mixture was concentrated in vacuo and the residue obtained was triturated with diethyl ether, filtered, and dried under high vacuum to afford compound 6 (6 g, 88%) as a yellow solid. TLC R$_f$=0.5 (CHCl$_3$-MeOH, 9:1); $^1$H NMR (CDCl$_3$) δ 7.92 (d, J=2.6 Hz, 2H), 7.78 (d, J=12.2 Hz, 1H), 6.93 (d, J=2.9 Hz, 2H), 5.71 (d, J=12.5 Hz, 1H), 3.84 (s, 3H), 3.02 (s, 6H); MS (ES) m/z 206 (M+H)$^+$.

7a

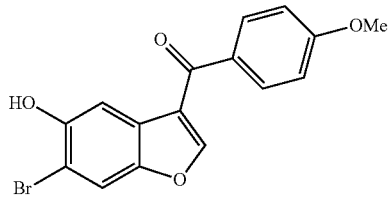 [SMILES: COc1ccc(C(=O)c2coc3cc(Br)c(O)cc23)cc1]

7b

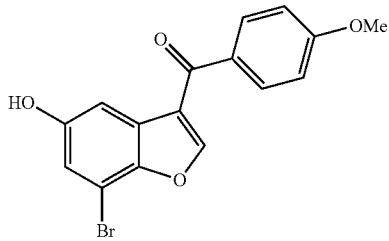 [SMILES: COc1ccc(C(=O)c2coc3c(Br)cc(O)cc23)cc1]

7c

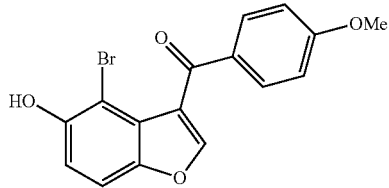 [SMILES: COc1ccc(C(=O)c2coc3ccc(O)c(Br)c23)cc1]

(6-Bromo-5-hydroxy-benzofuran-3-yl)-(4-methoxyphenyl)-methanone (7a), (7-Bromo-5-hydroxy-benzofuran-3-yl)-(4-methoxyphenyl)-methanone (7b) and (4-Bromo-5-hydroxy-benzofuran-3-yl)-(4-methoxyphenyl)-methanone (7c)

A suspension of enaminone 6 (3.0 g, 14.56 mmol) and compound Q-3 (3.5 g, 18.71 mmol) in acetic acid (20 mL) was stirred at room temperature under an atmosphere of N$_2$ for 5 h. The resulting precipitate was filtered to obtain a mixture of compounds 7a, 7b and 7c. Purification by column chromatography (silica gel, 3% ethyl acetate-pet. ether) furnished compound 7c (40 mg, 8%) as a dark brown solid along with a mixture of two different regioisomers. Preparative HPLC purification on the mixture of isomers afforded compound 7a (50 mg, 10%) and compound 7b (40 mg, 8%) as white solids. TLC: 7a & 7b: R$_f$=0.5 (petroleum ether-EtOAc, 6:4); 7c: R$_f$=0.55 (petroleum ether-EtOAc, 6:4); 7a: $^1$H NMR (DMSO-d$_6$) δ 10.28 (s, 1H), 8.62 (s, 1H), 7.97 (s, 1H), 7.91 (d, J=8.7 Hz, 2H), 7.67 (s, 1H), 7.10 (d, J=8.3 Hz, 2H), 3.87 (s, 3H); MS (ES) m/z 348 (M+H)$^+$; 7b: $^1$H NMR (DMSO-d$_6$) δ 9.85 (s, 1H), 8.68 (s, 1H), 7.92 (d, J=8.7 Hz, 2H), 7.46 (s, 1H), 7.12 (d, J=7.0 Hz, 2H), 7.1 (s, 1H), 3.87 (s, 3H); MS (ES) m/z 347 (M)$^+$; 7c: $^1$H NMR (DMSO-d$_6$) δ 10.08 (s, 1H), 8.35 (s, 1H), 7.84 (d, J=9.0 Hz, 2H), 7.57 (d, J=9.0 Hz, 1H), 7.08 (d, J=3.7 Hz, 2H), 3.85 (s, 3H); MS (ES) m/z 347 (M)$^+$.

SKC-BF-06

6-Bromo-3-(4-methoxybenzoyl)-benzofuran-4,5-dione (SKC-BF-06)

To a solution of compound 7a (50 mg, 0.14 mmol) in DMSO (2 mL) was added Dess-Martin periodinane (118 mg, 0.28 mmol) at 0° C. The resulting mixture was stirred at room temperature for 20 min and poured into ice water (2 mL). The resulting precipitate was filtered, washed with water, and dried under high vacuum to obtain compound SKC-BF-06 (25 mg, 48%) as a reddish brown solid. TLC $R_f$=0.5 (petroleum ether-EtOAc, 6:4); $^1$H NMR (CDCl$_3$) δ 7.86-7.81 (m, 4H), 6.95 (d, J=8.7 Hz, 2H), 3.88 (s, 3H); MS (ES) m/z 362 (M+H)$^+$.

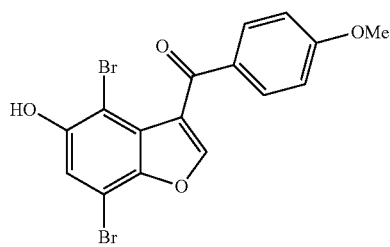

7d

(4,7-Dibromo-5-hydroxy-benzofuran-3-yl)-(4-methoxy-phenyl)-methanone (7d)

A suspension of enaminone 6 (2 g, 9.70 mmol) and compound Q-10 (2.6 g, 9.70 mmol) in acetic acid (10 mL) was stirred at room temperature for 5 h under an atmosphere of N$_2$. The reaction mixture was partitioned between ethyl acetate and water, and the aqueous layer was extracted with ethyl acetate (3×30 mL). The combined organic layers were dried (Na$_2$SO$_4$), filtered, and concentrated in vacuo to afford a yellow residue. Purification by column chromatography (silica gel, ethyl acetate-pet. ether, 1:5) afforded the desired product 7d (1.3 g, 32%) as a yellow solid. TLC $R_f$=0.5 (petroleum ether-EtOAc, 7:3); $^1$H NMR (DMSO-d$_6$) δ 10.48 (s, 1H), 8.47 (s, 1H), 7.85 (d, J=5.0 Hz, 2H), 7.26 (s, 1H), 7.06 (d, J=5.0 Hz, 2H), 3.86 (s, 3H); MS (ES) m/z 426 (M+H)$^+$.

SKC-BF-07

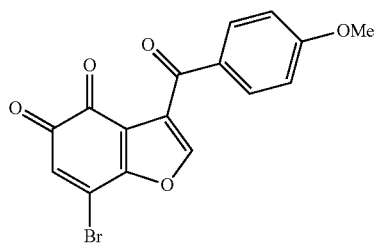

7-Bromo-3-(4-methoxybenzoyl)-benzofuran-4,5-dione (SKC-BF-07)

To a solution of compound 7d (50 mg, 0.12 mmol) in DMSO (1.5 mL) was added Dess-Martin periodinane (100 mg, 0.24 mmol) at 0° C. The resulting mixture was stirred at room temperature for 20 min and poured into ice water (2 mL). The resulting precipitate was filtered, washed with water, and dried under high vacuum to obtain compound SKC-BF-07 (25 mg, 55%) as a red solid. TLC $R_f$=0.45 (petroleum ether-EtOAc, 6:4); $^1$H NMR (CDCl$_3$) δ 7.89 (s, 1H), 7.85 (d, J=8.7 Hz, 2H), 6.95 (d, J=9.0 Hz, 2H), 6.78 (s, 1H), 3.89 (s, 3H); MS (ES) m/z 362 (M+H)$^+$.

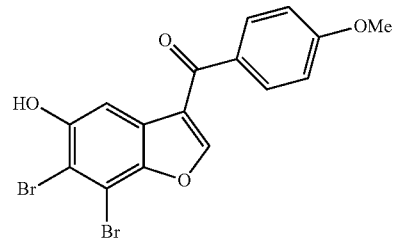

8

(6,7-Dibromo-5-hydroxy-benzofuran-3-yl)-(4-methoxyphenyl)-methanone (8)

A suspension of compound 6 (500 mg, 2.42 mmol) and Q-5 (640 mg, 2.42 mmol) in acetic acid (5 mL) was stirred at room temperature under an atmosphere of N$_2$ for 5 h. The resulting precipitate was filtered, washed with water, and dried under high vacuum to obtain compound 8 (400 mg, 40%) as an off-white solid. TLC $R_f$=0.6 (petroleum ether-EtOAc, 7:3); $^1$H NMR (DMSO-d$_6$) δ 10.69 (s, 1H), 8.73 (s, 1H), 7.92 (d, J=6.6 Hz, 2H), 7.68 (s, 1H), 7.12 (d, J=9.0 Hz, 2H), 3.88 (s, 3H); MS (ES) m/z 427 (M+H)$^+$.

SKC-BF-08

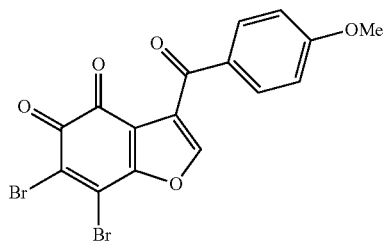

6,7-Dibromo-3-(4-methoxybenzoyl)-benzofuran-4,5-dione (SKC-BF-08)

To a suspension of compound 8 (200 mg, 0.47 mmol) in glacial acetic acid (2 mL) at room temperature was added nitric acid (0.1 mL, d 1.35) dropwise with vigorous stirring. The mixture was heated at 60° C. for 3 h, cooled to room temperature, and poured into cold water. The resulting precipitate was filtered, dried, dissolved in CH$_2$Cl$_2$, and triturated with pet. ether to furnish compound SKC-BF-08 (100 mg, 50%) as a red solid. TLC $R_f$=0.7 (CHCl$_3$-MeOH, 9:1); $^1$H NMR (CDCl$_3$) δ 7.88 (s, 1H), 7.85 (d, J=9.0 Hz, 2H), 6.95 (d, J=9.0 Hz, 2H), 3.89 (s, 3H); MS (ES) m/z 440 (M+H)$^+$.

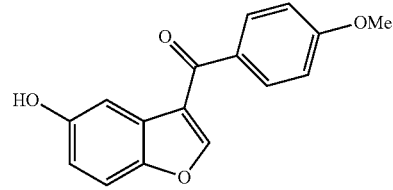 [SMILES: COc1ccc(C(=O)c2coc3ccc(O)cc23)cc1]

9

(5-Hydroxy-benzofuran-3-yl)-(4-methoxyphenyl)-methanone (9)

A suspension of enaminone 6 (1 g, 4.85 mmol) and compound Q-4 (524 mg, 4.85 mmol) in acetic acid (10 mL) was stirred at room temperature under an atmosphere of $N_2$ for 5 h. The resulting precipitate was filtered, washed with water, and dried under high vacuum to afford compound 9 (700 mg, 53%) as a light green solid. TLC $R_f$=0.5 (petroleum ether-EtOAc, 7:3); $^1$H NMR (DMSO-$d_6$) δ 9.43 (s, 1H), 8.58 (m, 1H), 7.9 (d, J=8.7 Hz, 2H), 7.51 (d, J=8.7 Hz, 1H), 7.45 (app s, 1H), 7.1 (d, J=8.7 Hz, 2H), 6.85 (dd, J=9.0 Hz, 2.6 Hz, 1H), 3.87 (s, 3H); MS (ES) m/z 269 (M+H)$^+$.

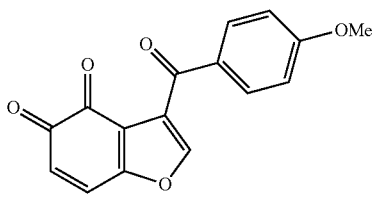

SKC-BF-02

3-(4-Methoxy-benzoyl)-benzofuran-4,5-dione (SKC-BF-02)

To a solution of compound 9 (100 mg, 0.371 mmol) in DMSO (1.5 mL) was added Dess-Martin periodinane (315 mg, 0.743 mmol) at 0° C. The resulting mixture was stirred at room temperature for 20 min and poured into ice water (2 mL). The resulting precipitate was filtered, washed with water, and dried under high vacuum to obtain compound SKC-BF-02 (50 mg, 50%) as a red solid. $R_f$=0.6 (CHCl$_3$-MeOH, 9:1); $^1$H NMR (CDCl$_3$) δ 7.85 (d, J=9.0 Hz, 2H), 7.81 (s, 1H), 7.40 (d, J=10.3 Hz, 1H), 6.93 (d, J=9.0 Hz, 2H), 6.32 (d, J=10.3 Hz, 1H), 3.88 (s, 3H); MS (ES) m/z 317 (M+H)$^+$.

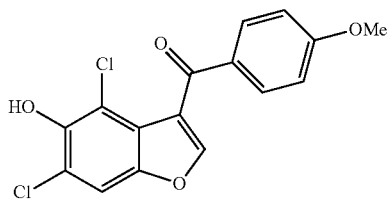 [SMILES: COc1ccc(C(=O)c2coc3cc(Cl)c(O)c(Cl)c23)cc1]

10d

(4,6-Dichloro-5-hydroxy-benzofuran-3-yl)-(4-methoxyphenyl)-methanone (10d)

A suspension of enaminone 6 (1.0 g, 4.87 mmol) and compound Q-11 (860 mg, 4.87 mmol) in acetic acid (10 mL) was stirred at room temperature under an atmosphere of $N_2$ for 5 h. The reaction mixture was then partitioned between ethyl acetate and water and the aqueous layer was extracted with ethyl acetate (3×20 mL). The combined organic layers were dried (Na$_2$SO$_4$), filtered, and concentrated in vacuo to afford a yellow residue. Purification by column chromatography (silica gel, ethyl acetate-pet. ether; 1:5) afforded the desired product 10d (660 mg 40%) as a pale yellow solid. TLC $R_f$=0.6 (7:3 petroleum ether-EtOAc); $^1$H NMR (DMSO-$d_6$) δ 9.92 (s, 1H), 8.45 (s, 1H), 7.94 (s, 1H), 7.87 (d, J=8.7 Hz, 2H), 7.08 (d, J=8.7 Hz, 2H), 3.86 (s, 3H); MS (ES) m/z 335 (M–H)$^−$.

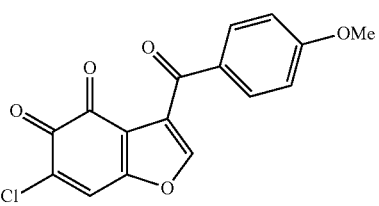

SKC-BF-04

6-Chloro-3-(4-methoxybenzoyl)-benzofuran-4,5-dione (SKC-BF-04)

To a suspension of compound 10d (100 mg, 0.29 mmol) in glacial acetic acid (1.5 mL) at room temperature was added nitric acid (0.1 mL, d 1.35) dropwise with vigorous stirring. The mixture was heated at 60° C. for 30 min, allowed to cool to room temperature, and poured into cold water. The resulting precipitate was filtered and recrystallized (CH$_2$Cl$_2$-pet. ether) to furnish compound SKC-BF-04 (50 mg, 53%) as a red solid. TLC $R_f$=0.4 (petroleum ether-EtOAc, 7:3); $^1$H NMR (CDCl$_3$) δ 7.86-7.80 (m, 3H), 7.54 (s, 1H), 6.95 (d, J=9.0 Hz, 2H), 3.88 (s, 3H); MS (ES) m/z 317 (M+H)$^+$.

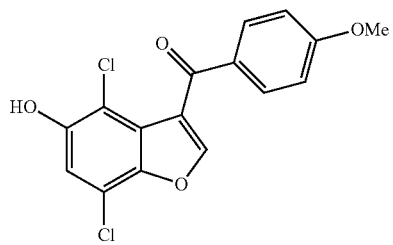 [SMILES: COc1ccc(C(=O)c2coc3c(Cl)cc(O)c(Cl)c23)cc1]

10e

(4,7-Dichloro-5-hydroxy-benzofuran-3-yl)-(4-methoxy-phenyl)-methanone (10e)

A suspension of enaminone 6 (1.0 g, 4.85 mmol) and compound Q-12 (850 mg, 4.8 mmol) in acetic acid (10 mL) was stirred at room temperature under an atmosphere of $N_2$ for 5 h. The reaction mixture was partitioned between ethyl acetate and water and the aqueous layer was extracted with ethyl acetate (20 mL×3). The combined organic layers were dried (Na$_2$SO$_4$), filtered, and concentrated in vacuo to afford a yellow residue. Purification by column chromatography (silica gel, ethyl acetate-pet. ether; 1:5) afforded the desired product 10e (700 mg, 43%) as an off-white solid. TLC $R_f$=0.55 (petroleum ether-EtOAc, 5:5). $^1$H NMR (DMSO-$d_6$) δ 10.46 (s, 1H), 8.49 (s, 1H), 7.87 (d, J=9.0 Hz, 2H), 7.17 (s, 1H), 7.08 (d, J=8.7 Hz, 2H), 3.86 (s, 3H); MS (ES) m/z 337 (M+H)$^+$.

SKC-BF-03

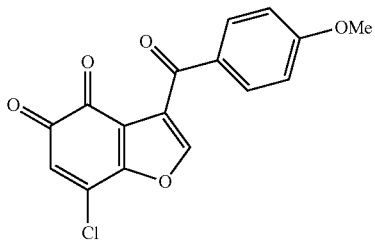

7-Chloro-3-(4-methoxybenzoyl)-benzofuran-4,5-dione (SKC-BF-03)

To a solution of compound 10e (100 mg, 0.29 mmol) in DMSO (1.5 mL) was added Dess-Martin periodinane (253 mg, 0.59 mmol) at 0° C. The resulting mixture was stirred at room temperature for 20 min and poured into ice-water (2 mL). The resulting precipitate was filtered, washed with water, and dried under high vacuum to obtain compound SKC-BF-03 (50 mg, 53%) as an orange solid. TLC $R_f$=0.5 (petroleum ether-EtOAc, 6:4); $^1$H NMR (CDCl$_3$) δ 7.90-7.84 (m, 3H), 6.95 (d, J=8.6 Hz, 2H), 6.53 (s, 1H), 3.88 (s, 3H); MS (ES) m/z 317 (M+H)$^+$.

10f

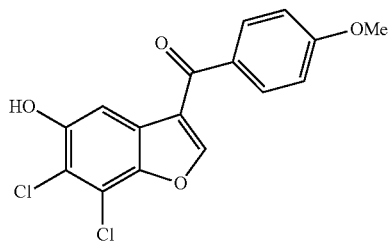 [SMILES: COc1ccc(C(=O)c2coc3c(Cl)c(Cl)c(O)cc23)cc1]

(6,7-Dichloro-5-hydroxy-benzofuran-3-yl)-(4-methoxyphenyl)-methanone (10f)

A suspension of enaminone 6 (1 g, 4.85 mmol) and compound Q-6 (850 mg, 4.85 mmol) in acetic acid (10 mL) was stirred at room temperature under an atmosphere of N$_2$ for 5 h. The resulting precipitate was filtered, washed with water, and dried under high vacuum to afford compound 10f (700 mg, 43%) as an off-white solid. TLC $R_f$=0.55 (petroleum ether-EtOAc, 5:5); $^1$H NMR (DMSO-d$_6$) δ 10.68 (s, 1H), 8.75 (s, 1H), 7.93 (d, J=9.0 Hz, 2H), 7.66 (s, 1H), 7.12 (d, J=8.7 Hz, 2H), 3.88 (s, 3H); MS (ES) m/z 337 (M+

SKC-BF-05

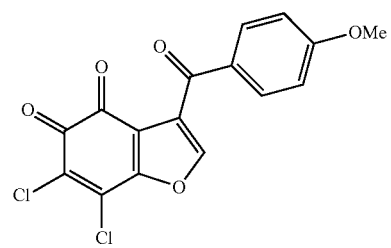

6,7-Dichloro-3-(4-methoxy-benzoyl)-benzofuran-4,5-dione (SKC-BF-05)

To a suspension of compound 10f (100 mg, 0.29 mmol) in glacial acetic acid (2 mL) at room temperature was added nitric acid (0.1 mL, d 1.35) dropwise with vigorous stirring. The mixture was heated at 60° C. for 3 hr, allowed to cool for 30 min, and poured into cold water. The resulting precipitate was filtered, washed with water, and dried under high vacuum to afford compound SKC-BF-05 (45 mg, 42%) as an orange solid. TLC $R_f$=0.7 (CHCl$_3$-MeOH, 9:1); $^1$H NMR (CDCl$_3$) δ 7.89 (s, 1H), 7.85 (d, J=9.0 Hz, 2H), 6.95 (d, J=9.0 Hz, 2H), 3.89 (s, 3H); MS (ES) m/z 351 (M+H)$^+$.

12

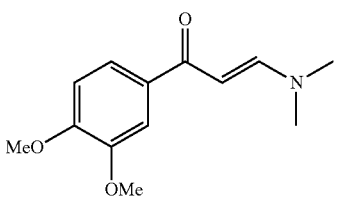

1-(3,4-Dimethoxy-phenyl)-3-dimethylamino-propenone (12)

A mixture of 3,4-dimethoxy acetophenone 11 (5 g, 27.47 mmol) and DMF-DMA (3.9 g, 111.1 mmol) in DMF (10 mL) was heated to 150° C. under an atmosphere of N$_2$. After stirring for 35 h 150° C., the reaction mixture was concentrated in vacuo. The resulting residue was triturated with diethylether and dried under high vacuum to afford compound 12 (5.0 g, 77%) as a yellow solid. TLC $R_f$=0.5 (CHCl$_3$-MeOH, 9:1); $^1$H NMR (CDCl$_3$) δ 7.8 (d, J=12.2 Hz, 1H), 7.56-7.51 (m, 3H), 6.86 (d, J=8.1 Hz, 1H), 5.71 (d, J=12.2 Hz, 1H), 3.95 (s, 3H), 3.92 (s, 3H), 3.03 (br, 6H); MS (ES) m/z 236 (M+H$^+$).

13

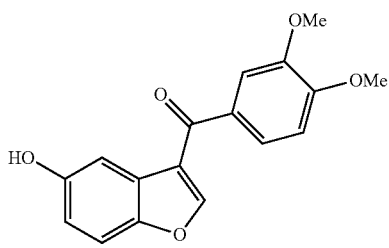 [SMILES: COc1ccc(C(=O)c2coc3ccc(O)cc23)cc1OC]

(3,4-Dimethoxy-phenyl)-(5-hydroxy-benzofuran-3-yl)-methanone (13)

A suspension of enaminone 12 (2 g, 8.43 mmol) and compound benzoquinone Q-4 (910 mg, 8.43 mmol) in acetic acid was stirred at room temperature under an atmosphere of N$_2$ for 5 h. The precipitate that formed was filtered, washed with water, and dried under high vacuum to afford compound 13 (1.2 g, 47%) as an off-white solid. TLC $R_f$=0.5 (petroleum ether-EtOAc, 7:3); $^1$H NMR (DMSO-d$_6$) δ 9.43 (s, 1H), 8.59 (s, 1H), 7.57-7.43 (band, 4H), 7.12 (d, J=8.3 Hz, 1H), 6.86 (dd, J=9.0 Hz, 2.6 Hz, 1H), 3.87 (s, 3H), 3.85 (s, 3H); MS (ES) m/z 299 (M+H)$^+$.

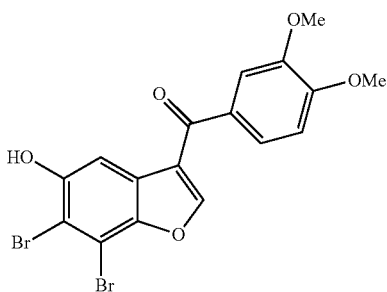 [SMILES: COc1ccc(C(=O)c2coc3c(Br)c(Br)c(O)cc23)cc1OC]

14

(6,7-Dibromo-5-hydroxy-benzofuran-3-yl)-(3,4-dimethoxy-phenyl)-methanone (14)

A suspension of enaminone 12 (500 mg, 2.11 mmol) and compound Q-5 (560 mg, 2.11 mmol) in acetic acid (10 mL) was stirred at room temperature under an atmosphere of $N_2$ for 5 h. The resulting precipitate was filtered, washed with water, and dried under high vacuum to afford compound 14 (600 mg, 62%) as an off-white solid. TLC $R_f$=0.6 ($CHCl_3$-MeOH, 9:1); $^1$H NMR (DMSO-$d_6$) δ 10.7 (s, 1H), 8.77 (s, 1H), 7.68 (s, 1H), 7.58 (d, J=6.3 Hz, 1H), 7.45 (app s, 1H), 7.13 (d, J=8.3 Hz, 1H), 3.87-3.85 (s, 6H); MS (ES) m/z 457 $(M+H)^+$.

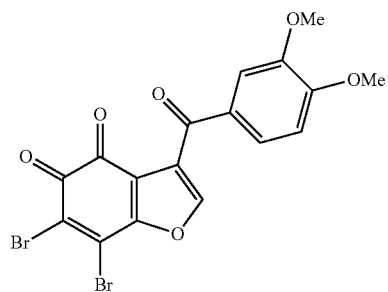

SKC-BF-12

6,7-Dibromo-3-(3,4-dimethoxy-benzoyl)-benzofuran-4,5-dione (SKC-BF-12)

To a suspension of compound 14 (100 mg, 0.22 mmol) in glacial acetic acid (2 mL) at room temperature was added nitric acid (0.1 mL, d 1.35) dropwise with vigorous stirring. The mixture was heated at 60° C. for 30 min, allowed to cool to room temperature, and poured into cold water. The resulting precipitate was filtered and recrystallized to obtain compound SKC-BF-12 (40 mg, 40%) as an orange solid. TLC $R_f$=0.7 ($CHCl_3$-MeOH, 9:1); $^1$H NMR ($CDCl_3$) δ 7.87 (s, 1H), 7.57 (app s, 1H), 7.37 (dd, J=8.4 Hz, 2.0 Hz, 1H), 6.84 (d, J=8.3, 1H), 3.95 (s, 6H); MS (ES) m/z 471 $(M+H)^+$.

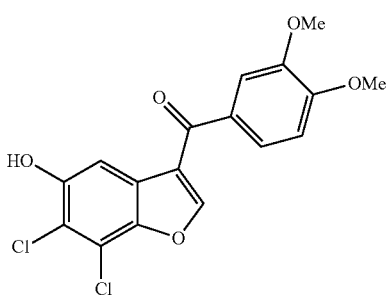 [SMILES: COc1ccc(C(=O)c2coc3c(Cl)c(Cl)c(O)cc23)cc1OC]

16

(6,7-Dichloro-5-hydroxy-benzofuran-3-yl)-(3,4-dimethoxy-phenyl)-methanone (16)

A suspension of enaminone 12 (500 mg, 2.11 mmol) and compound Q-6 (370 mg, 2.11 mmol) in acetic acid (10 mL) was stirred at room temperature under an atmosphere of $N_2$ for 5 h. The resulting precipitate was filtered, washed with water, and dried under high vacuum to obtain compound 16 (500 mg, 65%) as an off-white solid. TLC $R_f$=0.55 (petroleum ether-EtOAc, 5:5); $^1$H NMR (DMSO-$d_6$) δ 10.67 (s, 1H), 8.78 (s, 1H), 7.66 (s, 1H), 7.58 (d, J=6.7 Hz, 1H), 7.45 (app s, 1H), 7.13 (d, J=8.3 Hz, 1H), 3.88 (s, 3H), 3.86 (s, 3H); MS (ES) m/z 367 $(M+H^+)$.

SKC-BF-10

[Structure of SKC-BF-10]

6,7-Dichloro-3-(3,4-dimethoxy-benzoyl)-benzofuran-4,5-dione (SKC-BF-10)

To a suspension of compound 16 (100 mg, 0.27 mmol) in glacial acetic acid (2 mL) at room temperature was added nitric acid (0.1 mL, d 1.35) dropwise with vigorous stirring. The mixture was heated at 60° C. for 3 h, allowed to cool to room temperature, and poured into cold water. The resulting precipitate was filtered and recrystallized to furnish compound SKC-BF-10 (45 mg, 43%) as a red solid. TLC $R_f$=0.6 ($CHCl_3$-MeOH, 9:1); $^1$H NMR ($CDCl_3$) δ 7.89 (s, 1H), 7.57 (app s, 1H), 7.35 (app d, 1H), 6.84 (d, J=8.3 Hz, 1H), 3.96 (s, 6H); MS (ES) m/z 381 $(M+H)^+$.

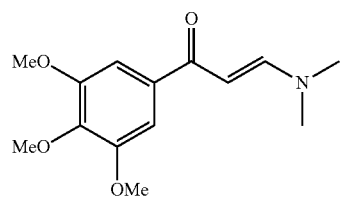

18

3-Dimethylamino-1-(3,4,5-trimethoxy-phenyl)-propenone (18)

A mixture of 3,4,5-trimethoxy acetophenone 17 (5.0 g, 23.47 mmol) and DMF-DMA (11.3 g, 94.9 mmol) in DMF (10 mL) was heated to 150° C. under an atmosphere of $N_2$. After stirring for 25 h at 150° C., the reaction mixture was concentrated in vacuo. The resulting residue was triturated with diethylether, filtered, and dried under high vacuum to afford compound 18 (4 g, 63%) as a yellow solid. TLC $R_f$=0.4 ($CHCl_3$-MeOH, 9:1); $^1$H NMR ($CDCl_3$) δ 7.8 (d, J=12.2 Hz, 1H), 7.16 (s, 2H), 5.65 (d, J=12.2 Hz, 1H), 3.92 (s, 6H), 3.89 (s, 3H), 3.04 (br, 6H); MS (ES) m/z 266 $(M+H)^+$.

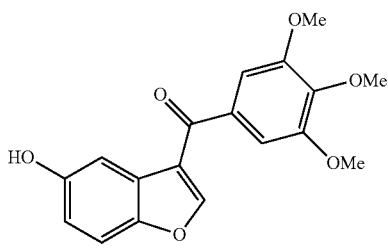 [SMILES: COc1cc(C(=O)c2coc3ccc(O)cc23)cc(OC)c1OC]

(5-Hydroxy-benzofuran-3-yl)-(3,4,5-trimethoxy-phenyl)-(-methanone (19)

A suspension of enaminone 18 (2.0 g, 7.46 mmol) and compound Q-4 (800 mg, 7.46 mmol) in acetic acid (10 mL) was stirred at room temperature under an atmosphere of $N_2$ for 5 h. The resulting precipitate was filtered, washed with water, and dried under high vacuum to obtain compound 19 (1.5 g, 60%) as a brown solid. TLC $R_f$=0.6 (petroleum ether-EtOAc, 5:5); $^1$H NMR (DMSO-$d_6$) δ 9.46 (s, 1H), 8.7 (s, 1H), 7.52-7.49 (m, 2H), 7.17 (s, 2H), 6.86 (dd, J=8.7, 2.7 Hz, 1H), 3.87 (s, 6H), 3.77 (s, 3H); MS (ES) m/z 329 (M+H)$^+$.

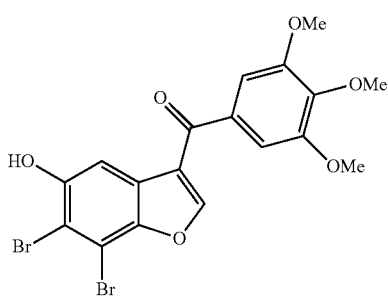 [SMILES: COc1cc(C(=O)c2coc3c(Br)c(Br)c(O)cc23)cc(OC)c1OC]

(6,7-Dibromo-5-hydroxy-benzofuran-3-yl)-(3,4,5-trimethoxy-phenyl)methanone(21)

A suspension of enaminone 18 (500 mg, 1.86 mmol) and compound Q-5 (500 mg, 2.1 mmol) in acetic acid (10 mL) was stirred at room temperature under an atmosphere of $N_2$ for 5 h. The resulting precipitate was filtered, washed with water, and dried under high vacuum to afford compound 21 (500 mg, 55%) as an off-white solid. TLC $R_f$=0.7 (CHCl$_3$-MeOH, 9:1); $^1$H NMR (DMSO-$d_6$) δ 8.66 (s, 1H), 7.72 (s, 1H), 7.20 (s, 2H), 3.88 (s, 6H), 3.78 (s, 3H); MS (ES) m/z 487 (M+H)$^+$.

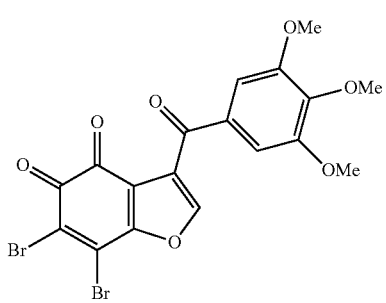

6,7-Dibromo-3-(3,4,5-trimethoxy-benzoyl)-benzofuran-4,5-dione (SKC-BF-13)

To a suspension of compound 21 (100 mg, 0.20 mmol) in glacial acetic acid (2 mL) at room temperature was added nitric acid (0.1 mL, d 1.35) dropwise with vigorous stirring. The mixture was heated at 60° C. for 3 h, allowed to cool to room temperature, and poured into cold water. The resulting precipitate was filtered and recrystallized to furnish compound SKC-BF-13 (50 mg, 49%) as an orange solid. TLC $R_f$=0.6 (CHCl$_3$-MeOH, 9:1); $^1$H NMR (CDCl$_3$) δ 7.89 (s, 1H), 7.26 (s, 2H), 3.88 (s, 3H), 3.87 (s, 6H); MS (ES) m/z 501 (M+H)$^+$.

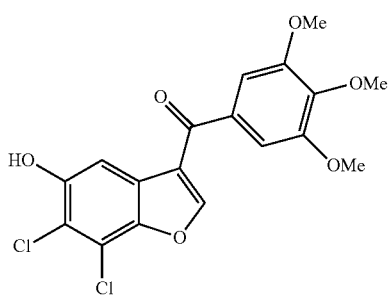 [SMILES: COc1cc(C(=O)c2coc3c(Cl)c(Cl)c(O)cc23)cc(OC)c1OC]

(6,7-Dichloro-5-hydroxy-benzofuran-3-yl)-(3,4,5-trimethoxy-phenyl)methanone (22)

A suspension of enaminone 18 (500 mg, 1.86 mmol) and compound Q-6 (330 mg, 1.87 mmol) in acetic acid (10 mL) was stirred at room temperature for 5 h under an atmosphere of $N_2$. The resulting precipitate was filtered, washed with water, and dried under high vacuum to afford compound 22 (500 mg, 67%) as an off-white solid. TLC $R_f$=0.5 (petroleum ether-EtOAc, 7:3); $^1$H NMR (DMSO-$d_6$) δ 10.7 (s, 1H), 8.88 (s, 1H), 7.7 (s, 1H), 7.2 (s, 2H), 3.87 (s, 6H), 3.77 (s, 3H); MS (ES) m/z 397 (M+H)$^+$.

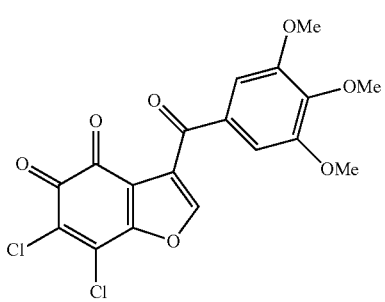

6,7-Dichloro-3-(3,4,5-trimethoxy-benzoyl)-benzofuran-4,5-dione (SKC-BF-11)

To a suspension of compound 22 (100 mg, 0.25 mmol) in glacial acetic acid (2 mL) at room temperature was added nitric acid (0.1 mL, d 1.35) dropwise with vigorous stirring. The mixture was heated at 60° C. for 3 h, left to cool for 30 min, and poured into cold water. The resulting precipitate was filtered and recrystallized to afford compound SKC-BF-11 (50 mg, 49%) as an orange solid. TLC $R_f$=0.6 (CHCl$_3$-MeOH, 9:1); $^1$H NMR (CDCl$_3$) δ 7.90 (s, 1H), 7.13 (s, 2H), 3.95 (s, 3H), 3.88 (s, 6H); MS (ES) m/z 411 (M+H)$^+$.

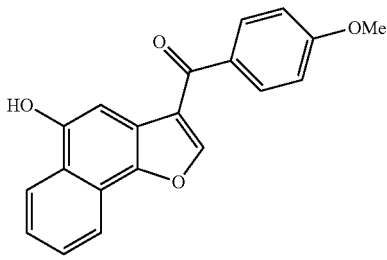

(5-Hydroxy-naphtho[1,2-b]furan-3-yl)-(4-methoxyphenyl)-methanone (23)

A suspension of enaminone 6 (500 mg, 2.42 mmol) and NQ-1 (380 mg, 2.42 mmol) in acetic acid (10 mL) was stirred at room temperature for 5 h under an atmosphere of $N_2$. The resulting precipitate was filtered, washed with water, and dried under high vacuum to obtain compound 23 (400 mg, 51%) as an off-white solid. TLC $R_f$=0.5 (petroleum ether-EtOAc, 7:3); $^1$H NMR (DMSO-$d_6$) δ 10.24 (s, 1H), 8.68 (s, 1H), 8.26 (d, J=8.3 Hz, 1H), 8.22 (d, J=8.0 Hz, 1H), 7.96 (d, J=8.7 Hz, 2H), 7.70 (app t, 1H), 7.67-7.55 (m, 2H), 7.12 (d, J=8.7 Hz, 2H), 3.89 (s, 3H); MS (ES) m/z 319 (M+H)$^+$.

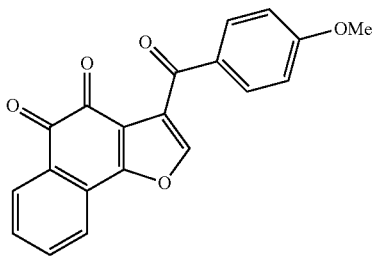

SKC-NF-01

3-(4-Methoxy-benzoyl)-naphtho[1,2-b]furan-4,5-dione (SKC-NF-01)

To a suspension of compound 23 (100 mg, 0.31 mmol) in glacial acetic acid (1.5 mL) at room temperature was added nitric acid (0.2 mL, d 1.35) dropwise with vigorous stirring. The mixture was then heated at 45° C. for 30 min, left to cool for 30 min, and poured into cold water. The resulting precipitate was filtered and recrystallized to obtain compound SKC-NF-01 (45 mg, 43%) as an orange solid. TLC $R_f$=0.4 ($CH_2Cl_2$-MeOH, 9:1); $^1$H NMR (CDCl$_3$) δ 8.13 (d, J=7.0 Hz, 1H), 7.90 (app d, 2H), 7.86-7.82 (m, 2H), 7.72 (app t, 1H), 7.54 (app t, 1H), 6.94 (m, 2H), 3.88 (s, 3H); MS (ES) m/z 333 (M+H)$^+$.

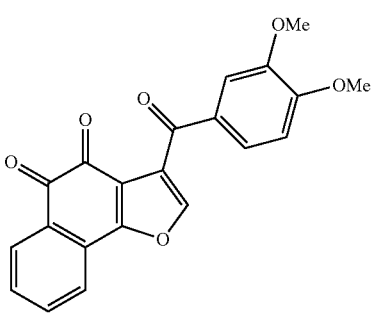

24

(3,4-Dimethoxy-phenyl)-(5-hydroxy-naphtho[1,2-b]furan-3-yl)-methanone (24)

A suspension of enaminone 12 (2.0 g, 8.43 mmol) and NQ-1 (1.33 g, 8.43 mmol) in acetic acid (20 ml) was stirred at room temperature for 5 h under an atmosphere of $N_2$. The resulting precipitate was filtered, washed with water, and dried under high vacuum to afford compound 24 (1.5 g, 50%) as an off-white solid. TLC $R_f$=0.5 (petroleum ether-EtOAc, 5:5); $^1$H NMR (DMSO-$d_6$) δ 8.72 (s, 1H), 8.28 (d, J=8.3 Hz, 1H), 8.22 (d, J=8.3 Hz, 1H), 7.70 (app t, 1H), 7.60-7.50 (band, 4H), 7.15 (d, J=8.3 Hz, 1H), 3.89 (s, 3H), 3.87 (s, 3H); MS (ES) m/z 349 (M+H)$^+$.

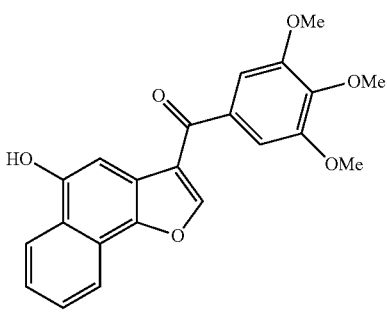

SKC-NF-02

3-(3,4-Dimethoxy-benzoyl)-naphtho[1,2-b]furan-4,5-dione (SKC-NF-02)

To a suspension of compound 24 (100 mg, 0.28 mmol) in glacial acetic acid (1.5 mL) at room temperature was added nitric acid (0.2 mL, d 1.35) dropwise with vigorous stirring. The mixture was heated at 45° C. for 30 min, allowed to cool to room temperature, and poured into cold water. The resulting precipitate was filtered and recrystallized to afford compound SKC-NF-02 (45 mg, 43%) as an orange solid. TLC $R_f$=0.4 (CHCl$_3$-MeOH, 9:1); $^1$H NMR (CDCl$_3$) δ 8.13 (d, J=7.0 Hz, 1H), 7.81 (m, 2H), 7.74 (app t, 1H), 7.61 (app s, 1H), 7.55 (app t, 1H), 7.43 (dd, J=8.4 Hz, 2.1 Hz, 1H), 6.85 (d, J=8.3 Hz, 1H), 3.96 (s, 6H); MS (ES) m/z 363 (M+H)$^+$.

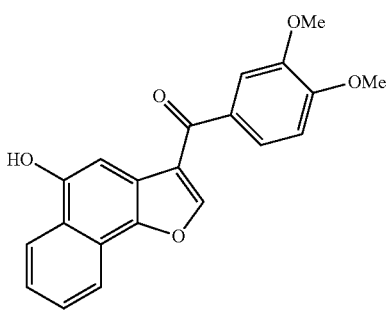

25

(5-hydroxy-naphtho[1,2-b]furan-3-yl)-(3,4,5-trimethoxyphenyl)-methanone (25)

A suspension of enaminone 18 (2.0 g, 7.46 mmol) and NQ-1 (1.18 g, 7.46 mmol) in acetic acid (20 mL) was stirred at room temperature for 5 h under an atmosphere of $N_2$. The resulting precipitate was filtered, washed with water, and dried under high vacuum to afford compound 25 (1.5 g, 53%) as an off-white solid. TLC $R_f$=0.5 (petroleum ether-EtOAc, 7:3); $^1$H NMR (DMSO-$d_6$) δ 10.30 (br s, 1H), 8.83 (s, 1H), 8.27 (d, J=8.3 Hz, 1H), 8.22 (d, J=8.3 Hz, 1H), 7.70 (app t, J=7.3 Hz, 1H), 7.58 (m, 2H), 7.23 (s, 2H), 3.89 (s, 6H), 3.79 (s, 3H); MS (ES) m/z 379 (M+H)$^+$.

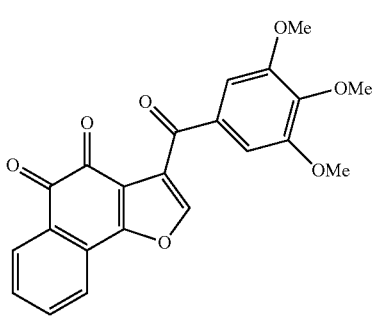

3-(3,4,5-Trimethoxy-benzoyl)-naphtho[1,2-b]furan-4,5-dione (SKC-NF-03)

To a suspension of compound 25 (250 mg, 0.66 mmol) in glacial acetic acid (1.5 mL) at room temperature was added nitric acid (0.4 mL, d 1.35) dropwise with vigorous stirring. The mixture was heated at 45° C. for 30 min, allowed to cool to room temperature, and poured into cold water. The resulting precipitate was filtered and recrystallized to furnish compound SKC-NF-03 (100 mg, 38%) as a yellow solid. TLC $R_f$=0.6 (CHCl$_3$-MeOH, 9.5:0.5); $^1$H NMR (CDCl$_3$) δ 8.15 (d, J=7.6 Hz, 1H), 7.84-7.80 (m, 2H), 7.73 (app t, 1H), 7.55 (app t, 1H), 7.18 (s, 2H), 3.95 (s, 3H), 3.87 (s, 6H); MS (ES) m/z 393 (M+H)$^+$.

Example 3

Figure 4:
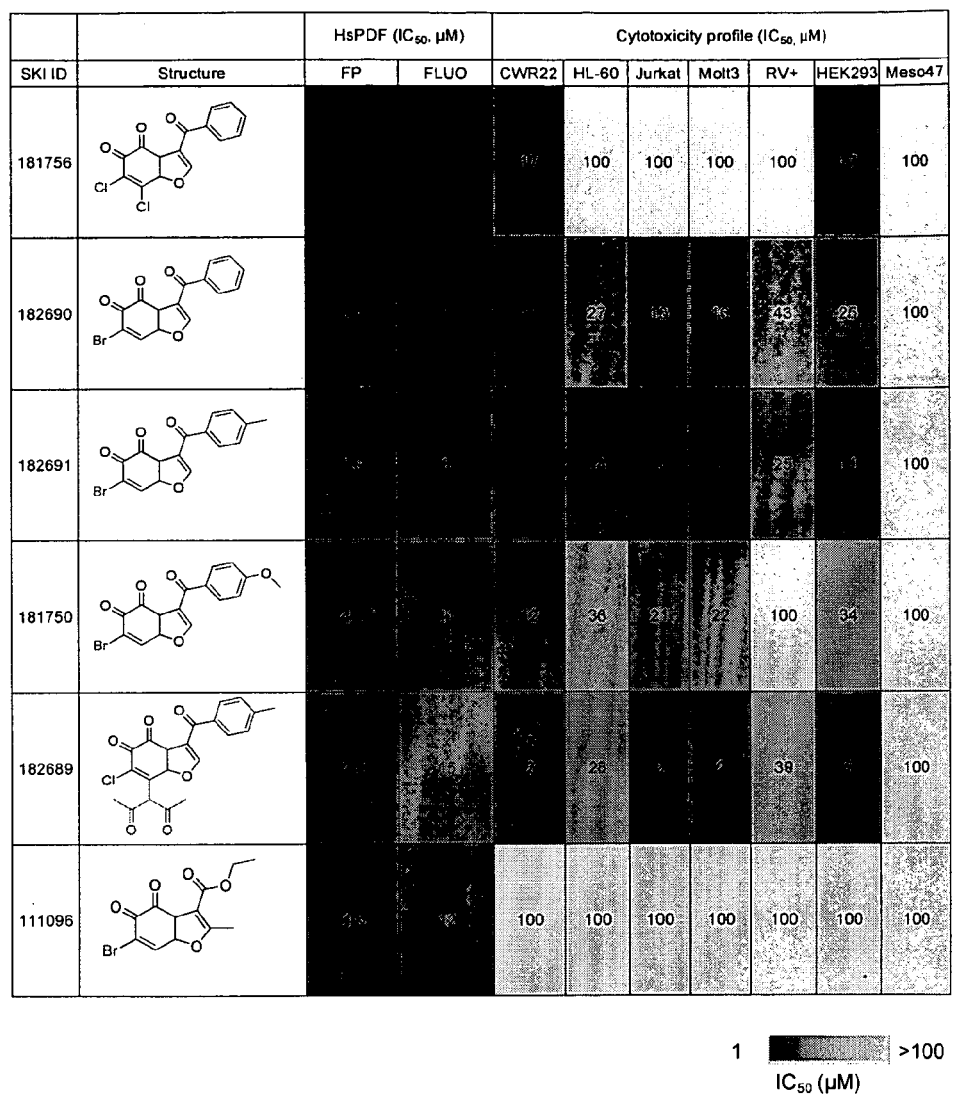
FIG. 4. The $IC_{50}$ in μM for HsPDF for each of the six primary hits and the cytotoxicity profile in seven different cell lines.

Specificity Profiling of the Newly Synthesized Benzofuran-4,5-Diones Derivatives Specificity profiling was performed on the newly synthesized benzofuran-4,5-diones using the aforementioned FP profiling method (Antczak et al., *J. Biomol. Screen* 2008, 13, 285-294). The panel of metalloproteases for this study comprised HsPDF, EcPDF, APN and MMP-1. The results of this study are summarized as a heat map (FIG. 4). Interestingly, all but three derivatives out of sixteen were potent against HsPDF and all three inactive derivatives resulted from modifications described above in (c). All synthetic intermediates analyzed were inactive toward HsPDF. Importantly, none of the tested derivatives were potent against EcPDF, indicating that the modifications undertaken on the benzofuran-4,5-dione core scaffold in this study did not alter its specificity for HsPDF over EcPDF. Finally, the derivatives had various degrees of specificity for HsPDF over aminopeptidase N (APN). SKC-BF-01 and SKC-BF-02 were the most selective HsPDF inhibitors when tested in a panel of metalloproteases.

Example 4

SAR of the Newly Synthesized Benzofuran-4,5-Diones Derivatives for the Inhibition of HsPDF and EcPDF Thirteen derivatives found to be potent toward HsPDF in the specificity profiling study and one of the inactive derivatives (SKC-NF-01) were selected for further study. Dose-response studies were performed for the fourteen selected derivatives toward HsPDF and EcPDF in the FP assay in order to assess the potency of those compounds toward HsPDF and to confirm their selectivity for HsPDF over EcPDF. A table summarizing the calculated IC$_{50}$ for each compound toward both enzymes is attached in FIG. 4. All tested derivatives were inactive or weakly potent toward EcPDF (i.e., SKC-BF-10, IC$_{50}$=67 μM; all other compounds, IC$_{50}$>100 μM), confirming that the modifications undertaken on the core scaffold in this study did not affect the selectivity of benzofuran-4,5-diones for HsPDF over EcPDF. Naphthofurandione derivative SKC-NF-01 was inactive toward HsPDF. All other tested derivatives were active toward HsPDF, with a calculated IC$_{50}$ ranging from 5.2 μM to 65 μM. This confirmed the potency of benzofuran-4,5-diones toward HsPDF. Interestingly, the number (1 or 2) or the nature (chloro versus bromo) of the halogen substitution on the 4,5-orthodione moiety (i.e., modification (a)) did not significantly affect the activity of benzofuran-4,5-diones. Only the absence of a halogen seemed to decrease the potency of the tested derivatives (SKC-BF-01 and SKC-BF-02, IC$_{50}$=59 and 34 μM respectively). Of the derivatives with modification (b), it was concluded that the presence of several methoxy substituents at −2, −3 and −4 positions on the benzoyl moiety is beneficial for activity toward HsPDF. The six most active derivatives bear one to three such moieties, while the six least potent derivatives bear either none or only one methoxy group (FIG. 5).

Example 5

Figure 6:
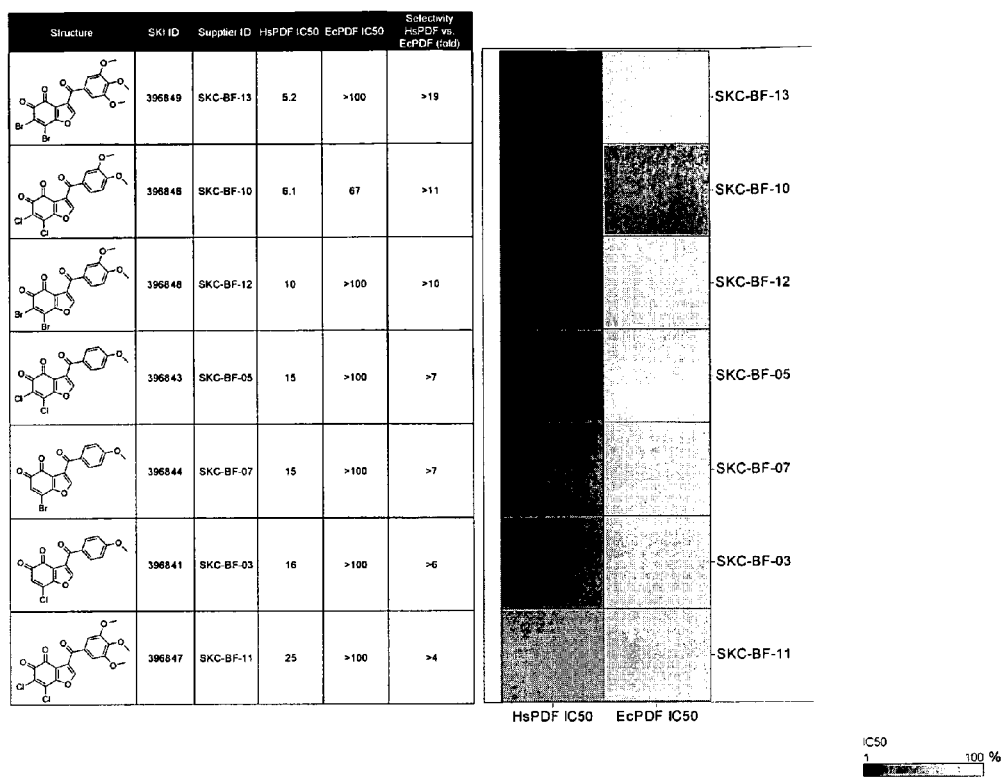
FIG. 6. Compared potency for fourteen newly synthesized derivatives of benzofuran-4,5-diones toward HsPDF and EcPDF. The $IC_{50}$ in µM for each compound for both enzymes as assessed using the FP assay is summarized in the table.
Figure 6:
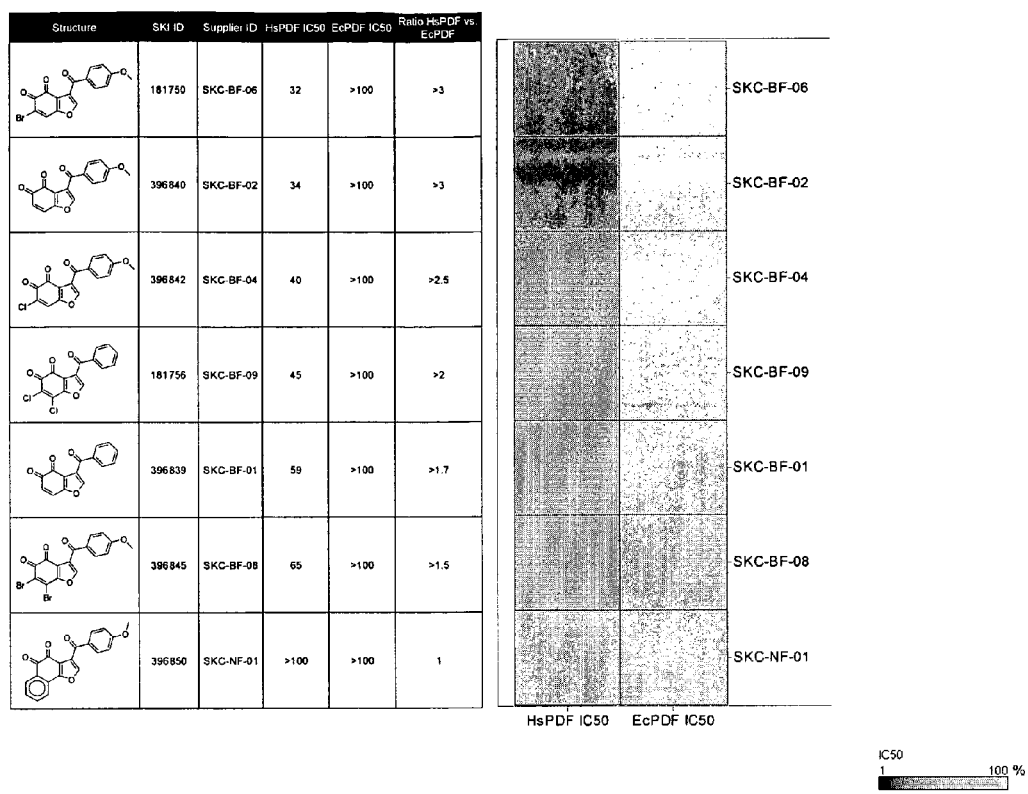

SAR of the Newly Synthesized Benzofuran-4,5-Diones Derivatives for In Vitro Anti-Cancer Activity Cytotoxicity assays were performed in order to profile the thirty-three newly synthesized benzofuran-4,5-dione derivatives on a panel of nine cancer cell lines. A heat map summarizes the calculated IC$_{50}$s (FIG. 6). Twelve out of thirteen derivatives potent toward HsPDF were also cytotoxic toward several cancer cell lines (FIG. 7). Only one outlier (i.e., SKC-BF-10) was not very active toward any cancer cell line tested, while being a potent HsPDF inhibitor. Similarly, sixteen out of twenty derivatives inactive toward HsPDF had no anti-cancer activity either. These results indicate that there is a good correlation between potency toward HsPDF and in vitro anti-cancer activity. Interestingly, the most potent HsPDF inhibitor identified in this study (i.e., SKC-BF-13, HsPDF IC$_{50}$=5.2 μM) was also the most potent anti-cancer agent (IC$_{50}$<10 μM on four cell lines). These results suggest that HsPDF constitutes an attractive target for novel, broad-acting anti-cancer agents and highlights SKC-BF-13 as a promising lead compound for future exploratory chemistry.

Assessment of the in vivo Toxicity of Benzofuran-4,5-diones

Lead compound SKC-BF-13 and another newly synthesized derivative SKC-BF-02 were selected in order to assess the in vivo toxicity of benzofuran-4,5-diones. Three mice per group were treated with BF-13 at three doses (i.e., 1, 5 and 10 mg/kg) or with SKC-BF-02 at two doses (i.e., 1 and 10 mg/kg). A control group of two mice were treated with the vehicle (i.e., 20% DMSO v/v). Mice were treated twice a day for four days via intraperitoneal administration. Their weight was monitored along with any other signs of toxicity for fourteen days. It was found that none of the treatments induced any sign of toxicity, indicating that benzofuran-4,5-diones are safe to use in vivo.

Example 6

Materials and Methods: Reagents

The probe SKI 267088 was synthesized at the Sloan-Kettering Organic Synthesis Core Facility. The molecular weight of SKI 267088 was confirmed by Mass Spectrometry analysis performed at the Sloan-Kettering Analytical Pharmacology Core Facility. The peptide N-formyl-Met-Ala-His-Ala was purchased from Biopeptide Co., Inc. (San Diego, Calif.). Fluorescamine, Actinonin, and L-Alanine were obtained from Sigma Chemical Co. (St Louis, Mo.). Human recombinant MMP-1, -2, -8, -9, -10 were obtained from Biomol International (Plymouth Meeting, Pa.). APN (microsomal Leucine Aminopeptidase from porcine kidney) was purchased from Sigma Chemical Co. (St Louis, Mo.). ADAM10 was kindly provided by Dimitar Nikolov (Structural Biology, Sloan-Kettering Institute, NY) and EcPDF by David A. Scheinberg (Molecular Pharmacology, Sloan-Kettering Institute, NY).

Expression and Purification of MBP-HsPDF

A 63 amino acid N-terminally truncated human peptide deformylase (HsPDF) was cloned as a fusion with maltose binding protein (MBP), with MBP at the N-terminus. HsPDF was cloned into the vector pIADL-16 (McCafferty et al., *Biochemistry* 1997, 36, 10498-10505), which contains the coding sequence for MBP expressed under the control of the T7 promoter. HsPDF was subcloned into pIADL-16 from a restriction digest of a pET-29b vector containing HsPDF (Lee et al., *Biochem. Biophys. Res. Commun.* 2003, 312, 309-315). Ligation of the NdeI/XhoI restriction fragment from pET-29b into pIADL-16 resulted in a vector (pIADL-16-MBP-HsPDF) coding for an MBP-HsPDF fusion with a C-terminal 6His-tag. BL21 (DE3) competent cells were transformed with pIADL-16-MBP-HsPDF and the plasmid GroES/EL, which codes for a chaperone. Transformed bacteria were inoculated in 100 mL of LB media containing ampicillin and kanamycin at 50 μg/mL and 10 μg/mL, respectively, and grown overnight at 37° C. The overnight culture was diluted 1:50 in 4 L of fresh LB with the same concentration of antibiotics described above. These cells were allowed to grow at 37° C. for approximately two hours, until the OD at 600 nm reached 0.4-0.8. Induction was initiated by addition of IPTG at a final concentration of 0.1 mM and 0.1 mM $CoCl_2$ followed by incubation at 20° C. for five hours. Cells were harvested by centrifuging at 5,000 rpm for 30 min. The cell pellet was again suspended in a 50 mL final volume of buffer (i.e., 50 mM HEPES pH 7.5, 50 mM NaCl, 0.1 mM $CoCl_2$) and lysed by passing through a french press twice. The cell lysate was centrifuged at 15,000 g for 45 minutes. The supernatant was applied to a column packed with 15 mL of amylose-resin slurry (New England Biolabs). MBP-HsPDF was eluted with a maltose gradient starting with lysis buffer without maltose, to reach a final concentration of 10 mM maltose in the same buffer. Fractions containing MBP-HsPDF, determined through SDS-PAGE, were pooled and the protein concentration measured using the Dc protein assay (Bio-rad). MBP-HsPDF purity was assessed by SDS-PAGE and GelCode Blue staining (Pierce). Per liter of cell culture, about 20-30 mg of MBP-HsPDF were obtained.

FP Binding Assay

Compounds or high/low controls were added to the wells at a volume of 2 μL. Low controls for this assay consisted of actinonin at a final concentration of 100 μM in 1% DMSO (v/v). High controls consisted of 1% DMSO (v/v). MBP-HsPDF or the metalloprotease to be tested was diluted in the assay buffer (25 mM Hepes, 50 mM NaCl, 0.005% Tween 20, pH 7.5), and 10 μL where added to the 384-well microplates (Low Volume Round Bottom NBS Treated, Corning) to achieve a final concentration of 1 μM. After addition of MBP-HsPDF to the tested compounds, the 384-well microplates were preincubated for one hour at room temperature. Then 8 μL of the probe SKI 267088 in solution in assay buffer was added to the wells at a final concentration of 5 nM. After one hour incubation at room temperature, the fluorescence polarization was read using the Amersham LEADseeker™ Multi-modality Imaging System equipped with Cy3 excitation/emission filters and Cy3 FP epi-mirror. Quench tests were performed in duplicate by measuring the fluorescence polarization of wells containing the probe, pre- and post-addition of the compounds at 100 μM. Compounds inducing a variation of fluorescence polarization greater than 20% were flagged as optically-active compounds.

Example 7

FLUO Assay

Compounds or high/low controls were added to the wells at a volume of 2 μL. Low controls for this assay consisted of actinonin at a final concentration of 100 μM in 1% DMSO (v/v). High controls consisted of 1% DMSO (v/v). MBP-HsPDF was diluted in the assay buffer (25 mM Hepes, 50 mM NaCl, 0.005% Tween 20, pH 7.5), and 10 μL of this solution was added to the wells of the 384 format microplates (Low Volume Round Bottom NBS Treated, Corning) at a final concentration of 1 μM. After one hour incubation at room temperature, 10 μL of the substrate peptide fMAHA diluted in the assay buffer was added to the wells at a final concentration of 0.5 mM. The deformylation reaction mixture was incubated for one hour at room temperature. A separate set of plates containing 3 μL of fluorescamine at 1 mg/mL in 100% DMSO was prepared for the labeling step. Then, 17 μL of the reaction mixture from the original set of plates was transferred to the plates containing the fluorescamine solution for the labeling step. The readout was performed on a Perkin Elmer VICTOR³ V™ Multi label counter, using an excitation wavelength of 355 nm, and an emission wavelength of 460 nm. Quench tests were performed in duplicate by measuring the fluorescence of wells containing L-alanine labeled with fluorescamine as a surrogate for the fluorescamine-labeled deformylated substrate, pre- and post-addition of the compounds at 100 μM. Compounds inducing a variation of fluorescence greater than 20% were flagged as optically active compounds.

Example 8

Cytotoxicity Assay

The cell lines HL-60 (human acute promyelocytic leukemia), Jurkat (human acute T cell leukemia), Molt3 (acute lymphoblastic leukemia), CWR22 (prostate carcinoma), HEK293 (human embryonic kidney), K562 (human chronic myeloid leukemia lymphoblasts), Y79 (human retinoblastoma) were obtained from the ATCC, and cultured following ATCC recommendations. The cell line NCEB-1 (human non-hodgkin lymphoma) was obtained from Dr. O'Connor (Sloan-Kettering Institute). The cell line HL-60/RV+ (a P-glycoprotein-overexpressing multi-drug resistant HL-60 variant selected by continuous exposure to vincristine) was described elsewhere (Weisburg et al., *J. Biol. Chem.* 1999, 274, 10877-10888). The cell line ALL-3 (acute lymphoblastic leukemia isolated from a patient treated at MSKCC and characterized as Philadelphia chromosome positive) was obtained from Dr. Mark Frattini (MSKCC). The assay used for the cytotoxicity studies is based on the dye resazurin and commercially sold as Alamar Blue (O'Brien et al., *Eur. J. Biochem.* 2000, 267, 5421-5426). Cells were added in 45 μL medium to the pre-plated compounds in 5 μL of 1% DMSO (v/v). After incubation for 72 hours, 5 μL of Alamar Blue was added. The cells were then incubated for another 24 hours, and the fluorescence intensity was read on the Amersham LEADseeker™ Multimodality Imaging System equipped with Cy3 excitation and excitation filters and FLINT epi-mirror. Quench tests were performed in duplicate by measuring the fluorescence of wells with cells grown in the same assay conditions, pre- and post-addition of the compounds at 100 Compounds inducing a variation of fluorescence greater than 20% were flagged as optically-active compounds.

Example 9

Dose Response Studies

In each assay, the signal inhibition induced by the compounds was expressed as a percentage compared to high and low controls located on the same plate, as defined as % Inhibition=(high control average−read value)/(high control average−low control average)×100. The dose response was assessed in duplicate and using 12 point doubling dilutions with 100 μM compound concentration as the upper limit. The dose response curve for each set of data was fitted separately, and the two $IC_{50}$ values obtained were averaged. For compounds having an $IC_{50}$ below $1_t$ μM, the dose response study was repeated using dilutions starting at 10 μM for more accurate determination of the $IC_{50}$ value.

Example 10

In vivo Studies

ICR/SCID male mice about three weeks old were used in this study. Three mice per group were treated with BF-13 at three doses (i.e., 1, 5 and 10 mg/kg) or with SKC-BF-02 at two doses (i.e., 1 and 10 mg/kg). A control group of two mice were treated with the vehicle (20% DMSO v/v). Mice were treated twice a day for four days via intraperitoneal administration. Their weight was monitored as well as any other sign of toxicity for 14 days.

Example 11

In vivo Studies of Three benzofuran-4,5-diones (SKI 396848, SKI 396840, and SKI 396849)

Assessment of the in vivo toxicity of benzofuran-4,5-diones.

Figure 8:
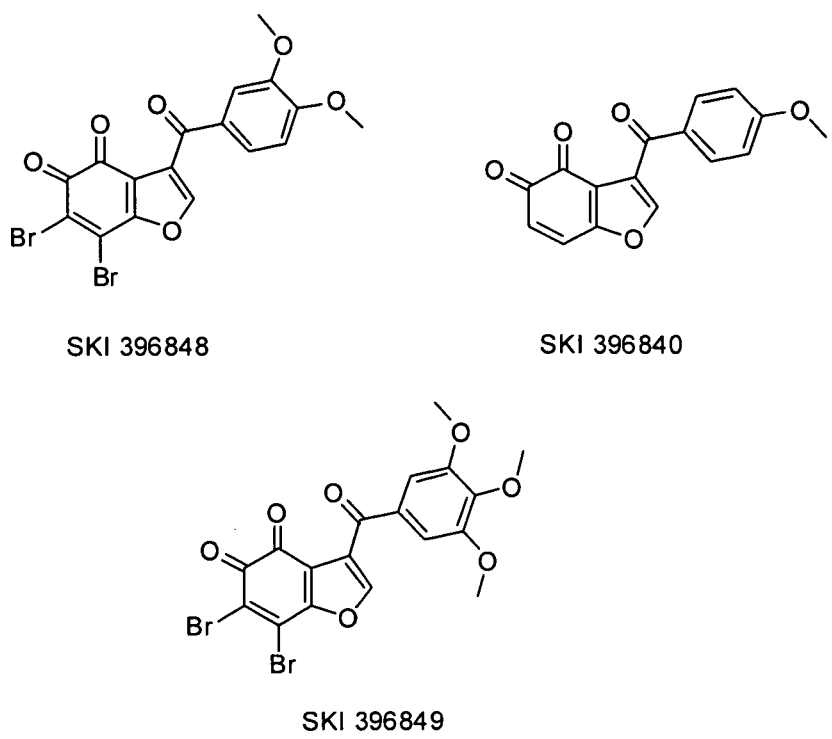
FIG. 8. Structures of the first generation benzofuran-4,5-dione derivatives evaluated in vivo.

SKI 396848 (SKC-BF-12) and SKI 396840 (SKC-BF-02) were synthesized during the first round of exploratory chemistry to assess the in vivo toxicity of benzofuran-4,5-diones (as shown in FIG. 8). Three ICR/SCID male mice per group were treated with SKI 396848 at three doses: 1, 5 and 10 mg/kg or with SKI 396840 at two doses: 1 and 10 mg/kg. A control group of two mice was treated with the vehicle (20% DMSO v/v). Mice were treated twice a day for four days i.p. Their weight was monitored as well as any other sign of toxicity for 14 days. One treated mouse per group was evaluated by a pathologist. None of the treatments were found to induce any signs of toxicity, indicating that benzofuran-4,5-diones are safe to use in vivo.

Assessment of the in vivo efficacy of benzofuran-4,5-diones.

Figure 9A:
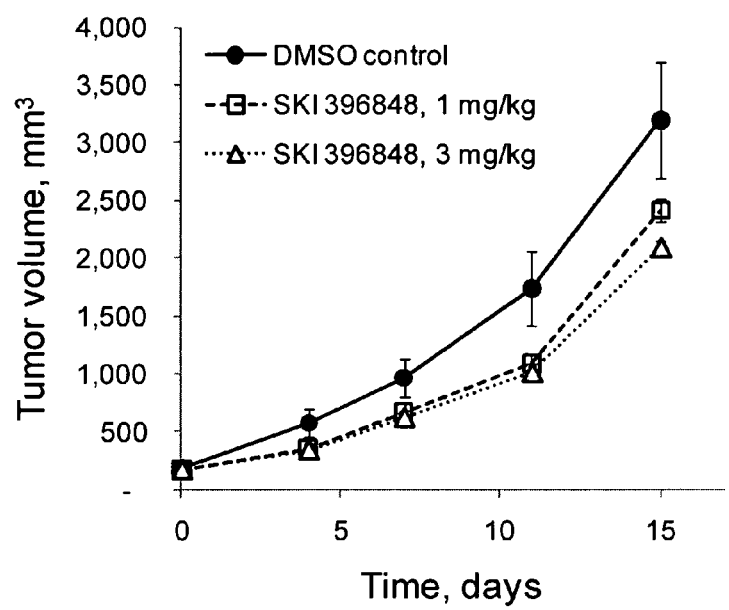
FIG. 9. In vivo efficacy assessment of the first generation benzo-4,5-diones SKI 396848 and SKI 3968489. A. In vivo assessment of SKI 396848 in a mouse xenogrant model using ALL-3 cells isolated from a patient with acute lymphoblastic leukemia refractory to imatinib. B. In vivo efficacy assessment of SKI 396849 in a mouse xenogrant model using acute T-cell leukemia Jurkat cells.
Figure 9B:
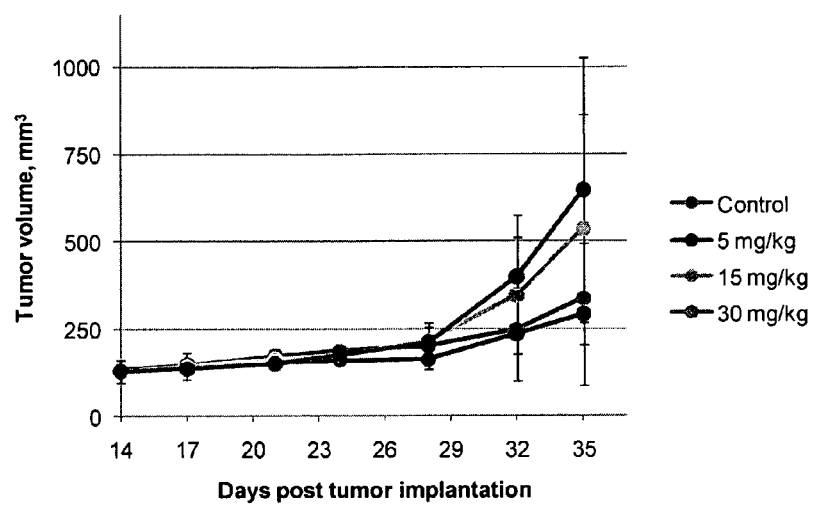

The in vivo efficacy of SKI 396848 (SKC-BF-12) was assessed in a mouse xenograft model using ALL-3 cells isolated from a patient with acute lymphoblastic leukemia refractory to imatinib. Three mice per group were treated at two doses: 1 and 3 mg/kg. A control group of three mice was treated with the vehicle (20% DMSO v/v). Mice were treated twice a week for two weeks i.p. Their weight was monitored as well as any other sign of toxicity for 14 days. As expected in respect to the somewhat low potency of this compound in vitro toward ALL3 cells ($IC_{50}$=36 μM), only a slight delay in tumor progression was observed in mice treated at the low doses of 1 and 3 mg/kg (FIG. 9). Nonetheless, the observed difference between the treated groups and the control group was significant, and our study provides a solid proof of concept for the use of benzofuran-4,5-dione based HsPDF inhibitors as novel antitumor agents in vivo.

In a second study, the in vivo efficacy of the compound SKI 396849 (SKC-BF-13) (FIG. 8) was assessed and found to be especially potent toward the Jurkat cell line (acute T-cell leukemia, $IC_{50}$=3 μM). In this study, higher doses could be achieved by injecting the drug in a small volume (100 μL) of 100% DMSO (v/v). Three mice per group were treated at three doses: 5, 15 and 30 mg/kg. A control group of three mice was treated with the vehicle (100% DMSO v/v). Mice were treated i.p. twice a week for three weeks. Unfortunately, a large variability in the growth of the Jurkat tumors caused data interpretation to be difficult. Nonetheless, this experiment demonstrates that the benzofurandione SKI 396849 was well tolerated up to 30 mg/kg, since no loss of weight was observed for any of the treated groups.

Example 12

Further Exploratory Chemistry of benzofuran-4,5-diones

In the first round of SAR described above, three areas for modification of the benzofuran-4,5-dione scaffold were focused on: (FIG. 3):

A. Halogen substitutions at α- and β-positions on the 4,5-orthodione moiety;

B. Effect of methoxy substituents at −2, −3 and −4 positions on the benzoyl moiety; and C. Replacement of the benzofurandione moiety by a naphtofurandione moiety From this first round of SAR, we concluded that while halogen substitutions at α- and β-positions on the 4,5-orthodione moiety are not required for HsPDF activity, they do seem to increase the potency of benzofuran-4,5-diones toward HsPDF. In addition, methoxy substituents at 2-, 3-, and 4-positions on the benzoyl moiety seemed to increase the potency of benzofuran-4,5-diones in cell-based viability assays. Finally, replacement of the benzofurandione moiety by a naphtofurandione moiety abrogates the enzymatic activity as well as the cell-based activity of these derivatives.

Figure 10:
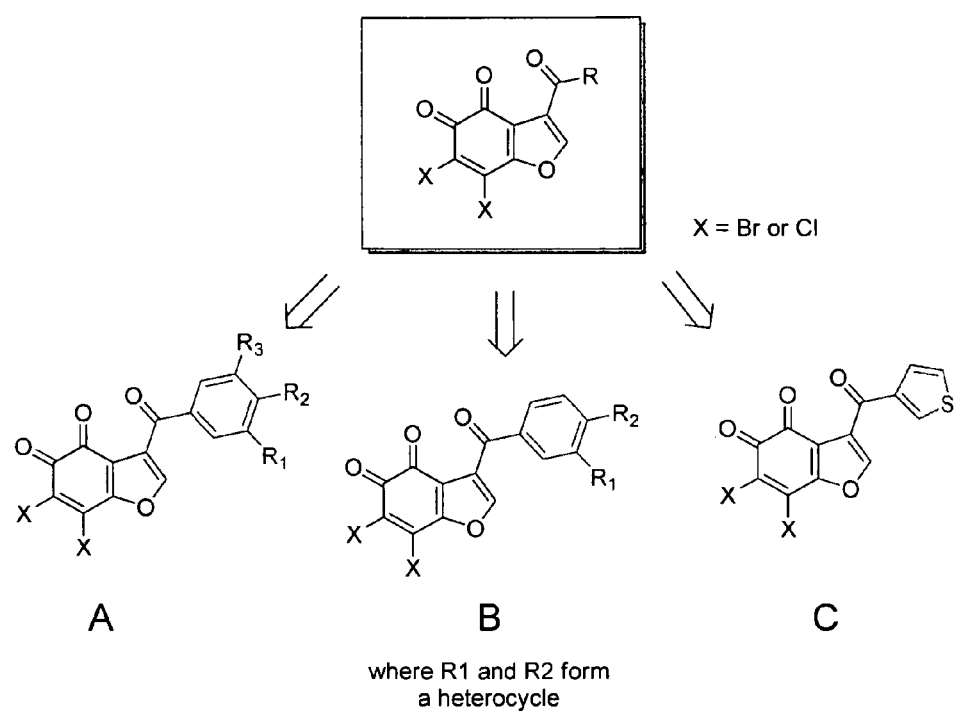
FIG. 10. Design of benzofuran-4,5-dione derivatives. A. Exploration of various substituents at the meta and para positions of the phenyl ring B. Replacement of the phenyl ring with a bicyclic heterocycle. C. Replacement of the phenyl ring with a heterocycle.

For this new round of exploratory chemistry, our objective was to further examine the SAR of benzofuran-4,5-diones to improve the potency of benzofuran-4,5-diones in enzymatic assays as well as cell-based assays. Halogen substitutions at α- and β-positions on the 4,5-orthodione moiety were kept constant and we explored both dichloro- and dibromo-derivatives. Based on the results of the first round of SAR, we focused on different R groups from the pendant phenyl ring and/or replacement of this ring with heterocycles (FIG. 10):

A. Exploration of various substituents in meta and para of the phenyl ring

B. Replacement of the phenyl ring with a bicyclic heterocycle

C. Replacement of the phenyl ring with a heterocycle

A total of 26 novel benzofuran-4,5-dione derivatives were synthesized:
- 20 derivatives with A modifications;
- 4 derivatives with B modifications; and
- 2 derivatives with C modifications.

Figure 11:
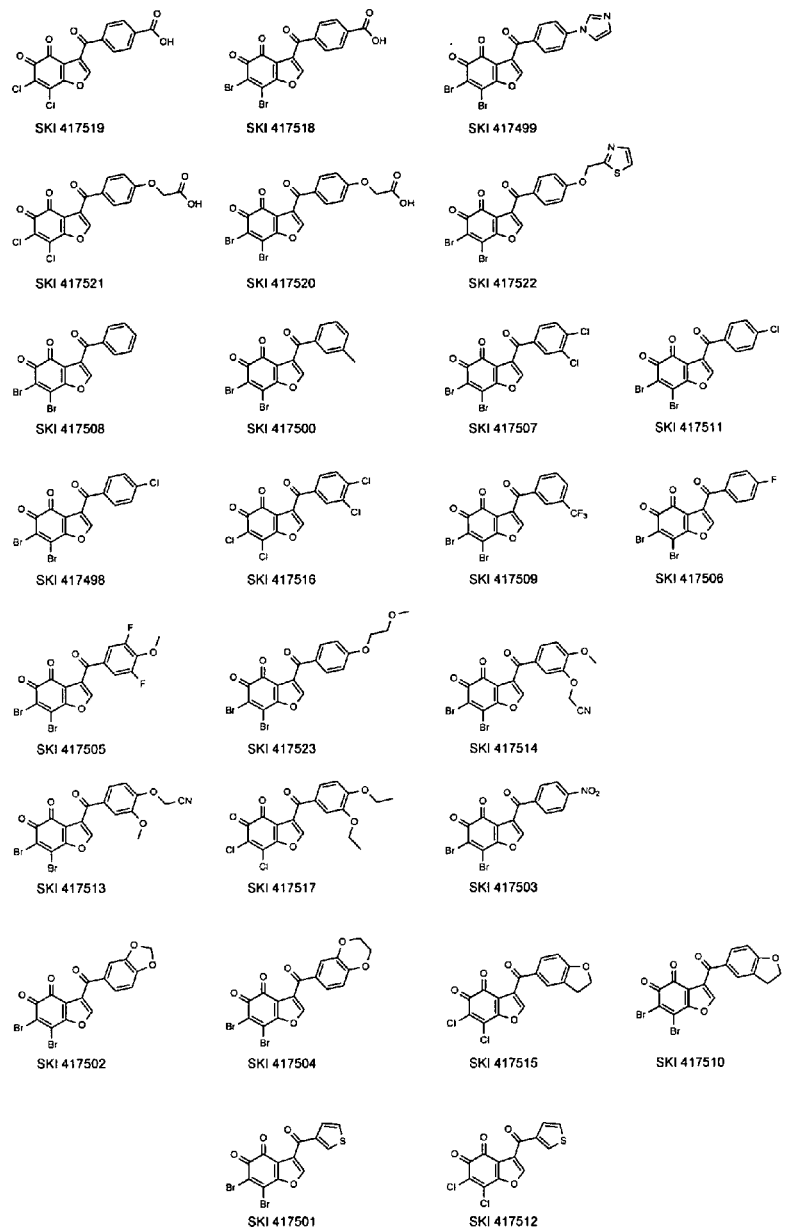
FIG. 11. Structures of 26 benzofuran-4,5-dione derivatives with A, B, and C modifications as described in FIG. 10.
Figure 12:
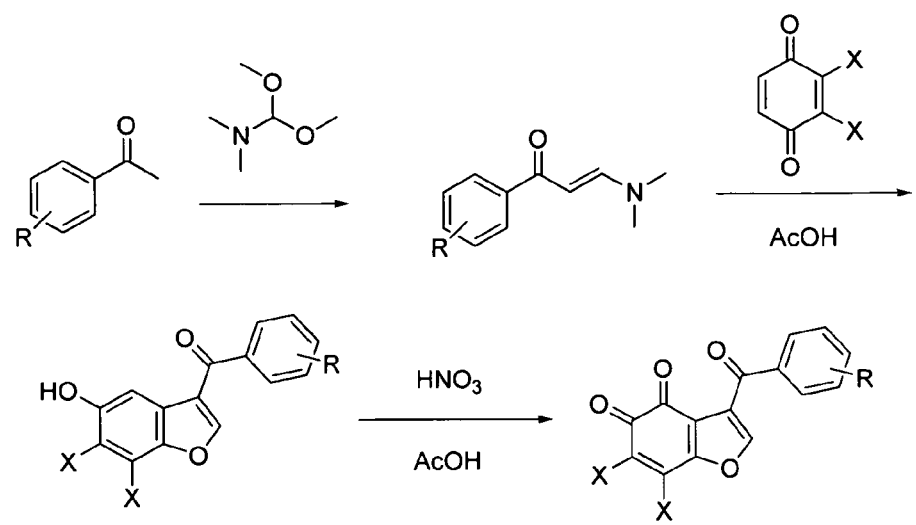
FIG. 12. Exemplary scheme for synthesizing benzofuran-4,5-dione derivatives.
Figure 13:
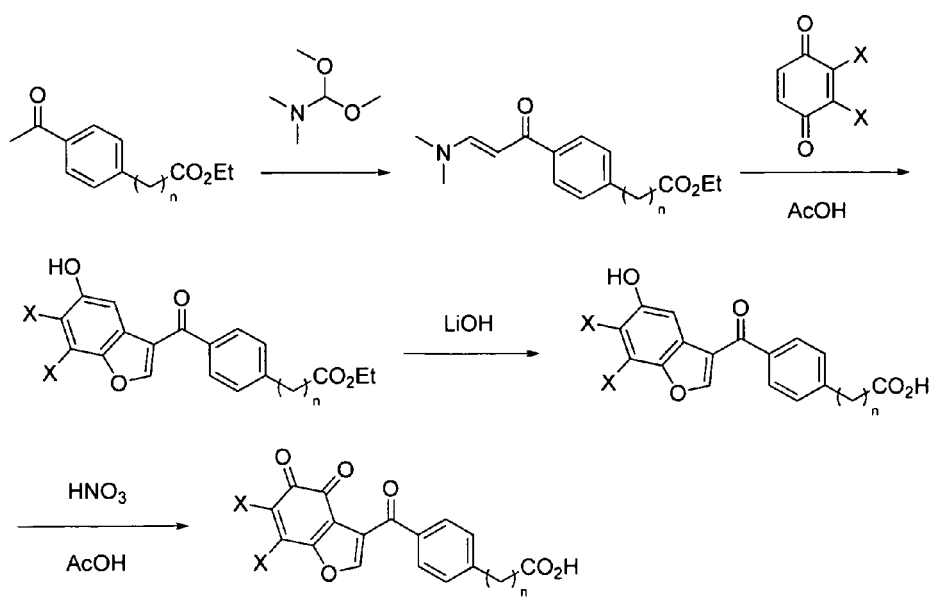
FIG. 13. Exemplary scheme for synthesizing acid derivatives of benzofuran-4,5-diones.

The structures of the 26 novel derivatives are shown in FIG. 11. The experimental methods and characterization of the novel derivatives are described below.

Solubility Limit Assessment of 26 Novel Benzofuran-4,5-Diones.

We assessed the aqueous solubility limit for the 26 novel benzofuran-4,5-diones using laser nephelometry. Laser nephelometry has been shown to be a reliable and sensitive technique for the measurement of solubility in 384-well plate format (Bevan C D, Lloyd R S: A high-throughput screening method for the determination of aqueous drug solubility using laser nephelometry in microtiter plates. *Anal Chem* 2000; 72:1781-1787). We assessed the solubility limit for each compound in dose response in duplicate and using 12 point doubling dilutions with 10 µM compound concentration as the upper limit. Data were compared to standards of known turbidity to assess the solubility limit for each compound. All compounds were found to have an aqueous solubility limit greater than 10 µM, except for the compound SKI 417516, which has an aqueous solubility limit of 5 µM. These results suggest that we were successful in preserving the aqueous solubility of the newly designed benzofurandione derivatives.

SAR of the 26 Newly Synthesized Benzofuran-4,5-Diones Derivatives for the Inhibition of HsPDF and EcPDF.

We assessed the dose response of the 26 benzofuran-4,5-diones derivatives of second generation toward HsPDF and EcPDF in a functional assay to assess their potency toward HsPDF, and to confirm their selectivity for HsPDF vs. EcPDF.

Compounds or high/low controls were added to the wells at a volume of 2 µL. Low controls for this assay consisted of actinonin at a final concentration of 100 µM in 1% DMSO (v/v). High controls consisted of 1% DMSO (v/v). MBP-HsPDF or MBP-EcPDF was diluted in the assay buffer (25 mM Hepes, 50 mM NaCl, 0.005% Tween 20, pH 7.5), and 104 of this solution was added to the wells of the 384 format microplates (Low Volume Round Bottom NBS Treated, Corning) at a final concentration of 0.5 µM for HsPDF and 0.1 µM for EcPDF. After 1 hour incubation at room temperature, 10 µl of the substrate peptide fMAHA diluted in the assay buffer was added to the wells at a final concentration of 0.5 mM. The deformylation reaction mixture was incubated for one hour at room temperature. A separate set of plates containing 3 µL of fluorescamine at 1 mg/mL in 100% DMSO was prepared for the labeling step. Then, 17 µL of the reaction mixture from the original set of plates was transferred to the plates containing the fluorescamine solution for the labeling step. The readout was performed on a Perkin Elmer VICTOR3 V™ Multi label counter, using an excitation wavelength of 355 nm, and an emission wavelength of 460 nm. The signal inhibition induced by the compounds was expressed as a percentage compared to high and low controls located on the same plate, as defined as % Inhibition=(high control average−read value)/(high control average−low control average)×100. For each assay, the dose response for each compound was assessed in duplicate and using 12 point doubling dilutions with 10 µM compound concentration as the upper limit. The dose response curve for each set of data was fitted separately, and the two $IC_{50}$ values obtained were averaged.

A table summarizing the calculated $IC_{50}$ for each compound toward both enzymes is attached in FIG. 14. Importantly, all tested derivatives were inactive toward EcPDF, confirming that the modifications undertaken on the core scaffold in this study did not affect the selectivity of benzofuran-4,5-diones for HsPDF vs. EcPDF. Nine out 26 compounds were potent toward HsPDF, with an $IC_{50}$ ranging from 0.62 to 3.4 µM. This result is significant, since we have therefore identified during this second round of exploratory chemistry the first non-hydroxamic acid-based and non-peptidomimetic-based compounds ever reported with an $IC_{50}$ lower than 1 µM in the HSPDF functional assay—and inactive toward EcPDF. Our results therefore confirm that benzofuran-4,5-diones constitute an attractive scaffold for the development of PDF inhibitors specific for the human enzyme. In addition, the increase in potency observed after this second round of exploratory chemistry implies that the potency of benzofuran-4,5-diones can be further improved—and the SAR data gathered in this study constitutes a major step toward this goal. We found that at least one compound resulting from either A, B or C modification was potent toward HsPDF, suggesting that none of the approaches we undertook to modify the benzofuran-4,5-dione scaffold abbrogates its activity. Interestingly, replacing the phenyl ring with a bicyclic heterocycle can lead to an improvement in activity toward HsPDF (SKI 417504, $IC_{50}$=2.3 µM vs. SKI 417508, $IC_{50}$=3.4 µM). Similarly, replacing the phenyl ring with a heterocycle can lead to improved activity toward HsPDF (SKI 417512, $IC_{50}$=1.8 µM vs. SKI 417508, $IC_{50}$=3.4 µM). The most potent compounds we have identified result from the substitution of the phenyl ring in para with a carboxylic acid group (SKI 417518 and SKI 417519, $IC_{50}$=2.3 and 0.69 µM) or with a chain carrying a carboxylic acid group (SKI 417520 and SKI 417521, $IC_{50}$=0.68 and 0.62 µM). Together with the finding that derivatives with the phenyl ring replaced with a heterocycle (SKI 417512, $IC_{50}$=1.8 µM) or with the phenyl ring substituted in para with a heterocycle (SKI 417499, $IC_{50}$=1.8 µM) constitute potent inhibitors of HsPDF, we hypothesize that the presence of a hydrogen bond acceptor in para of the phenyl moiety is important for activity toward HsPDF. This important observation will be of tremendous help for designing benzofuran-4,5-dione derivatives with even more improved potency in the next round of exploratory chemistry, while preserving the specificity of this scaffold toward HsPDF.

SAR of the 26 Newly Synthesized benzofuran-4,5-diones Derivatives for In Vitro Anti-Cancer Activity.

Cytotoxicity profiling for the 26 newly synthesized benzofuran-4,5-diones derivatives was performed on a panel of eight cancer cell lines.

The cell lines HL-60 (human acute promyelocytic leukemia), Jurkat (human acute T cell leukemia), Molt3 (acute lymphoblastic leukemia), CWR22 (prostate carcinoma), K562 (human chronic myeloid leukemia lymphoblasts), and Y79 (human retinoblastoma) were obtained from the ATCC, and cultured following ATCC recommendations. The cell line HL-60/RV+ (a P-glycoprotein-overexpressing multi-drug resistant HL-60 variant selected by continuous exposure to vincristine) was described elsewhere (Weisburg J H, Roepe P D, Dzekunov S, Scheinberg D A: Intracellular pH and multi-drug resistance regulate complement-mediated cytotoxicity of nucleated human cells. *J Biol Chem* 1999; 274:10877-10888). The cell line ALL-3 (acute lymphoblastic leukemia isolated from a patient treated at MSKCC and characterized as Philadelphia chromosome positive) was obtained from Dr.

Mark Frattini (MSKCC). The viability assay we used in this study is based on the dye resazurin and commercially sold as Alamar Blue (O'Brien J, Wilson I, Orton T, Pognan F: Investigation of the Alamar Blue (resazurin) fluorescent dye for the assessment of mammalian cell cytotoxicity. *Eur J Biochem* 2000; 267:5421-5426). Cells were added in 45 µL medium to the pre-plated compounds in 5 µL of 1% DMSO (v/v). After 72 h incubation was added 5 µL Alamar Blue. The cells were then incubated for another 24 h, and the fluorescence intensity was read on the Amersham LEADseeker™ Multimodality Imaging System equipped with Cy3 excitation and excitation filters and FLINT epi-mirror. Plates were then fixed and nuclei were stained using Hoechst for the nuclear count proliferation assay. Imaging for Hoechst staining of nuclei count were acquired with an IN Cell Analyzer 2000 epifluorescence automated microscope (INCA 1000) (GE Healthcare, Piscataway, N.J.) equipped with a 4× objective, using D360/40 excitation filter (360 nm excitation peak; +/−40 nm bandpass), HQ535/50 emission filter (535 nm emission peak; +/−50 nm bandpass) and Q505LP dichroic, and exposing fields for 200 milliseconds in the blue channel. Image analysis was conducted with the IN Cell Developer 1.7 software (GE Healthcare) using custom-developed analysis modules. The analysis module used for nuclei count performs object segmentation in the blue channel to automatically define and count the number of nuclei. Data is reported as the sum of imaged nuclei.

For both assays, the signal inhibition induced by the compounds was expressed as a percentage compared to high and low controls located on the same plate, as defined as % Inhibition=(high control average−read value)/(high control average−low control average)×100. In addition of the Alamar Blue viability assay readout, for the adherent cell lines of this panel (CWR22 and Meso47) we performed a direct nuclei count to assess the effect of the novel derivatives on cell proliferation. For each assay, the dose response for each compound was assessed in duplicate and using 12 point doubling dilutions with 10 µM compound concentration as the upper limit. The dose response curve for each set of data was fitted separately, and the two $IC_{50}$ values obtained were averaged.

The calculated $IC_{50}$s are summarized in the SAR table in Appendix 8. Fifteen out of 26 derivatives were potent toward at least one cell line of the panel, with $IC_{50}$s ranging from 1.6 to 7.5 µM. Interestingly, one derivative (SKI 417516) was active against all cell lines of our panel except Meso47, including the multidrug resistant HL60/RV+ cells. However, since this compound has a solubility limit of 5 µM, non-specific toxicity at the highest concentrations may contribute to the overall cytotoxic effects observed with this compound. Importantly, we found that all nine compounds that were potent toward HsPDF in the enzymatic assay had in vitro anti-cancer activity, as reflected by their $IC_{50}$ below 10 µM for at least one cell line of the panel. In addition, compared to the first generation derivatives, we have significantly improved the cell-based activity of benzofuran-4,5-diones. Only seven out of the 33 derivatives of first generation had an $IC_{50}$ in the Alamar Blue viability assay lower than 10 µM; in contrast, 15 out of the 26 new derivatives have sub-10 µM $IC_{50}$s in the same panel of cell lines. This result demonstrates that we were successful in improving the cell-based activity of benzofuran-4,5-diones. The observation that the most potent HsPDF inhibitors we have identified so far (SKI 417519, SKI 417521, SKI 417520) were not active toward most of the cell lines tested in this panel is consistent with the fact that these compounds bear a carboxylic acid moiety, which when charged under physiological pH most likely prevents these compounds to diffuse inside the cell. Masking this carboxylic acid moiety with functional groups such as esters should allow our next generation derivatives to penetrate the cell before esterases restore the precursor compound bearing the carboxylic acid moiety. We are therefore confident that the next round of exploratory chemistry will allow us to identify potent HsPDF inhibitors with improved in vitro anti-cancer activity.

General Reaction Scheme

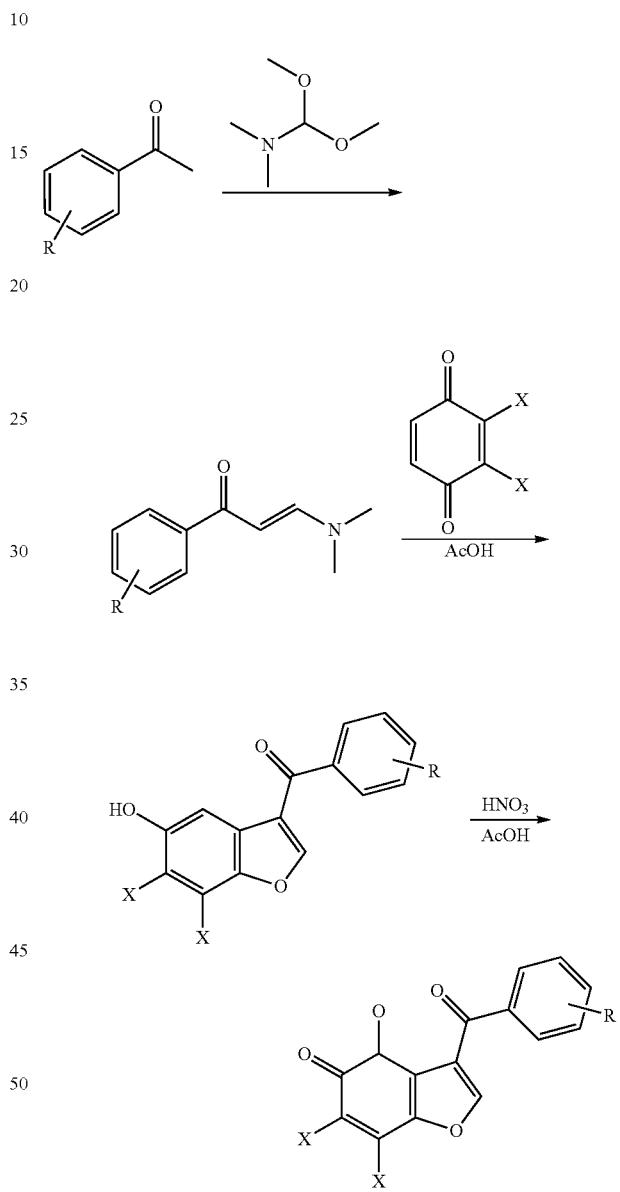

General Reaction Scheme for Acid Derivatives

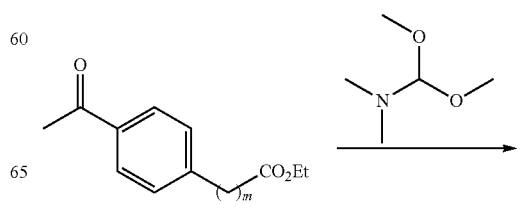

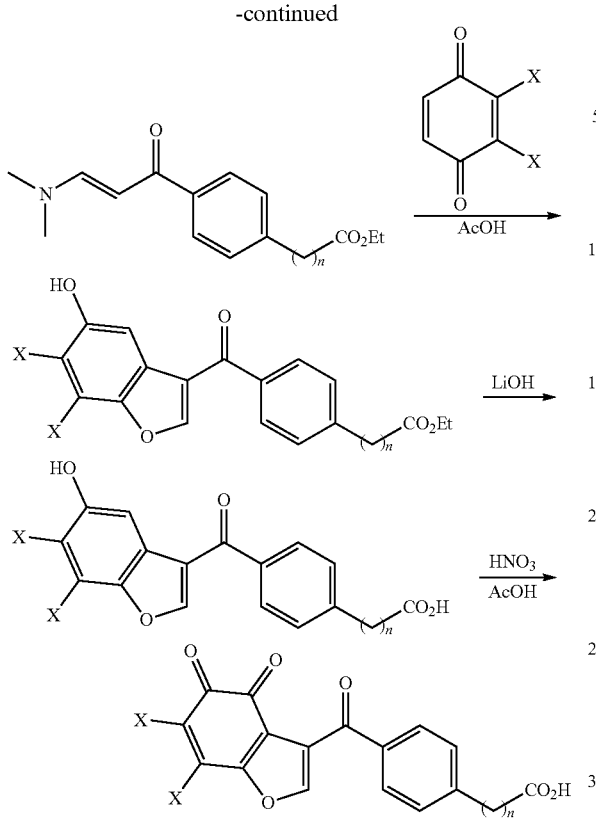

Synthesis of Non-Commercial Acetophenones

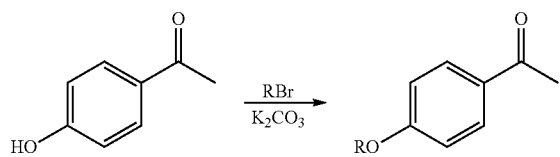

Synthesis of Quinones

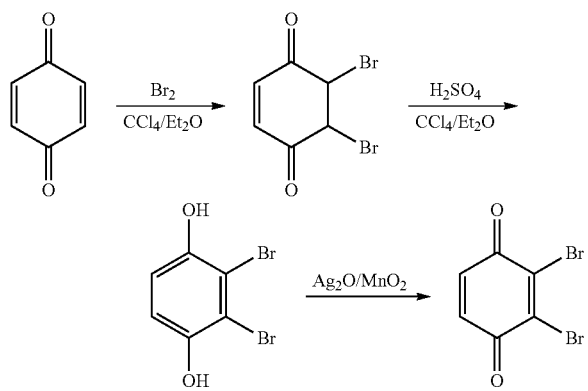

2,3-dibromocyclohexa-2,5-diene-1,4-dione:[1,2]

To a solution of benzoquinone (7.5 g, 69.4 mmol) in carbon tetrachloride (100 mL) was added a solution of Bromine (3.55 mL, 69.4 mmol) in 10% $Et_2O$ in carbon tetrachloride (85 mL). The mixture was stirred in the dark at room temperature for 20 minutes before partially removing solvents under vacuum, forming a green precipitate. The suspension was diluted with iso-hexanes (20 mL), sonicated for a few minutes, filtered and the solid washed with iso-hexanes (30 mL). $^1$H NMR (CDCl$_3$) indicated remaining starting material, so the material was diluted with 10% $Et_2O/CCl_4$ (180 mL), re-subjected to the bromination conditions and left to stir for 1 hour in the dark before the addition of conc. H2SO4 (40 mL) at 0° C. The mixture was stirred overnight and allowed to warm to room temperature. The reaction was poured onto iced water (200 mL) and partitioned over $Et_2O$ (100 mL). The layers were separated and the aqueous washed with $Et_2O$ (100 mL). The organic layers were combined and treated with silver (I) oxide (11.18 g, 56 mmol). After stirring at room temperature for 1 hour, the mixture was filtered, concentrated, then suspended in chloroform (20 mL) and treated with manganese (IV) oxide (12.17 g, 140 mmol). After stirring at room temperature for 4 hours, the mixture was filtered through celite and the filtrate concentrated to dryness. The resultant solid was re-crystallised from hexanes (60 mL) then purified by flash chromatography eluting with a shallow gradient of EtOAc/Iso-Hexanes (0-20%, holding at 5%) to afford compound x (4.4 g, 30%).

[1] J. Chem. Soc. Perkin Trans. II 1983, 271-279
[2] Synthetic Communications, 1999, 29 (5), 821-825

$^1$H NMR (400 MHz, CDCl$_3$) δ 7.03 (s, 2H)

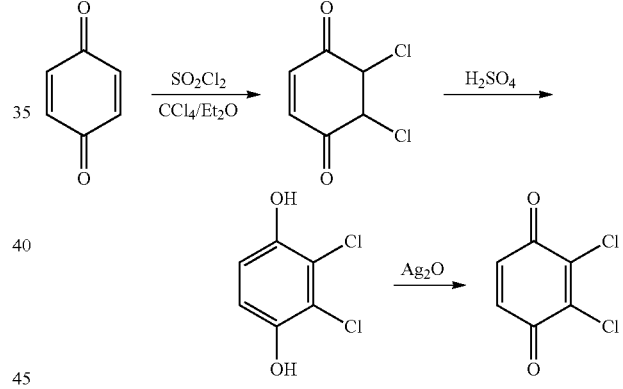

2,3-dichlorocyclohexa-2,5-diene-1,4-dione:[2]

1,4-Benzoquinone (2.01 g, 18.59 mmol) was dissolved in dry ether (50 mL) and dry chloroform (20 mL). The flask was placed under a constant flow of nitrogen and sulfuryl dichloride (5.02 g, 37.2 mmol) added dropwise over 15 minutes at 0° C. After 30 minutes the mixture was warmed to room temperature, stirred for another 30 minutes, returned to the ice-bath and treated with $Et_2O$ (25 mL) and conc. H2SO4 (30 mL). After 45 minutes the mixture was poured onto ice-water and extracted with further $Et_2O$ (3×75 mL). The combined organics were dried (MgSO4), filtered and concentrated to ca. 125 mL volume, whereupon silver oxide (9.96 g, 43 mmol) was added and the mixture stirred in the absence of light for 1 hour. The mixture was filtered through celite, washing with ether and chloroform. Evaporation of the filtrate afforded an orange/yellow solid. The mixture was purified by flash chromatography, loading onto silica, eluting with a gradient of 0 to 20% EtOAc/Iso-Hexanes, holding at 9%, then re-purified by flash chromatography, loading onto silica, eluting with a gradient of 5 to 60% EtOAc/Iso-Hexanes, holding at 35%. This afforded compound x (1.15 g, 34.9%) as a bright yellow powder.

¹H NMR (400 MHz, CDCl₃) δ 6.97 (s, 2H)

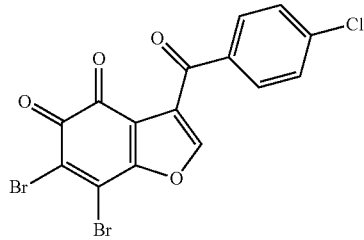 [SMILES: O=C1C(=O)c2c(C(=O)c3ccc(Cl)cc3)coc2C(Br)=C1Br]

6,7-dibromo-3-(4-chlorobenzoyl)benzofuran-4,5-dione (SKI 417498)

To a solution of (4-chlorophenyl)(6,7-dibromo-5-hydroxybenzofuran-3-yl)methanone (40 mg, 0.093 mmol) in AcOH (1 mL) was added nitric acid—69% (28.7 µl, 0.465 mmol) at room temperature. The mixture was heated to 60° C. After 30 minutes, a bright red suspension was observed. On cooling to room temperature, the mixture was poured onto crushed ice and the suspension was filtered under vacuum. The bright red precipitate was washed with water (2 mL) and dried under vacuum to afford compound x (28 mg, 68%).

¹H NMR (400 MHz, CDCl₃) δ 7.93 (s, 1H), 7.79 (d, J=8.7 Hz, 2H), 7.47 (d, J=8.8 Hz, 2H); MS (ES) m/z 465/467/469 (M+Na+H)⁺

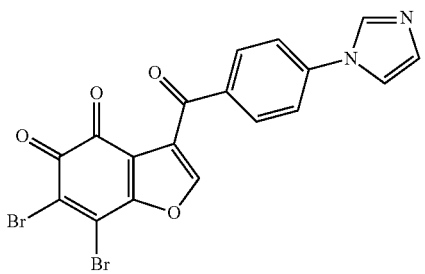 [SMILES: O=C1C(=O)c2c(C(=O)c3ccc(-n4ccnc4)cc3)coc2C(Br)=C1Br]

3-(4-(1H-imidazol-1-yl)benzoyl)-6,7-dibromobenzofuran-4,5-dione (SKI 417499)

To a solution of (4-(1H-imidazol-1-yl)phenyl)(6,7-dibromo-5-hydroxybenzofuran-3-yl)methanone (55 mg, 0.119 mmol) in AcOH (1 mL) was added nitric acid—69% (36.7 µl, 0.595 mmol) at room temperature. The mixture was heated to 60° C. for 1 hour then cooled to room temperature, poured onto iced water (3 mL) and the suspension filtered under vacuum to furnish 42 mg of a red/orange solid. ¹H NMR (DMSO-d₆) was consistent with two species—product and starting material. The material was re-subjected to the above conditions for a further hour and then worked up as before to afford compound x (25 mg, 44%).

¹H NMR (400 MHz, DMSO) δ 9.36 (s, 1H), 8.60 (s, 1H), 8.27 (s, 1H), 8.10 (d, J=8.8 Hz, 2H), 7.91 (d, J=8.8 Hz, 2H), 7.70 (s, 1H); MS (ES) m/z 475/477/479 (M+H)⁺

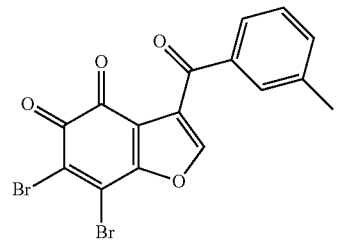

6,7-dibromo-3-(3-methylbenzoyl)benzofuran-4,5-dione (SKI 417500)

To a solution of (6,7-dibromo-5-hydroxybenzofuran-3-yl)(m-tolypmethanone (30 mg, 0.073 mmol) in AcOH (1 mL) was added nitric acid—69% (22.57 µl, 0.366 mmol) at room temperature. The mixture was then heated to 60° C. for 1 hour, cooled to room temperature, poured onto iced water (3 mL) and the suspension filtered. A bright red solid was isolated which was dried under vacuum to afford compound x (31 mg, 100%).

¹H NMR (400 MHz, DMSO) δ 8.51 (s, 1H), 7.75-7.65 (m, 2H), 7.52 (d, J=7.5 Hz, 1H), 7.42 (t, J=7.6 Hz, 1H); MS (ES) m/z 445/447/449 (M+Na+H)⁺

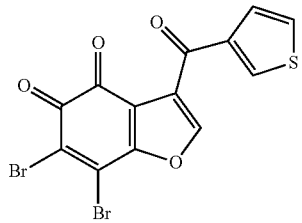 [SMILES: O=C1C(=O)c2c(C(=O)c3ccsc3)coc2C(Br)=C1Br]

6,7-dibromo-3-(thiophene-3-carbonyl)benzofuran-4,5-dione (SKI 417501)

To a solution of (6,7-dibromo-5-hydroxybenzofuran-3-yl)(thiophen-3-yl)methanone (30 mg, 0.075 mmol) in AcOH (1 mL) was added nitric acid—69% (23.02 µl, 0.373 mmol) at room temperature. The mixture was heated to 60° C. for 1 hour, cooled to room temperature, poured onto iced water (3 mL) and the suspension filtered. An orange/red solid was isolated which was dried under vacuum to afford compound x (30 mg, 97%).

¹H NMR (400 MHz, DMSO) δ 8.57 (s, 1H), 8.42 (dd, J=2.8, 1.3 Hz, 1H), 7.70 (dd, J=5.1, 2.8 Hz, 1H), 7.57 (dd, J=5.1, 1.3 Hz, 1H); MS (ES) m/z 437/439/441 (M+Na+H)⁺

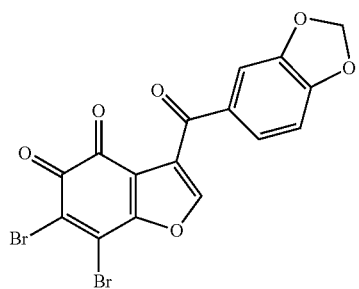 [SMILES: O=C1C(=O)c2c(C(=O)c3ccc4c(c3)OCO4)coc2C(Br)=C1Br]

3-(benzo[d][1,3]dioxole-5-carbonyl)-6,7-dibromobenzofuran-4,5-dione (SKI 417502)

To a solution of benzo[d][1,3]dioxol-5-yl(6,7-dibromo-5-hydroxybenzofuran-3-yl)methanone, (30 mg, 0.068 mmol) in AcOH (1 mL) was added nitric acid—69% (21.03 µl, 0.341 mmol) at room temperature. The mixture was heated to 60° C. for 3 hours, cooled to room temperature, poured onto iced water and the suspension filtered. An orange/red solid was isolated which was dried under vacuum to afford compound x (20 mg, 65%).

$^1$H NMR (400 MHz, CDCl$_3$) δ 7.88 (s, 1H), 7.42-7.36 (m, 2H), 6.84 (dd, J=7.7, 0.8 Hz, 1H), 6.09 (s, 2H); MS (ES) m/z 475/477/479 (M+Na+H)$^+$

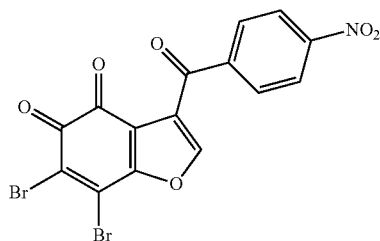 [SMILES: O=C1C(=O)c2c(C(=O)c3ccc([N+](=O)[O-])cc3)coc2C(Br)=C1Br]

6,7-dibromo-3-(4-nitrobenzoyl)benzofuran-4,5-dione (SKI 417503)

To a solution of (6,7-dibromo-5-hydroxybenzofuran-3-yl)(4-nitrophenyp methanone (30 mg, 0.068 mmol) in AcOH (1 mL) was added nitric acid—69% (20.99 µl, 0.340 mmol) at room temperature. The mixture was heated to 60° C. for 3 hours, cooled to room temperature, poured onto iced water and the suspension filtered. A red/orange solid was isolated which was dried under vacuum to afford compound x (20 mg, 65%).

$^1$H NMR (400 MHz, CDCl$_3$) δ 8.36-8.31 (m, 2H), 8.03 (s, 1H), 8.00-7.96 (m, 2H); MS (ES) m/z 476/478/480 (M+Na+H)$^+$

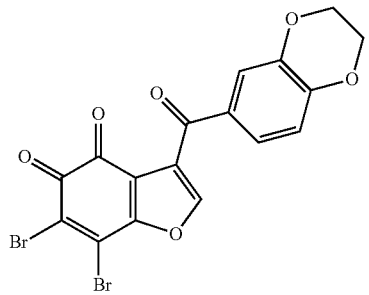

6,7-dibromo-3-(2,3-dihydrobenzo[b][1,4]dioxine-6-carbonyl)benzofuran-4,5-dione (SKI 417504)

To a solution of (6,7-dibromo-5-hydroxybenzofuran-3-yl)(2,3-dihydrobenzo[b][1,4]dioxin-6-yl)methanone (30 mg, 0.066 mmol) in AcOH (1 mL) was added nitric acid—69% (20.38 µl, 0.330 mmol) at room temperature. The mixture was heated to 60° C. for 3 hours then cooled to room temperature. Iced water (3 mL) was added, followed by EtOAc (4 mL) and the organic layer was collected and concentrated under vacuum to afford compound x (22 mg, 71%).

$^1$H NMR (400 MHz, CDCl$_3$) δ 7.87 (s, 1H), 7.43-7.37 (m, 2H), 6.92 (d, J=8.7 Hz, 1H), 4.34 (dd, J=5.5, 2.1 Hz, 2H), 4.29 (dd, J=5.5, 2.2 Hz, 2H); MS (ES) m/z 489/491/493 (M+Na+H)$^+$

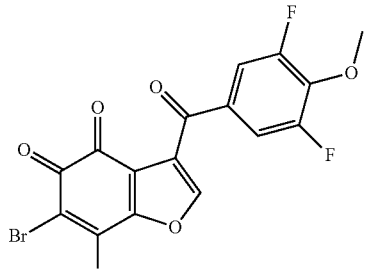

6,7-dibromo-3-(3,5-difluoro-4-methoxybenzoyl)benzofuran-4,5-dione (SKI 417505)

To a solution of (6,7-dibromo-5-hydroxybenzofuran-3-yl)(3,5-difluoro-4-methoxyphenyl)methanone (30 mg, 0.065 mmol) in AcOH (1 mL) was added nitric acid—69% (20.03 µl, 0.325 mmol) at room temperature. The mixture was heated to 60° C. for 3 hours, cooled to room temperature, poured onto iced water and the suspension filtered. A red/orange solid was isolated which was dried under vacuum to afford the product (28 mg, 91%).

$^1$H NMR (400 MHz, CDCl$_3$) δ 7.93 (s, 1H), 7.46-7.37 (m, 2H), 4.19-4.10 (m, 3H); MS (ES) m/z 497/499/501 (M+Na+H)$^+$

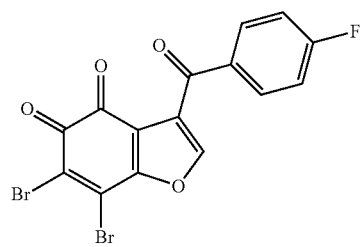 [SMILES: O=C1C(=O)c2c(C(=O)c3ccc(F)cc3)coc2C(Br)=C1Br]

6,7-dibromo-3-(4-fluorobenzoyl)benzofuran-4,5-dione (SKI 417506)

To a solution of (6,7-dibromo-5-hydroxybenzofuran-3-yl)(4-fluorophenyl)methanone (62 mg, 0.150 mmol) in AcOH (1 mL) was added nitric acid—69% (46.2 µl, 0.749 mmol) at room temperature. The mixture was heated to 60° C. for 3 hours, cooled to room temperature, poured onto iced water and the suspension filtered. A solid was isolated which was dried under vacuum to afford the product (14 mg, 17%).

$^1$H NMR (400 MHz, CDCl$_3$) δ 7.91 (s, 1H), 7.90-7.84 (m, 2H), 7.18-7.11 (m, 2H); MS (ES) m/z 449/451/453 (M+Na+H)$^+$

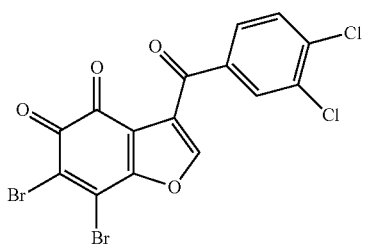

6,7-dibromo-3-(3,4-dichlorobenzoyl)benzofuran-4,5-dione (SKI 417507)

To a solution of (6,7-dibromo-5-hydroxybenzofuran-3-yl)(3,4-dichlorophenyl)methanone (50 mg, 0.108 mmol) in AcOH (1 mL) was added nitric acid—69% (33.2 μl, 0.538 mmol) at room temperature. The mixture was heated to 60° C. for 3 hours, cooled to room temperature, poured onto iced water and the suspension filtered. The resultant solid was further purified using a small pipette flash column to afford compound x (12 mg, 23%).

$^1$H NMR (400 MHz, CDCl$_3$) δ 7.96 (s, 1H), 7.93 (d, J=1.9 Hz, 1H), 7.66 (dd, J=8.3, 2.0 Hz, 1H), 7.57 (d, J=8.4 Hz, 1H); MS (ES) m/z 499/501/503 (M+Na+H)$^+$

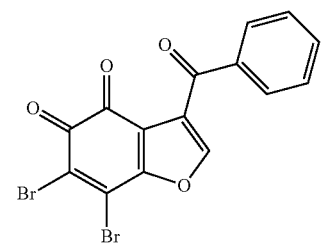

3-benzoyl-6,7-dibromobenzofuran-4,5-dione (SKI 417508)

To a solution of (6,7-dibromo-5-hydroxybenzofuran-3-yl)(phenyl)methanone (51 mg, 0.129 mmol) in AcOH (1 mL) was added nitric acid—69% (39.7 μl, 0.644 mmol) at room temperature. The mixture was heated to 60° C. for 3 hours, cooled to room temperature, poured onto iced water and the suspension filtered. The resultant solid was further purified using a small pipette flash column to afford compound x (11 mg, 17%).

$^1$H NMR (400 MHz, CDCl$_3$) δ 7.90 (s, 1H), 7.86-7.81 (m, 2H), 7.62 (t, J=7.4 Hz, 1H), 7.47 (t, J=7.7 Hz, 2H); MS (ES) m/z 431/433/435 (M+Na+H)$^+$

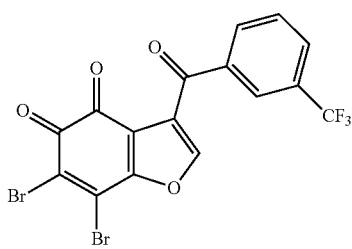 [SMILES: O=C1C(=O)c2c(C(=O)c3cccc(C(F)(F)F)c3)coc2C(Br)=C1Br]

6,7-dibromo-3-(3-(trifluoromethyl)benzoyl)benzofuran-4,5-dione (SKI 417509)

To a solution of (6,7-dibromo-5-hydroxybenzofuran-3-yl)(3-(trifluoromethyl)phenyl)methanone (44 mg, 0.095 mmol) in AcOH (1 mL) was added nitric acid—69% (29.3 μl, 0.474 mmol) at room temperature. The mixture was heated to 60° C. for 3 hours, cooled to room temperature, poured onto iced water and the suspension filtered. The resultant solid was dried under vacuum to afford compound x (14 mg, 31%).

$^1$H NMR (400 MHz, CDCl$_3$) δ 8.09 (s, 1H), 8.00 (d, J=7.4 Hz, 1H), 7.96 (s, 1H), 7.88 (d, J=7.8 Hz, 1H), 7.62 (t, J=7.7 Hz, 1H); MS (ES) m/z 498/500/502 (M+Na+H)$^+$

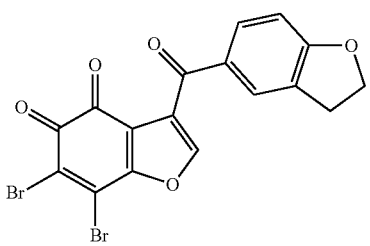 [SMILES: O=C1C(=O)c2c(C(=O)c3ccc4c(c3)CCO4)coc2C(Br)=C1Br]

6,7-dibromo-3-(2,3-dihydrobenzofuran-5-carbonyl)benzofuran-4,5-dione (SKI 417510)

To a solution of (6,7-dibromo-5-hydroxybenzofuran-3-yl)(2,3-dihydrobenzofuran-5-yl)methanone (62 mg, 0.142 mmol) in AcOH (1 mL) was added nitric acid—69% (43.7 μl, 0.708 mmol) at room temperature. The mixture was heated to 60° C. for 4 hours, cooled to room temperature, poured onto iced water and the suspension filtered. The resultant solid was further purified using a small pipette flash column to afford compound x (13 mg, 20%).

$^1$H NMR (400 MHz, CDCl$_3$) δ 7.85 (s, 1H), 7.81-7.74 (m, 1H), 7.64 (dd, J=8.4, 1.9 Hz, 1H), 6.78 (d, J=8.4 Hz, 1H), 4.68 (t, J=8.8 Hz, 2H), 3.24 (t, J=8.7 Hz, 2H); MS (ES) m/z 473/475/477 (M+Na+H)$^+$

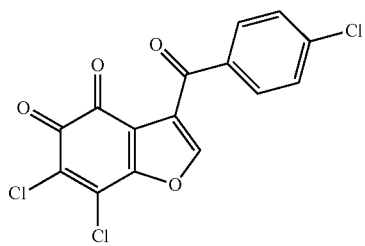 [SMILES: O=C1C(=O)c2c(C(=O)c3ccc(Cl)cc3)coc2C(Cl)=C1Cl]

6,7-dichloro-3-(4-chlorobenzoyl)benzofuran-4,5-dione (SKI 417511)

To a solution of (4-chlorophenyl)(6,7-dichloro-5-hydroxybenzofuran-3-yl)methanone (35 mg, 0.102 mmol) in AcOH (1 mL) was added nitric acid—69% (31.6 μl, 0.512 mmol) at room temperature. The mixture was heated to 60° C. for 3 hours, cooled to room temperature, poured onto iced water and the suspension filtered. The resultant solid was dried under vacuum to afford compound x (14 mg, 39%).

$^1$H NMR (400 MHz, CDCl$_3$) δ 7.94 (s, 1H), 7.78 (d, J=8.5 Hz, 2H), 7.45 (d, J=8.4 Hz, 2H). MS (ES) m/z 377/379/381 (M+Na+H)$^+$

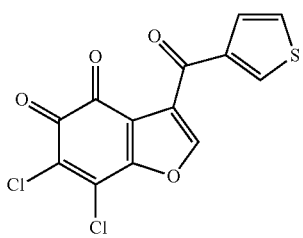 [SMILES: O=C1C(=O)c2c(C(=O)c3ccsc3)coc2C(Cl)=C1Cl]

6,7-dichloro-3-(thiophene-3-carbonyl)benzofuran-4,5-dione (SKI 417512)

To a solution of (6,7-dichloro-5-hydroxybenzofuran-3-yl)(thiophen-3-yl)methanone (32 mg, 0.102 mmol) in AcOH (1 mL) was added nitric acid—69% (31.5 µl, 0.511 mmol) at room temperature. The mixture was heated to 60° C. for 3 hours, cooled to room temperature, poured onto iced water and the suspension filtered. The resultant solid was dried under vacuum to afford compound x (14 mg, 42%).

$^1$H NMR (400 MHz, CDCl$_3$) δ 7.98 (dd, J=2.9, 1.3 Hz, 1H), 7.96 (s, 1H), 7.57 (dd, J=5.1, 1.3 Hz, 1H), 7.39 (dd, J=5.1, 2.9 Hz, 1H); MS (ES) m/z 349/351/353 (M+Na+H)$^+$

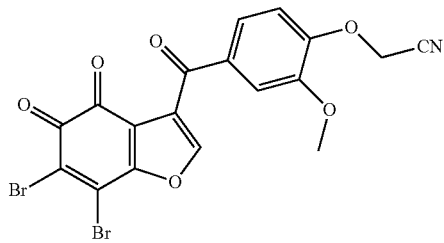 [SMILES: COc1cc(C(=O)c2coc3c2C(=O)C(=O)C(Br)=C3Br)ccc1OCC#N]

2-(4-(6,7-dibromo-4,5-dioxo-4,5-dihydrobenzofuran-3-carbonyl)-2-methoxyphenoxy)acetonitrile (SKI 417513)

To a solution of 2-(4-(6,7-dibromo-5-hydroxybenzofuran-3-carbonyl)-2-methoxyphenoxy)acetonitrile (40 mg, 0.083 mmol) in AcOH (1 mL) was added nitric acid—69% (25.7 µl, 0.416 mmol) at room temperature. The mixture was heated to 60° C. for 2 hours. After this time, the mixture was poured onto iced water (4 mL) and the resulting suspension filtered. The material was adsorbed onto silica (200 mg) and purified by column chromatography (Companion, 4 g cartridge) eluting with a DCM and Et$_{2O}$ gradient. One clean fraction was obtained which was concentrated to dryness under vacuum to afford compound x (12 mg, 29%).

$^1$H NMR (400 MHz, CDCl$_3$) δ 7.92 (s, 1H), 7.62 (d, J=2.0 Hz, 1H), 7.37 (dd, J=8.3, 2.0 Hz, 2H), 7.02 (d, J=8.3 Hz, 1H), 4.92 (s, 2H), 3.97 (s, 3H); MS (ES) m/z 516/518/520 (M+Na+H)$^+$

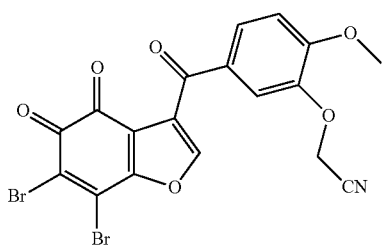 [SMILES: COc1ccc(C(=O)c2coc3c2C(=O)C(=O)C(Br)=C3Br)cc1OCC#N]

2-(5-(6,7-dibromo-4,5-dioxo-4,5-dihydrobenzofuran-3-carbonyl)-2-methoxyphenoxy)acetonitrile (SKI 417514)

To a solution of 2-(5-(6,7-dibromo-5-hydroxybenzofuran-3-carbonyl)-2-methoxyphenoxy)acetonitrile (40 mg, 0.083 mmol) in AcOH (1 mL) was added nitric acid—69% (25.7 µl, 0.416 mmol) at room temperature. The mixture was heated to 60° C. for 3 hours. After this time, the mixture was cooled to room temperature, poured onto iced water (5 mL) and the suspension filtered. A red/orange solid was isolated which was dried under vacuum to afford compound x (23 mg, 56%).

$^1$H NMR (400 MHz, CDCl$_3$) δ 7.94 (s, 1H), 7.66 (dd, J=8.5, 2.0 Hz, 1H), 7.59 (d, J=2.0 Hz, 1H), 6.99 (d, J=8.6 Hz, 1H), 4.84 (s, 2H), 3.98 (s, 3H); MS (ES) m/z 516/518/520 (M+Na+H)$^+$

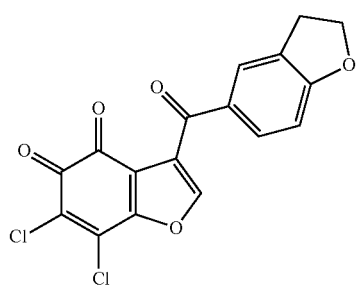 [SMILES: O=C1C(=O)c2c(C(=O)c3ccc4c(c3)CCO4)coc2C(Cl)=C1Cl]

6,7-dichloro-3-(2,3-dihydrobenzofuran-5-carbonyl)benzofuran-4,5-dione (SKI 417515)

To a suspension of (6,7-dichloro-5-hydroxybenzofuran-3-yl)(2,3-dihydrobenzofuran-5-yl)methanone (35 mg, 0.100 mmol) in AcOH (1 mL) was added nitric acid—69% (30.9 µl, 0.501 mmol) at room temperature. The mixture was then heated at 60° C. for 4 hours, forming a red precipitate which was filtered on cooling and was washed with acetic acid, water and ether to afford compound x (14 mg, 38%).

$^1$H NMR (400 MHz, DMSO) δ 8.48 (s, 1H), 7.82-7.78 (m, 1H), 7.72 (dd, J=8.4, 2.0 Hz, 1H), 6.86 (d, J=8.4 Hz, 1H), 4.67 (t, J=8.8 Hz, 2H), 3.23 (t, J=8.7 Hz, 2H); MS (ES) m/z 385/387/389 (M+Na+H)$^+$

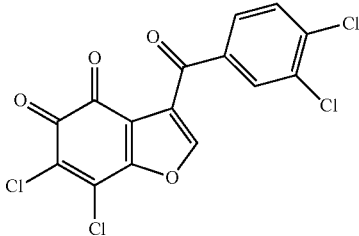 [SMILES: O=C1C(=O)c2c(C(=O)c3ccc(Cl)c(Cl)c3)coc2C(Cl)=C1Cl]

6,7-dichloro-3-(3,4-dichlorobenzoyl)benzofuran-4,5-dione (SKI 417516)

To a suspension of (6,7-dichloro-5-hydroxybenzofuran-3-yl)(3,4-dichlorophenyl)methanone (35 mg, 0.093 mmol) in AcOH (1 mL) was added nitric acid—69% (30.9 µl, 0.501 mmol) at room temperature. The mixture was then heated at 60° C. for 4 hours, forming a red precipitate which was filtered on cooling and was washed with acetic acid, water and ether to afford compound x (16 mg, 44%).

$^1$H NMR (400 MHz, Acetone) δ 8.49 (s, 1H), 8.05 (d, J=2.0 Hz, 1H), 7.90 (dd, J=8.4, 2.0 Hz, 1H), 7.73 (dd, J=8.3, 4.0 Hz, 1H); MS (ES) m/z 411/413/415 (M+Na+H)$^+$

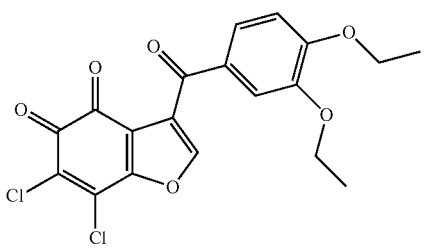 [SMILES: CCOc1ccc(C(=O)c2coc3c2C(=O)C(=O)C(Cl)=C3Cl)cc1OCC]

6,7-dichloro-3-(3,4-diethoxybenzoyl)benzofuran-4,5-dione (SKI 417517)

To a suspension of (6,7-dichloro-5-hydroxybenzofuran-3-yl)(3,4-diethoxyphenyl)methanone (35 mg, 0.089 mmol) in AcOH (1 mL) was added nitric acid—69% (30.9 µl, 0.501 mmol) at room temperature. The mixture was then heated at 60° C. for 4 hours, forming a red precipitate which was filtered on cooling and was washed with acetic acid, water and ether to afford compound x (15 mg, 42%).
$^1$H NMR (400 MHz, DMSO) δ 8.51 (s, 1H), 7.47 (dd, J=8.4, 2.1 Hz, 1H), 7.43 (d, J=2.1 Hz, 1H), 7.03 (d, J=8.5 Hz, 1H), 4.15 (q, J=7.0 Hz, 2H), 4.09 (q, J=7.0 Hz, 2H), 1.41-1.29 (m, 6H); MS (ES) m/z 431/433/435 (M+Na+H)$^+$

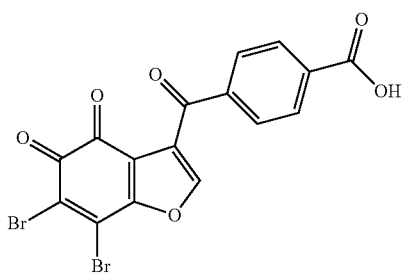 [SMILES: O=C1C(=O)c2c(C(=O)c3ccc(C(=O)O)cc3)coc2C(Cl)=C1Cl]

4-(6,7-dibromo-4,5-dioxo-4,5-dihydrobenzofuran-3-carbonyl)benzoic acid (SKI 417518)

To a suspension of 4-(6,7-dibromo-5-hydroxybenzofuran-3-carbonyl)benzoic acid (15 mg, 0.034 mmol) in AcOH (0.5 ml) was added nitric acid—69% (10.52 µl, 0.170 mmol) at room temperature. The mixture was then heated at 60° C. for 2 hours, forming a red precipitate which was filtered on cooling and was washed with acetic acid, water and ether to afford compound x (11 mg, 74%).
$^1$H NMR (400 MHz, DMSO) δ 13.42 (s, 1H), 8.59 (s, 1H), 8.07-8.02 (m, 2H), 8.01-7.96 (m, 2H); MS (ES) m/z 475/477/479 (M+Na+H)$^+$

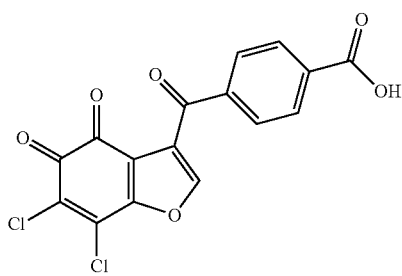

4-(6,7-dichloro-4,5-dioxo-4,5-dihydrobenzofuran-3-carbonyl)benzoic acid (SKI 417519)

To a suspension of 4-(6,7-dichloro-5-hydroxybenzofuran-3-carbonyl)benzoic acid (50 mg, 0.142 mmol) in AcOH (1 mL) was added nitric acid—69% (43.9 µl, 0.712 mmol) at room temperature. The mixture was then heated at 60° C. for 2 hours, forming a red precipitate which was filtered on cooling and was washed with acetic acid, water and ether to afford compound x (12 mg, 23%).
$^1$H NMR (400 MHz, DMSO) δ 13.42 (s, 1H), 8.63 (s, 1H), 8.08-8.02 (m, 2H), 8.01-7.95 (m, 2H); MS (ES) m/z 387/389/391 (M+Na+H)$^+$

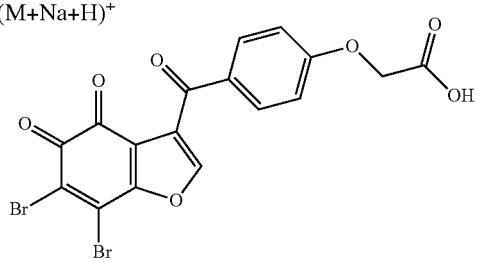

2-(4-(6,7-dibromo-4,5-dioxo-4,5-dihydrobenzofuran-3-carbonyl)phenoxy)acetic acid (SKI 417520)

To a suspension of 2-(4-(6,7-dibromo-5-hydroxybenzofuran-3-carbonyl)phenoxy)acetic acid (40 mg, 0.085 mmol) in AcOH (1 mL) was added nitric acid—69% (26.3 µl, 0.425 mmol) at room temperature. The mixture was then heated at 60° C. for 2 hours, forming a red precipitate which was filtered on cooling and washed with acetic acid, water and ether to afford compound x (12 mg, 29%).
$^1$H NMR (400 MHz, DMSO) δ 13.15 (s, 1H), 8.48 (s, 1H), 7.87 (d, J=9.0 Hz, 2H), 7.01 (d, J=9.0 Hz, 2H), 4.83 (s, 2H); MS (ES) m/z 504/506/508 (M+Na+H)$^+$

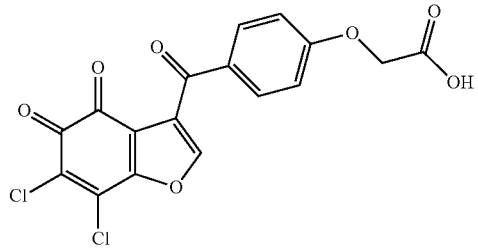

2-(4-(6,7-dichloro-4,5-dioxo-4,5-dihydrobenzofuran-3-carbonyl)phenoxy)acetic acid (SKI 417521)

To a suspension of 2-(4-(6,7-dichloro-5-hydroxybenzofuran-3-carbonyl)phenoxy)acetic acid, (50.8 mg, 0.133 mmol) in AcOH (1 mL) was added nitric acid—69% (41.1 µl, 0.666 mmol) at room temperature. The mixture was then heated at 60° C. for 2 hours, forming a red precipitate which was filtered on cooling and washed with acetic acid, water and ether to afford compound x (16 mg, 30%).
$^1$H NMR (400 MHz, DMSO) δ 13.16 (s, 1H), 8.52 (s, 1H), 7.87 (d, J=9.0 Hz, 2H), 7.02 (d, J=9.0 Hz, 2H), 4.83 (s, 2H); MS (ES) m/z 417/419/421 (M+Na+H)$^+$

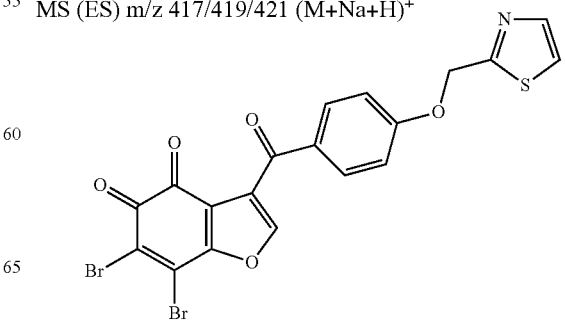

6,7-dibromo-3-(4-(thiazol-2-ylmethoxy)benzoyl)benzofuran-4,5-dione (SKI 417522)

To a suspension of (6,7-dibromo-5-hydroxybenzofuran-3-yl)(4-(thiazol-2-ylmethoxy)phenyl)methanone (70 mg, 0.137 mmol) in acetic acid (1 mL) was added nitric acid—69% (44.2 μl, 0.687 mmol) and the mixture heated at 60° C. for 1 hour. During this time the suspension turned bright red/orange and partially dissolved. After this time, the mixture was added to ice-water, then filtered to afford crude product as a red solid.

This was evaporated onto silica and purified by column chromatography (0-30% EtOAc in DCM) to afford compound x (23.5 mg, 33%) as a red powder.

$^1$H NMR (400 MHz, DMSO) δ 9.14 (d, J=2.0 Hz, 1H), 8.48 (s, 1H), 7.89 (d, J=9.0 Hz, 2H), 7.86 (d, J=2.0 Hz, 1H), 7.15 (d, J=9.0 Hz, 2H), 5.35 (s, 2H); MS (ES) m/z 544/546/548 (M+Na+H)$^+$

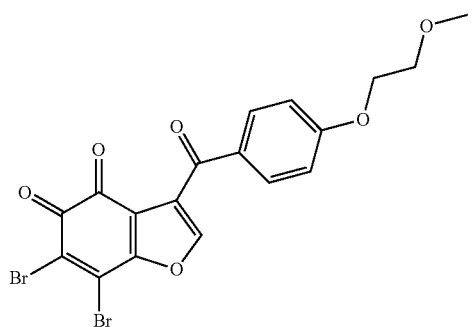 [SMILES: COCCOc1ccc(C(=O)c2coc3c2C(=O)C(=O)C(Br)=C3Br)cc1]

6,7-dibromo-3-(4-(2-methoxyethoxy)benzoyl)benzofuran-4,5-dione (SKI 417523)

To (6,7-dibromo-5-hydroxybenzofuran-3-yl)(4-(2-methoxyethoxy)phenyl)methanone (35 mg, 0.074 mmol) in acetic acid (0.75 mL) was added nitric acid—69% (17.51 μl, 0.389 mmol) and the reaction heated at 60° C. for 1.5 hours. The reaction was then allowed to cool to room temperature, and poured onto ice-water (10 mL) and allowed to stand for one hour after which time a red precipitate had formed. The solid was filtered, washed with water to afford crude product as a red solid. This was evaporated onto silica and purified by column chromatography (0-10% Et$_2$O in DCM) to afford compound x (22 mg, 61%) as a red powder.

$^1$H NMR (400 MHz, Acetone) δ 8.30 (s, 1H), 7.93 (d, J=9.0 Hz, 2H), 7.03 (d, J=9.0 Hz, 2H), 4.27-4.22 (m, 2H), 3.77-3.71 (m, 2H), 3.36 (s, 3H); MS (ES) m/z 505/507/509 (M+Na+H)$^+$

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:
1. A compound of the formula:

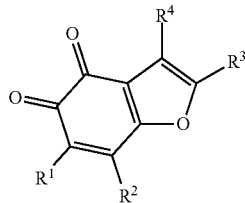

wherein:

$R^1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$^a$; —C(=O)R$^a$; —CO$_2$R$^a$; —CN; —SCN; —SR$^a$; —SOR$^a$; —SO$_2$R$^a$; —NO$_2$; —N$_3$; —N(R$^a$)$_2$; —NR$^a$C(=O)R$^a$; —NR$^a$C(=O)N(R$^a$)$_2$; —OC(=O)OR$^a$; —OC(=O)R$^a$; —OC(=O)N(R$^a$)$_2$; —NR$^a$C(=O)OR$^a$; or —C(R$^a$)$_3$; wherein each occurrence of R$^a$ is independently hydrogen; halogen; a protecting group; an optionally substituted aliphatic or heteroaliphatic moiety; an acyl moiety; or an optionally substituted aryl or heteroaryl moiety;

$R^2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$^b$; —C(=O)R$^b$; —CO$_2$R$^b$; —CN; —SCN; —SR$^b$; —SOR$^b$; —SO$_2$R$^b$; —NO$_2$; —N$_3$; —N(R$^b$)$_2$; —NR$^b$C(=O)R$^a$; —NR$^b$C(=O)N(R$^b$)$_2$; —OC(=O)OR$^b$; —OC(=O)R$^b$; —OC(=O)N(R$^b$)$_2$; —NR$^b$C(=O)OR$^b$; or —C(R$^b$)$_3$; wherein each occurrence of R$^b$ is independently hydrogen; halogen; a protecting group; an optionally substituted aliphatic or heteroaliphatic moiety; an acyl moiety; or an optionally substituted aryl or heteroaryl moiety;

wherein R$^1$ and R$^2$ when taken together form an optionally substituted, saturated or unsaturated aromatic, heteroaromatic, or nonaromatic 3-8 membered monocyclic or bicyclic ring optionally containing one or more heteroatoms selected from the group consisting of N, O, or S;

$R^3$ is hydrogen; halogen; cyclic or acyclic, substituted or unsubstituted, branched or unbranched aliphatic; cyclic or acyclic, substituted or unsubstituted heteroaliphatic; substituted or unsubstituted, branched or unbranched acyl; substituted or unsubstituted aryl; substituted or unsubstituted heteroaryl; —OR$^c$; —C(=O)R$^c$; —CO$_2$R$^c$; —CN; —SCN; —SR$^c$; —SOR$^c$; —SO$_2$R$^c$; —NO$_2$; —N$_3$; —N(R$^c$)$_2$; —NR$^c$C(=O)R$^c$; —NR$^c$C(=O)N(R$^c$)$_2$; —OC(=O)OR$^c$; —OC(=O)R$^c$; —OC(=O)N(R$^c$)$_2$; —NR$^c$C(=O)OR$^c$; or —C(R$^c$)$_3$; wherein each occurrence of R$^c$ is independently hydrogen; halogen; a protecting group; an optionally substituted aliphatic or heteroaliphatic moiety; an acyl moiety; or an optionally substituted aryl or heteroaryl moiety; and $R^4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$^d$; —C(=O)R$^d$; —CO$_2$R$^d$; —CN; —SCN; —SR$^d$; —SOR$^b$; —SO$_2$R$^d$; —NO$_2$; —N$_3$; —N(R$^d$)$_2$; —NR$^d$C(=O)R$^d$; —NR$^d$C(=O)N(R$^d$)$_2$; —OC(=O)OR$^d$; —OC(=O)R$^d$; —OC(=O)N(R$^d$)$_2$; —NR$^d$C(=O)OR$^d$; or —C(R$^d$)$_3$; wherein each occurrence of R$^d$ is independently hydrogen; halogen; a protecting group; an optionally substituted aliphatic or heteroaliphatic moiety; an acyl moiety; or an optionally substituted aryl or heteroaryl moiety, or a pharmaceutically acceptable salt thereof; and wherein the compound is not of one of the formulae:

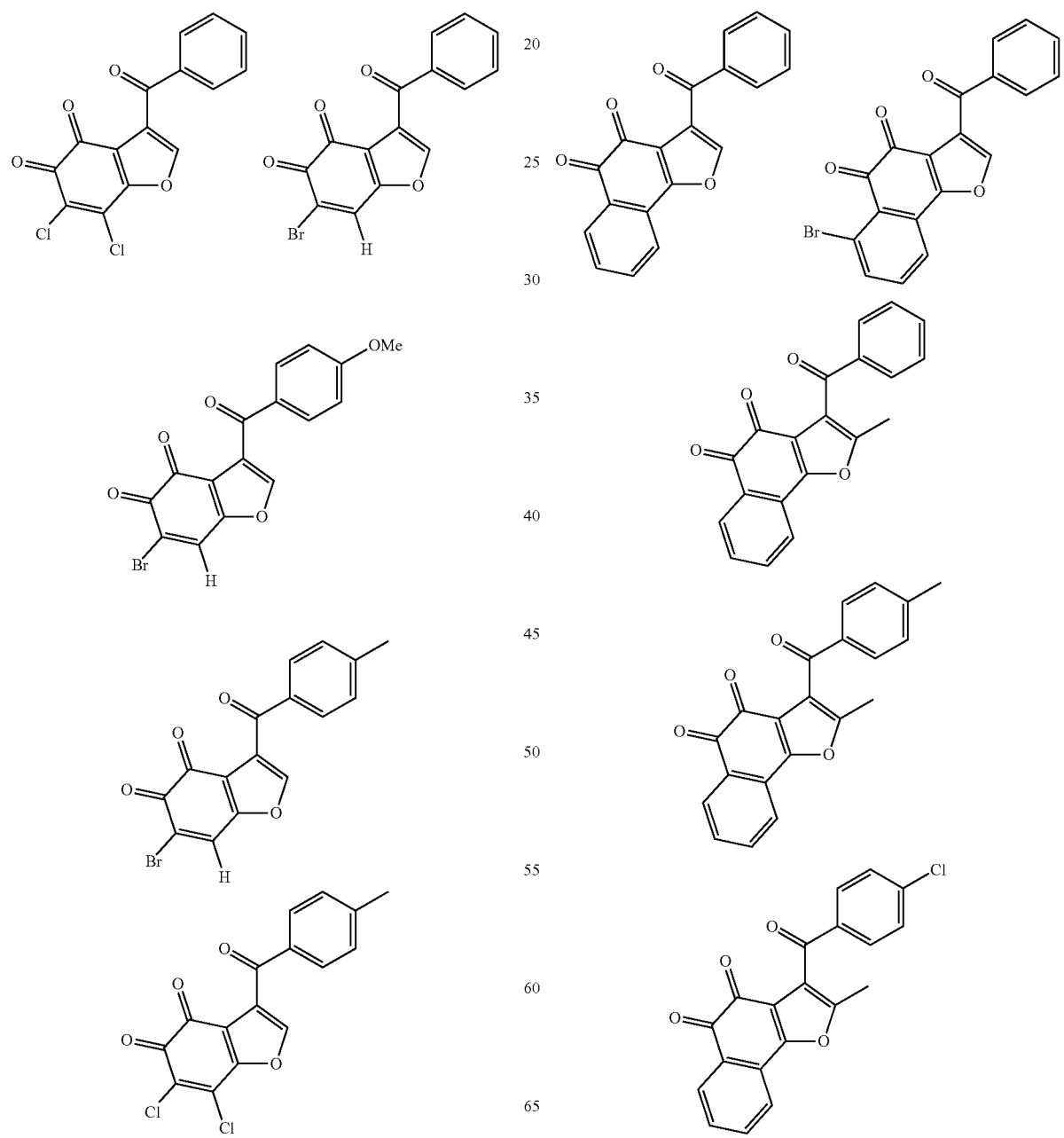

-continued

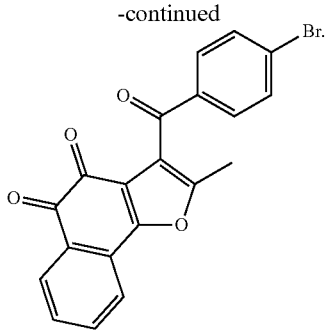

2. The compound of claim 1, wherein at least one occurrence of $R^1$ and $R^2$ is hydrogen.

3. The compound of claim 1, wherein at least one occurrence of $R^1$ and $R^2$ is a halogen.

4. The compound of claim 1, wherein $R^1$ and $R^2$ taken together form a fused aryl or heteroaryl.

5. The compound of claim 1, wherein $R^3$ is hydrogen or $C_1$-$C_6$ alkyl.

6. The compound of claim 1, wherein $R^4$ is acyl.

7. The compound of claim 1 of the formula:

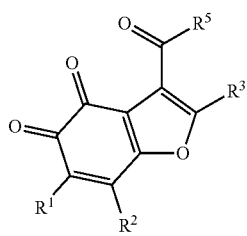

wherein $R^5$ is hydrogen; cyclic or acyclic, substituted or unsubstituted, branched or unbranched aliphatic; cyclic or acyclic, substituted or unsubstituted, branched or unbranched heteroaliphatic; substituted or unsubstituted aryl; substituted or unsubstituted heteroaryl; —$OR^e$; —$SR^e$; —$N(R^e)_2$; —$NR^eC(=O)R^e$; —$NR^eC(=O)N(R^e)_2$; —$OC(=O)OR^e$; —$OC(=O)R^e$; —$OC(=O)N(R^e)_2$; —$NR^eC(=O)OR^e$; or —$C(R^e)_3$; wherein each occurrence of $R^e$ is independently independently hydrogen; halogen; a protecting group; an optionally substituted aliphatic or heteroaliphatic moiety; an acyl moiety; or an optionally substituted aryl or heteroaryl moiety, or a pharmaceutically acceptable salt thereof.

8. The compound of claim 1 of the formula:

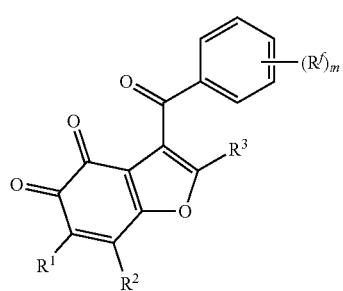

wherein:

m is an integer between 0 and 5, inclusive; and each occurrence of $R^f$ is independently hydrogen; halogen; cyclic or acyclic, substituted or unsubstituted, branched or unbranched aliphatic; cyclic or acyclic, substituted or unsubstituted heteroaliphatic; substituted or unsubstituted, branched or unbranched acyl; substituted or unsubstituted aryl; substituted or unsubstituted heteroaryl; —$OR^g$; —$C(=O)R^g$; —$CO_2R^g$; —CN; —SCN; —$SR^g$; —$SOR^g$; —$SO_2R^g$; —$NO_2$; —$N_3$; —$N(R^g)_2$; —$NR^gC(=O)R^g$; —$NR^gC(=O)N(R^g)_2$; —$OC(=O)OR^g$; —$OC(=O)R^g$; —$OC(=O)N(R^g)_2$; —$NR^gC(=O)OR^g$; or —$C(R^g)_3$; wherein each occurrence of $R^9$ is independently hydrogen; halogen; a protecting group; an optionally substituted aliphatic or heteroaliphatic moiety; an acyl moiety; or an optionally substituted aryl or heteroaryl moiety.

9. The compound of claim 7, wherein $R^5$ is one of the formulae:

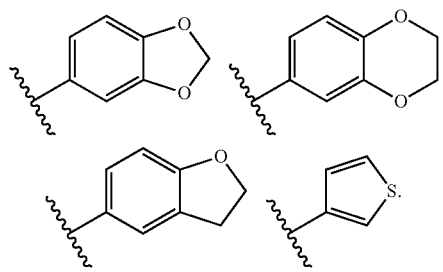

10. The compound of claim 8, wherein at least one occurrence of $R^f$ is —$OR^g$.

11. The compound of claim 8 of the formula:

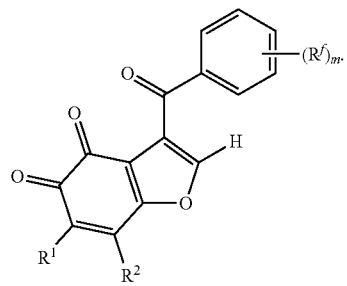

12. The compound of claim 1 of one of the formulae:

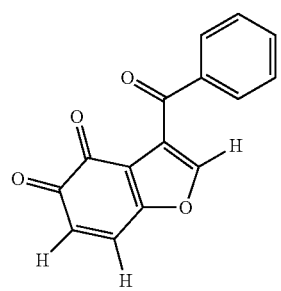

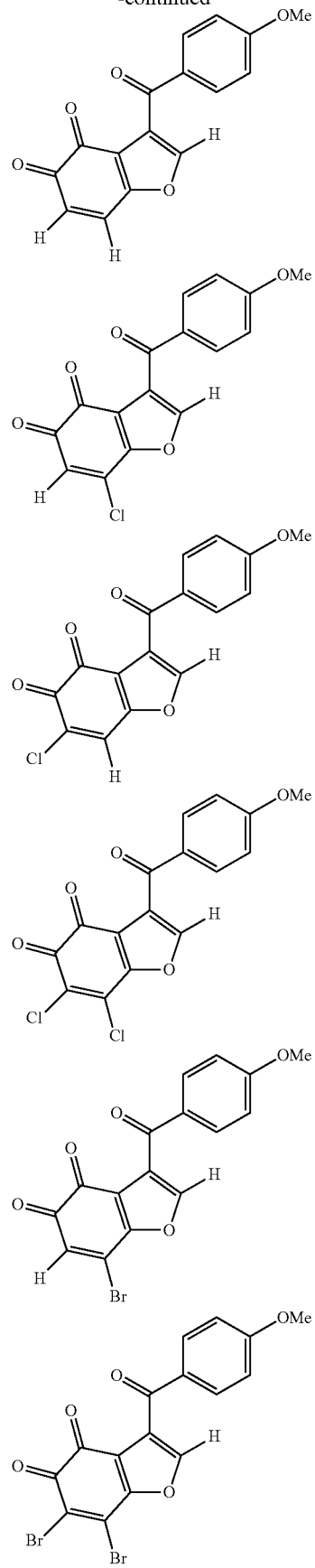
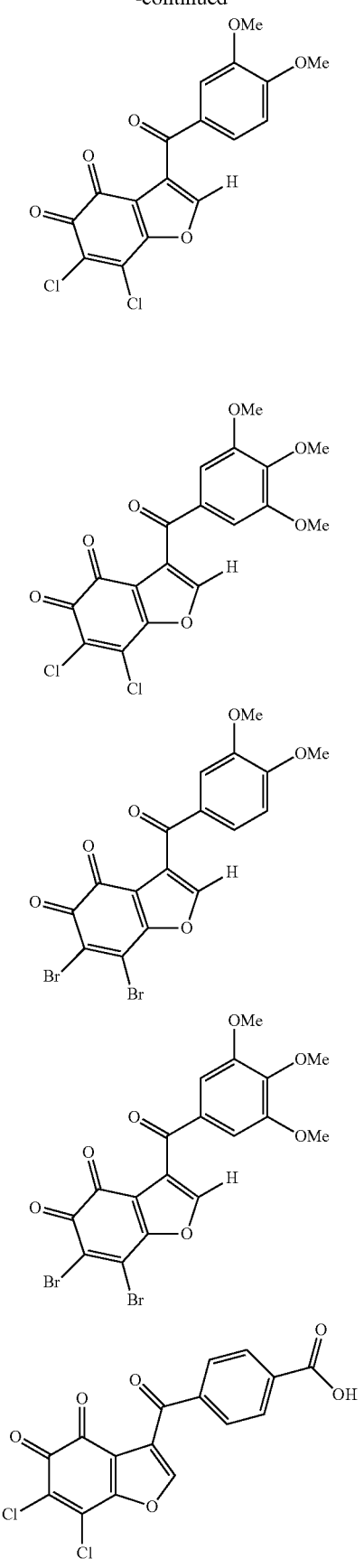

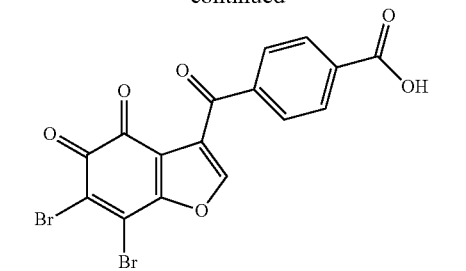
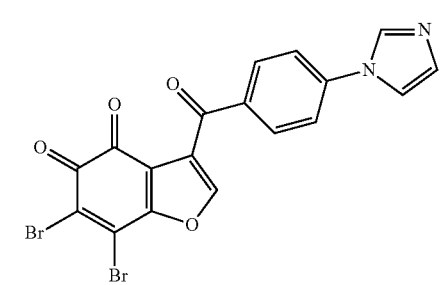
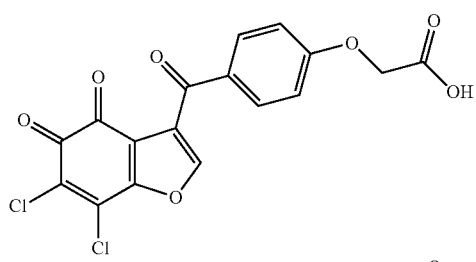
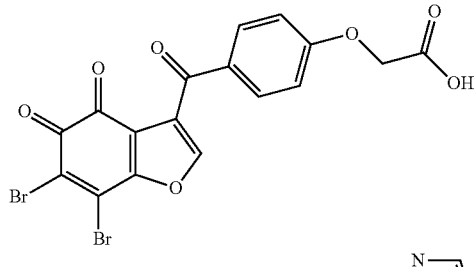
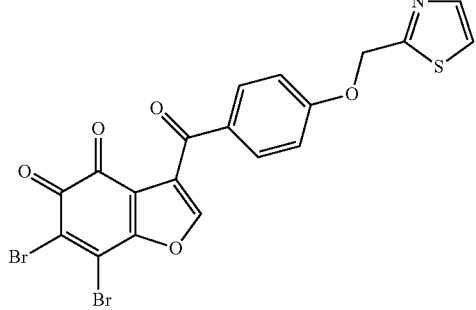
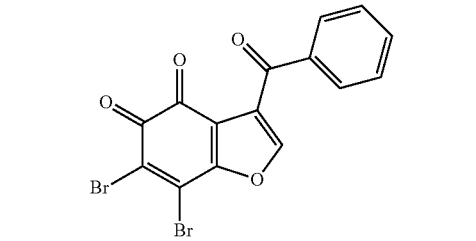
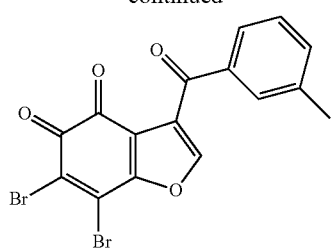
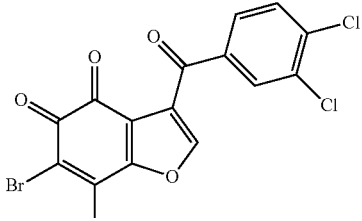
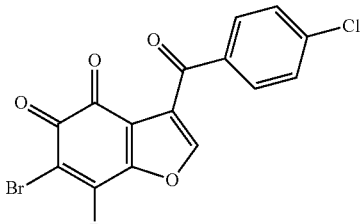
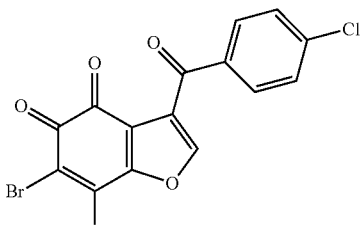
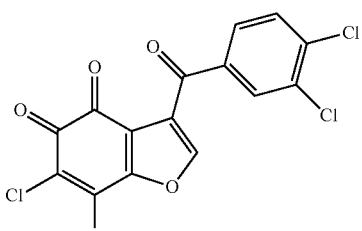
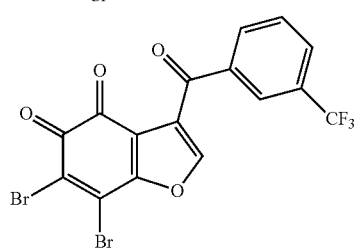
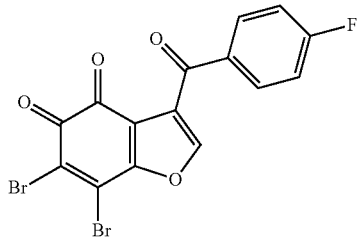

197
-continued
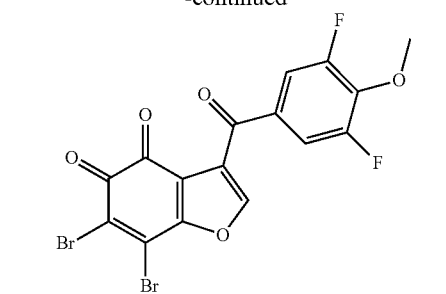
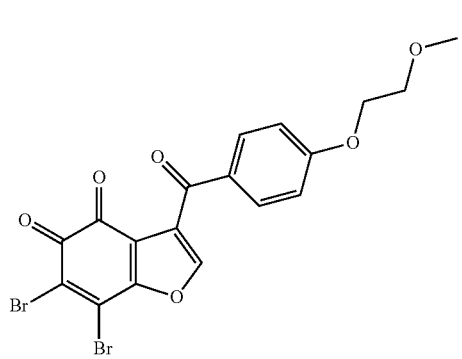
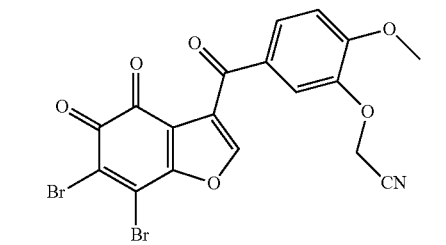
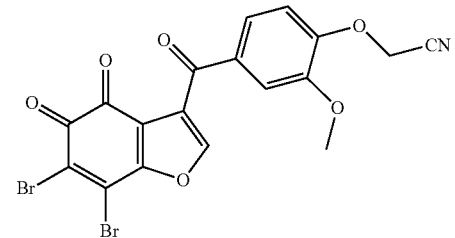
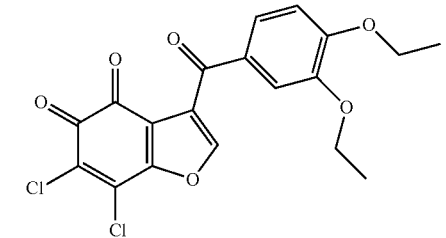
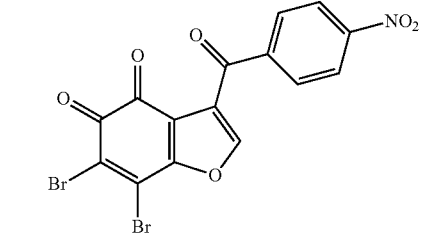
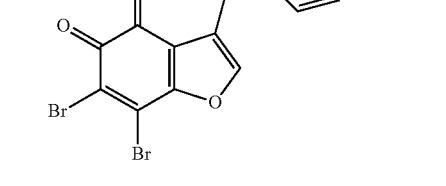
198
-continued
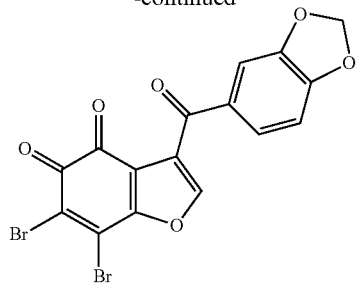
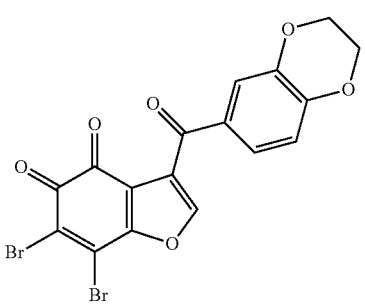
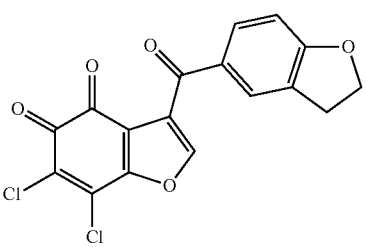
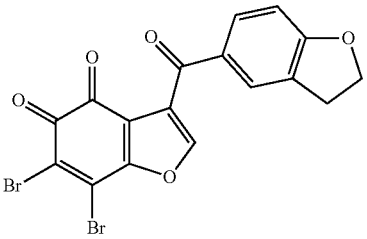
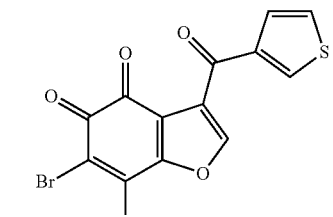
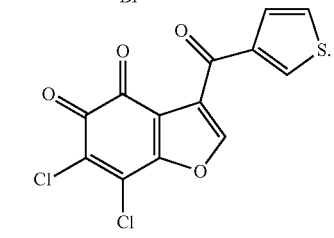

13. The compound of claim 1 of the formula:

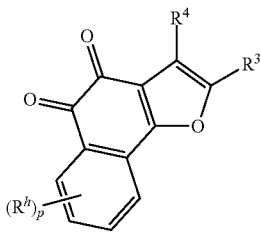

wherein:
p is an integer between 0 and 4, inclusive; and
each occurrence of $R^h$ is independently hydrogen; halogen; cyclic or acyclic, substituted or unsubstituted, branched or unbranched aliphatic; cyclic or acyclic, substituted or unsubstituted heteroaliphatic; substituted or unsubstituted, branched or unbranched acyl; substituted or unsubstituted aryl; substituted or unsubstituted heteroaryl; —$OR^i$; —$C(=O)R^i$; —$CO_2R^i$; —CN; —SCN; —$SR^i$; —$SOR^i$; —$SO_2R^i$; —$NO_2$; —$N_3$; —$N(R^i)_2$; —$NR^iC(=O)R^i$; —$NR^iC(=O)N(R^i)_2$; —$OC(=O)OR^i$; —$OC(=O)R^i$; —$OC(=O)N(R^i)_2$; —$NR^iC(=O)OR^i$; or —$C(R^i)_3$; wherein each occurrence of $R^i$ is independently hydrogen; halogen; a protecting group; an optionally substituted aliphatic or heteroaliphatic moiety; an acyl moiety; or an optionally substituted aryl or heteroaryl moiety.

14. The compound of claim 1 of one of the formulae:

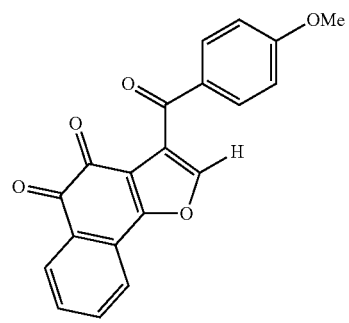

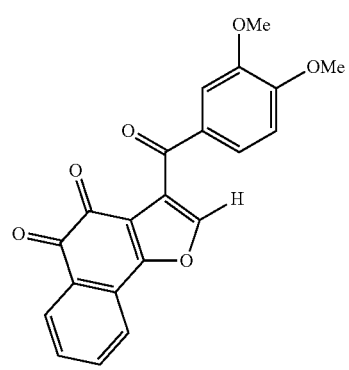

-continued

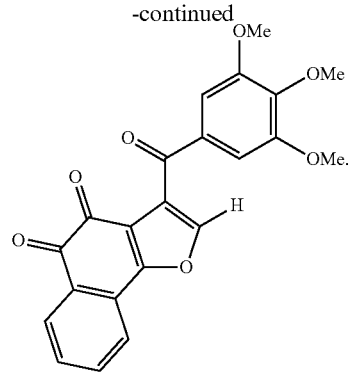

15. A pharmaceutical composition comprising a therapeutically effective amount of a compound of the formula:

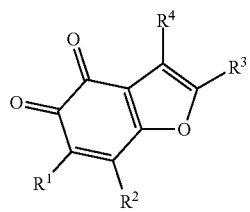

wherein:
$R^1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^a$; —$C(=O)R^a$; —$CO_2R^a$; —CN; —SCN; —$SR^a$; —$SOR^a$; —$SO_2R^a$; —$NO_2$; —$N_3$; —$N(R^a)_2$; —$NR^aC(=O)R^a$; —$NR^aC(=O)N(R^a)_2$; —$OC(=O)OR^a$; —$OC(=O)R^a$; —$OC(=O)N(R^a)_2$; —$NR^aC(=O)OR^a$; or —$C(R^a)_3$; wherein each occurrence of $R^a$ is independently hydrogen; halogen; a protecting group; an optionally substituted aliphatic or heteroaliphatic moiety; an acyl moiety; or an optionally substituted aryl or heteroaryl moiety;

$R^2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^b$; —$C(=O)R^b$; —$CO_2R^b$; —CN; —SCN; —$SR^b$; —$SOR^b$; —$SO_2R^b$; —$NO_2$; —$N_3$; —$N(R^b)_2$; —$NR^bC(=O)R^a$; —$NR^bC(=O)N(R^b)_2$; —$OC(=O)OR^b$; —$OC(=O)R^b$; —$OC(=O)N(R^b)_2$; —$NR^bC(=O)OR^b$; or —$C(R^b)_3$; wherein each occurrence of $R^b$ is independently hydrogen; halogen; a protecting group; an optionally substituted aliphatic or heteroaliphatic moiety; an acyl moiety; or an optionally substituted aryl or heteroaryl moiety;

wherein $R^1$ and $R^2$ when taken together form an optionally substituted, saturated or unsaturated aromatic, heteroaromatic, or nonaromatic 3-8 membered monocyclic or bicyclic ring optionally containing one or more heteroatoms selected from the group consisting of N, O, or S;

R³ is hydrogen; halogen; cyclic or acyclic, substituted or unsubstituted, branched or unbranched aliphatic; cyclic or acyclic, substituted or unsubstituted heteroaliphatic; substituted or unsubstituted, branched or unbranched acyl; substituted or unsubstituted aryl; substituted or unsubstituted heteroaryl; —OR$^c$; —C(=O)R$^c$; —CO$_2$R$^c$; —CN; —SCN; —SR$^c$; —SOR$^c$; —SO$_2$R$^c$; —NO$_2$; —N$_3$; —N(R$^c$)$_2$; —NR$^c$C(=O)R$^c$; —NR$^c$C(=O)N(R$^c$)$_2$; —OC(=O)OR$^c$; —OC(=O)R$^c$; —OC(=O)N(R$^c$)$_2$; —NR$^c$C(=O)OR$^c$; or —C(R$^c$)$_3$; wherein each occurrence of R$^c$ is independently hydrogen; halogen; a protecting group; an optionally substituted aliphatic or heteroaliphatic moiety; an acyl moiety; or an optionally substituted aryl or heteroaryl moiety; and R⁴ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$^d$; —C(=O)R$^d$; —CO$_2$R$^d$; —CN; —SCN; —SR$^d$; —SOR$^d$; —SO$_2$R$^d$; —NO$_2$; —N$_3$; —N(R$^d$)$_2$; —NR$^d$C(=O)R$^d$; —NR$^d$C(=O)N(R$^d$)$_2$; —OC(=O)OR$^d$; —OC(=O)R$^d$; —OC(=O)N(R$^d$)$_2$; —NR$^d$C(=O)OR$^d$; or —C(R$^d$)$_3$; wherein each occurrence of R$^d$ is independently hydrogen; halogen; a protecting group; an optionally substituted aliphatic or heteroaliphatic moiety; an acyl moiety; or an optionally substituted aryl or heteroaryl moiety, or a pharmaceutically acceptable salt thereof, and a pharmaceutically acceptable excipient.

16. The composition of claim 15, wherein the compound is of one of the formulae:

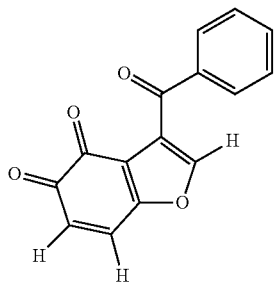

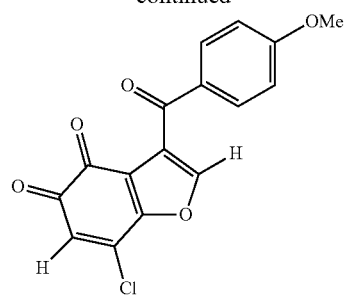

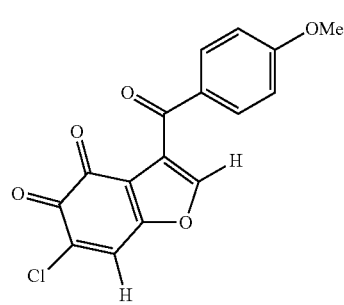

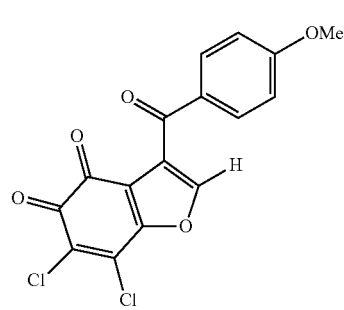

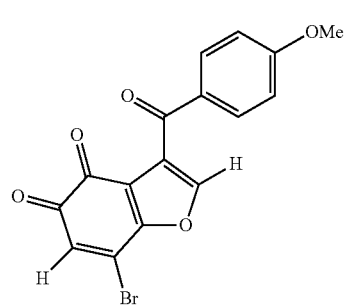

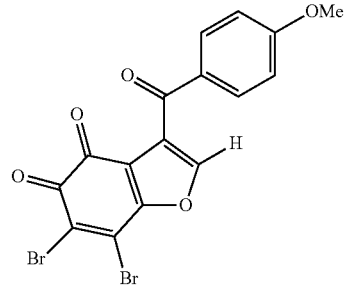

-continued
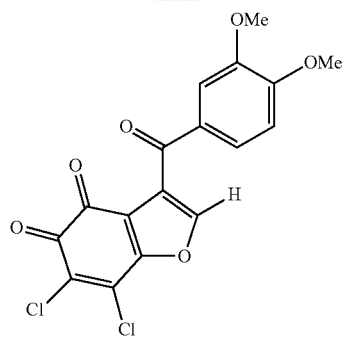
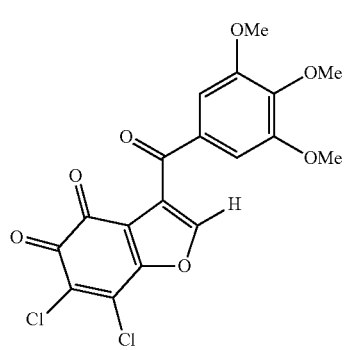
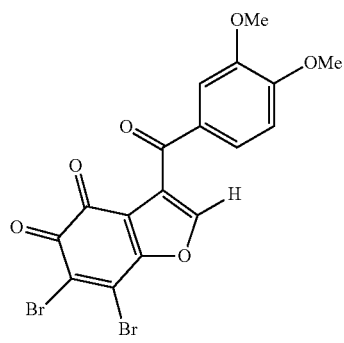
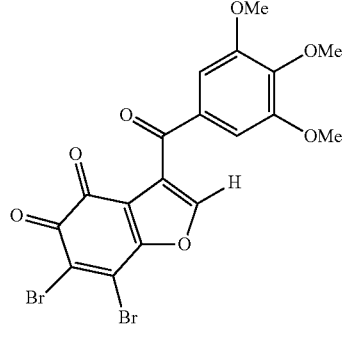
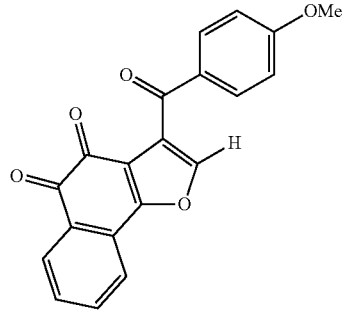
-continued
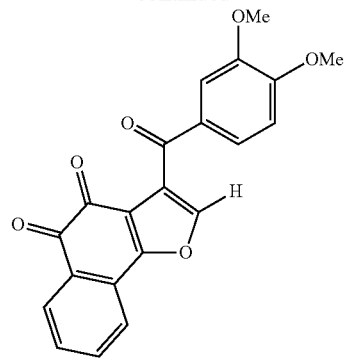
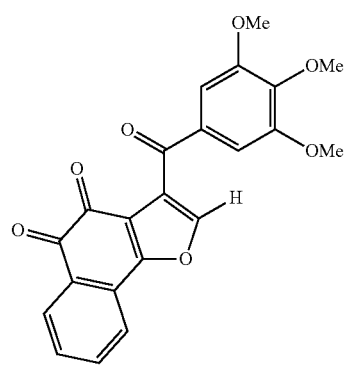
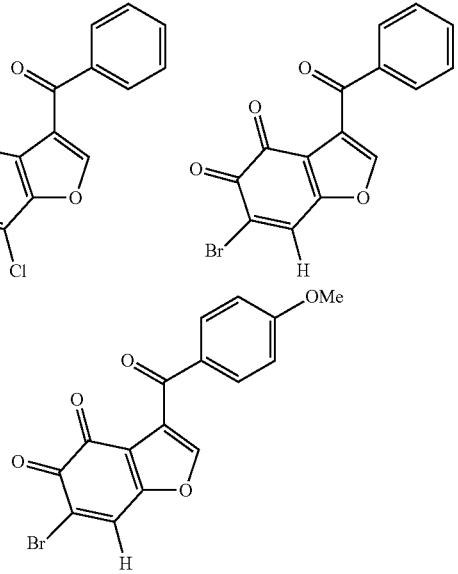
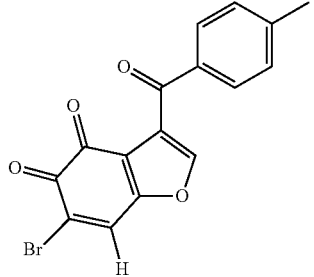

-continued

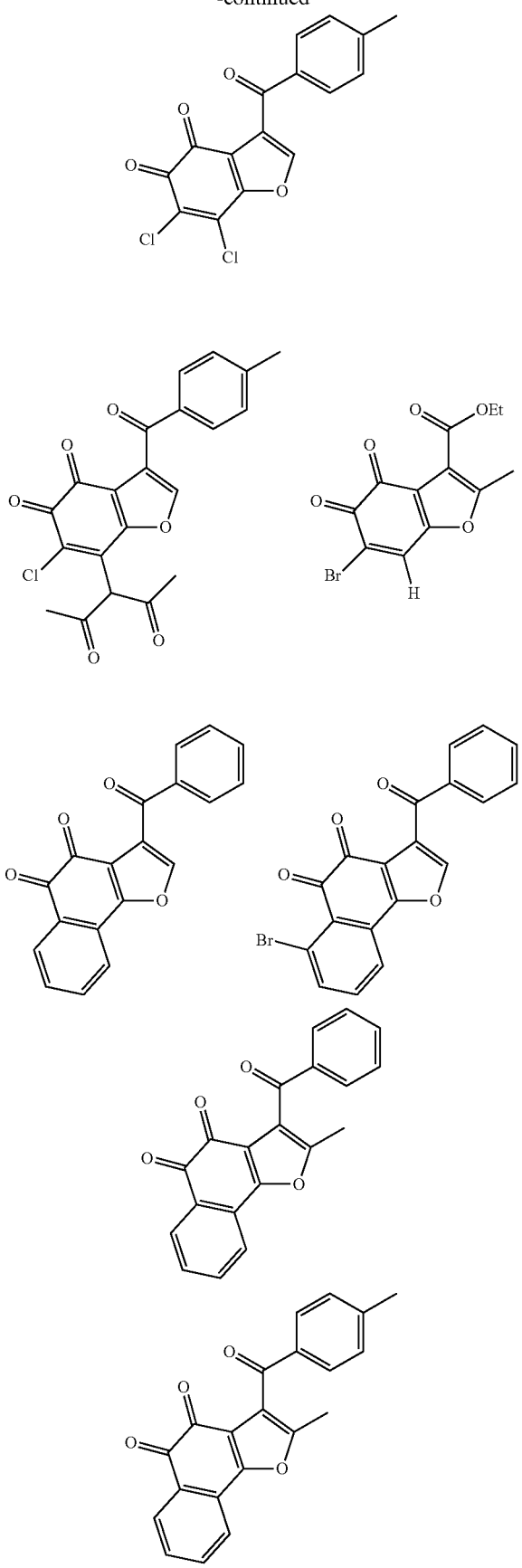

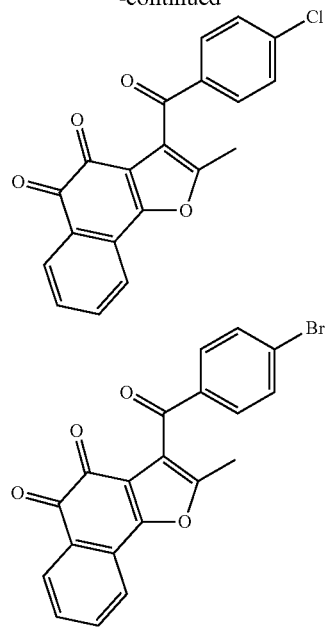

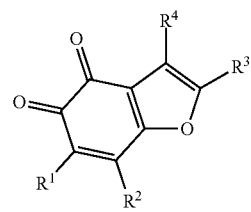

or a pharmaceutically acceptable salt thereof.

17. A method for inducing apoptosis comprising contacting a cell with a compound of the formula:

wherein:
$R^1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^a$; —$C(=O)R^a$; —$CO_2R^a$; —CN; —SCN; —$SR^a$; —$SOR^a$; —$SO_2R^a$; —$NO_2$; —$N_3$; —$N(R^a)_2$; —$NR^aC(=O)R^a$; —$NR^aC(=O)N(R^a)_2$; —$OC(=O)OR^a$; —$OC(=O)R^a$; —$OC(=O)N(R^a)_2$; —$NR^aC(=O)OR^a$; or —$C(R^a)_3$; wherein each occurrence of $R^a$ is independently hydrogen; halogen; a protecting group; an optionally substituted aliphatic or heteroaliphatic moiety; an acyl moiety; or an optionally substituted aryl or heteroaryl moiety;

$R^2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^b$; —$C(=O)R^b$; —$CO_2R^b$; —CN; —SCN; —$SR^b$; —$SOR^b$; —$SO_2R^b$; —$NO_2$; —$N_3$; —$N(R^b)_2$; —$NR^bC(=O)R^a$; —$NR^bC(=O)N(R^b)_2$; —$OC(=O)OR^b$; —$OC(=O)R^b$; —$OC(=O)N(R^b)_2$; —$NR^bC(=O)OR^b$; or —$C(R^b)_3$; wherein each occurrence of $R^b$ is independently hydrogen; halogen; a protecting group; an optionally substituted aliphatic or heteroaliphatic moiety; an acyl moiety; or an optionally substituted aryl or heteroaryl moiety;

wherein $R^1$ and $R^2$ when taken together form an optionally substituted, saturated or unsaturated aromatic, heteroaromatic, or nonaromatic 3-8 membered monocyclic or bicyclic ring optionally containing one or more heteroatoms selected from the group consisting of N, O, or S;

$R^3$ is hydrogen; halogen; cyclic or acyclic, substituted or unsubstituted, branched or unbranched aliphatic; cyclic or acyclic, substituted or unsubstituted heteroaliphatic; substituted or unsubstituted, branched or unbranched acyl; substituted or unsubstituted aryl; substituted or unsubstituted heteroaryl; —$OR^c$; —$C(=O)R^c$; —$CO_2R^c$; —CN; —SCN; —$SR^c$; —$SOR^c$; —$SO_2R^c$; —$NO_2$; —$N_3$; —$N(R^c)_2$; —$NR^cC(=O)R^c$; —$NR^cC(=O)N(R^c)_2$; —$OC(=O)OR^c$; —$OC(=O)R^c$; —$OC(=O)N(R^c)_2$; —$NR^cC(=O)OR^c$; or —$C(R^c)_3$; wherein each occurrence of $R^c$ is independently hydrogen; halogen; a protecting group; an optionally substituted aliphatic or heteroaliphatic moiety; an acyl moiety; or an optionally substituted aryl or heteroaryl moiety; and $R^4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^d$; —$C(=O)R^d$; —$CO_2R^d$; —CN; —SCN; —$SR^d$; —$SOR^d$; —$SO_2R^d$; —$NO_2$; —$N_3$; —$N(R^d)_2$; —$NR^dC(=O)R^d$; —$NR^dC(=O)N(R^d)_2$; —$OC(=O)OR^d$; —$OC(=O)R^d$; —$OC(=O)N(R^d)_2$; —$NR^dC(=O)OR^d$; or —$C(R^d)_3$; wherein each occurrence of $R^d$ is independently hydrogen; halogen; a protecting group; an optionally substituted aliphatic or heteroaliphatic moiety; an acyl moiety; or an optionally substituted aryl or heteroaryl moiety, or a pharmaceutically acceptable salt thereof, in an amount effective to induce apoptosis.

18. A method for treating a proliferative disease comprising administering to a subject in need thereof a therapeutically effective amount of a compound of the formula:

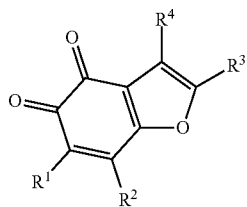

wherein:

$R^1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^a$; —$C(=O)R^a$; —$CO_2R^a$; —CN; —SCN; —$SR^a$; —$SOR^a$; —$SO_2R^a$; —$NO_2$; —$N_3$; —$N(R^a)_2$; —$NR^aC(=O)R^a$; —$NR^aC(=O)N(R^a)_2$; —$OC(=O)OR^a$; —$OC(=O)R^a$; —$OC(=O)N(R^a)_2$; —$NR^aC(=O)OR^a$; or —$C(R^a)_3$; wherein each occurrence of $R^a$ is independently hydrogen; halogen; a protecting group; an optionally substituted aliphatic or heteroaliphatic moiety; an acyl moiety; or an optionally substituted aryl or heteroaryl moiety;

$R^2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^b$; —$C(=O)R^b$; —$CO_2R^b$; —CN; —SCN; —$SR^b$; —$SOR^b$; —$SO_2R^b$; —$NO_2$; —$N_3$; —$N(R^b)_2$; —$NR^bC(=O)R^a$; —$NR^bC(=O)N(R^b)_2$; —$OC(=O)OR^b$; —$OC(=O)R^b$; —$OC(=O)N(R^b)_2$; —$NR^bC(=O)OR^b$; or —$C(R^b)_3$; wherein each occurrence of $R^b$ is independently hydrogen; halogen; a protecting group; an optionally substituted aliphatic or heteroaliphatic moiety; an acyl moiety; or an optionally substituted aryl or heteroaryl moiety;

wherein $R^1$ and $R^2$ when taken together form an optionally substituted, saturated or unsaturated aromatic, heteroaromatic, or nonaromatic 3-8 membered monocyclic or bicyclic ring optionally containing one or more heteroatoms selected from the group consisting of N, O, or S;

$R^3$ is hydrogen; halogen; cyclic or acyclic, substituted or unsubstituted, branched or unbranched aliphatic; cyclic or acyclic, substituted or unsubstituted heteroaliphatic; substituted or unsubstituted, branched or unbranched acyl; substituted or unsubstituted aryl; substituted or unsubstituted heteroaryl; —$OR^c$; —$C(=O)R^c$; —$CO_2R^c$; —CN; —SCN; —$SR^c$; —$SO^c$; —$SO_2R^c$; —$NO_2$; —$N_3$; —$N(R^c)_2$; —$NR^cC(=O)R^c$; —$NR^cC(=O)N(R^c)_2$; —$OC(=O)OR^c$; —$OC(=O)R^c$; —$OC(=O)N(R^c)_2$; —$NR^cC(=O)OR^c$; or —$C(R^c)_3$; wherein each occurrence of $R^c$ is independently hydrogen; halogen; a protecting group; an optionally substituted aliphatic or heteroaliphatic moiety; an acyl moiety; or an optionally substituted aryl or heteroaryl moiety; and $R^4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR_d$; —$C(=O)R^d$; —$CO_2R^d$; —CN; —SCN; —$SR^d$; —$SOR^d$; —$SO_2R^d$; —$NO_2$; —$N_3$; —$N(R^d)_2$; —$NR^dC(=O)R^d$; —$NR^dC(=O)N(R^d)_2$; —$OC(=O)OR^d$; —$OC(=O)R^d$; —$OC(=O)N(R^d)_2$; —$NR^dC(=O)OR^d$; or —$C(R^d)_3$; wherein each occurrence of $R^d$ is independently hydrogen; halogen; a protecting group; an optionally substituted aliphatic or heteroaliphatic moiety; an acyl moiety; or an optionally substituted aryl or heteroaryl moiety, or a pharmaceutically acceptable salt thereof.

19. A method for treating an infectious bacterial disease comprising contacting a cell with a therapeutically effective amount of a compound of the formula:

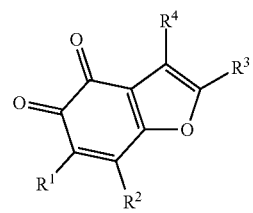

wherein:

$R^1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^a$; —$C(=O)R^a$; —$CO_2R^a$; —CN; —SCN; —$SR^a$; —$SOR^a$; —$SO_2R^a$; —$NO_2$; —$N_3$; —$N(R^a)_2$; —$NR^aC(=O)R^a$; —$NR^aC(=O)N(R^a)_2$; —$OC(=O)OR^a$; —$OC(=O)R^a$; —$OC(=O)N(R^a)_2$; —$NR^aC(=O)OR^a$; or —$C(R^a)_3$; wherein each occurrence of $R^a$ is independently hydrogen; halogen; a protecting group; an optionally substituted aliphatic or heteroaliphatic moiety; an acyl moiety; or an optionally substituted aryl or heteroaryl moiety;

$R^2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^b$; —$C(=O)R^b$; —$CO_2R^b$; —CN; —SCN; —$SR^b$; —$SOR^b$; —$SO_2R^b$; —$NO_2$; —$N_3$; —$N(R^b)_2$; —$NR^bC(=O)R^a$; —$NR^bC(=O)N(R^b)_2$; —$OC(=O)OR^b$; —$OC(=O)R^b$; —$OC(=O)N(R^b)_2$; —$NR^bC(=O)OR^b$; or —$C(R^b)_3$; wherein each occurrence of $R^b$ is independently hydrogen; halogen; a protecting group; an optionally substituted aliphatic or heteroaliphatic moiety; an acyl moiety; or an optionally substituted aryl or heteroaryl moiety;

wherein $R^1$ and $R^2$ when taken together form an optionally substituted, saturated or unsaturated aromatic, heteroaromatic, or nonaromatic 3-8 membered monocyclic or bicyclic ring optionally containing one or more heteroatoms selected from the group consisting of N, O, or S;

$R^3$ is hydrogen; halogen; cyclic or acyclic, substituted or unsubstituted, branched or unbranched aliphatic; cyclic or acyclic, substituted or unsubstituted heteroaliphatic; substituted or unsubstituted, branched or unbranched acyl; substituted or unsubstituted aryl; substituted or unsubstituted heteroaryl; —$OR^c$; —$C(=O)R^c$; —$CO_2R^c$; —CN; —SCN; —$SR^c$; —$SOR^c$; —$SO_2R^c$; —$NO_2$; —$N_3$; —$N(R^c)_2$; —$NR^cC(=O)R^c$; —$NR^cC(=O)N(R^c)_2$; —$OC(=O)OR^c$; —$OC(=O)R^c$; —$OC(=O)N(R^c)_2$; —$NR^cC(=O)OR^c$; or —$C(R^c)_3$; wherein each occurrence of $R^c$ is independently hydrogen; halogen; a protecting group; an optionally substituted aliphatic or heteroaliphatic moiety; an acyl moiety; or an optionally substituted aryl or heteroaryl moiety; and $R^4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR^d$; —$C(=O)R^d$; —$CO_2R^d$; —CN; —SCN; —$SR^d$; —$SOR^d$; —$SO_2R^d$; —$NO_2$; —$N_3$; —$N(R^d)_2$; —$NR^dC(=O)R^d$; —$NR^dC(=O)N(R^d)_2$; —$OC(=O)OR^d$; —$OC(=O)R^d$; —$OC(=O)N(R^d)_2$; —$NR^dC(=O)OR^d$; or —$C(R^d)_3$; wherein each occurrence of $R^d$ is independently hydrogen; halogen; a protecting group; an optionally substituted aliphatic or heteroaliphatic moiety; an acyl moiety; or an optionally substituted aryl or heteroaryl moiety, or a pharmaceutically acceptable salt thereof, to treat the infectious disease.

\* \* \* \* \*

UNITED STATES PATENT AND TRADEMARK OFFICE
CERTIFICATE OF CORRECTION

PATENT NO.        : 8,614,237 B2
APPLICATION NO.   : 13/318573
DATED             : December 24, 2013
INVENTOR(S)       : Hakim Djaballah et al.

It is certified that error appears in the above-identified patent and that said Letters Patent is hereby corrected as shown below:

*In the Claims*

In claim 12, at column 196, lines 25-35, the following structure is repeated:

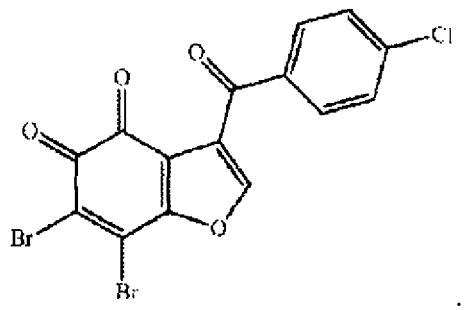

. Please remove the second occurrence of this structure.

In claim 18, at column 208, line 32, "-SO$^{c}$" should be: -- -SOR$^{c}$ --.

Signed and Sealed this
Thirteenth Day of May, 2014

Michelle K. Lee
*Deputy Director of the United States Patent and Trademark Office*